US011076536B2

United States Patent
Lys et al.

(10) Patent No.: US 11,076,536 B2
(45) Date of Patent: Aug. 3, 2021

(54) FLUID-COOLED LED-BASED LIGHTING METHODS AND APPARATUS FOR CONTROLLED ENVIRONMENT AGRICULTURE WITH INTEGRATED CAMERAS AND/OR SENSORS AND WIRELESS COMMUNICATIONS

(71) Applicant: Agnetix, Inc., San Diego, CA (US)

(72) Inventors: Ihor Lys, La Jolla, CA (US); Nicholas Maderas, Richmond, CA (US)

(73) Assignee: Agnetix, Inc., San Diego, CA (US)

( * ) Notice: Subject to any disclaimer, the term of this patent is extended or adjusted under 35 U.S.C. 154(b) by 0 days.

(21) Appl. No.: 17/083,461

(22) Filed: Oct. 29, 2020

(65) Prior Publication Data

US 2021/0059123 A1 Mar. 4, 2021

Related U.S. Application Data

(63) Continuation of application No. PCT/US2019/061324, filed on Nov. 13, 2019.

(Continued)

(51) Int. Cl.
*A01G 7/04* (2006.01)
*F21V 29/56* (2015.01)
(Continued)

(52) U.S. Cl.
CPC .............. *A01G 7/045* (2013.01); *A01G 9/24* (2013.01); *F21V 23/003* (2013.01);
(Continued)

(58) Field of Classification Search
CPC .......... A01G 7/045; A01G 9/24; A01G 9/246; A01G 31/06; F21V 29/56; F21V 23/003;
(Continued)

(56) References Cited

U.S. PATENT DOCUMENTS

| 3,869,605 A | 3/1975 | Davis |
| 4,300,623 A | 11/1981 | Meckler |

(Continued)

FOREIGN PATENT DOCUMENTS

| CA | 2632307 A1 | 11/2009 |
| CN | 102421281 A | 4/2012 |

(Continued)

OTHER PUBLICATIONS

Notice of Allowance in U.S. Appl. No. 16/404,192, dated Mar. 30, 2021, 9 pages.

(Continued)

*Primary Examiner* — Bao Q Truong
(74) *Attorney, Agent, or Firm* — Smith Baluch LLP

(57) ABSTRACT

A fluid-cooled LED-based lighting fixture for Controlled Environment Agriculture (CEA) to improve energy efficiency, recycle waste heat, and support the operation of environmental sensors in a controlled agricultural environment. In one example, a lighting fixture frame mechanically supports and houses respective components of the lighting fixture and includes a light spine to mechanically couple the lighting fixture to a support structure. One or more coolant pipes formed from copper and coupled to the lighting fixture frame conduct a fluid coolant through the lighting fixture to remove heat. The lighting fixture comprises one or more LED modules to emit light, one or more onboard sensors and/or cameras, wireless communication functionality, and multiple electrical power and communication ports to facilitate interconnection of the lighting fixture in a variety of controlled agricultural environments. In some examples, the lighting fixture includes a multispectral imaging system to acquire multispectral images of the environment.

30 Claims, 75 Drawing Sheets
(3 of 75 Drawing Sheet(s) Filed in Color)

Related U.S. Application Data

(60) Provisional application No. 62/760,572, filed on Nov. 13, 2018.

(51) Int. Cl.

| | | |
|---|---|---|
| *A01G 9/24* | (2006.01) | |
| *F21V 23/00* | (2015.01) | |
| *F21V 23/04* | (2006.01) | |
| *G01N 33/00* | (2006.01) | |
| *G06T 5/50* | (2006.01) | |
| *H04N 5/225* | (2006.01) | |
| *H04N 5/235* | (2006.01) | |
| *H04N 5/247* | (2006.01) | |
| *F21Y 113/10* | (2016.01) | |
| *F21Y 115/10* | (2016.01) | |

(52) U.S. Cl.
CPC ............ *F21V 23/045* (2013.01); *F21V 29/56* (2015.01); *G01N 33/0098* (2013.01); *G06T 5/50* (2013.01); *H04N 5/2252* (2013.01); *H04N 5/2256* (2013.01); *H04N 5/2354* (2013.01); *H04N 5/247* (2013.01); *F21Y 2113/10* (2016.08); *F21Y 2115/10* (2016.08); *G06T 2207/10048* (2013.01); *G06T 2207/20221* (2013.01)

(58) Field of Classification Search
CPC ........ F21V 23/045; F21V 29/51; F21V 29/59; F21V 29/503; F21V 29/508; F21V 29/71; F21V 29/713; F21V 29/502; G01N 33/0098; G06T 5/50; G06T 2207/10048; G06T 2207/20221; H04N 5/2252; H04N 5/2256; H04N 5/2354; H04N 5/247; F21Y 2113/10; F21Y 2115/10; F24F 2221/02

See application file for complete search history.

(56) References Cited

U.S. PATENT DOCUMENTS

| | | | |
|---|---|---|---|
| 5,012,609 A | 5/1991 | Ignatius et al. | |
| 6,431,723 B1 | 8/2002 | Schubert et al. | |
| 6,683,970 B1 | 1/2004 | Satake et al. | |
| 7,095,053 B2 | 8/2006 | Mazzochette et al. | |
| 7,252,408 B2 | 8/2007 | Mazzochette et al. | |
| 7,456,733 B2 | 11/2008 | Joy et al. | |
| 7,635,205 B2 | 12/2009 | Yu et al. | |
| 7,905,051 B2 | 3/2011 | Lysa | |
| 7,933,060 B2 | 4/2011 | Ishii et al. | |
| 8,297,782 B2 | 10/2012 | Bafetti et al. | |
| 8,358,097 B2 | 1/2013 | Cartwright | |
| 8,373,361 B2 | 2/2013 | Smits et al. | |
| 8,390,454 B2 | 3/2013 | Lyon et al. | |
| 8,558,413 B1 | 10/2013 | Lepard | |
| 8,651,704 B1 | 2/2014 | Gordin et al. | |
| 8,668,350 B2 | 3/2014 | Wells et al. | |
| 8,850,742 B2 | 10/2014 | Dube | |
| 8,920,001 B2 | 12/2014 | Part | |
| 9,137,874 B2 | 9/2015 | Maxik et al. | |
| 9,310,027 B2 | 4/2016 | Wells | |
| 9,310,049 B2 | 4/2016 | Wells | |
| 9,392,753 B2 | 7/2016 | Krijn et al. | |
| 9,404,648 B2 | 8/2016 | Druchinin | |
| D768,901 S | 10/2016 | Hillberg et al. | |
| 9,516,822 B2 | 12/2016 | Gonyer et al. | |
| 9,644,828 B1 | 5/2017 | May | |
| 9,688,951 B2 | 6/2017 | Krenbrink et al. | |
| 9,693,512 B2 | 7/2017 | Chen et al. | |
| 9,857,068 B2* | 1/2018 | Nguyen .............. F21V 15/015 | |
| 10,021,838 B1 | 7/2018 | Gustafik | |
| 10,034,435 B2 | 7/2018 | Helene et al. | |
| 10,175,215 B2 | 1/2019 | Ozcan et al. | |
| 10,188,046 B2 | 1/2019 | Wik et al. | |
| 10,261,493 B2 | 4/2019 | Hillberg et al. | |
| 10,339,380 B2 | 7/2019 | Greenberg et al. | |
| 10,426,099 B2 | 10/2019 | Clendinning et al. | |
| 10,512,221 B2 | 12/2019 | Wells | |
| 10,517,226 B2 | 12/2019 | Lee | |
| 10,555,466 B2 | 2/2020 | Gonyer et al. | |
| 10,627,785 B2 | 4/2020 | King et al. | |
| 10,635,274 B2 | 4/2020 | Greenberg et al. | |
| 10,660,170 B2 | 5/2020 | Wells | |
| 10,674,677 B2 | 6/2020 | Pohjanvouri et al. | |
| 10,750,671 B2 | 8/2020 | Wik et al. | |
| 10,856,470 B2* | 12/2020 | Lys .................. A01G 7/045 | |
| 10,881,051 B2* | 1/2021 | Lys .................. F21S 2/005 | |
| 10,949,974 B2 | 3/2021 | King et al. | |
| 2003/0216837 A1 | 11/2003 | Reich et al. | |
| 2005/0103473 A1 | 5/2005 | Todd et al. | |
| 2005/0152143 A1 | 7/2005 | Lee et al. | |
| 2008/0205030 A1 | 8/2008 | Hargreaves | |
| 2009/0027888 A1 | 1/2009 | Yu et al. | |
| 2009/0040759 A1 | 2/2009 | Zhang et al. | |
| 2010/0321950 A1 | 12/2010 | Wong | |
| 2011/0037369 A1 | 2/2011 | Van Elmpt | |
| 2012/0033431 A1 | 2/2012 | Martinez et al. | |
| 2012/0162976 A1 | 6/2012 | Claeys | |
| 2012/0211201 A1 | 8/2012 | Kunstwadl et al. | |
| 2012/0257375 A1 | 10/2012 | Tickner et al. | |
| 2013/0003382 A1 | 1/2013 | Ohura et al. | |
| 2013/0006401 A1 | 1/2013 | Shan | |
| 2013/0057247 A1 | 3/2013 | Russell et al. | |
| 2013/0293156 A1 | 11/2013 | Wells | |
| 2014/0259920 A1 | 9/2014 | Wilson | |
| 2014/0301067 A1 | 10/2014 | Morgan | |
| 2015/0250106 A1 | 9/2015 | Wik et al. | |
| 2015/0254738 A1 | 9/2015 | Wright, III et al. | |
| 2015/0313092 A1 | 11/2015 | Pocock et al. | |
| 2015/0356894 A1 | 12/2015 | Petrocy et al. | |
| 2016/0007424 A1 | 1/2016 | Maxik et al. | |
| 2016/0081178 A1 | 3/2016 | D'Onofrio | |
| 2016/0113211 A1 | 4/2016 | MacKenzie | |
| 2016/0113213 A1* | 4/2016 | Berinsky ............ H05B 47/19 47/58.1 LS |
| 2016/0209020 A1 | 7/2016 | Sprankle et al. | |
| 2016/0217562 A1 | 7/2016 | Ulman | |
| 2016/0235013 A1 | 8/2016 | Pohjanvouri et al. | |
| 2016/0262313 A1 | 9/2016 | Szeto et al. | |
| 2016/0278300 A1 | 9/2016 | Clendinning et al. | |
| 2016/0360712 A1 | 12/2016 | Yorio et al. | |
| 2016/0366833 A1 | 12/2016 | Pohjanvouri et al. | |
| 2017/0023193 A1 | 1/2017 | Thosteson et al. | |
| 2017/0055474 A1 | 3/2017 | Storey | |
| 2017/0095639 A1 | 4/2017 | Trzecieski | |
| 2017/0146226 A1 | 5/2017 | Storey et al. | |
| 2017/0215252 A1 | 7/2017 | Wells | |
| 2017/0231169 A1 | 8/2017 | Gillard et al. | |
| 2017/0241632 A1 | 8/2017 | Nguyen et al. | |
| 2017/0244934 A1 | 8/2017 | Chien | |
| 2017/0303478 A1 | 10/2017 | Smith et al. | |
| 2017/0311414 A1* | 10/2017 | Kido ............... H05B 45/20 | |
| 2017/0339839 A1 | 11/2017 | Carstensen et al. | |
| 2018/0007845 A1 | 1/2018 | Martin | |
| 2018/0014485 A1 | 1/2018 | Whitcher et al. | |
| 2018/0054985 A1 | 3/2018 | Li | |
| 2018/0116025 A1 | 4/2018 | Adams et al. | |
| 2018/0128472 A1 | 5/2018 | Nguyen et al. | |
| 2018/0259550 A1 | 9/2018 | Nakamura et al. | |
| 2018/0309941 A1 | 10/2018 | Lopez et al. | |
| 2018/0313760 A1 | 11/2018 | Kramer et al. | |
| 2019/0008096 A1 | 1/2019 | Lee | |
| 2019/0364743 A1 | 1/2019 | Lys et al. | |
| 2019/0116739 A1 | 4/2019 | Lys et al. | |
| 2019/0141911 A1 | 5/2019 | Nguyen et al. | |
| 2019/0221044 A1 | 7/2019 | Motta et al. | |
| 2019/0234797 A1 | 8/2019 | Ramer et al. | |
| 2019/0244417 A1 | 8/2019 | Ashdown et al. | |
| 2019/0244428 A1 | 8/2019 | Greenberg et al. | |
| 2019/0246278 A1 | 8/2019 | Dorfman et al. | |
| 2019/0303164 A1 | 10/2019 | King | |
| 2019/0353341 A1 | 11/2019 | Spiro | |

(56) References Cited

U.S. PATENT DOCUMENTS

| | | |
|---|---|---|
| 2020/0077598 A1 | 3/2020 | Wells |
| 2020/0134741 A1 | 4/2020 | Bongartz et al. |
| 2020/0163183 A1 | 5/2020 | Lys et al. |
| 2020/0236862 A1 | 7/2020 | Lys et al. |
| 2020/0236870 A1 | 7/2020 | Lys et al. |

FOREIGN PATENT DOCUMENTS

| | | |
|---|---|---|
| CN | 203628582 U | 6/2014 |
| CN | 203656872 U | 6/2014 |
| CN | 203686764 U | 7/2014 |
| CN | 104520636 A | 4/2015 |
| CN | 105423198 A | 3/2016 |
| CN | 106151982 A | 11/2016 |
| CN | 106402746 A | 2/2017 |
| CN | 107091467 A | 8/2017 |
| CN | 107208871 A | 9/2017 |
| CN | 207369705 U | 5/2018 |
| DK | 2129212 T3 | 3/2016 |
| EP | 3123823 A1 | 2/2017 |
| EP | 3269231 A1 | 1/2018 |
| EP | 3281514 A1 | 2/2018 |
| EP | 3324099 A1 | 5/2018 |
| EP | 3326452 A1 | 5/2018 |
| EP | 3065535 B1 | 7/2020 |
| FR | 2173912 A1 | 10/1973 |
| JP | 2010192152 A | 9/2010 |
| JP | 2011054529 A | 3/2011 |
| JP | 2016214153 A | 12/2016 |
| KR | 10-0941000 B1 | 2/2010 |
| KR | 101020063 B1 | 3/2011 |
| KR | 101068315 B1 | 9/2011 |
| KR | 201125871 A | 9/2011 |
| KR | 101234587 B1 | 2/2013 |
| KR | 20150033363 A | 4/2015 |
| KR | 20150035102 A | 4/2015 |
| KR | 20170021662 A | 2/2017 |
| KR | 10-1730069 B1 | 4/2017 |
| KR | 20170115987 A | 10/2017 |
| KR | 20170127406 A | 11/2017 |
| TW | M471005 U | 1/2014 |
| TW | 201501570 A | 1/2015 |
| WO | WO 2008/112822 | 9/2008 |
| WO | WO 2009/074602 A3 | 6/2009 |
| WO | WO 2012/067499 A1 | 5/2012 |
| WO | WO-2014/011444 A3 | 3/2014 |
| WO | WO-2014/064893 A1 | 5/2014 |
| WO | WO 2014/098735 A1 | 6/2014 |
| WO | WO 2015/004179 A1 | 1/2015 |
| WO | WO 2015/144660 A1 | 10/2015 |
| WO | WO-2016/115314 A1 | 7/2016 |
| WO | WO-2016/166311 | 10/2016 |
| WO | WO-2017/044177 A1 | 3/2017 |
| WO | WO-2017/134623 A1 | 8/2017 |
| WO | WO 2017/184448 A1 | 10/2017 |
| WO | WO-2017/192566 A1 | 11/2017 |
| WO | WO 2018/010946 A1 | 1/2018 |
| WO | WO 2018/013161 A1 | 1/2018 |
| WO | WO 2018/017451 A1 | 1/2018 |
| WO | WO 2018/091560 A1 | 5/2018 |
| WO | WO 2019/014703 A1 | 1/2019 |
| WO | WO 2019/040944 A2 | 2/2019 |
| WO | WO 2019/204805 A1 | 10/2019 |
| WO | WO 2019/213652 A1 | 11/2019 |
| WO | WO 2020/219832 | 10/2020 |

OTHER PUBLICATIONS

Notice of Allowance in U.S. Appl. No. 17/141,173, dated Mar. 30, 2021, 24 pages.
International Search Report and Written Opinion in International Patent Application No. PCT/US2020/064837 dated Mar. 31, 2021, 13 pages.
Corrected Notice of Allowance in U.S. Appl. No. 16/390,501, dated Apr. 8, 2021, 2 pages.
Extended European Search Report in European Patent Application No. 18848610.4 dated Mar. 2, 2021, 11 pages.
LED Application. Odtech 2014. Accessed at http://www.od-tech.com/eng/subl/s42.php?Phpsessid=64d5029f1b80d6df54ab87468d7f9172 on Apr. 23, 2018, 1 page.
PFLi Water-cooled LED Bar. NewLux Horticultural LED Lighting. Accessed at http://newlux.com/product/pfli-water-cooled-led-bar/ on Apr. 23, 2018, 8 pages.
Our Grow Light Models. GS Thermal Solutions 2018. Accessed at http://gsgrow.com/technology/liguid-cooled-led-models/ on Apr. 23, 2018.
GC-Plus Control System. Agrowtek Inc. Accessed at http://agrowtek.com/component/page,shop.product_details/flypage,flypage.tpl/product_id,53/category_id,14/option,com_virtuemart/Itemid,26/ on May 25, 2018, 4 pages.
Cooking Hacks. Accessed at https://www.cooking-hacks.com/documentation/tutorials/open-garden-hydroponics-irrigation-system-sensors-plant-monitoring on May 25, 2018, 11 pages.
LED Lighting for Horticulture, Aquabar LED Grow System brochure. Genesis Scientific. Accessed at www.gs.horti.com on Oct. 31, 2017, 4 pages.
Intravision Spectra R&D, Water-cooled 7-LED band Plant Research Rig., Accessed at <www.intravisiongroup.com> on Apr. 7, 2016, 1 page.
LED Grow World, Liquid Cooled LED Grow Light brochure, Model BLE-GL9015, 2017. Accessed at www.ledgrowworld.co, 3 pages.
JPFA Plant Factory Association. Accessed at http://npoplantfactory.org/english.html on May 18, 2018, 6 pages.
Harper, 2017: The OpenAG Ecosystem Expands Research, Non-Profit Ventrures. The Medium, Jan. 27, 2017. Accessed at https://medium.com/@calebgrowsfood/2017-the-openag-ecosystem-expands-research-non-profit-ventures-b5762beed64b, 10 pages.
Fenome. Vimeo. Accessed at https://vimeo.com/219601049, 3 pages, 2018.
Agnetix—The A3 Product Brochure, 2 pages, Aug. 24, 2017.
Agnetix—A3 Cables, 5 pages, Feb. 26, 2018.
Agnetix—Liquid-cooled, intelligent LED horticultural platform, 25 pages, Jan. 31, 2018.
Agnetix—A3 Horticulture LED, 6 pages, Jan. 31, 2018.
Agnetix—4' x 1 A3 Light Assembly, 1 page, Jan. 24, 2018.
Agnetix—8' x 2 A3 Light Assembly, 1 page, Jan. 24, 2018.
Agnetix—12' x 3 A3 Light Assembly, 1 page, Jan. 24, 2018.
Agnetix—16' x 3 A3 Light Assembly, 1 page, Jan. 23, 2018.
Agnetix—20' x 4 A3 Light Assembly, 1 page, Jan. 23, 2018.
Agnetix—20' x 5 A3 Light Assembly, 1 page, Mar. 8, 2018.
Agnetix—24' x 5 A3 Light Assembly, 1 page, Apr. 3, 2018.
Agnetix—24' x 6 A3 Light Assembly, 1 page, Jan. 16, 2018.
Agnetix—36' x 9 A3 Light Assembly, 1 page, Dec. 5, 2017.
Agnetix—32' x 8 A3 Light Assembly, 1 page, Feb. 12, 2017.
Agnetix—24'x12'x8' Growth Chamber, 1 page, Mar. 1, 2018.
Agnetix—42'x180'x12' Greenhouse, 1 page, Jan. 29, 2018.
Agnetix—20'x8'x9.5' 3-Light Isopod, 1 page, Mar. 17, 2018.
Agnetix—Hydronics Loop Diagram, 1 page, Mar. 9, 2018.
Bah, A. et al., "Sensor Technologies for Precision Soil Nutrient Management and Monitoring," American Journal of Agriculture and Biological Sciences 7(1): pp. 43-49, 2012.
Chandra, S. et al., "Photosynthetic response of Cannabis sativa L. To variations in Photosynthetic photon flux densities, temperature and $CO_2$ conditions," Physiol. Mol. Biol. Plants, vol. 14, No. 4, pp. 299-306, 2008.
Hamza, B. et al., "Distributed Polymer Optical Fibre Sensing of Moisture and pH in Soils: Feasibility for E-Agriculture," retrieved from https://www.research.manchester.ac.ukportal/files/38209074/FULL_TEXT.pdf, 7 pages, Nov. 3, 2017.
Nakano, A., "Plant Factories in Japan—An Integrated Approach," NARO Institute of Vegetable and Floriculture Science, National Agriculture and Food Research Organization (NARO), Tsukuba, Ibaraki, Japan, 11 pages. Sep. 11, 2017.

(56) References Cited

OTHER PUBLICATIONS

Nelson, J. A. et al., "Economic Analysis of Greenhouse Lighting: Light Emitting Diodes vs. High Intensity Discharge Features," PLoS One, vol. 9, Issue 6, e99010, 10 pages, 2014.
Photosynthetically Active Radiation (PAR) Units, 1 page, Aug. 16, 2000.
Sihombing, P. et al., "Automated hydroponics nutrition plants systems using arduino uno microcontroller based on android," 2nd International Conference on Computing and Applied Informatics, IPO Conf. Series: Journal of Physics 978 012014, 6 pages, 2018.
Vellidis, G., "The University of Georgia Smart Sensor Array," <http://scienceinhydroponics.com/2017/03/automating-a-hydroponic-system-sensors-and-monitoring.html>, 11 pages, 2018.
Vellidis, G. et al., "A real-time wireless smart sensor array for scheduling irrigation," Computers and Electronics in Agriculture 61, pp. 44-50, 2008.
Vijay, N., "Application of sensor networks in agriculture," https://ieeexplore.ieee.org/document/6719103/, Third International Conference on Sustainable Energy and Intelligent System, Dec. 27-29, 2012.
AgNetix Liquid Cooled Horitcultural Lighting and Agnetix Water-Cooled LED & Sensory Platform, Jan. 31, 2018, 25 pages.
Products—Thrive Agritech. Accessed at http://www.thriveagritech.com/products/on May 16, 2019. 9 pages.
Intravision Products. Accessed at https://www.intravisiongroup.com/products on May 16, 2019. 2 pages.
Smart LED Grow Lights with Wireless Control LumiGrow. Accessed at https://www.lumigrow.com/ accessed on May 16, 2019. 8 pages.
PlantLab. Accessed at https://www.plantlab.com/ on May 16, 2019. 8 pages.
Aquabar. Genesis Scientific. Accessed at https://gs-horti.com/products/led-grow-lights/aquabar.html on May 16, 2019. 7 pages.
Viparspectra. Accessed at http://www.viparspectra.com/ on May 16, 2019. 10 pages.
Which regions of the electromagnetic spectrum do plants use to drive photosynthesis? Heliospectra. Accessed at www.heliospectra.com, Oct. 5, 2012.
International Search Report and Written Opinion in International Patent Application No. PCT/US2018/048190 dated Feb. 8, 2019, 100 pages.
Guidelines for Measuring and Reporting Environmental Parameters for Experiments in Greenhouses. International Committee for Controlled Environment Guidelines, Feb. 2016, 37 pages.
2JCIE-BU Environment Sensor (USB Type). Omron Electronic Components. Accessed at https://www.components.omron.com/product-detail?partNumber=2JCIE-BU on Apr. 13, 2019, 5 pages.
Environment Sensor Integrating various sensing capabilities into one single loT sensor. Accessed at https://www.components.omron.com/solutions/mems-sensors/environment-sensor on Apr. 13, 2019, 6 pages.
Environment Sensor 2JCIE Series Catalog. Omron Electronic Components. Accessed at https://www.components.omron.com/solutions/mems-sensors/environment-sensor on May 16, 2019, 16 pages.
Schriber, Smart Agriculture Sensors: Helping Small Farmers and Positively Impacting Global Issues, Too. Mouser Electronics. Accessed at https://www.mousercom/applications/smart-agriculture-sensors/ on Apr. 13, 2019, 4 pages.
Lakhiar et al., "Monitoring and Control Systems in Agriculture Using Intelligent Sensor Techniques: A Review of the Aeroponic System." Journal of Sensors 2018 (2018), 19 pages.
Hwang et al., "Study on an agricultural environment monitoring server system using wireless sensor networks." Sensors 10.12 (2010): 11189-11211.
Kerns et al., "Automated aeroponics system using loT for smart farming." European Scientific Journal, ESJ 13.10 (2017), 7 pages.
Tsitsimpelis et al., "Development of a grow-cell test facility for research into sustainable controlled-environment agriculture." Biosystems Engineering 150 (2016): 40-53.

Keshtgary et al., "An efficient wireless sensor network for precision agriculture." Canadian Journal on Multimedia and Wireless Networks 3.1 (2012): 1-5.
Jawad et al., "Energy-efficient wireless sensor networks for precision agriculture: A review." Sensors 17.8 (2017): 1781, 45 pages.
Shamshiri et al., "Advances in greenhouse automation and controlled environment agriculture: A transition to plant factories and urban agriculture." (2018), 22 pages.
Ruiz-Garcia et al., "A review of wireless sensor technologies and applications in agriculture and food industry: state of the art and current trends." sensors 9.6 (2009): 4728-4750.
Dener et al., "Smart technologies with wireless sensor networks." Procedia-Social and Behavioral Sciences 195 (2015): 1915-1921.
Pahuja et al., "A wireless sensor network for greenhouse climate control." IEEE Pervasive Computing 12.2 (2013): 49-58.
Balendonck et al., "Monitoring spatial and temporal distribution of temperature and relative humidity in greenhouses based on wireless sensor technology." International Conference on Agricultural Engineering-AgEng. 2010, 10 pages.
Chaudhary et al., "Application of wireless sensor networks for greenhouse parameter control in precision agriculture." International Journal of Wireless & Mobile Networks (IJWMN) 3.1 (2011): 140-149.
Ferentinos et al., "Wireless sensor networks for greenhouse climate and plant condition assessment." Biosystems engineering 153 (2017): 70-81.
Vox et al., "A wireless telecommunications network for real-time monitoring of greenhouse microclimate." Journal of Agricultural Engineering 45.2 (2014): 70-79.
Sánchez-Álvarez et al., "A Framework to Design the Computational Load Distribution of Wireless Sensor Networks in Power Consumption Constrained Environments." Sensors 18.4 (2018): 954, 20 pages.
Laamrani et al., "Using a Mobile Device "App" and Proximal Remote Sensing Technologies to Assess Soil Cover Fractions on Agricultural Fields." Sensors 18.3 (2018): 708, 16 pages.
Peng et al., "Comparative study of the detection of chromium content in rice leaves by 532 nm and 1064 nm laser-induced breakdown spectroscopy." Sensors 18.2 (2018): 621, 18 pages.
Pichorim et al., "Two solutions of soil moisture sensing with RFID for landslide monitoring." Sensors 18.2 (2018): 452, 11 pages.
Behmann et al., "Specim IQ: evaluation of a new, miniaturized handheld hyperspectral camera and its application for plant phenotyping and disease detection." Sensors 18.2 (2018): 441, 20 pages.
Nie et al., "Research on the effects of drying temperature on nitrogen detection of different soil types by near infrared sensors." Sensors 18.2 (2018): 391, 22 pages.
Cui et al., "Plant pest detection using an artificial nose system: a review." Sensors 18.2 (2018): 378, 18 pages.
Kafarski et al., "Evaluation of apple maturity with two types of dielectric probes." Sensors 18.1 (2018): 121, 13 pages.
Lim et al., "Application of near infrared reflectance spectroscopy for rapid and non-destructive discrimination of hulled barley, naked barley, and wheat contaminated with Fusarium." Sensors 18.1 (2018): 113, 16 pages.
Barriuso et al., "Combination of multi-agent systems and wireless sensor networks for the monitoring of cattle." Sensors 18.1 (2018): 108, 27 pages.
Meng et al., "A Compound Sensor for Simultaneous Measurement of Packing Density and Moisture Content of Silage." Sensors 18.1 (2018): 73, 10 pages.
Brinkhoff et al., "Multisensor capacitance probes for simultaneously monitoring rice field soil-water-crop-ambient conditions." Sensors 18.1 (2018): 53, 14 pages.
Bengochea-Guevara et al., "A low-cost approach to automatically obtain accurate 3D models of woody crops." Sensors 18.1 (2018): 30, 17 pages.
Skovsen et al., "Estimation of the Botanical Composition of Clover-Grass Leys from RGB Images Using Data Simulation and Fully Convolutional Neural Networks." Sensors 17.12 (2017): 2930, 18 pages.

(56) References Cited

OTHER PUBLICATIONS

Ravichandran et al., "In vivo non-destructive monitoring of capsicum annuum seed growth with diverse nacl concentrations using optical detection technique." Sensors 17.12 (2017): 2887, 12 pages.
Mao et al., "Contamination Event Detection with Multivariate Time-Series Data in Agricultural Water Monitoring." Sensors 17.12 (2017): 2806, 19 pages.
Castrignanò et al., "A combined approach of sensor data fusion and multivariate geostatistics for delineation of homogeneous zones in an agricultural field." Sensors 17.12 (2017): 2794, 20 pages.
Al-Saddik et al., "Development of spectral disease indices for 'Flavescence Dorée'grapevine disease identification." Sensors 17.12 (2017): 2772, 25 pages.
Wojnowski et al., "Portable electronic nose based on electrochemical sensors for food quality assessment." Sensors 17.12 (2017): 2715, 14 pages.
Dong et al., "Estimating crop area at county level on the North China Plain with an indirect sampling of segments and an adapted regression estimator." Sensors 17.11 (2017): 2638, 9 pages.
Kragh et al., "Fieldsafe: dataset for obstacle detection in agriculture." Sensors 17.11 (2017): 2579, 11 pages.
Zou et al., "A Real-Time Smooth Weighted Data Fusion Algorithm for Greenhouse Sensing Based on Wireless Sensor Networks." Sensors 17.11 (2017): 2555, 14 pages.
Fan et al., "Fast detection of striped stem-borer (Chilo suppressalis Walker) infested rice seedling based on visible/near-infrared hyperspectral imaging system." Sensors 17.11 (2017): 2470, 13 pages.
Nawar et al., "Comparison between random forests, artificial neural networks and gradient boosted machines methods of on-line Vis-NIR spectroscopy measurements of soil total nitrogen and total carbon." Sensors 17.10 (2017): 2428, 22 pages.
Moorhead et al., "Evaluation of sensible heat flux and evapotranspiration estimates using a surface layer scintillometer and a large weighing lysimeter." Sensors 17.10 (2017): 2350, 23 pages.
Corwin et al., "Evaluating Oilseed Biofuel Production Feasibility in California's San Joaquin Valley Using Geophysical and Remote Sensing Techniques." Sensors 17.10 (2017): 2343, 25 pages.
Nader et al., "Assessing white wine viscosity variation using polarized laser speckle: A promising alternative to wine sensory analysis." Sensors 17.10 (2017): 2340, 12 pages.
Tamouridou et al., "Application of multilayer perceptron with automatic relevance determination on weed mapping using UAV multispectral imagery." Sensors 17.10 (2017): 2307, 9 pages.
Lim et al., "Classification of Fusarium-Infected Korean Hulled Barley Using Near-Infrared Reflectance Spectroscopy and Partial Least Squares Discriminant Analysis." Sensors 17.10 (2017): 2258, 15 pages.
Jia et al., "Hyperspectral imaging analysis for the classification of soil types and the determination of soil total nitrogen." Sensors 17.10 (2017): 2252, 14 pages.
Fuentes et al., "A robust deep-learning-based detector for real-time tomato plant diseases and pests recognition." Sensors 17.9 (2017): 2022, 21 pages.
Alexandridis et al., "Novelty detection classifiers in weed mapping: Silybum marianum detection on UAV multispectral images." Sensors 17.9 (2017): 2007, 12 pages.
Feng et al., "Discrimination of transgenic maize kernel using NIR hyperspectral imaging and multivariate data analysis." Sensors 17.8 (2017): 1894, 14 pages.
Schmittmann et al., "A True-Color Sensor and Suitable Evaluation Algorithm for Plant Recognition." Sensors 17.8 (2017): 1823, 16 pages.
Villarrubia et al., "Combining multi-agent systems and wireless sensor networks for monitoring crop irrigation." Sensors 17.8 (2017): 1775, 23 pages.
Kicherer et al., "Phenoliner: A new field phenotyping platform for grapevine research." Sensors 17.7 (2017): 1625, 18 pages.
Wei et al., "Leaf area index estimation using Chinese GF-1 wide field view data in an agriculture region." Sensors 17.7 (2017): 1593, 14 pages.
Martinez-Guanter et al., "Optical sensing to determine tomato plant spacing for precise agrochemical application: Two scenarios." Sensors 17.5 (2017): 1096, 19 pages.
Shi et al., "Spectroscopic diagnosis of arsenic contamination in agricultural soils." Sensors 17.5 (2017): 1036, 15 pages.
Kameoka et al., "A wireless sensor network for growth environment measurement and multi-band optical sensing to diagnose tree vigor." Sensors 17.5 (2017): 966, 21 pages.
Sniffler, Smart Sensors in Farming: 10 Startups to Watch in 2018. Mar. 7, 2018. Accessed at https://www.disruptordaily.com/smart-sensors-farming-10-startups-watch-2018/ on May 17, 2019, 10 pages.
Danckwerts, A decentralized future for food: Indoor Farming, the Internet of Things and Blockchain Technology. Medium. Jun. 11, 2017. Accessed at https://medium.com/@forbesdanckwerts/a-decentralized-future-for-food-indoor-farming-the-internet-of-things-and-blockchain-technology-8d905b6dcb27 on May 17, 2019, 10 pages.
Agriculture Market 2018-2023: Focus on Systems (Sensing, Communication, Cloud Computing, Data), Applications (Precision Crop, Indoor, Livestock Monitoring, Aquaculture). Research and Markets Nov. 23, 2018. Accessed at https://www.prnewswire.com/news-releases/global iot in agriculture-market-2018-2023-focus-on-systems-sensing-communication-cloud-computing-data-applications-precision-crop-indoor-livestock-monitoring-aquaculture-300754772.html on May 17, 2019, 8 pages.
Global IoT in Agriculture Market: Focus on Systems (Sensing, Communication, Cloud Computing, Data Management), Applications (Precision Crop Farming, Indoor Farming, Livestock Monitoring, Aquaculture)-Analysis and Forecast (2018-2023) Description. Nov. 2018 Research and Markets. Accessed at https://www.researchandmarkets.com/research/w5t7j8/global iot in?w=5 on May 21, 2019. 14 pages.
Environmental Monitoring & Aiflow for Climate Uniformity. The University of Arizona Controlled Environment Agriculture Center. Accessed at http://ceac.arizona.edu/environmental-monitoring on May 17, 2019, 6 pages.
Multi-Sensor Modules Ease Indoor Agriculture Design Challenges. Techmezine Feb. 19, 2019. Accessed at https://www.techmezine.com/internet-of-things/multi-sensor-modules-ease-indoor-agriculture-design-challenges/ on May 17, 2019, 8 pages.
Indoor Precision Farming in American medical marijuana plantations. Libelium Dec. 13, 2016. Accessed at http://www.libelium.com/indoor-precision-farming-in-american-medical-marijuana-plantations/ on May 17, 2019, 7 pages.
<https://sensorinsight.io/> Accessed on May 17, 2019, 7 pages.
Internet of Things Hardware Distributor. Accessed at https://sensorinsight.io/hardware/ on May 17, 2019, 4 pages.
Modular Farming Systems. Cityblooms. Accessed at https://cityblooms.com/modular-farms/ on May 17, 2019, 6 pages.
The Orchestra Conductor for Your Farm. The Cityblooms Commander. Accessed at https://cityblooms.com/commander/ on May 17, 2019, 12 pages.
New controlled-environment agriculture solution in Chile enables up to 50% energy saving. Advanticsys Feb. 3, 2018. Accessed at https://www.advanticsys.com/new-controlled-environment-agriculture-solution-in-chile-enables up to 50 energy saving/ on May 17, 2019, 3 pages.
4-In-1 Sensor. Growlink. Accessed at https://growlink.com/shop/4-in-1-sensor/ on May 17, 2019, 7 pages.
Growlink Climate Sensor. Growlink. Accessed at https://growlink.com/shop/environment-sensor-module/ on May 17, 2019, 7 pages.
Smart Sense Wireless Module. Growlink. Accessed at https://growlink.com/shop/remotesense/ on May 17, 2019, 7 pages.
Blink XP Plant Vision Cameras. Growlink. Accessed at https://growlink.com/shop/plant-vision-camera-system/ on May 17, 2019, 6 pages.
Advanced Soil Moisture Sensing. Growlink. Accessed at https://growlink.com/shop/terros12/ on May 17, 2019, 6 pages.
Small Soil Moisture Sensor. Growlink. Accessed at https://growlink.com/shop/ec-5-small-soil-moisture-sensor/ on May 17, 2019, 7 pages.

(56) References Cited

OTHER PUBLICATIONS

TE Connectivity AmbiMate Sensor Module MS4 Series. Mouser Electronics. Accessed at https://www.mouser.com/new/Te-Connectivity/te-connectivity-ambimate-sensor-module/ on May 17, 2019, 2 pages.
LED Grow Lights. Heliospectra. Accessed at https://www.heliospectra.com/led-grow-lights/ on May 17, 2019, 9 pages.
Oreon Grow Light 2.1 (GL 600 2.1 XXX) Installation Manual. Oreon. Jan. 22, 2018. Accessed at https://www.oreon-led.com/cache/InstallationMan ual20180122USCA.107/ InstallationManual20180122USCA.pdf, 18 pages.
Oreon Grow Light 2.1. Oreon 2016. Accessed at https://hortinext.com/wp-content/uploads/2016/08/Lemnis-Oreon-Brochure_EN.pdf, 2 pages.
International Search Report and Written Opinion in International Patent Application No. PCT/US19/28493 dated Jul. 25, 2019, 15 pages.
Purwar, "In-situ Real-time Field Imaging and Monitoring of Leaf Stomata by High-resolution Portable Microscope." bioRxiv (2019): 677450. 24 pages.
Roots Corporate Presentation. Roots Sustainable Agricultural Technologies Ltd. Oct. 2018. 28 pages.
Model-W LED Grow Light. ThinkGrow 2019. Accessed at https://www.thinkgrowled.com/First/IndexW on Mar. 11, 2020. 3 pages.
Rosenthal, Light Dep vs Outdoor: Why Light Deprivation Greenhouses Are A Good Investment. Ed Rosenthal.com May 3, 2019. Accessed at https://www.edrosenthal.com/the-guru-of-ganja-blog/light-dep-vs-outdoor on Mar. 11, 2020. 10 pages.
YellowScan Forestry. Accessed at https://www.yellowscan-lidar.com/applications/forestry/ on Mar. 16, 2020. 9 pages.
Bowen, GreenThumb 10 Platform. GreenThumb.IO. Feb. 16, 2019. Accessed at https://medium.com/greenthumbio/greenthumb-io-platform-d6d09ca7fafb on Mar. 16, 2020. 4 pages.
Smarter Farming. TortugaAgTech. Accessed at https://www.tortugaagtech.com/ on Mar. 24, 2020. 10 pages.
PlantEye F500 multispectral 3D scanner for plants. Phenospec Smart Plant Analysis. Accessed at https://phenospex.com/products/plant-phenotyping/planteye4500-multispectral-3d-laser-scanner/?gclid=CjOKCQjwmdzzBRC7ARIsANdoRRn6Q05qmhOwwGnIkROEuy sd8CaRKe94 kmoBIPuJzwlvcQGzgWGksMaAmt EALw wcB on Mar. 24, 2020.
Russo, "The case for the entourage effect and conventional breeding of clinical cannabis: no "strain," no gain." Frontiers in plant science 9 (2019): 1969. 8 pages.
US Energy Use Intensity by Property Type. Energy Star PortfolioManager Technical Reference. Aug. 2018. 6 pages.
International Search Report and Written Opinion in International Patent Application No. PCT/US2019/030889 dated Sep. 26, 2019, 22 pages.
Rodrigues, Agnetix—Most Powerful and Efficient LED Horticulture Lighting Platform. YouTube Jan. 8, 2018. Accessed at https://www.youtube.com/watch?v=y6rZeJ6V8Ug. 7 pages.
International Search Report and Written Opinion in International Patent Application No. PCT/US2019/061324 dated Mar. 18, 2020, 92 pages.
Spectranomics. Carnegie Airborne Observatory as of Dec. 5, 2019. Accessed at https://web.archive.org/web/20191205203624/https://cao.carnegiescience.edu/spectranomics on Apr. 17, 2020. 2 pages.
TerrAvion Product Info. Accessed at https://www.terravion.com/product-info/ on Apr. 17, 2020. 3 pages.
Story et al., "Design and implementation of a computer vision-guided greenhouse crop diagnostics system." Machine vision and applications 26.4 (2015): 495-506.
Canopy Scanalyzer. LemnaTec. Accessed at https://www.lemnatec.com/products/canopy-scanalyzer/ on Apr. 17, 2020. 2 pages.
Pam Chlorophyll Fluorescence Imaging. LemnaTec. Accessed at https://www.lemnatec.com/pam-chlorophyll-fluorescence-imaging/ on Apr. 17, 2020. 2 pages.
Cerna® Modular Microscopes. Thorlabs May 10, 2018. Accessed at https://www.thorlabs.com/images/BrochuresiThorlabs Cerna Brochure.pdf on Apr. 17, 2020. 6 pages.

Murphy et al., "OpenFluor—an online spectral library of autofluorescence by organic compounds in the environment." Analytical Methods 6.3 (2014): 658-661.
Ubbens et al., "Deep plant phenomics: a deep learning platform for complex plant phenotyping tasks." Frontiers in plant science 8 (2017): 1190. 11 pages.
YellowScan Reliable UAV LiDAR Mapping. Accessed at https://www.yellowscan-lidarcom/ on Apr. 17, 2020. 3 pages.
Earles et al., "Beyond porosity: 3D leaf intercellular airspace traits that impact mesophyll conductance." Plant physiology 178.1 (2018): 148-162.
Li-6400XT Portable Photosynthesis System. Li-Cor . Accessed at. https://www.licor.com/env/products/photosynthesis/ on Apr. 17, 2020. 1 page.
Controlled Environment Agriculture. Cornell University college of Agriculture and Life Sciences Sep. 2, 2019. Accessed at https://web.archive.org/web/20190902094759/http://cea.cals.cornell.edu/bestPractices/lightControl.html on Apr. 17, 2020. 2 pages.
Sentera. Accessed at https://sentera.com/sensors/ on Apr. 17, 2020. 4 pages.
Accesssories: UV & NIR Illuminators, Filter Modules. Eigen Imaging. Accessed at https://www.eigenimaging.com/collections/uv-nir-illuminator on Apr. 17, 2020. 5 pages.
360 Soilscan. 360YIELDCENTER.Com. Decebmer 24, 2014. Accessed at http://nebula.wsimg.com/45a21444c39dcfb4b9ca43dedf13076e?AccessKeyld= 42F03180740870DBAOEF&disposition=0 &alloworigin=1 on Apr. 17, 2020. 2 pages.
TerrAvion + FluroSense: nitrogen management. TerrAvion Jun. 3, 2019. Accessed at https://blog.terravion.com/blog/terravion-flurosat-nitrogen-management on Apr. 17, 2020. 4 pages.
Osburn et al., "Predicting sources of dissolved organic nitrogen to an estuary from an agro-urban coastal watershed." Environmental science & technology 50.16 (2016): 8473-8484.
Excitation-Emission Matrix (EEM) Fluorescence Spectroscopy for Analysis of Dissolved Organic Matter (DOM) in Natural Water and Wastewaters. Application News No. AD-0133 Shimadzu Nov. 15, 2016. Accessed at https://solutions.shimadzu.co.jp/an/n/en/rf/apa417010. pdf?_ga=2.70350806.735204626.1575945001-871956823. 1575945001 on Apr. 16, 2020.
Abramowitz et al., Overview of Fluorescence Excitation and Emission Fundamentals. Olympus. Accessed at https://www.olympus-lifescience.com/en/microscope-resource/primer/lightandcolor/fluoroexcitation/ on Apr. 17, 2020. 4 pages.
Fluorescence Imaging Filters. ThorLabs. Accessed at https://www.thorlabs.com/newgrouppage9.cfm?objectgroup_id=2990 on Apr. 17, 2020. 4 pages.
Shortwave Infrared Camera Core Tau ™ SWIR. FLIR. Accessed at https://www.flir.com/products/tau-swir/?model=Tau-Vis-Swir on Apr. 17, 2020. 2 pages.
Natali et al., "Light-harvesting complexes (LHCs) cluster spontaneously in membrane environment leading to shortening of their excited state lifetimes." Journal of Biological Chemistry 291.32 (2016): 16730-16739.
Ghassemi et al., "Evaluation of mobile phone performance for near-infrared fluorescence imaging." IEEE Transactions on Biomedical Engineering 64.7 (2016): 1650-1653.
310nm UV LED Fluorescence using iPhone 6s. Youtube Jul. 15, 2018. Accessed at https://www.youtube.com/watch?v=hA6VPmJWE_8 on Apr. 17, 2020. 3 pages.
Tran et al., Smartphone Multi-Spectral Imaging. Eigen Imaging Inc., Apr. 2013. Accessed at https://sites.google.com/a/eigenimaging.com/eigen/learn-more/smartphone-multi-spectral-imaging on Apr. 17, 2020. 5 pages.
The Greencube. Youtube Nov. 5, 2015. Accessed at https://www.youtube.com/watch?v=iqoENjkruMc on Apr. 17, 2020. 3 pages.
Executive Summary EDEN ISS. Apr. 2019. Accessed at https://eden-iss.net/wp-content/uploads/Eden-Iss-Complete-Brochure_ONLINE_small.pdf on Apr. 17, 2020.
Non Final Office Action in U.S. Appl. No. 16/824,495 dated May 22, 2020, 47 pages.
Non Final Office Action in U.S. Appl. No. 16/114,088 dated May 5, 2020, 38 pages.

(56) References Cited

OTHER PUBLICATIONS

Notice of Allowance in U.S. Appl. No. 16/114,088 dated Jul. 24, 2020, 20 pages.
Non Final Office Action in U.S. Appl. No. 16/828,521 dated Jul. 28, 2020, 30 pages.
Notice of Allowance in U.S. Appl. No. 16/824,495 dated Jul. 29, 2020, 21 pages.
Notice of Allowance in U.S. Appl. No. 16/390,501 dated Aug. 24, 2020, 10 pages.
Lai—theory and practice. Accessed at https://www.metergroup.com/environment/articles/lai-theory-practice/ on Sep. 2, 2020. 35 pages.
Nynomic—The Photonics Group. Company Presentation Nynomic AG Dec. 10, 2019. Accessed at https://www.nynomic.com/wp-content/uploads/2019/12/Nynomic_28.MKK_2019.pdf. 34 pages.
Apogee Instruments. Accessed at https://www.apogeeinstruments.com/ on Sep. 2, 2020. 6 pages.
OCO-3 Instrument. NASA Jet Propulsion Laboratory California Institute of Technology. Accessed at https://ocov3.jpl.nasa.gov/instrument/ on Sep. 2, 2020. 3 pages.
Sensors, Sonars, and Cameras. BlueRobotics. Accessed at https://bluerobotics.com/product-category/sensors-sonars-cameras/ on Sep. 2, 2020. 6 pages.
Aidukas et al., "Low-cost, sub-micron resolution, wide-field computational microscopy using opensource hardware." Scientific reports 9.1 (2019): 1-12.
Koyama et al., "High-image quality, high-resolution camera with high sensitivity up to 1,100 nm." Ultra-High-Definition Imaging Systems. vol. 10557. International Society for Optics and Photonics, 2018. 32 pages.
About LCI. Bliportal. Accessed at https://www.bli.eu/about-multi-light/about-lci/ on Sep. 2, 2020. 5 pages.
Prairie et al., "An accurate, precise, and affordable light emitting diode spectrophotometer for drinking water and other testing with limited resources." Plos one 15.1 (2020): e0226761. 32 pages.
Spectral Indices. L3Harris Geospatial. Accessed at https://www.harrisgeospatial.com/docs/spectralindices.html on Sep. 2, 2020. 12 pages.
Wünsch et al., "Fluorescence quantum yields of natural organic matter and organic compounds: Implications for the fluorescence-based interpretation of organic matter composition." Frontiers in Marine Science 2 (2015): 98. 15 pages.
Terra Mepp. Accessed at https://terra-mepp.illinois.edu/ on Sep. 2, 2020. 9 pages.
Valle et al., "PYM: a new, affordable, image-based method using a Raspberry Pi to phenotype plant leaf area in a wide diversity of environments." Plant methods 13.1 (2017): 98. 17 pages.
Mudhar, Using near IR to look for photosynthesis and plant health with NDVI. Richard Mudhar Blog. Jul. 21, 2015. Accessed at https://www.richardmudhar.com/blog/2015/07/using-near-ir-to-look-for-photosynthesis-and-plant-health-with-ndvi/. 7 pages.
LAPA, Raspberry + NoIR cam + Sensors to detect water stress of the plants during their growing. Public Lab Mar. 31, 2016. Accessed at https://publiclab.org/notes/LaPa/Mar. 31, 2016/raspberry-noir-cam-sensors-to-detect-water-stress-of-the-plants-during-their-growing. 11 pages.
Blonquist, Using Infrared Thermometers for Plant Science Research. Apogee Insturments Inc. Youtube Jul. 31, 2017. Accessed at https://www.youtube.com/watch?time continue=120&v=U azOSSvBW8&feature=emb logo. 3 pages.
Notice of Allowance in U.S. Appl. No. 16/114,088 dated Sep. 30, 2020, 5 pages.
Notice of Allowance in U.S. Appl. No. 16/390,501 dated Oct. 15, 2020, 7 pages.
Notice of Allowance in U.S. Appl. No. 16/824,495 dated Oct. 23, 2020, 5 pages.
Notice of Allowance in U.S. Appl. No. 16/828,521 dated Nov. 9, 2020, 5 pages.
Goossens et al., "Broadband image sensor array based on graphene—CMOS integration." Nature Photonics 11.6 (2017): 366. 6 pages.
Tokarz et al., "Carotenoid based bio-compatible labels for third harmonic generation microscopy." Physical Chemistry Chemical Physics 14.30 (2012): 10653-10661.
Lichtenthaler et al., "Chlorophylls and carotenoids: Measurement and characterization by UV-VIS spectroscopy." Current protocols in food analytical chemistry 1.1 (2001): F4-3. 8 pages.
Lopez-Ruiz et al., "Portable multispectral imaging system based on Raspberry Pi." Sensor Review (2017). 9 pages.
Osroosh et al., "Using the power of IoT to improve irrigation water management." Irrigation Today (Apr. 2018). 2 pages.
Campbell, "Can Canopy Measurements Determine Soil Moisture?" (Part 1) Environmental Biophysics Aug. 29, 2016. 4 pages.
Campbell, "Can Canopy Measurements Determine Soil Moisture?" (Part 2) Environmental Biophysics Sep. 5, 2016. 3 pages.
Osroosh et al., "Automatic irrigation scheduling of apple trees using theoretical crop water stress index with an innovative dynamic threshold." Computers and Electronics in Agriculture 118 (2015): 193-203.
Osroosh et al., "Daylight crop water stress index for continuous monitoring of water status in apple trees." Irrigation science 34.3 (2016): 209-219.
Osroosh et al., "Comparison of irrigation automation algorithms for drip-irrigated apple trees." Computers and Electronics in Agriculture 128 (2016): 87-99.
Osroosh et al., "Economical thermal-RGB imaging system for monitoring agricultural crops." Computers and Electronics in Agriculture 147 (2018): 34-43.
Osroosh et al., "Detecting fruit surface wetness using a custom-built low-resolution thermal-RGB imager." Computers and Electronics in Agriculture 157 (2019): 509-517.
Osroosh et al., "Estimating potential transpiration of apple trees using theoretical non-water-stressed baselines." Journal of Irrigation and Drainage Engineering 141.9 (2015): 04015009. 13 pages.
Osroosh et al., "Estimating actual transpiration of apple trees based on infrared thermometry." Journal of Irrigation and Drainage Engineering 141.8 (2015): 04014084. 13 pages.
Notice of Allowance in U.S. Appl. No. 16/390,501 dated Feb. 10, 2021, 10 pages.
International Search Report and Written Opinion in International Patent Application No. PCT/US2020/064382 dated May 27, 2021, 15 pages.

* cited by examiner

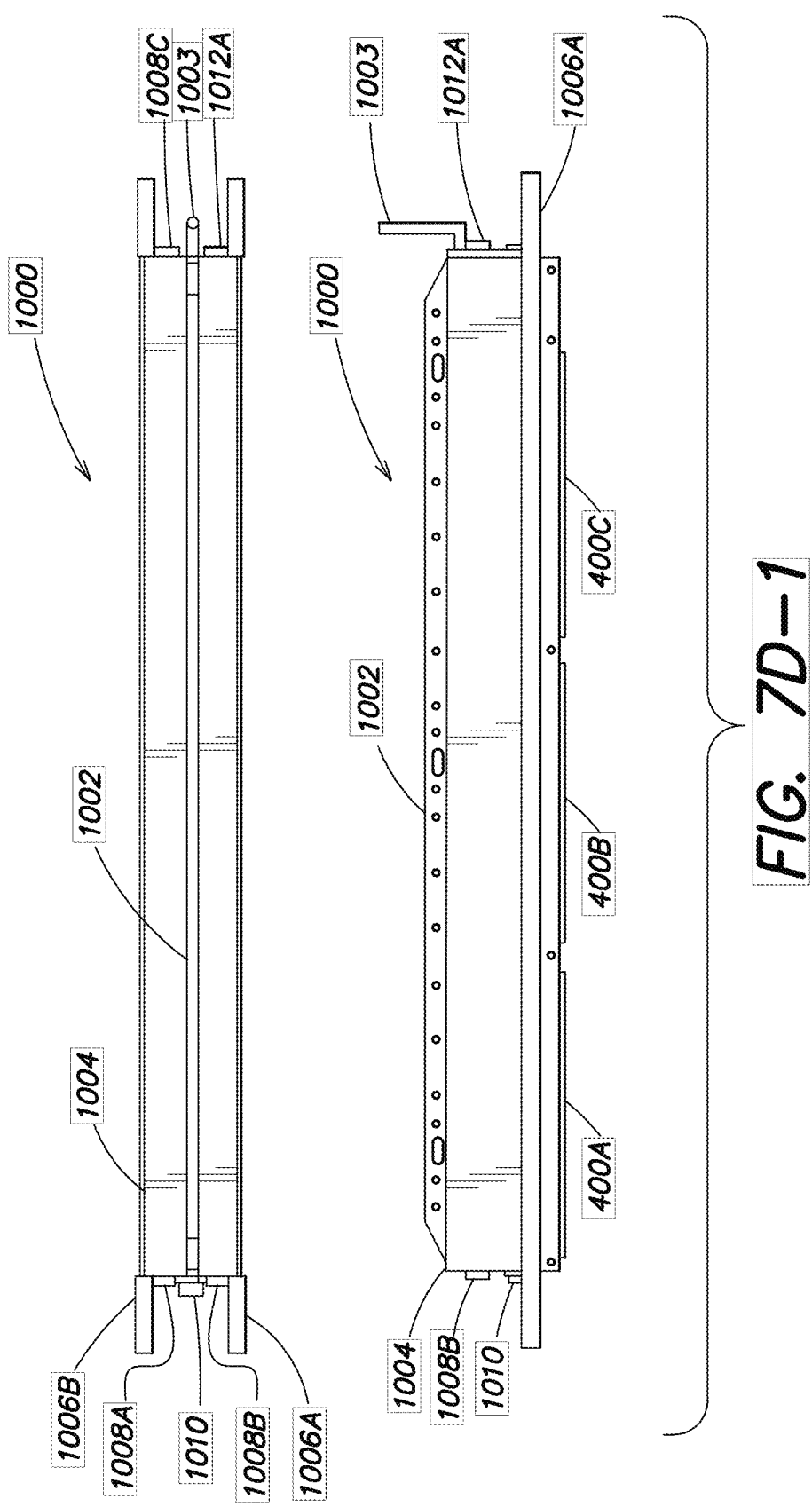

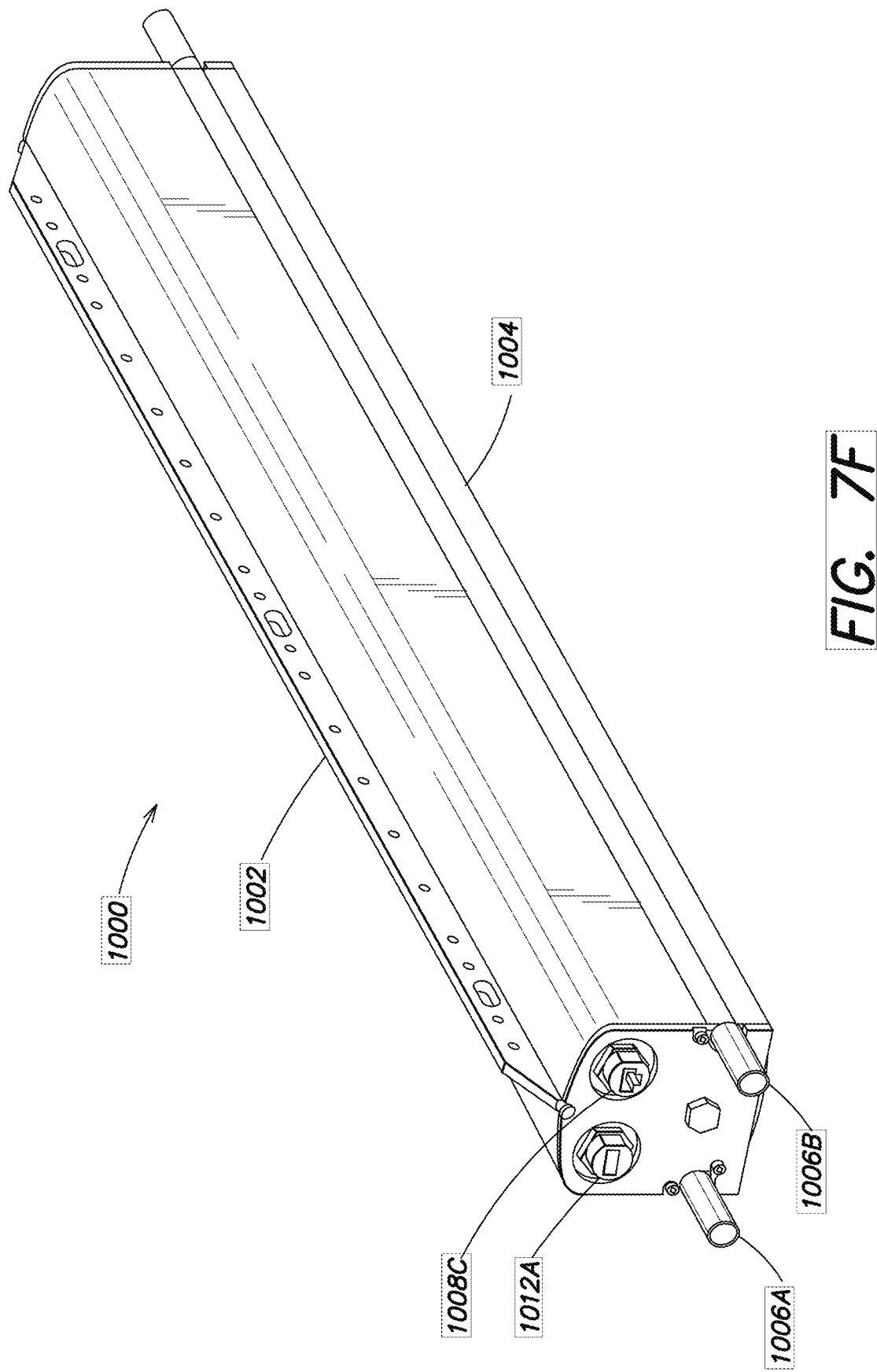

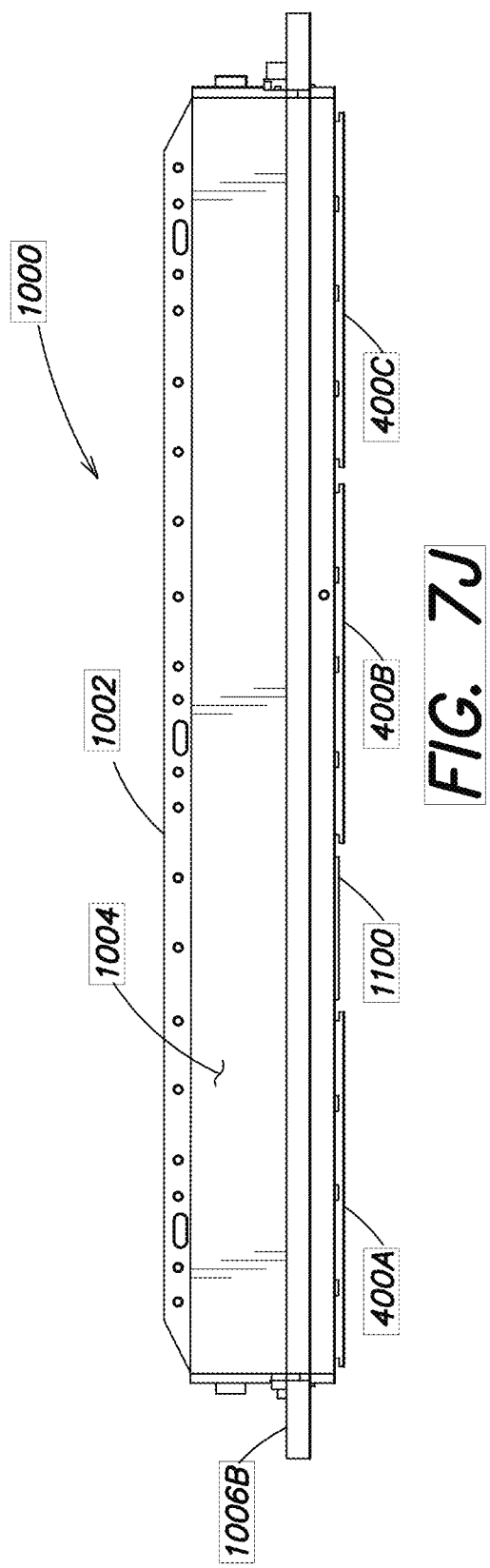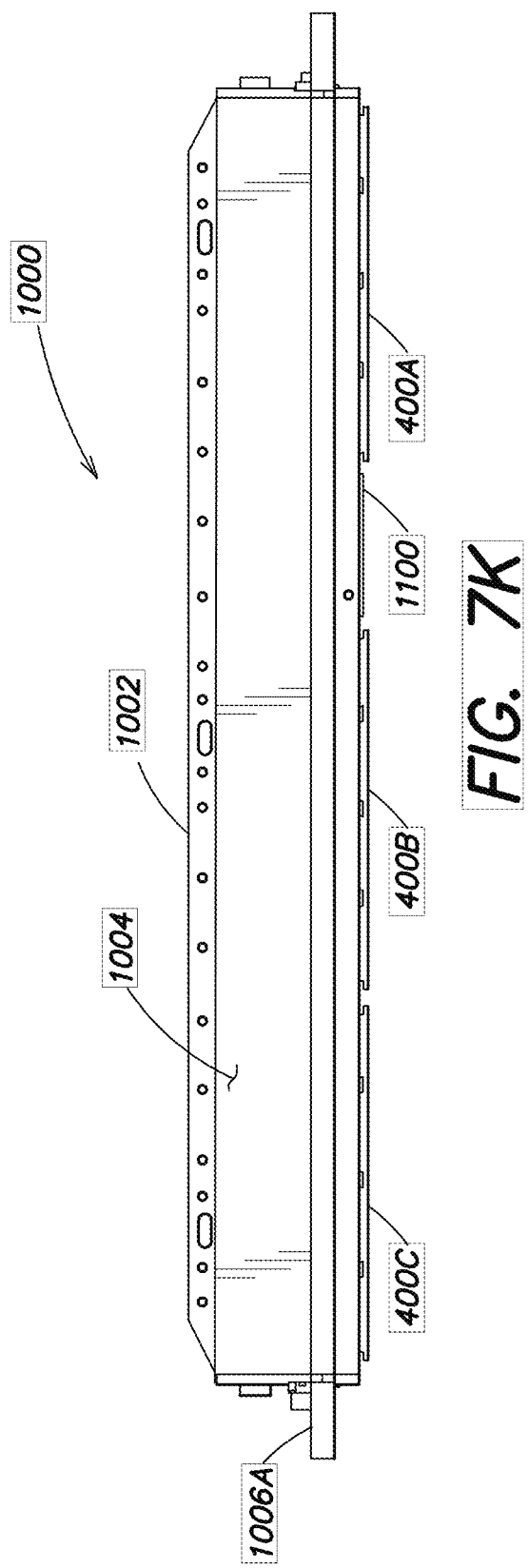

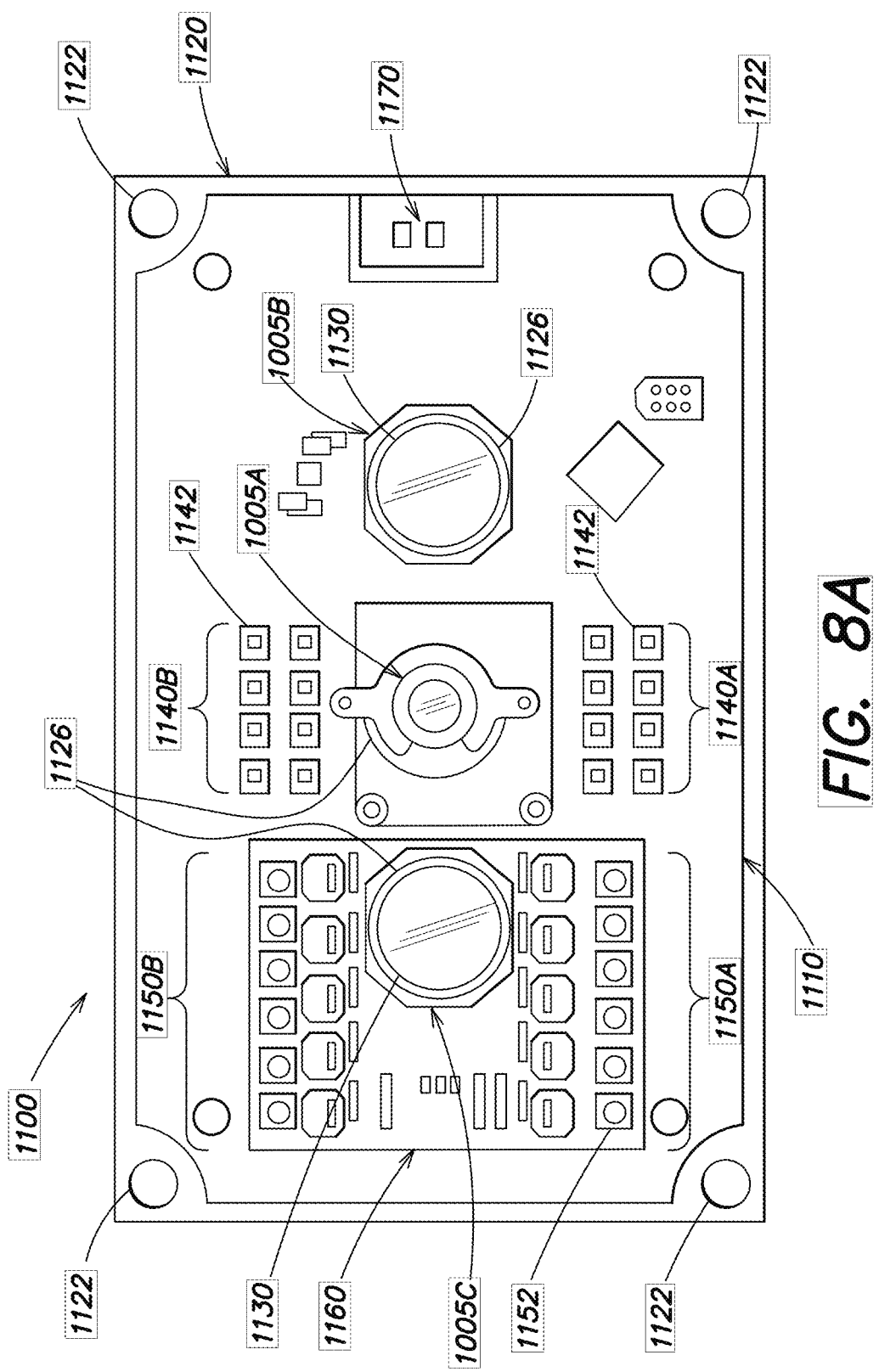

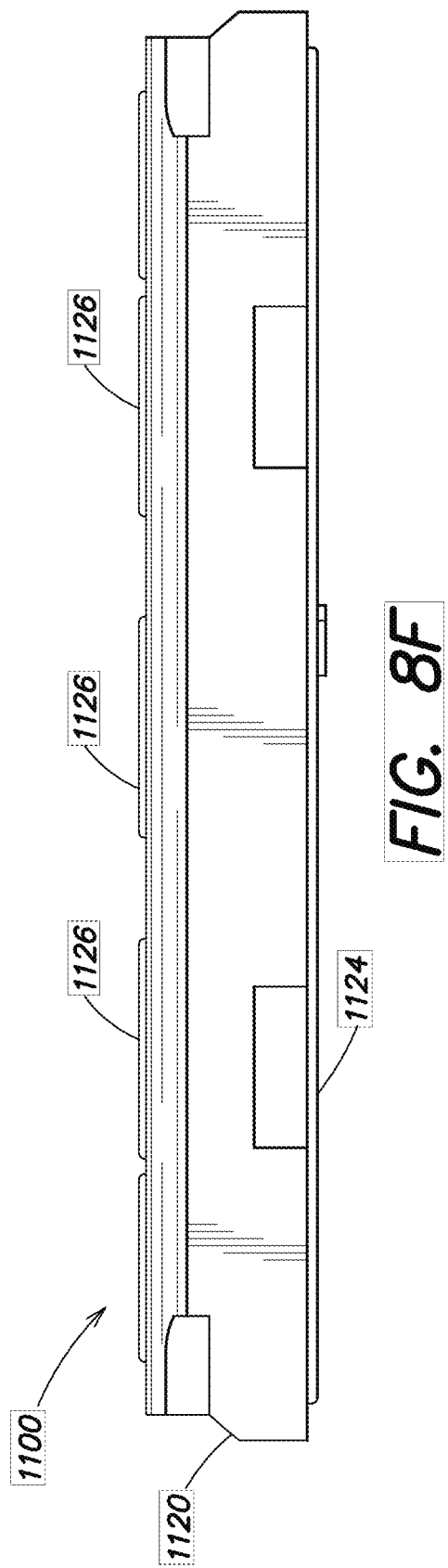
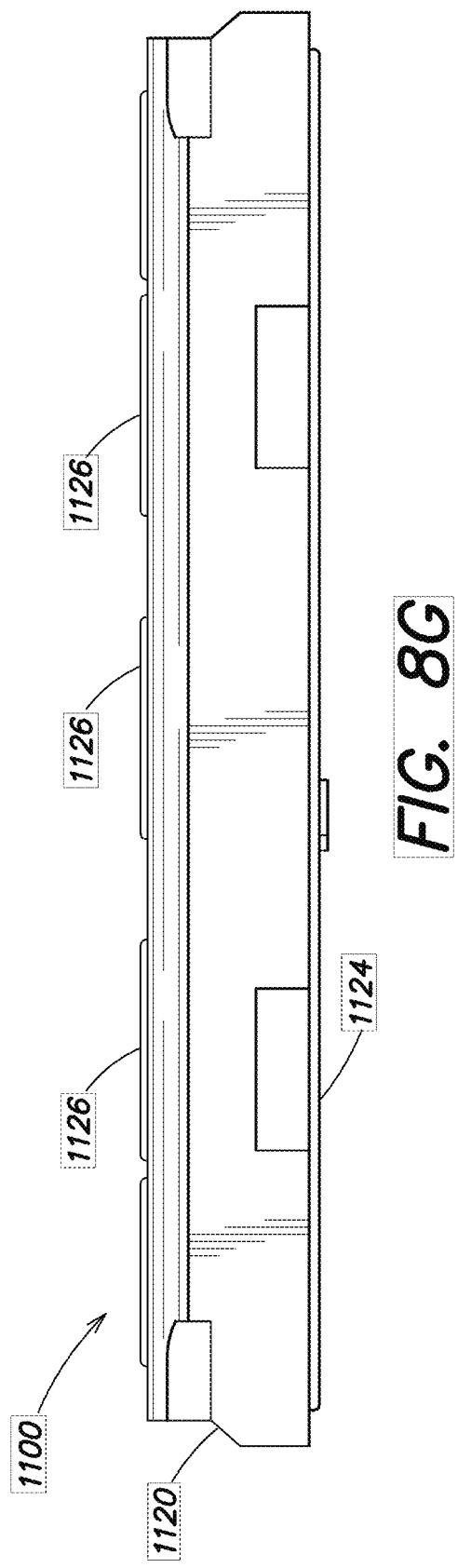

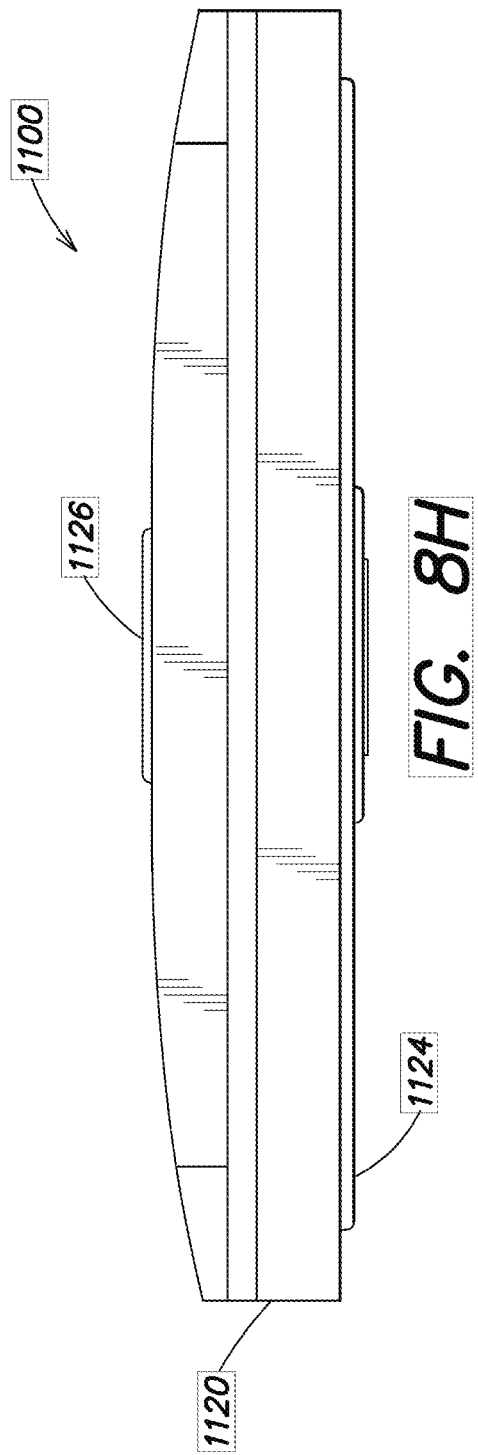
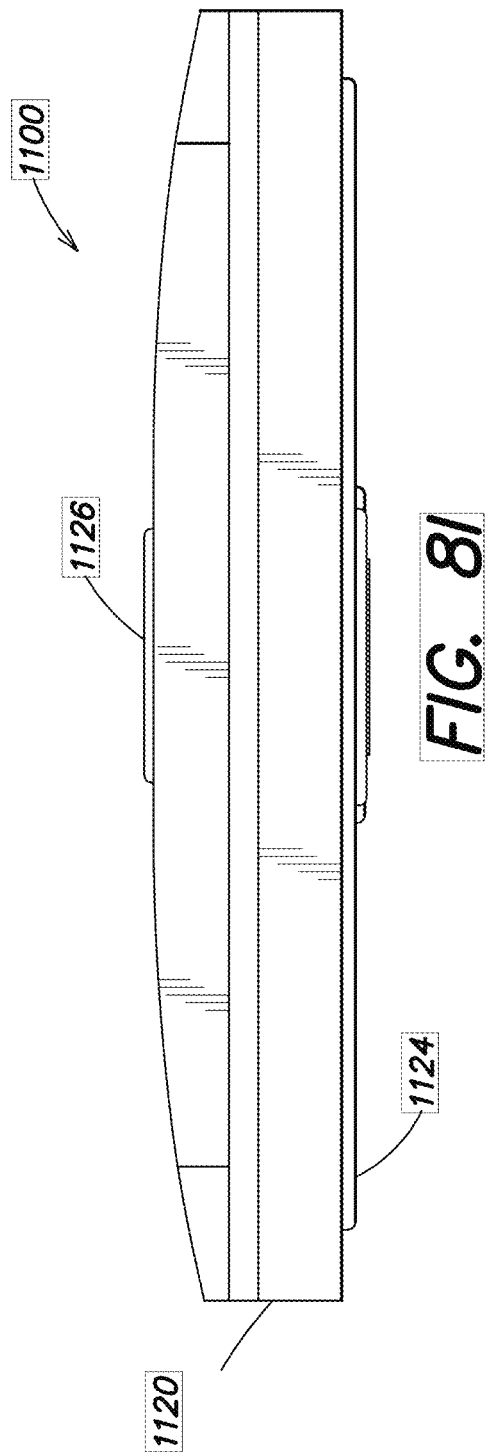

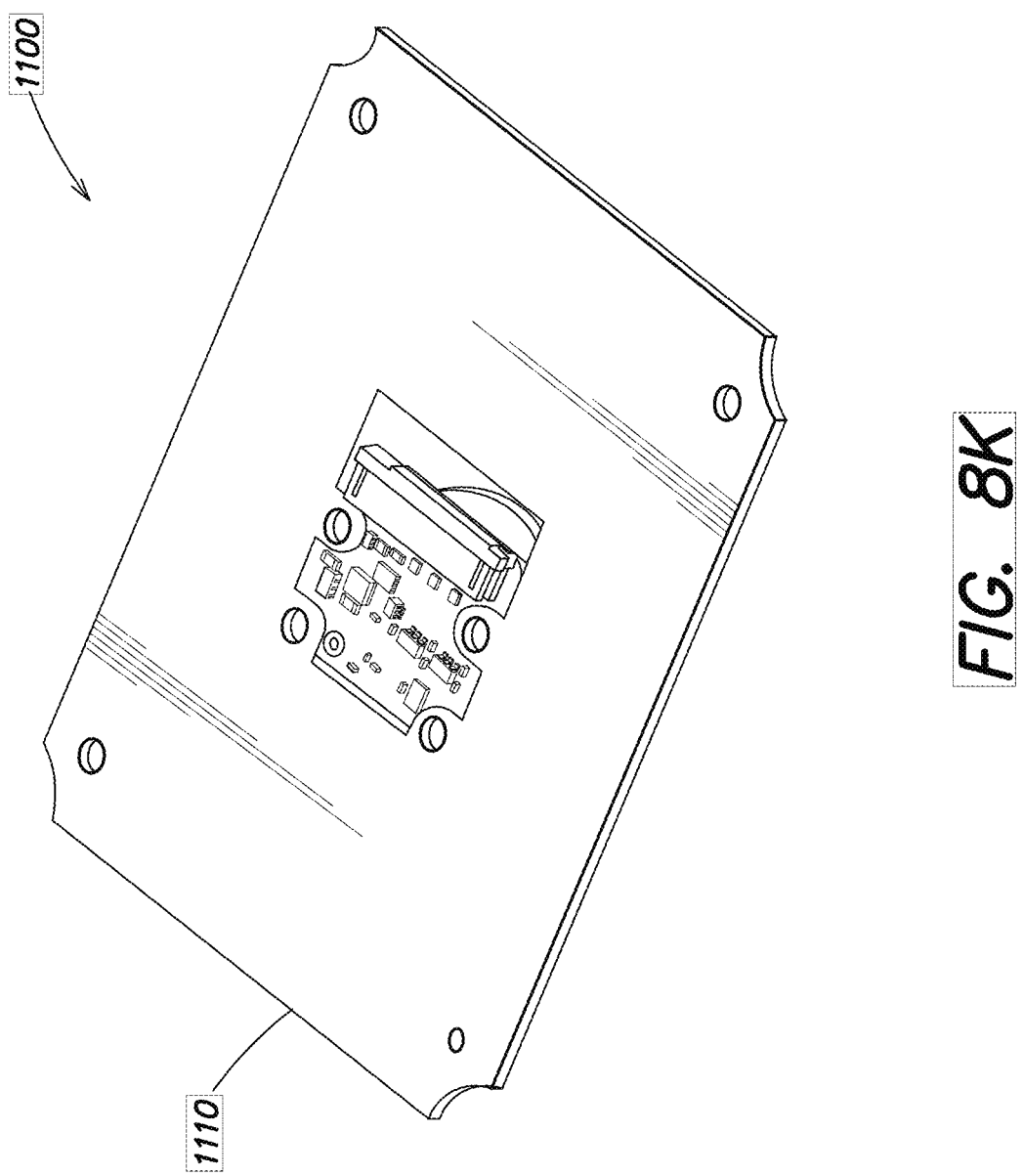

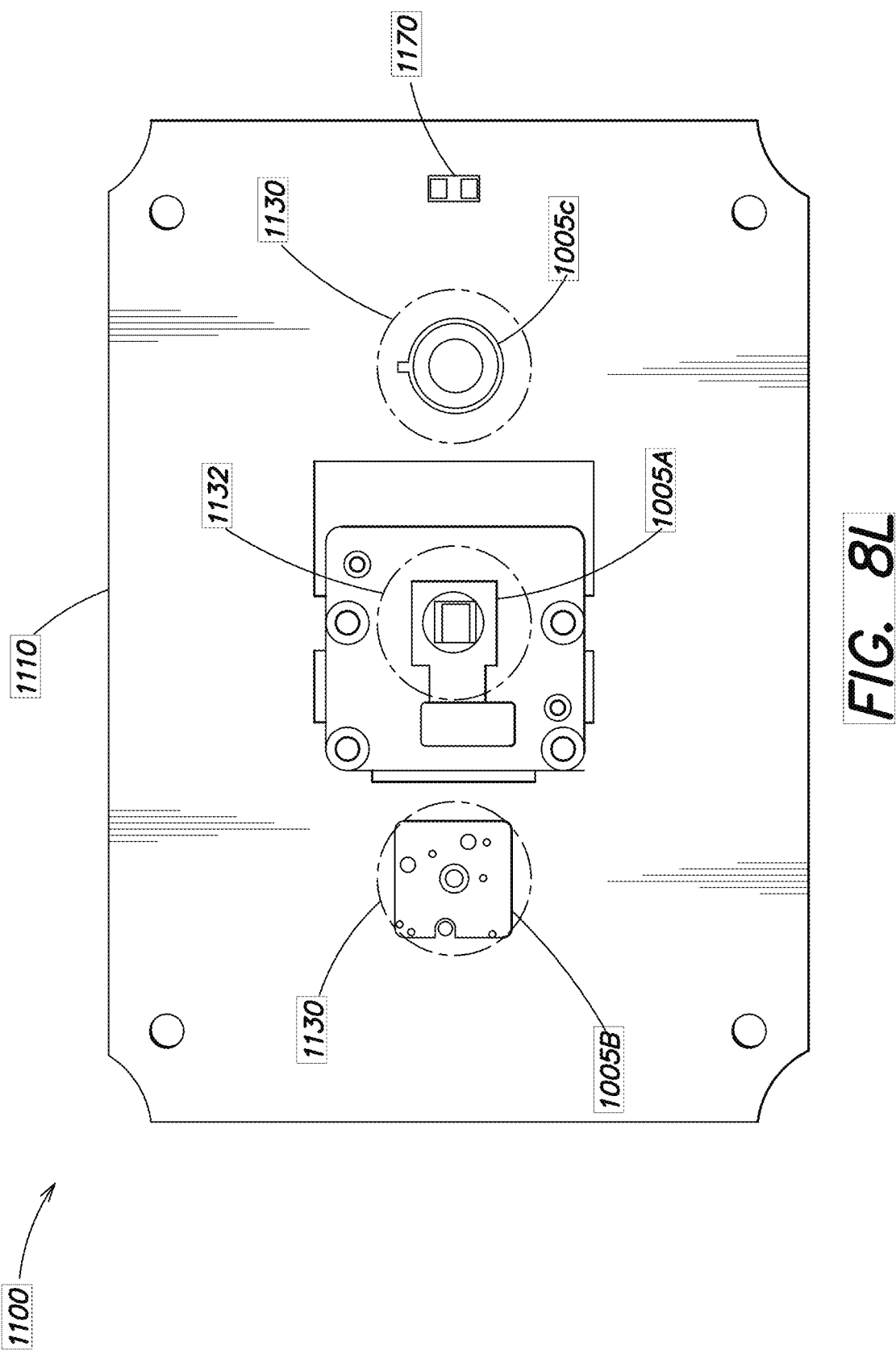

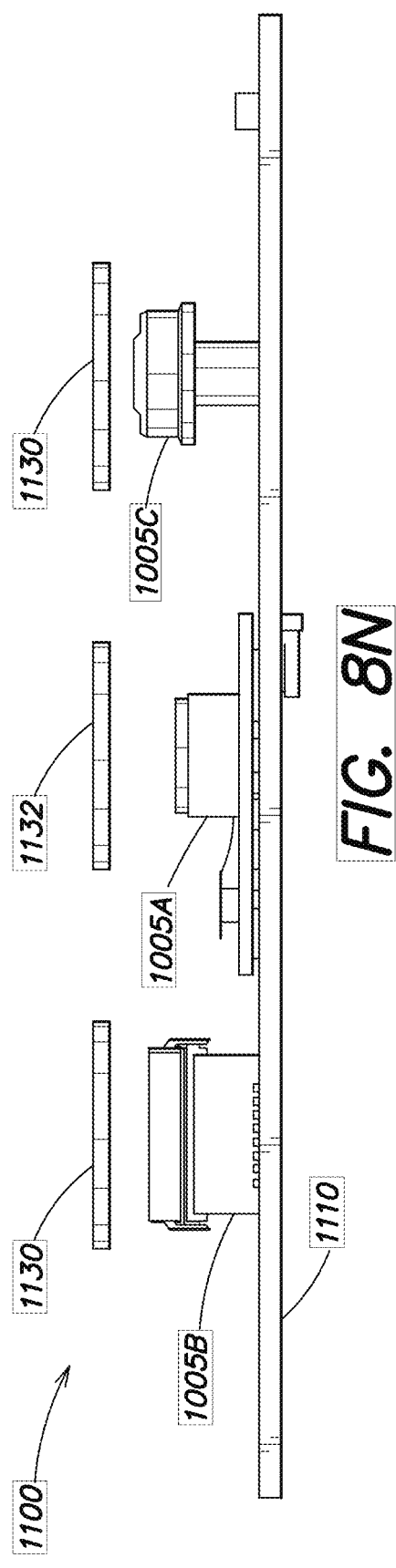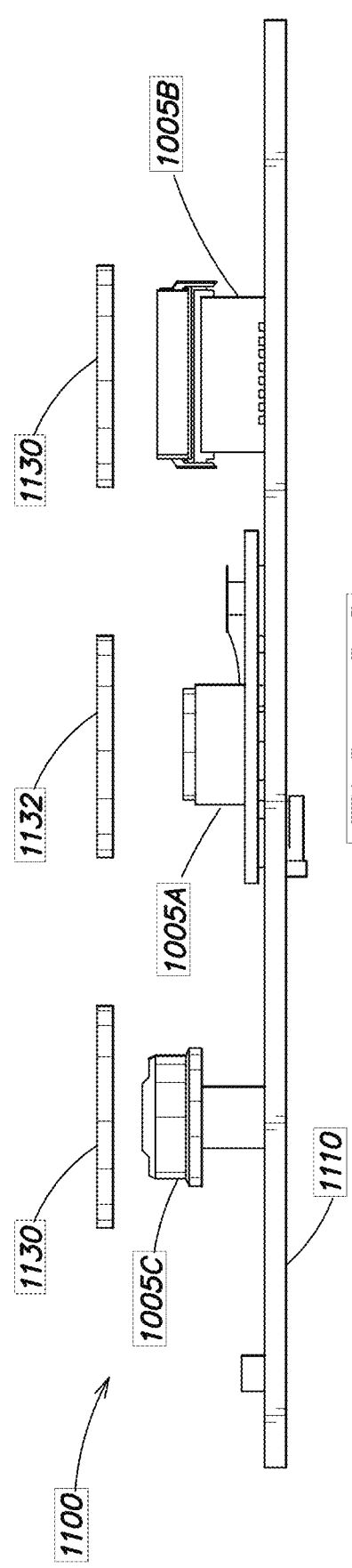

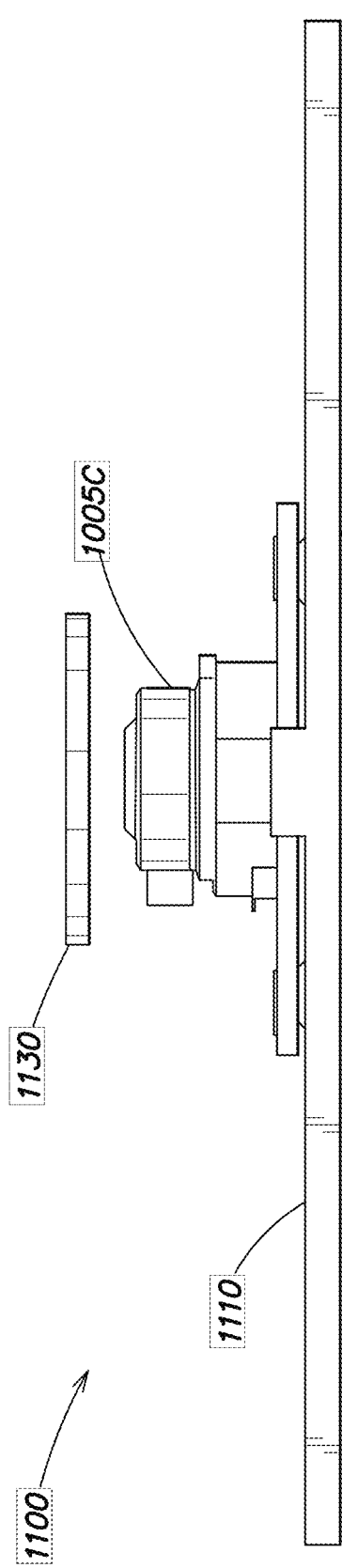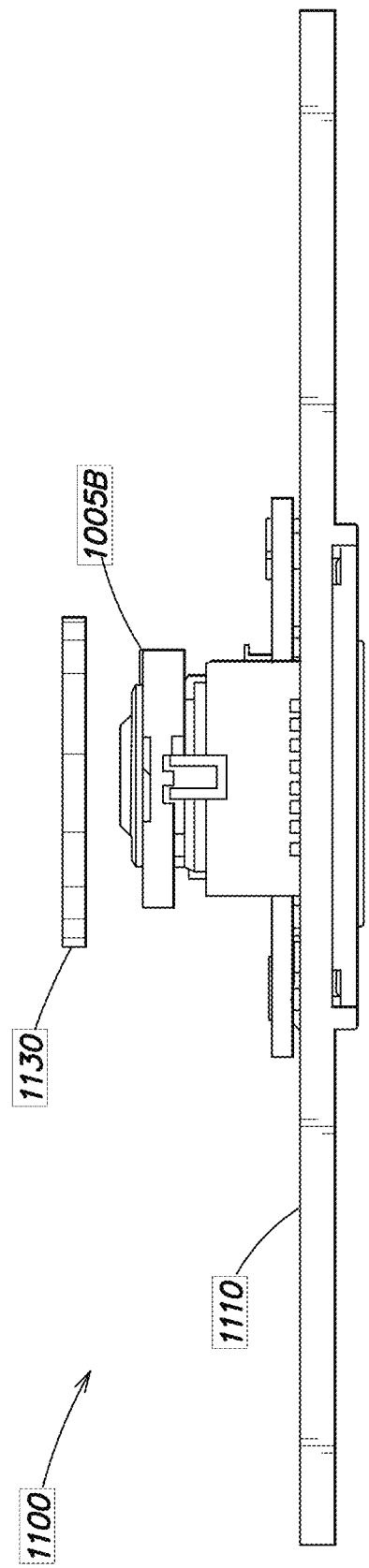

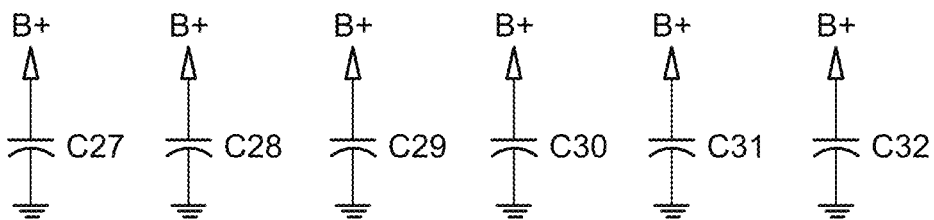
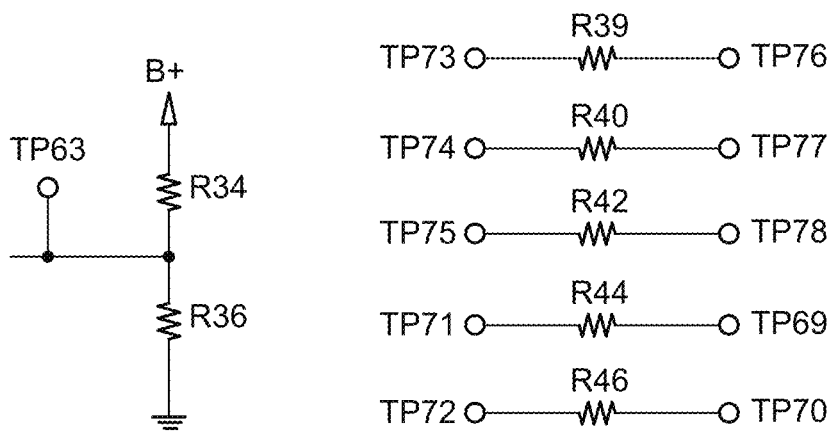
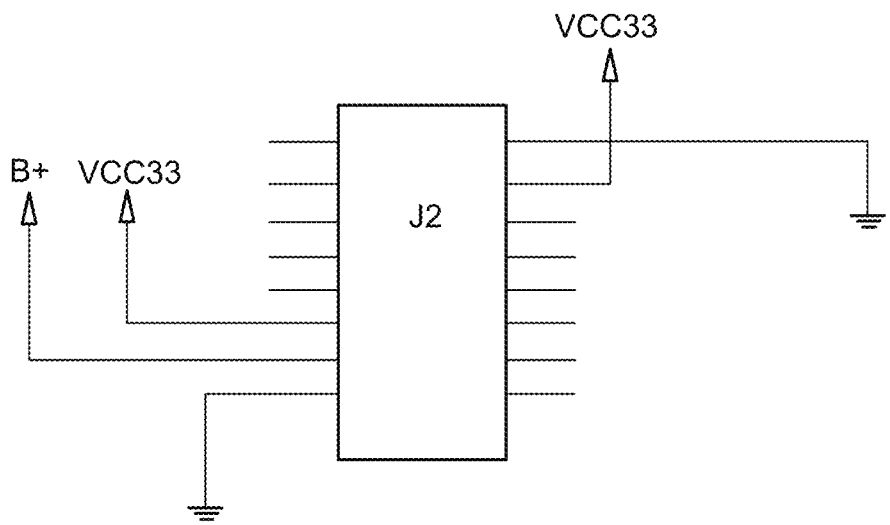
*FIG. 90-2*

FLUID-COOLED LED-BASED LIGHTING METHODS AND APPARATUS FOR CONTROLLED ENVIRONMENT AGRICULTURE WITH INTEGRATED CAMERAS AND/OR SENSORS AND WIRELESS COMMUNICATIONS

CROSS-REFERENCE TO RELATED PATENT APPLICATION(S)

The present application is a bypass continuation application of International Application No. PCT/US2019/061324, filed on Nov. 13, 2019, entitled "FLUID-COOLED LED-BASED LIGHTING METHODS AND APPARATUS FOR CONTROLLED ENVIRONMENT AGRICULTURE WITH INTEGRATED CAMERAS AND/OR SENSORS AND WIRELESS COMMUNICATIONS," which in turn claims priority to U.S. provisional application No. 62/760,572, filed on Nov. 13, 2018, entitled "FLUID-COOLED LED-BASED LIGHTING METHODS AND APPARATUS FOR CONTROLLED ENVIRONMENT AGRICULTURE WITH INTEGRATED CAMERAS AND/OR SENSORS AND WIRELESS COMMUNICATIONS." Each of the aforementioned applications is incorporated herein by reference in its entirety.

BACKGROUND

Controlled Environment Agriculture (CEA) (also referred to as controlled environment horticulture or CEH) is the process of growing plants in a controlled environment where various environmental parameters are monitored and adjusted to improve the quality and yield of the plants grown. Compared to conventional approaches of plant cultivation, CEA may enable year-round production of plants, insensitivity to variable weather conditions, reduce pests and diseases, and reduce the amount of resources consumed on a per plant basis. A controlled agricultural environment is typically enclosed, at least in part, by a building structure such as a greenhouse, a grow room, or a covered portion of a field in order to provide some degree of control over environmental conditions. One or more artificial lighting systems are often used in such controlled agricultural environments to supplement and/or replace natural sunlight that may be obstructed by the building structure or insufficient during certain periods of the year (e.g., winter months). Various types of artificial lighting systems may be used including, but not limited to, a high intensity discharge lamp, a light emitting diode (LED), and a fluorescent lamp.

SUMMARY

The present disclosure is directed to various implementations of a fluid-cooled light emitting diode (LED)-based lighting fixture (also referred to hereafter as a "lighting fixture") for Controlled Environment Agriculture (CEA), respective components of the lighting fixture, and methods relating to the same. The lighting fixture may be coupled to a fluid cooling system (also referred to hereafter as a "coolant circuit") that flows fluid coolant through the lighting fixture to capture heat generated by one or more LED modules in the lighting fixture. In this manner, heat generated by the lighting fixture may be removed from the controlled agricultural environment, thus reducing the cooling load and improving energy efficiency. The lighting fixture described herein may be coupled to one or more other lighting fixtures in a daisy-chain configuration where plumbing, electrical power, and communication connections are shared to facilitate the creation of a continuous electrical circuit and coolant circuit. In some implementations, the lighting fixture may be coupled to a hydronics system that utilizes waste heat generated by the lighting fixture (and extracted from the lighting fixture by the coolant circuit) for various applications such as regulating the temperature of the controlled agricultural environment or a space near the controlled agricultural environment. The lighting fixture may also function as an integrated sensor platform by providing electrical power and data communication connections to one or more sensors that may monitor various environment conditions of the controlled agricultural environment.

In one exemplary implementation, a lighting fixture includes a frame (also referred to herein as a "housing") to mechanically support and house various components of the lighting fixture. A light spine is formed onto the frame with features to mechanically couple and secure the lighting fixture to a support structure disposed in the controlled agricultural environment. The frame includes one or more channels and corresponding coolant pipes that fit into the one or more channels. The coolant pipes are formed from copper and used to flow fluid coolant through the lighting fixture to remove heat. One or more LED modules are disposed on the frame to emit photosynthetically active radiation (PAR) for growing plants. A processor is coupled to the frame to facilitate the operation of the lighting fixture with functions including power conversion, network connectivity, and data processing. One or more electrical power ports are disposed on the frame to supply electrical power from an external source (e.g., a building electrical supply system) to various components of the lighting fixture including the LED modules, the processor, and auxiliary devices coupled to the lighting fixture. One or more communication ports are disposed on the frame to facilitate electrical communication and data transmission.

In some implementations, a coolant pipe may be press-fit or crush-fit into a channel of a frame to improve thermal contact, thereby increasing the amount of heat removed by the fluid coolant flowing through the lighting fixture. The coolant pipe of the lighting fixture may be coupled to another coolant pipe of another lighting fixture using push-to-connecting plumbing fittings. In this manner, multiple lighting fixtures may be coupled to form a continuous coolant circuit. One or more pumps, regulators, and/or valves may be incorporated into the coolant circuit to generate and direct the fluid coolant through the coolant circuit. A heat rejection device, such as a cooling tower, may also be incorporated into the coolant circuit to remove heat from fluid coolant, thus reducing the temperature of the fluid coolant for reuse in the coolant circuit. The coolant circuit may also be used to remove heat from other components in the controlled agricultural environment, such as a dehumidifier.

In some implementations, a coolant circuit having multiple lighting fixtures may be coupled to a hydronics system to recycle waste heat generated by the lighting fixtures and captured by the fluid coolant. The hydronics system may distribute heat to regulate the temperature of at least a portion of the controlled agricultural environment (e.g., a growing area) or another space near the controlled agricultural environment (e.g., a residential building, a cogeneration plant, a factory). The hydronics system may include a fluid storage tank to store fluid coolant and one or more piping subsystems to direct relatively cool fluid coolant and relatively hot fluid coolant through the coolant circuit and/or other spaces. Fluid coolant may also be stored at various temperatures for later distribution and/or to regulate the temperature of the fluid coolant.

In some implementations, a controlled agricultural environment with one or more fluid-cooled LED-based lighting fixtures does not require additional cooling or air-conditioning. In other words, excess heat generated in the environment from a variety of heat sources (e.g., the lighting fixtures, the plants themselves, walls of a building structure constituting the environment, one or more dehumidifiers) is effectively captured by the fluid coolant and removed by a heat rejection device (e.g., a cooling tower) or recycled in a hydronics system. By significantly reducing, or in some instances eliminating, the need for air-conditioning, a significant source of required energy for the controlled agricultural environment is accordingly significantly reduced or eliminated. The energy savings may lead to substantial reductions in energy costs for controlled agricultural environments on a variable energy budget or increase the energy available to grow larger and crops and larger crop yields for controlled agricultural environments on a fixed energy budget. For example, at least a portion of the energy budget formerly used for cooling/air-conditioning may instead be used for additional artificial lighting to provide PAR and thereby promote plant growth for a greater number of plants.

In various implementations, the lighting fixture disclosed herein may include one or more communication and/or auxiliary power ports, for example, to provide auxiliary DC power to one or more auxiliary devices coupled to the port(s). Example of such ports include, but are not limited to, one or more Power over Ethernet (PoE) ports and/or one or more Universal Serial Bus (USB) ports to communicatively couple multiple lighting fixtures together and/or support operation of one or more auxiliary devices (e.g., sensors, actuators, or other external electronic devices). Examples of various sensors that may be coupled to one or more lighting fixtures via one or more of the PoE or USB ports include, but is not limited to, air temperature sensors, near-infrared (NIR) leaf moisture sensors, hyperspectral cameras, finite spectral cameras, IR leaf temperature sensors, relative humidity sensors, and carbon dioxide sensors. Other examples of auxiliary devices that may be coupled to one or more lighting fixtures via PoE or USB ports include, but are not limited to, one or more fans, security cameras, smart phones, and multi-spectral cameras (e.g., to analyze soil moisture, nutrient content, leaves of the plants). In this manner, various auxiliary devices may be particularly distributed in the controlled agricultural environment due to the flexible placement of communication ports on the lighting fixtures.

In some implementations, the processor of the lighting fixture may be used to control one or more auxiliary devices and/or process data from the auxiliary devices. The processor may then utilize the data to adjust and control operation of one or more lighting fixtures (e.g., adjusting the PAR output from the lighting fixture) one or more coolant circuits or other fluid coolant loops (e.g., adjusting the fluid flow through the coolant circuit/lighting loop, heating loop, and cooling loops), one or more fans, one or more dehumidifiers, or one or more air conditioners in the controlled agricultural environment. In some implementations, various environmental conditions are measured and controlled to provide target vapor pressure deficits in the environment.

In some implementations, the lighting fixture may be used in a leased lighting system where a customer pays a recurring fee to rent and operate one or more lighting fixtures. In one exemplary implementation, the lighting fixture may be communicatively coupled to a license server that controls the amount of time the lighting fixtures operates according to payments by the customer. Encryption keys and a token exchange with a license server may be used operate the leased lighting system for a controlled agricultural environment.

In sum, one example implementation is directed to a fluid-cooled LED-based lighting fixture, comprising: an extruded aluminum frame including at least a first channel, a second channel, and at least one enclosed cavity formed therein, the extruded aluminum frame further including a fin protruding from the frame and having a plurality of holes to facilitate mechanical coupling of the lighting fixture to at least one support structure; at least one LED light source mechanically supported by the extruded aluminum frame; a first copper pipe to carry a fluid coolant to extract heat generated by at least the at least one LED light source during operation of the lighting fixture, wherein the first copper pipe is press-fit into the first channel of the extruded aluminum frame so as to establish a first thermal connection between the first copper pipe and the extruded aluminum frame; a second copper pipe to carry the fluid coolant, wherein the second copper pipe is press-fit into the second channel of the extruded aluminum frame so as to establish a second thermal connection between the second copper pipe and the extruded aluminum frame; control circuitry, disposed in the at least one enclosed cavity of the extruded aluminum frame, to receive AC power and to control the at least one LED light source; and a plurality of ports, electrically coupled to at least some of the control circuitry, to provide DC power to at least one auxiliary device coupled to at least one of the plurality of ports.

Another example implementation is directed to a method for controlling an agricultural environment, the method Another example implementation is directed to a method for controlling an agricultural environment, the method comprising: A) flowing a fluid coolant in a coolant circuit, wherein the coolant circuit comprises at least one LED-based lighting fixture from which the fluid coolant extracts fixture-generated heat as the fluid coolant flows in the coolant circuit through the at least one LED-based lighting fixture and at least one hydronics loop, coupled to the at least one LED-based lighting fixture, to facilitate temperature regulation in at least a portion of the agricultural environment; B) irradiating a plurality of plants with photosynthetically active radiation (PAR) output by at least one LED-based lighting fixture; and C) sensing at least one condition in the agricultural environment via at least one sensor communicatively coupled to the at least one LED-based lighting fixture.

Another example implementation is directed to a method for controlling an agricultural environment, the method comprising: A) flowing a fluid coolant in a coolant circuit, wherein the coolant circuit comprises at least one LED-based lighting fixture from which the fluid coolant extracts fixture-generated heat as the fluid coolant flows in the coolant circuit through the at least one LED-based lighting fixture and at least one hydronics loop, coupled to the at least one LED-based lighting fixture, to facilitate temperature regulation in at least a portion of the agricultural environment; B) irradiating a plurality of plants with photosynthetically active radiation (PAR) output by at least one LED-based lighting fixture; C) sensing at least one condition in the agricultural environment via at least one sensor communicatively coupled to the at least one LED-based lighting fixture, wherein the at least one sensor includes least one of: an air temperature sensor; a near infrared (NIR) sensor; a relative humidity sensor; a camera; a carbon dioxide (CO2) sensor; and an infrared (IR) sensor; and D) controlling at least one of 1) the PAR output by the at least one LED lighting fixture and 2) a flow of the fluid coolant in at least one of the at least one LED lighting fixture and the hydronics loop, based at least in part on the at least one sensed condition in C), wherein: the at least one LED-based lighting fixture includes at least a first copper pipe and a second copper pipe forming at least a portion of the coolant circuit; and A) comprises flowing the fluid coolant in opposite directions in the first copper pipe and the second copper pipe, respectively.

This application incorporates by reference U.S. provisional application Ser. No. 62/550,379 filed on Aug. 25, 2017, U.S. provisional application Ser. No. 62/635,501 filed on Feb. 26, 2018, and U.S. non-provisional application Ser. No. 16/114,008, filed on Aug. 27, 2018.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 7D-1 shows various views of a lighting fixture including one or more onboard cameras and wireless communications functionality, according to some implementations of the disclosure.

FIG. 7D-2 shows several views of the lighting fixture of FIG. 7D-1.

FIG. 7F shows a top, front, left perspective view of the lighting fixture of FIG. 7E.

FIG. 7J shows a front view of the lighting fixture of FIG. 7E.

FIG. 7K shows a rear view of the lighting fixture of FIG. 7E.

FIG. 7O shows a magnified view of the lighting fixture of FIG. 7N.

FIG. 8A shows a photograph of an exemplary multispectral imaging system, according to some implementations of the disclosure.

FIG. 8F shows a front view of the imaging system of FIG. 8A.

FIG. 8G shows a rear view of the imaging system of FIG. 8A.

FIG. 8H shows a right view of the imaging system of FIG. 8A.

FIG. 8I shows a left view of the imaging system of FIG. 8A.

FIG. 8K shows a bottom, rear, right perspective view of the imaging system of FIG. 8I.

FIG. 8L shows a top view of the imaging system of FIG. 8I.

FIG. 8N shows a front view of the imaging system of FIG. 8I.

FIG. 8O shows a rear view of the imaging system of FIG. 8I.

FIG. 8P shows a right view of the imaging system of FIG. 8I.

FIG. 8Q shows a left view of the imaging system of FIG. 8I.

FIG. 9O-1 shows a first portion of a circuit diagram of a digital signal converter and FIG. 9O-2 shows a second portion of the circuit diagram of the digital signal converter.

DETAILED DESCRIPTION

Figure 1:
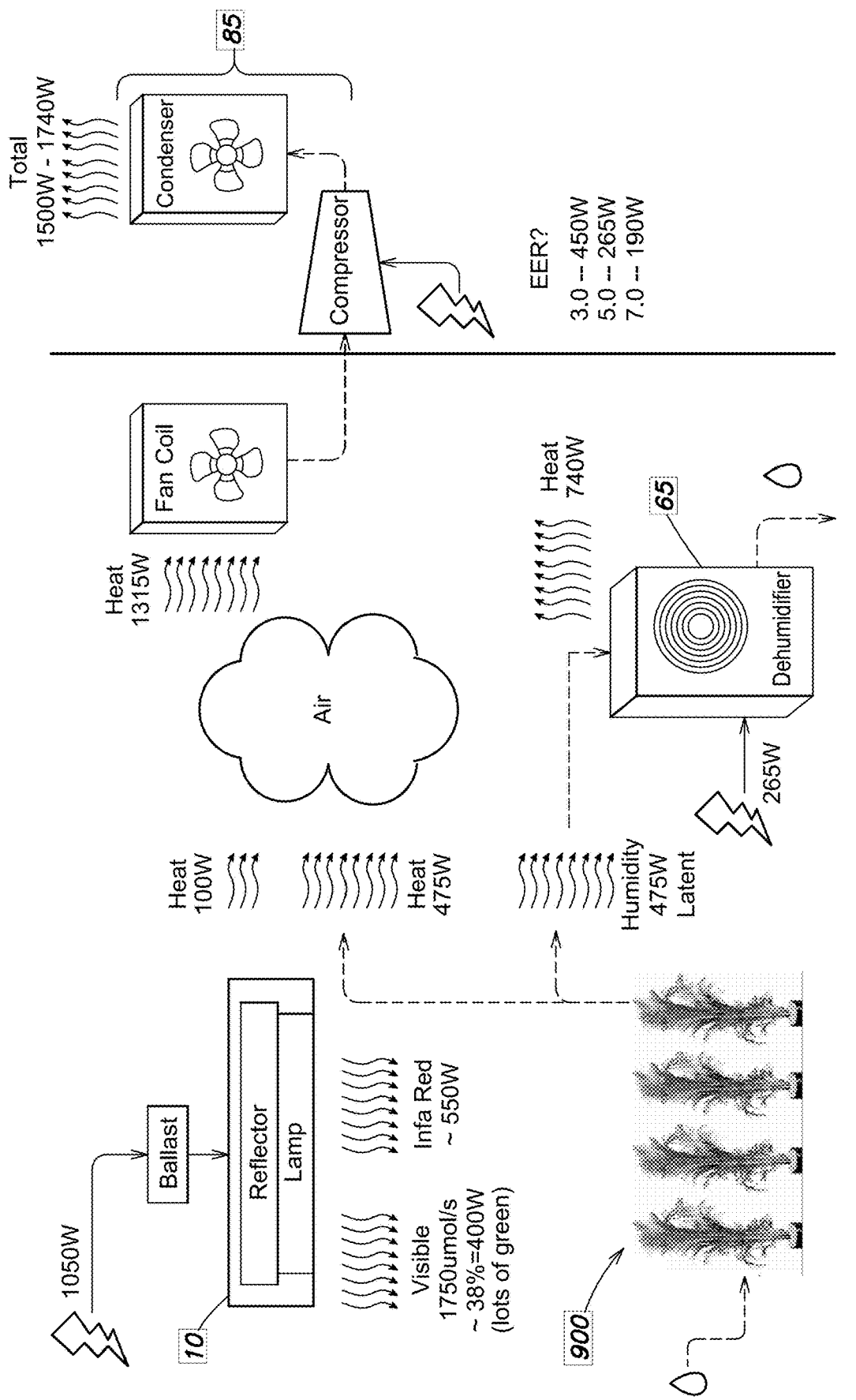
FIG. 1 is an illustration of a conventional controlled agricultural environment where one or more HPS lamps are used.

Following below are more detailed descriptions of various concepts related to, and implementations of, fluid-cooled LED-based lighting methods and apparatus for controlled environment agriculture. It should be appreciated that various concepts introduced above and discussed in greater detail below may be implemented in numerous ways. Examples of specific implementations and applications are provided primarily for illustrative purposes so as to enable those skilled in the art to practice the implementations and alternatives apparent to those skilled in the art.

The figures and example implementations described below are not meant to limit the scope of the present implementations to a single embodiment. Other implementations are possible by way of interchange of some or all of the described or illustrated elements. Moreover, where certain elements of the disclosed example implementations may be partially or fully implemented using known components, in some instances only those portions of such known components that are necessary for an understanding of the present implementations are described, and detailed descriptions of other portions of such known components are omitted so as not to obscure the present implementations.

In the discussion below, various examples of inventive lighting fixtures and multispectral imaging systems are provided, wherein a given example or set of examples showcases one or more particular features of a lighting fixture, cooling system, sensors (e.g., a multispectral imaging system), and an agricultural system deploying one or more lighting fixtures. It should be appreciated that one or more features discussed in connection with a given example of a frame, LED module, coolant pipe, wireless device, camera, and/or sensor may be employed in other examples of a lighting fixture according to the present disclosure, such that the various features disclosed herein may be readily combined in a given system according to the present disclosure (provided that respective features are not mutually inconsistent).

Controlled Environment Agriculture

Controlled Environment Agriculture (CEA) (also referred to as controlled environment horticulture or CEH) is the process of growing plants in a controlled environment where various environmental parameters, such as lighting, temperature, humidity, nutrient levels, and carbon dioxide ($CO_2$) concentrations are monitored and adjusted to improve the quality and yield of the plants. Compared to conventional approaches of plant cultivation, CEA may enable year-round production of plants, insensitivity to variable weather conditions, reduce pests and diseases, and reduce the amount of resources consumed on a per plant basis. Additionally, CEA may support various types of growing systems including, but not limited to soil-based systems and hydroponics systems.

A controlled agricultural environment is typically enclosed, at least in part, by a building structure such as a greenhouse, a grow room, or a covered portion of a field in order to provide some degree of control over environmental conditions. One or more artificial lighting systems are often used in such controlled agricultural environments to supplement and/or replace natural sunlight that may be obstructed by the building structure or insufficient during certain periods of the year (e.g., winter months). The use of an artificial lighting system may also provide yet another measure of control where the intensity and spectral characteristics of the lighting system may be tailored to improve the photosynthetic rates of plants. Various types of artificial lighting systems may be used including, but not limited to, a high intensity discharge lamp, a light emitting diode (LED), and a fluorescent lamp.

Artificial lighting systems, however, generate heat, which when dissipated into the environment may contribute significantly to the cooling load of the controlled agricultural environment. In order to accommodate the higher cooling load and thus maintain the controlled agricultural environment within a desired temperature envelope, the cooling capacity of a cooling system may need to be increased resulting in greater energy consumption. For a controlled agricultural environment on a variable energy budget, greater energy consumption may lead to higher energy costs. Alternatively, for a controlled environment on a fixed energy budget, a larger portion of the energy budget may be consumed by the cooling system, thus reducing the energy and capacity available to support a larger crop size and yield.

To illustrate the impact excess heat generated by an artificial lighting system may have on energy consumption, FIG. 1 shows a conventional controlled agricultural environment with one or more high pressure sodium (HPS) lamps 10, a particular type of high intensity discharge lamp, which irradiates a plurality of plants 900. The exemplary controlled agricultural environment shown in FIG. 1 further includes a dehumidifier 65 to manage the relative humidity of the environment and an air conditioner 85, which may include a fan coil, compressor, and condenser. Energy consumption by the air conditioner 85 generally depends on (1) the total cooling load of the environment and (2) the energy efficiency ratio (EER) of the air conditioner 85. The EER of an air conditioner is defined as the ratio of the cooling capacity (in Watts) to the input power (in Watts) at a given operating point. The EER was calculated with a 35° C. (95° F.) outside temperature and an inside (return air) temperature of 26.7° C. (8° F.) and 50% relative humidity. A higher EER indicates the air conditioner 85 is more efficient.

As shown in FIG. 1, the HPS lamps 10 may increase the cooling load of the environment by (1) dissipating heat convectively and/or radiatively directly into the environment and (2) increasing the relative humidity of the environment and thus, the power input and resultant heat generated by the dehumidifier 65. The cooling load in this exemplary controlled agricultural environment is about 1315 W. For an EER ranging from 3 to 7, the input power for the air conditioner thus ranges from 450 to 190 W, respectively. Based on the input power to the HPS lamps 10 of 1009 W and the dehumidifier 65 of 265 W, the air conditioner 85 thus consumes about 13% and 26% of the total energy budget, corresponding to an EER of 7 and 3, respectively.

Figure 2:
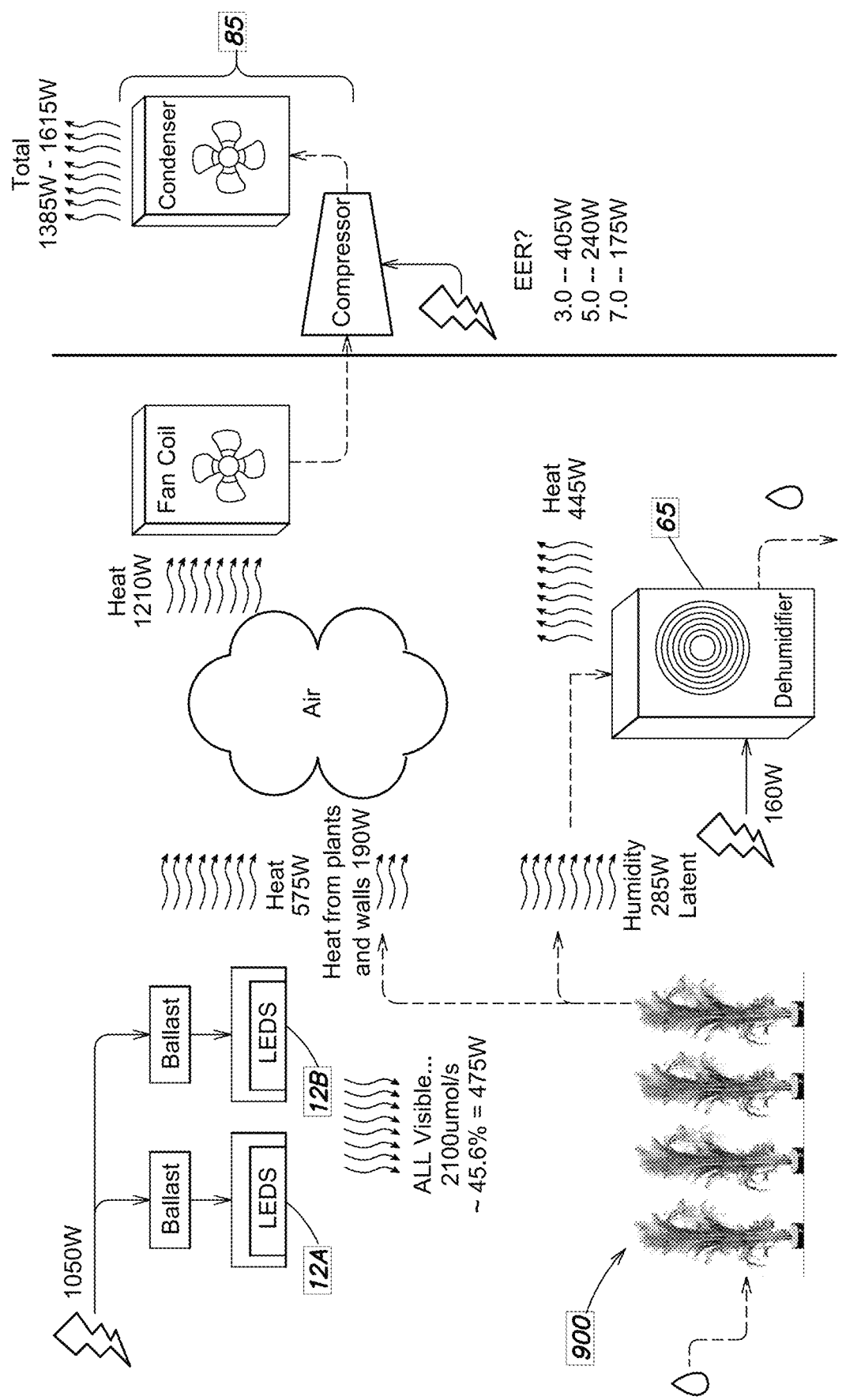
FIG. 2 is an illustration of a conventional controlled agricultural environment where one or more conventional LED-based lighting fixtures are used.

The amount of heat generated may vary depending on the type of lighting system used. However, artificial lighting systems for controlled agricultural environments generally have large power inputs (e.g., greater than 1000 W) in order to sustain a sufficient level of photosynthetically active radiation (PAR). Thus, the heat generated by various types of lighting systems may still constitute a large portion of heat produced within the environment. In another example, FIG. 2 illustrates a conventional controlled agricultural environment where one or more conventional LED-based lighting fixtures 12A and 12B irradiate a plurality of plants 900. In this exemplary controlled agricultural environment, the LED-based lighting fixtures 12A and 12B dissipates heat primarily via convection, which may reduce the power input and heat generated by the dehumidifier 65. In this example, the total cooling load is about 1210 W. For an EER ratio ranging from 3 to 7, the input power for the air conditioner 85 ranges from 405 W to 175 W. Compared to the first example, the use of LED-based lighting fixtures 12A and 12B decreases the total energy budget of the controlled agricultural environment. However, the proportion of energy used by the air conditioner 85 remains similar to the first example at about 13% and 25% for an EER ratio of 7 and 3, respectively. As shown in the two exemplary controlled agricultural environments, artificial lighting systems may generate a substantial amount of heat, which may result in air conditioning systems consuming a significant portion of the total energy budget in a controlled agricultural environment.

The present disclosure is thus directed to a fluid-cooled LED-based lighting fixture. In some implementations, a fluid cooling system may be integrated into the lighting fixture such that a substantial portion of the heat generated by one or more LED's in the lighting fixture is captured by the fluid cooling system. In this manner, the amount of heat transferred to the environment by the lighting fixture may be substantially reduced, thus decreasing the cooling load and the energy input for any air conditioning systems that may be in the controlled agricultural environment. In some implementations, the fluid cooling system may be coupled to a hydronics system to distribute waste heat from the lighting fixture to control the temperature of the growing area or a separate interior space (e.g., a residential building). In some implementations, two or more lighting fixtures may be connected in series, or "daisy-chained," where electrical and piping connections are shared to support a continuous electrical circuit and coolant circuit. The lighting fixture may also provide electrical connections to power one or more sensors to monitor various environmental conditions. In this manner, the fluid-cooled LED-based lighting fixture may also function as an integrated sensor platform.

Figure 3:
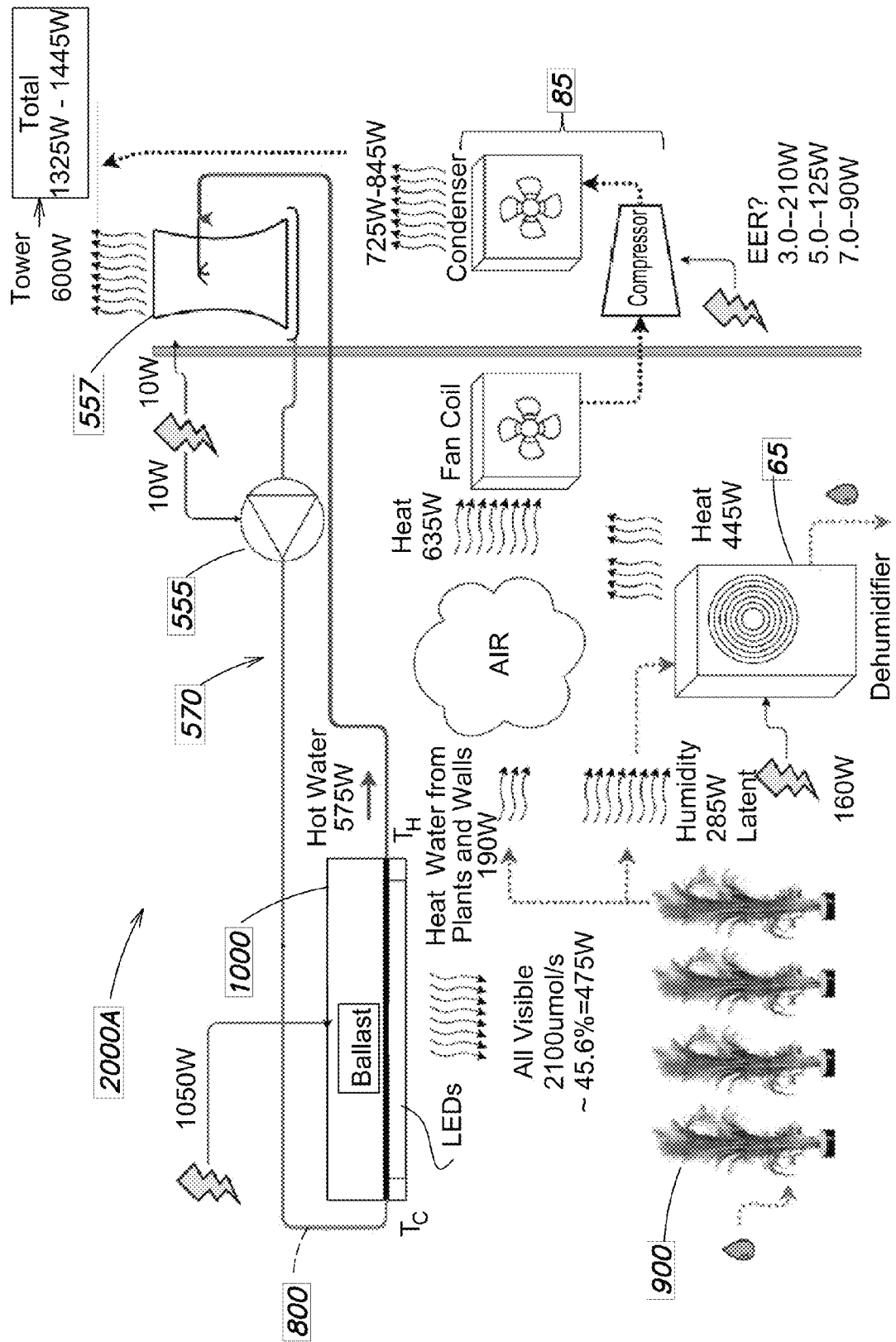
FIG. 3 is an illustration of a controlled agricultural environment where one or more fluid-cooled LED-based lighting fixtures are retrofit into a pre-existing environment, according to some implementations of the disclosure.

To illustrate the benefits of a fluid-cooled LED-based lighting fixture disclosed herein, FIG. 3 shows an exemplary implementation of a controlled agricultural environment 2000A where a lighting fixture 1000 is retrofit into a pre-existing environment that includes a dehumidifier 65 and an air conditioner 85. While not shown explicitly in FIG. 3, the environment may be constituted, at least in part, by a building structure to house a plurality of plants 900, one or more lighting fixtures 1000, and other equipment. The lighting fixture 1000 is cooled by a fluid coolant 800 that circulates through a coolant circuit 570. Heat carried by the fluid coolant 800 is removed by a cooling tower 557 located outside of the controlled agricultural environment 2000A. The coolant circuit 570 may include one or more pumps, regulators and/or valves 555 to control the flow of the fluid coolant 800 in the coolant circuit 570.

As shown in FIG. 3, the one or more pumps, regulators, and/or valves 555 may produce a flow of fluid coolant 800 that exhibits a relatively colder temperature $T_C$ upon entry into the lighting fixture 1000 and a relatively hotter temperature $T_H$ upon exit from the lighting fixture 1000. The rise in temperature of the fluid coolant 800 is due, in part, to convective heating of the fluid as it passes through the lighting fixture 1000 due to heat generated from one or more LED modules within the lighting fixture 1000. The fluid coolant 800 may thus be used to capture and transport heat generated by the lighting fixture 1000, which may substantially reduce the cooling load of the environment and the power inputs to the air conditioner 85 and/or the dehumidifier 65. As shown in FIG. 3, the cooling load for the exemplary controlled agricultural environment 2000A is about 635 W, which is approximately 50% the cooling load in the exemplary controlled agricultural environments shown in FIGS. 1 and 2. For an EER ranging from 3 to 7, the input power for the air conditioner thus ranges from 210 W to 90 W, respectively. Based on the input power to the lighting fixture 1000 of 1009 W and the dehumidifier 65 of 160 W, the air conditioner 85 thus consumes about 7% and 15% of the total energy budget, corresponding to an EER of 7 and 3, respectively.

Although a cooling tower 557 is shown in FIG. 3 to facilitate evaporative cooling of the heated fluid coolant exiting the lighting fixture 1000, it should be appreciated that various types of heat rejection devices may be employed in the coolant circuit 570 to remove heat from the fluid coolant 800. Some examples of heat rejection devices include, but are not limited to, various types of evaporative coolers, "free" coolers, chillers, dry coolers, air source coolers, ground source heat exchangers, water source heat exchangers, or any combinations of the foregoing.

Figure 4:
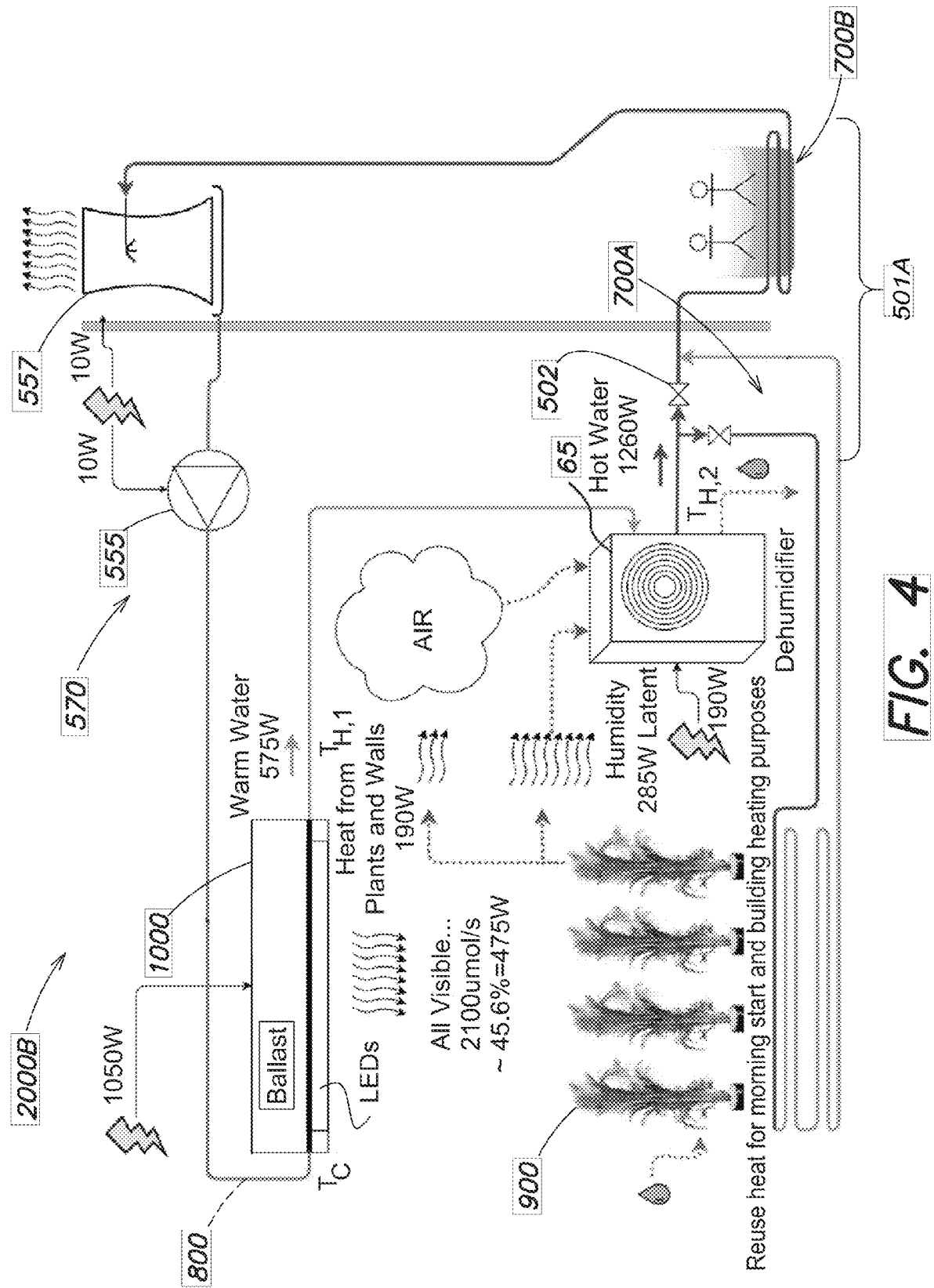
FIG. 4 is an illustration of a controlled agricultural environment where one or more fluid-cooled LED-based lighting fixtures are coupled to a hydronics system, according to some implementations of the disclosure.

In another example, FIG. 4 shows an exemplary controlled agricultural environment 2000B where a lighting fixture 1000 is coupled to a coolant circuit 570 that directs the fluid coolant 800 to a hydronics system 501A having multiple plumbing subsystems 700A and 700B (also referred to herein as "hydronics loops"), which regulate and/or maintain the temperature of various portions of the controlled agricultural environment 2000B and/or space near the controlled agricultural environment 2000B (e.g., a hot pool, the growing area) by utilizing the waste heat generated by the lighting fixture 1000 as a heat source. The coolant circuit 570 may receive heat from the lighting fixture 1000 and other environment sources (e.g., a dehumidifier 65, the ambient air) such that excess heat generated in the environment may be substantially removed, thus further improving the energy savings to operate the controlled agricultural environment 2000B. In some implementations, the cooling load may be sufficiently reduced so as to eliminate the need for any air conditioning systems (i.e., there is no air conditioner fan coil, compressor or condenser).

As shown in FIG. 4, the controlled agricultural environment 2000B may include a dehumidifier 65 to regulate the relative humidity of the environment. The coolant circuit 570 may direct fluid coolant 800 heated by the lighting fixture 1000 into the dehumidifier 65 to further remove heat generated by the dehumidifier 65 in a convective manner similar to the removal of heat from the lighting fixture 1000. The coolant circuit 570 may then direct the fluid coolant 800 to the hydronics loops 700A and 700B, which may be used to heat the plurality of plants 900 and a hot pool, respectively. The coolant circuit 570 may distribute and direct heated fluid coolant 800 in a controlled manner by one or valves 502 before dissipating the remaining heat by the cooling tower 557.

In some implementations, the hydronics system 501A may also be used to regulate the temperature of the ambient environment itself. For example, the hydronics system 501A may be used to heat the controlled agricultural environment 2000B convectively and/or radiatively as the fluid coolant 800 flows through the hydronics system 501A. Furthermore, while FIG. 4 shows a coolant circuit 570 passing through the dehumidifier 65, it should be appreciated that in other implementations the coolant circuit 570 need not include the dehumidifier 65, e.g. the coolant need not flow through the humidifier 65.

An Exemplary Lighting Fixture

Figure 5:
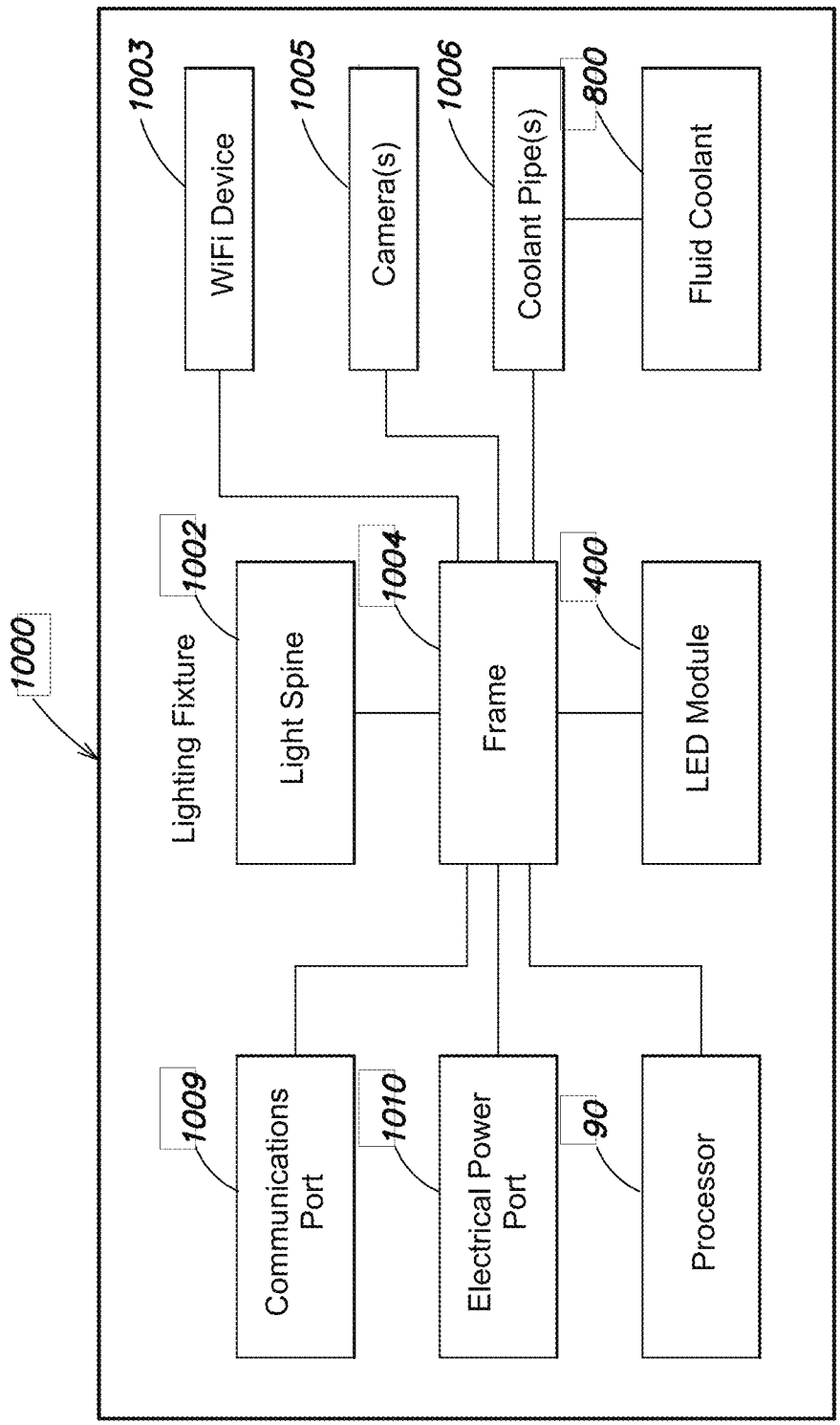
FIG. 5 is a block diagram of a lighting fixture, according to some implementations of the disclosure.

An exemplary implementation of a fluid-cooled LED-based lighting fixture 1000 is shown in FIG. 5. The lighting fixture 1000 may include a frame 1004 to mechanically support and house various components of the lighting fixture 1000. A light spine 1002 may be incorporated onto one or more sides of the frame 1004 with features to mechanically couple and secure the lighting fixture 1000 to a support structure disposed within a controlled agricultural environment. One or more coolant pipes 1006 may be coupled to the frame 1004, where each coolant pipe 1006 may be used to flow a fluid coolant 800 to cool the lighting fixture 1000. One or more LED modules 400 may be disposed on the frame 1004 to emit PAR towards a plurality of plants. A processor 90 may be coupled to the frame 1004 to facilitate the operation of the lighting fixture 1000 including, but not limited to power conversion, network connectivity, and data processing. One or more electrical power ports 1010 may be disposed on the frame 1004 to supply electrical power to various components of the lighting fixture 1000, including, but not limited to the LED modules 400, the processor 90, and other sensors that may be coupled to the lighting fixture 1000. One or more communication ports 1009 may be disposed on the frame 1004 to facilitate electrical communication and data transmission (and in some instances power, e.g., Power over Ethernet as discussed further below). One or more devices 1003 relating to wireless communications ("WiFi 1003;" e.g., wireless antenna, chip set with encryption functionality, etc.) may be disposed on and/or included within the frame 1004 to facilitate wireless communications that may or may not be encrypted to and from the lighting fixture 1000. One or more cameras 1005 and/or other sensing devices (onboard cameras/sensors) also may be disposed on and/or included within the frame 1004 (as opposed to coupled to the electrical power ports and/or the communication ports 1009), to facilitate image acquisition within various spectral regions of interest and/or other sensing functionalities.

The frame 1004 may be a mechanically rigid, hollow structure that forms a substantially enclosed housing. The interior cavity of the frame 1004 may be dimensioned to house a plurality of components in the lighting fixture 1000, such as various electronics in the processor 90. The frame 1004 may include one or more mounting features within the interior cavity to securely couple the plurality components to the frame 1004. For example, the frame 1004 may include one or more slots disposed within the interior cavity of the frame 1004 and arranged so as to mechanically support at least two opposing edges of a printed circuit board. Other mounting features may include, but are not limited to mounting posts and mounting stubs.

One or more removable panels may be included in the frame 1004 to provide access to the interior space. The one or more removable panels may be coupled to a portion of the frame 1004 using various types of coupling mechanisms including, but not limited to screw fasteners, bolt fasteners, clips, and clamps. In some implementations, the frame 1004 may form a sufficiently airtight enclosure or cavity to protect components, e.g., electronics, that may be sensitive to the environmental conditions of the controlled agricultural environment. For example, the controlled agricultural environment may operate at a relative humidity that may cause moisture to condense onto various surfaces of the lighting fixture 1000, causing damage to components including exposed electronics. In instances where the frame 1004 is an airtight enclosure, moisture may be substantially restricted from infiltrating the interior space of the frame 1004 to reduce the likelihood of condensation forming onto components disposed within the frame 1004.

The frame 1004 may also include a recessed portion disposed along at least one side of the frame 1004, e.g., the bottom side, with sidewalls that at least partially surround one or more LED modules 400. The recessed portion may be used to direct light emitted by the one or more LED modules 400 along a preferred direction and angular distribution. For example, the recessed portion may be used to substantially illuminate a growing area containing one or more plants located below the frame 1004. In some implementations, the surface quality and orientation of the interior surfaces of the sidewalls forming the recessed portion may form an integrated reflector to reflect light emitted by the one or more LED modules 400. For example, the interior surfaces of the sidewalls may be polished to reflect light in a substantially specular manner and oriented such that light is reflected towards a preferred direction, e.g., the growing area.

The frame 1004 may also include one or more channels formed along one or more sides of the frame 1004 where each channel may be used to secure a corresponding coolant pipe 1006 to the frame 1004. The cross-sectional shape of the channel may be substantially similar to the cross-sectional shape of the coolant pipe 1006 to facilitate insertion of the coolant pipe 1006 into the channel. The coolant pipe 1006 may be secured to the channel of the frame 1004 using several approaches. For example, the cross-section dimensions of the channel may be equal to or smaller than the cross-sectional dimensions of the coolant pipe 1006 to facilitate a press fit where the coolant pipe 1006 is secured to the channel via friction. In other examples, the coolant pipe 1006 may be clamped to the frame 1004 using one or more clamps, which may include, but are not limited to zip ties and clamps with a worm drive fastener. The clamps may be removable to allow replacement of the coolant pipes 1006. The surface of the one or more channels may also be polished to improve thermal contact with the coolant pipe 1006, thus enabling greater heat dissipation into the fluid coolant 800. In yet other examples, the coolant pipes 1006 may be adhered or bonded to the frame 1004 using various methods including, but not limited to adhesive bonding, welding, and brazing. Thermal interface material may also be disposed between the channel and the coolant pipe to improve thermal contact.

The frame 1004 may also be, at least in part, thermally conducting to transfer heat from the one or more LED modules 400 to the coolant pipe 1006. In particular, a first portion of the frame 1004 disposed between the LED module 400 and the coolant pipe 1006 may be formed from a thermally conducting material with dimensions to (1) reduce the distance between the LED module 400 and the coolant pipe 1006 and (2) increase the lateral cross-sectional area between the LED module 400 and the coolant pipe 1006. In this manner, the thermal resistance between the LED module 400 and the coolant pipe 1006 may be reduced. In some implementations, the frame 1004 may be formed entirely from the thermally conducting material to simplify manufacture and assembly. In some implementations, the first portion of the frame 1004 may be formed from a thermally conducting material while the remainder of the frame 1004 is formed from another material, such as a polymer in order to reduce material costs.

The frame 1004 may be formed from various metals, ceramics, polymers, or composites including, but not limited to, copper, aluminum, stainless steel, carbon steel, polyethylene, acrylic, and porcelain. Depending on the materials used to form the frame 1004, various method of manufacture may be utilized including, but not limited to extrusion, sandcasting, milling, injection molding, and manual molding. For instances where the frame 1004 is assembled form multiple parts, various coupling mechanisms may be used for assembly including, but not limited to snap fits, screw fasteners, bolt fasteners, adhesives, brazing, and welding.

The light spine 1002 may be used to secure the lighting fixture 1000 to a support structure in the controlled agricultural environment. The support structure may be various types of structures including, but not limited to a railing, a suspended platform, a ceiling, and a wall. The light spine 1002 may be a protruding fin formed onto the frame 1004 that includes one or more holes of varying size to accommodate different sizes and types of coupling mechanisms used to secure the lighting fixture 1000 to the support structure. The coupling mechanisms may include, but are not limited to bolt fasteners, screw fasteners, hooks, and shackles. The light spine 1002 may be dimensioned to span the length of the frame 1004, thus providing multiple locations along the frame 1004 to couple the lighting fixture 1000 to the support structure in a stable manner. For example, the light spine 1002 may be disposed on the top side of the frame 1004 with a length that spans the length of the frame 1004. The light spine 1002 may include a plurality of holes where the center axis of each hole is parallel to the top side of the frame 1004. Multiple bolt fasteners may be installed at each end and the center of the light spine 1002 to secure the lighting fixture 1000 to a sidewall of a support structure. Multiple light spines 1002 may also be distributed along the length of the frame 1004 or on multiple sides of the frame 1004 to allow the lighting fixture 1000 to be coupled to different support structures.

As described above, the coolant pipe 1006 may be used to flow fluid coolant 800 to capture heat generated by the LED module 400. The coolant pipe 1006 may be dimensioned to have a length longer than the frame 1004 such that a portion of the coolant pipe 1006 may extend beyond the sides of the frame 1004 to facilitate coupling of the coolant pipe 1006 to a pipe from a coolant circuit, a hydronics system, or another lighting fixture 1000. Various types of coupling mechanisms may be used to couple the coolant pipe 1006 to another pipe including, but not limited to threaded fittings, where the ends of the coolant pipe 1006 have corresponding threads, and bolt fasteners, where the end of the coolant pipe 1006 have a flange that mates to a corresponding flange on another pipe. In a preferred implementation, push-to-connect plumbing fittings may be used as a coupling mechanism where the ends of the coolant pipe 1006 are left bare. In this manner, internal seals and O-rings do not need to be used.

Multiple coolant pipes 1006 may be incorporated into the frame 1004 where each coolant pipe 1006 may be used to flow fluid coolant 800 along the same or opposing directions. For example, the lighting fixture 1000 may include two coolant pipes 1006 disposed on opposing sides of the frame 1004. For a lighting fixture 1000 that supports multiple LED modules 400, an opposing flow configuration (e.g., fluid coolant 800 flows in opposing directions between the two coolant pipes 1006) may more uniformly remove heat from the multiple LED modules 400. In comparison, a same flow configuration will result in more heat removed from the LED module 400 closest to the fluid coolant 800 input and less heat removed from the LED module 400 furthest from the fluid coolant 800 input. Additionally, the opposing flow configuration may more readily facilitate implementation of a closed coolant circuit. For example, the two coolant pipes 1006 may be connected at one end by a plumbing fitting such that fluid coolant 800 entering the lighting fixture 1000 flows through a first coolant pipe 1006 and then a second coolant pipe 1006 serially before exiting the lighting fixture 1000 on the same side.

The coolant pipe 1006 may be formed from various materials including copper, aluminum, and stainless steel. In a preferred implementation, the coolant pipes 1006 may be formed from copper to reduce algae growth, fouling, and corrosion. Thus, by coupling copper coolant pipes 1006 using the push-to-connect plumbing fittings described above, the fluid coolant 800 may pass through a coolant circuit made up of only copper without contacting other materials in the lighting fixture (e.g., an aluminum frame 1004).

The cross-sectional dimensions of the coolant pipe 1006 may vary depending on multiple factors including, but not limited to a desired flow rate, fluid coolant properties (e.g., dynamic viscosity, density), and a desired type of flow. For example, it may be desirable for the fluid coolant to be in a turbulent flow regime, which engenders a higher heat transfer coefficient, thus dissipating more heat from the lighting fixture 1000. In some implementations, the cross-sectional dimensions of the coolant pipe 1006 may be chosen such that a particular Reynold's number, Re, is greater than a desired threshold (e.g., Re>4000 for turbulent flow) for a given pump power and coolant circuit geometry. The interior surface of the coolant pipe 1006 may also be roughened to increase the surface area and the convective heat transfer coefficient. The effective depth and pitch of the interior surface roughness may be chosen so as to not substantially increase pumping requirements (e.g., due to a larger pressure drop) and maintains wettability of the interior surface to the fluid coolant 800 (e.g., remains hydrophilic, oleophilic).

The fluid coolant 800 used to capture and carry heat from the lighting fixture 1000 may be chosen based on several factors. First, it is preferable for the fluid coolant 800 to exhibit a high thermal conductivity and a high specific heat in order to increase heat dissipation from the LED module 400 to the fluid coolant 800. Second, the fluid coolant 800 should remain in a liquid phase within the operating temperature and pressure range of the controlled agricultural environment. For example, the fluid coolant 800 should not freeze or boil as it passes through the lighting fixture 1000, the coolant circuit, the hydronics system, or a cooling tower. Third, the fluid coolant 800 should also be chosen so as not to substantially corrode the coolant pipe 1006. For controlled agricultural environments, the fluid coolant 800 may be various fluids including, but not limited to water, mineral oil, glycol, and mixtures.

The lighting fixture 1000 also may include one or more communication and/or auxiliary power ports, for example, to provide auxiliary DC power to one or more auxiliary devices coupled to the port(s), and/or facilitate communications between the lighting fixture and the one or more auxiliary devices. Example of such ports include, but are not limited to, one or more Power over Ethernet (PoE) ports and/or one or more Universal Serial Bus (USB) ports.

For example, the lighting fixture 1000 may include at least one electrical power port 1010 to supply electrical power to various components in the lighting fixture 1000 (e.g., the LED module 400) and/or various components electrically coupled to the lighting fixture 1000 (e.g., other lighting fixtures 1000 or auxiliary sensors). The electrical power port 1010 may receive as input alternating current (AC) power, such as from a building electrical supply system, which may be converted into direct current (DC) power via the processor 90. The processor 90 may include electronics to facilitate conversion between DC and AC power, as will be discussed in greater detail below.

One or more communication ports 1009 may also be used in the lighting fixture 1000 to facilitate data transmission to and from the lighting fixture 1000. For example, the communication port 1009 may be used to remotely control various aspects of the lighting fixture 1000 including, but not limited to adjustments to electrical power (e.g., high voltage and low voltage modes), adjustments to the spectral content of the light emission (e.g., directing more power to blue or red LED elements), and commands to operate auxiliary sensor devices (e.g., frequency of data recording). In another example, the communication port 1009 may be used to send various status and monitoring data to a remote user including, but not limited to electrical power consumption, temperature, and data measured by auxiliary sensor devices. The data received and transmitted by the communication port 1009 may be managed, in part, by the processor 90, as will be discussed in more detail below.

The communication port 1009 may accommodate various types of electrical cabling including, but not limited to universal serial bus (USB) cables and Power over Ethernet (PoE) cables. In some implementations, multiple communication ports 1009 including both USB and PoE ports may be used to enable greater flexibility and compatibility with more types of cabling and auxiliary devices. One or more communication ports 1009 may be disposed on one or more sides of the frame 1004. For example, a set of communication ports 1009 may be disposed on opposite sides of the frame 1004 (e.g., left and right sides or front and rear sides) to facilitate connectivity between a plurality of lighting fixtures 1000 in a daisy-chain configuration. Communication ports 1009 may also be disposed on the frame 1004 where auxiliary sensors are likely to be deployed. For example, communication ports 1009 may be disposed on the bottom side of the frame 1004 to provide electrical connection to auxiliary sensors that are used to monitor ambient conditions near the plants located below the lighting fixture 1000. In some implementations, the communication port 1009 may also supply DC power. For example, the lighting fixture 1000 may include a USB port that may electrically power an auxiliary sensor device and receive data measured by the auxiliary sensor device through the same communication port 1009.

Figure 6A:
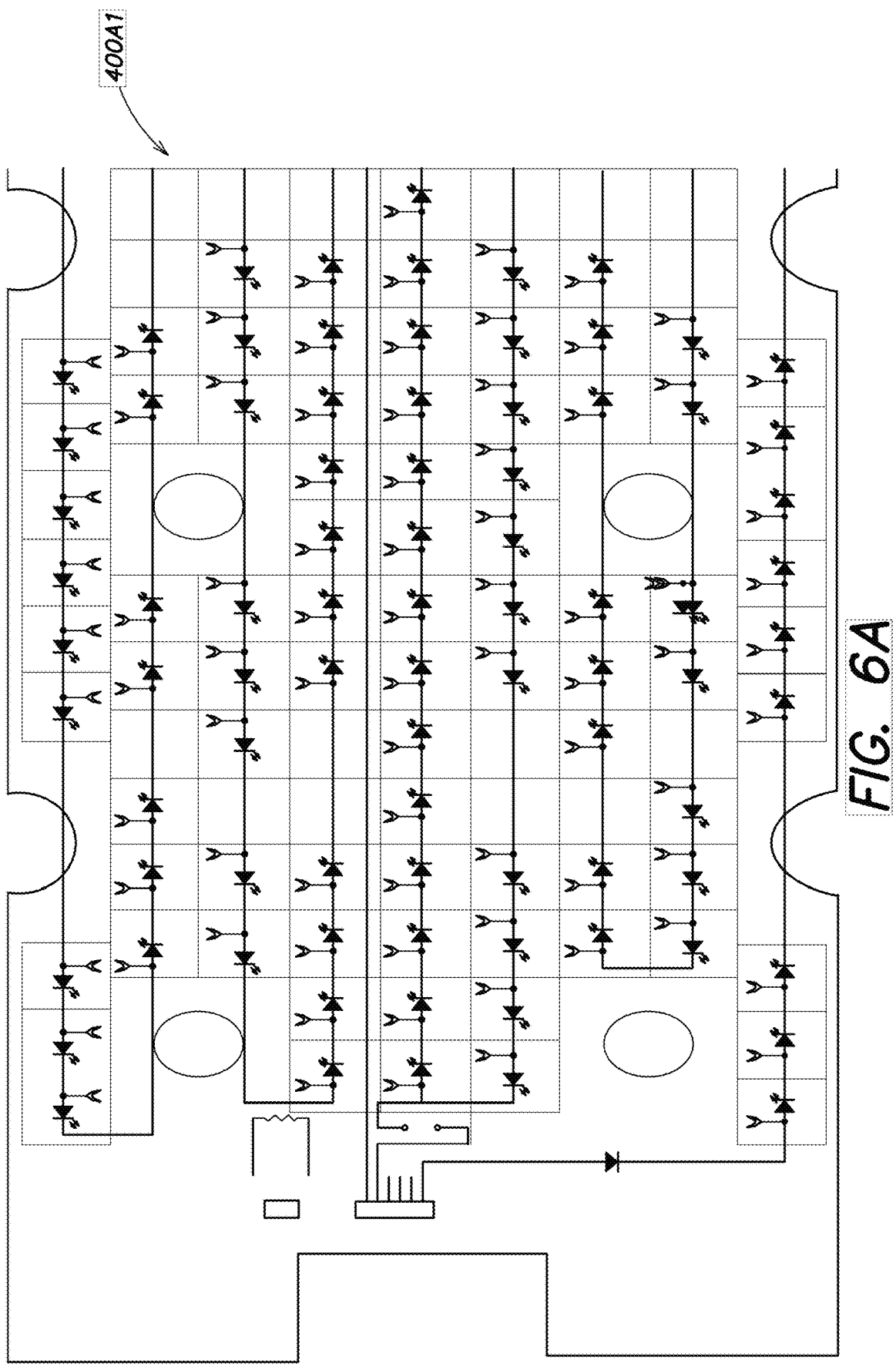
FIG. 6A is a circuit diagram detailing a first half of an exemplary LED module of a lighting fixture, according to some implementations of the disclosure.
Figure 6B:
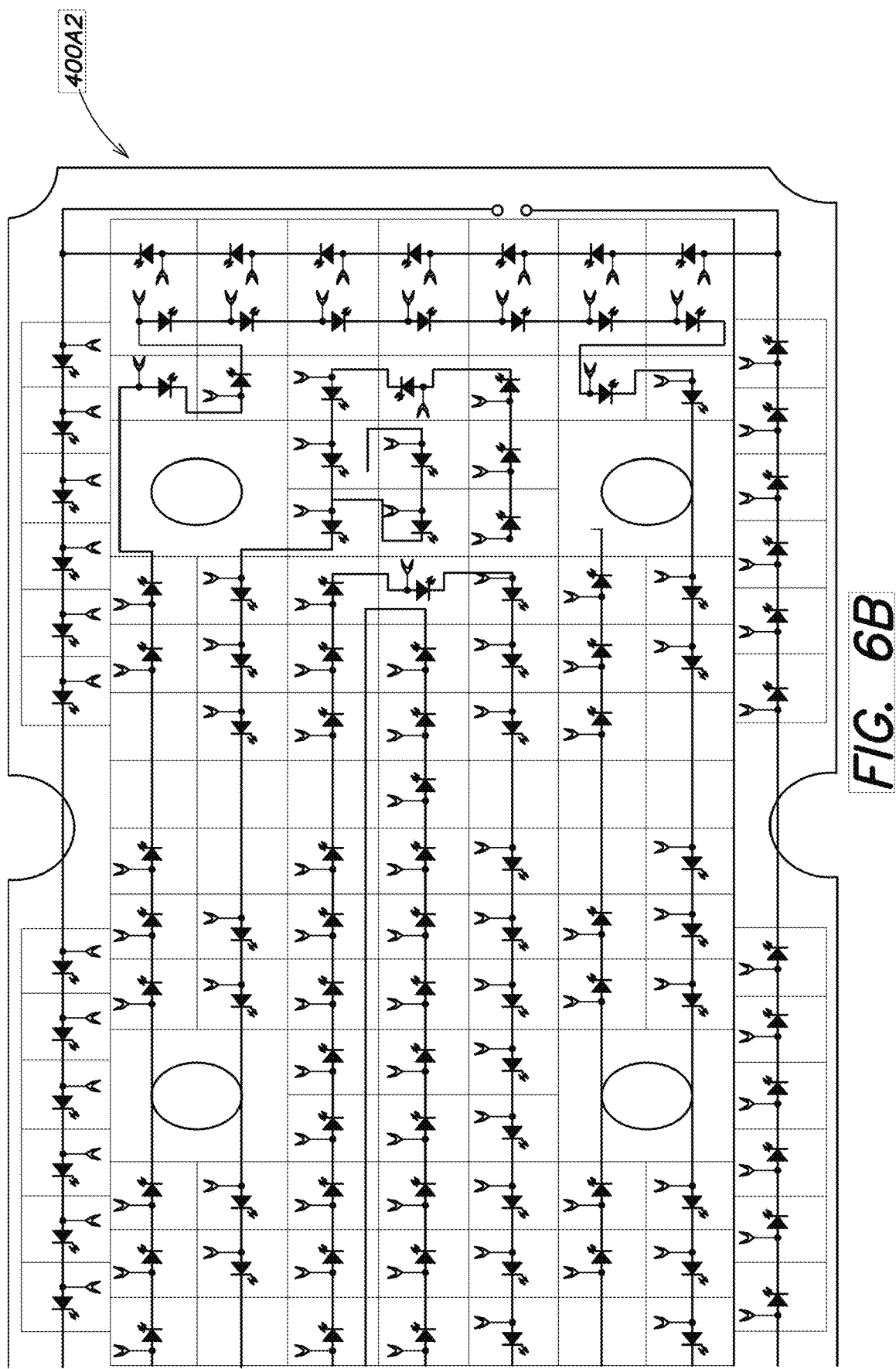
FIG. 6B is a circuit diagram detailing the second half of the exemplary LED module of FIG. 6B.

The LED module 400 may include one or more LED elements arranged into an array. The one or more LED elements of the LED module 400 may each emit light at a particular wavelength such that in combination, the LED module 400 irradiates plants with light at multiple wavelengths tailored to improve various aspects related to the growth of plants and operation of the controlled agricultural environment including, but not limited to improving photosynthetic rates of the plants, growth modification, and ultraviolet (UV) sterilization. The one or more LED elements may be assembled onto the frontside of a printed circuit board. An exemplary circuit layout of an LED module 400 according to one inventive implementation is shown in FIGS. 6A and 6B, which illustrates the respective halves 400A1 and 400A2 of the LED module 400A. As shown, the LED module 400A may include multiple LED elements that are distributed across the printed circuit board.

The printed circuit board may be a metal core printed circuit board (MCPCB) to facilitate heat dissipation generated by the one or more LED elements. The LED module 400 may be coupled to the frame 1004 such that the backside of the printed circuit board is in contact with the bottom side of the frame 1004 located in the recessed portion as described above. The LED module 400 may be coupled to the frame 1004 using various coupling mechanisms including, but not limited to screw fasteners, bolt fasteners, clips, and clamps. The coupling mechanism may be adjusted such that a clamping force is applied to the LED module 400, thus improving the thermal contact between the LED module 400 and the frame 1004. Additionally, thermal interface material may also be placed between the LED module 400 and the frame 1004 to improve thermal contact.

In some implementations, the lighting fixture 1000 may also include an optic located on the recessed portion of the frame 1004, which covers the LED module 400. The optic may be used to modify the direction and angular distribution of the light emitted by the LED module 400. For example, a portion of the optic may have a convex surface to focus light emitted from the LED module 400 onto plants located directly below the lighting fixture 1000. The optic may be coupled to the frame 1004 using various coupling mechanisms including, but not limited to screw fasteners, bolt fasteners, clips, and clamps. In some implementations, the optic may form a substantially airtight enclosure around the LED module 400, thus substantially isolating the LED module 400 from the ambient environment in the controlled agricultural environment. Similar to the airtight enclosure that may be formed by the frame 1004, the optic may reduce moisture infiltration, thus reducing the risk of condensation damaging the LED module 400.

Figure 7A:
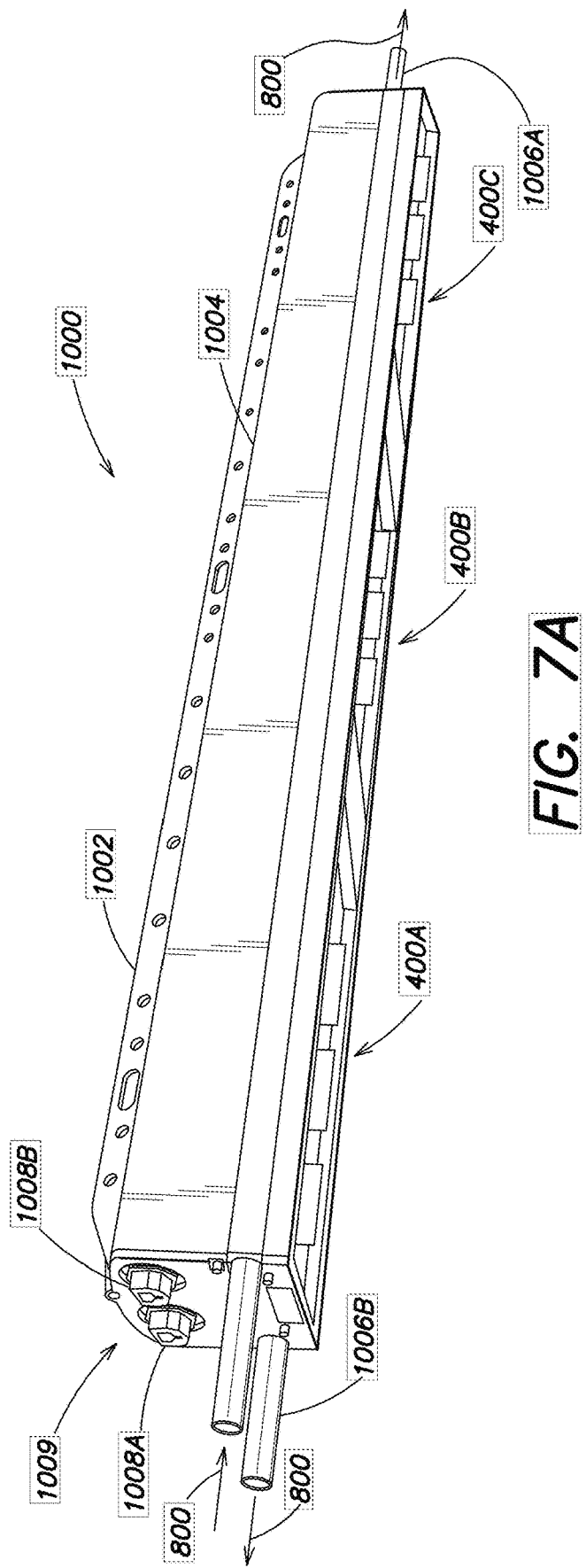
FIG. 7A shows a bottom, front perspective view of a lighting fixture, according to some implementations of the disclosure.
Figure 7B:
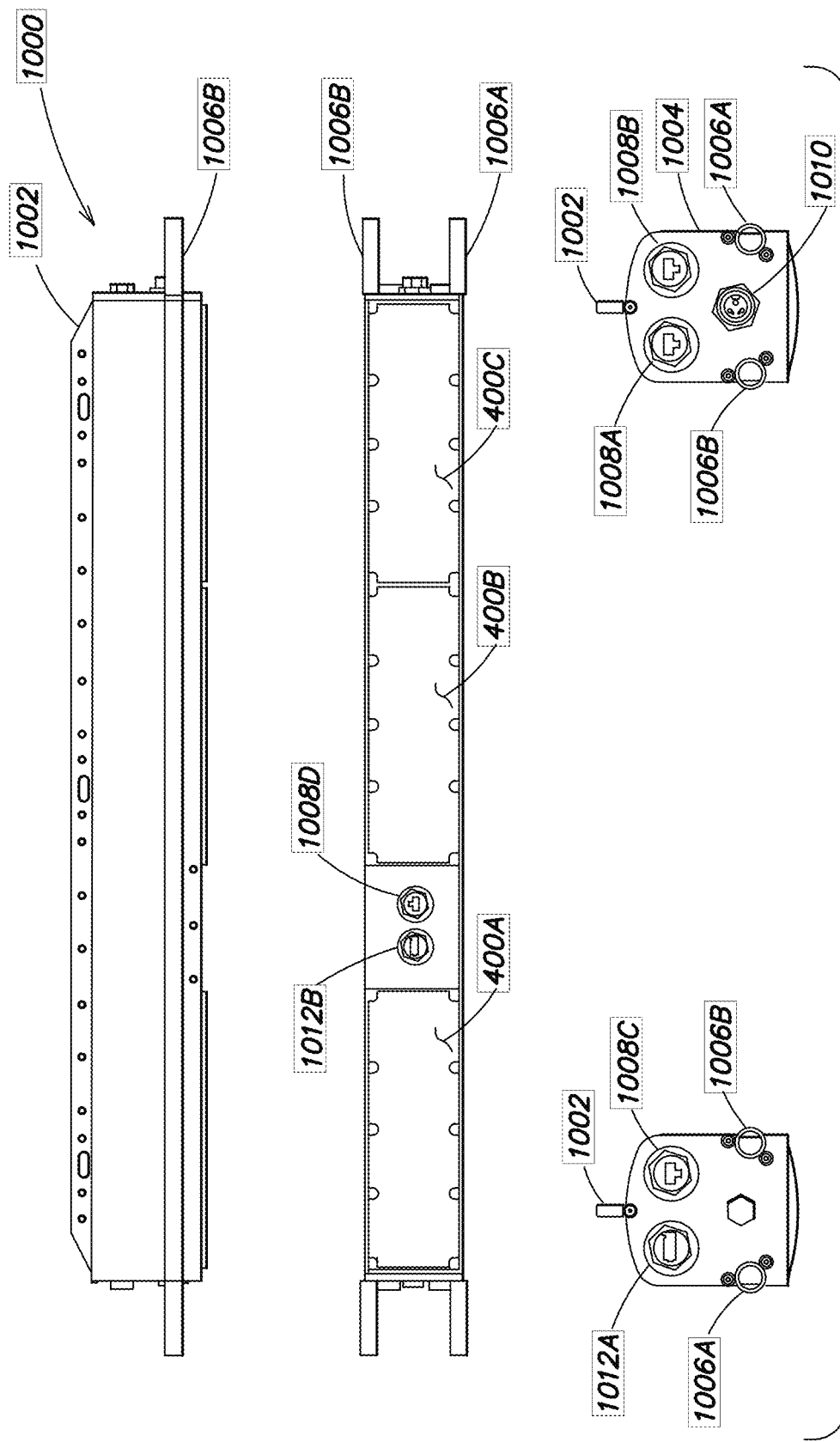
FIG. 7B shows front, bottom, left side, and right side views of the lighting fixture of FIG. 7A.
Figure 7C:
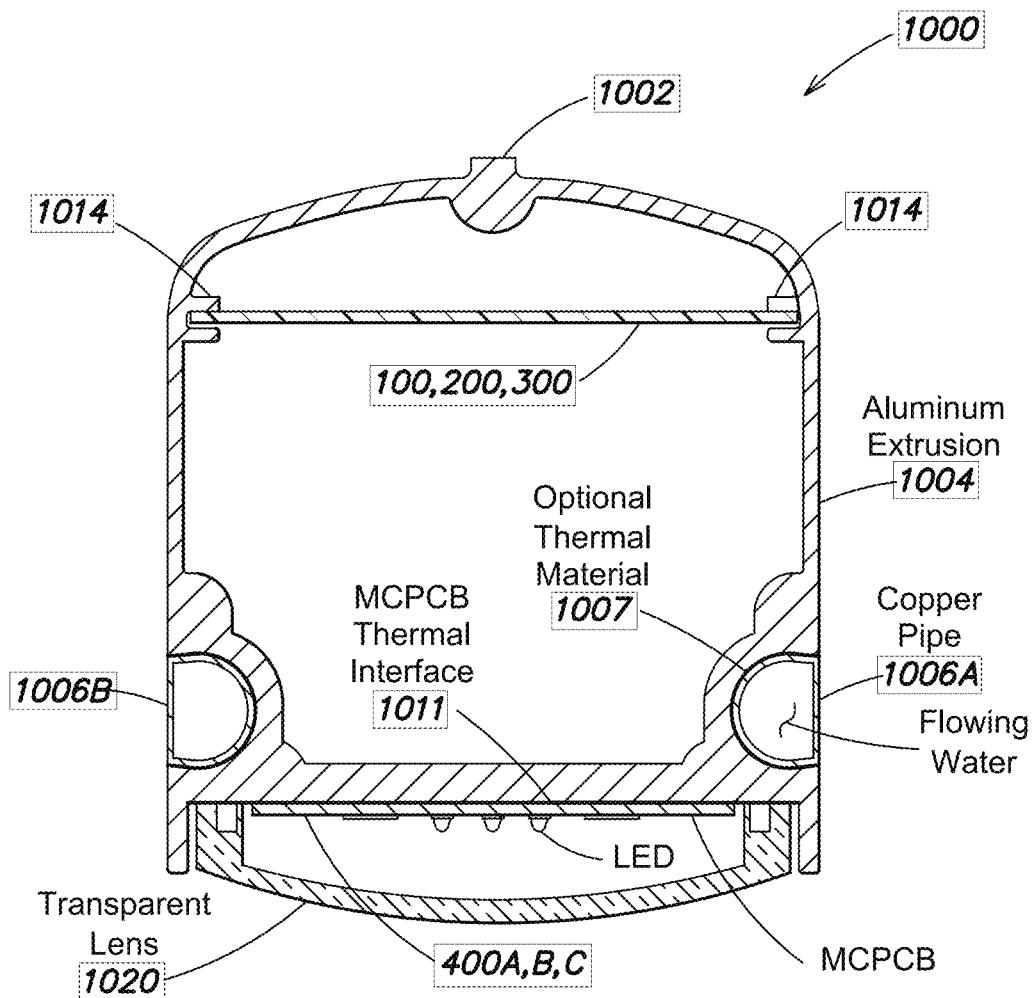
FIG. 7C shows a cross-sectional view of the lighting fixture of FIG. 7B along the plane A-A.

An exemplary lighting fixture 1000 according to one inventive implementation is shown in FIGS. 7A-7C. FIG. 7A shows a bottom perspective view of the lighting fixture 1000 and FIG. 7B shows a front, bottom, left and right side view of the lighting fixture 1000. As shown, the lighting fixture 1000 includes a frame 1004 dimensioned to support three LED modules 400A, 400B, and 400C positioned in a row and disposed on the bottom side of the frame 1004. A light spine 1002 may be formed on the top of the frame 1004 that substantially spans the entire length of the frame 1004. The light spine 1002 may include a plurality of different sized holes to facilitate coupling of the lighting fixture 1000 to a support structure in the controlled agricultural environment. The left and right-side panels of the frame 1004 may be secured by a plurality of screw fasteners and hence, may be removed to allow access into the interior cavity of the frame 1004. The left side panel of the frame 1004 may include two communication ports 1009, e.g., a USB port 1012A and a PoE port 1008C. The right-side panel of the frame 1004 may also include two communication ports 1009, e.g., two PoE ports 1008A and 1008B, as well as an electrical power port 1010. Two communication ports, e.g., a USB port 1012B and a PoE port 1008D, may be disposed on the bottom side of the frame 1004 to facilitate connectivity to auxiliary senor devices that may be used to monitor ambient conditions near the plants. The lighting fixture 1000 also includes two coolant pipes 1006A and 1006B disposed along the front and rear sides of the frame 1004. The frame 1004 may be formed from an aluminum extrusion to include a corresponding pair of channels. The coolant pipes 1006A and 1006B, which may be formed form copper, may be press-fit or crush-fit into the corresponding channels. In this manner, the likelihood that fluid coolant flowing through the coolant pipes 1006A and 1006B contacts the frame 1004 is substantially reduced.

FIG. 7C shows a cross-sectional view of the lighting fixture 1000 where the coolant pipes 1006A and 1006B are shown to be press-fit into the channels of the frame 1004. Thermal interface material 1007 may be disposed between the channels and the coolant pipes 1006A and 1006B to improve thermal contact. The LED modules 400A-400C are disposed substantially in a recessed portion of the bottom side of the frame 1004 and in close proximity to the coolant pipes 1006A and 1006B to facilitate heat dissipation. As shown, a small portion of the frame 1004, which is formed from a thermally conducting material, is present between the coolant pipes 1006A and 1006B and the LED modules 400A-400C. FIG. 7C also shows mounting features 1014 used to support various control circuitry boards 100, 200, and 300, which are collectively referred to hereafter as a processor 90. The mounting features 1014 are a pair of protruding slots disposed along the front and rear sides of the frame 1004, which are dimensioned to support the opposing edges of the processor 90. The processor 90 is positioned above the coolant pipes 1006A and 1006B and LED modules 400A-400C in order to reduce thermal effects due to heat generated by the LED modules 400A-400C. An optic 1020 is also included, which may be coupled to the frame 1004 via a plurality of screw fasteners. The optic 1020 may be a transparent lens with a convex surface used to redirect light emitted by the LED modules 400A-400C along a desired direction and angular distribution. The optic 1020 may also substantially enclose and isolate the LED modules 400A-400C from the surrounding ambient environment.

Figures 2, 7D:
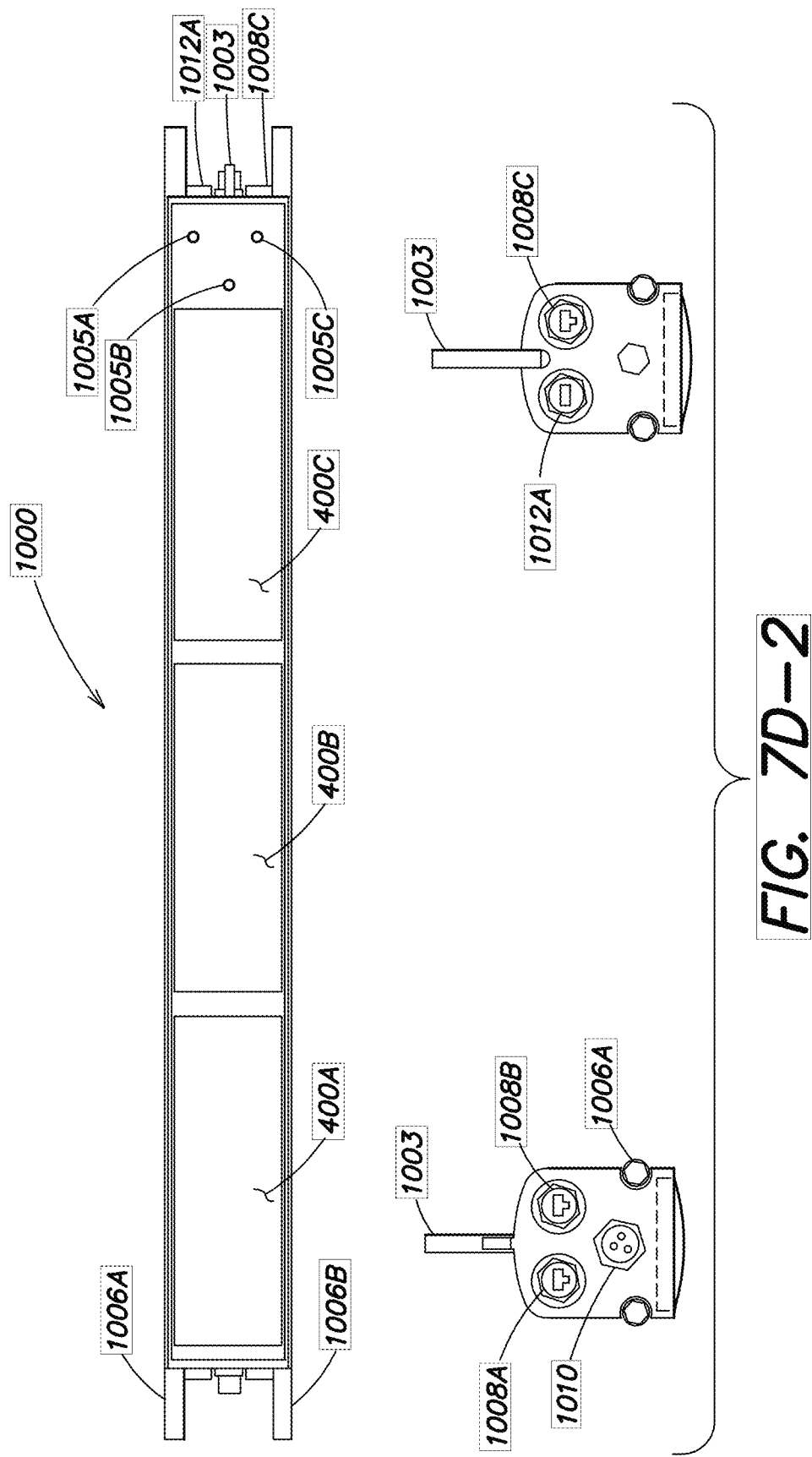
Figure 7E:
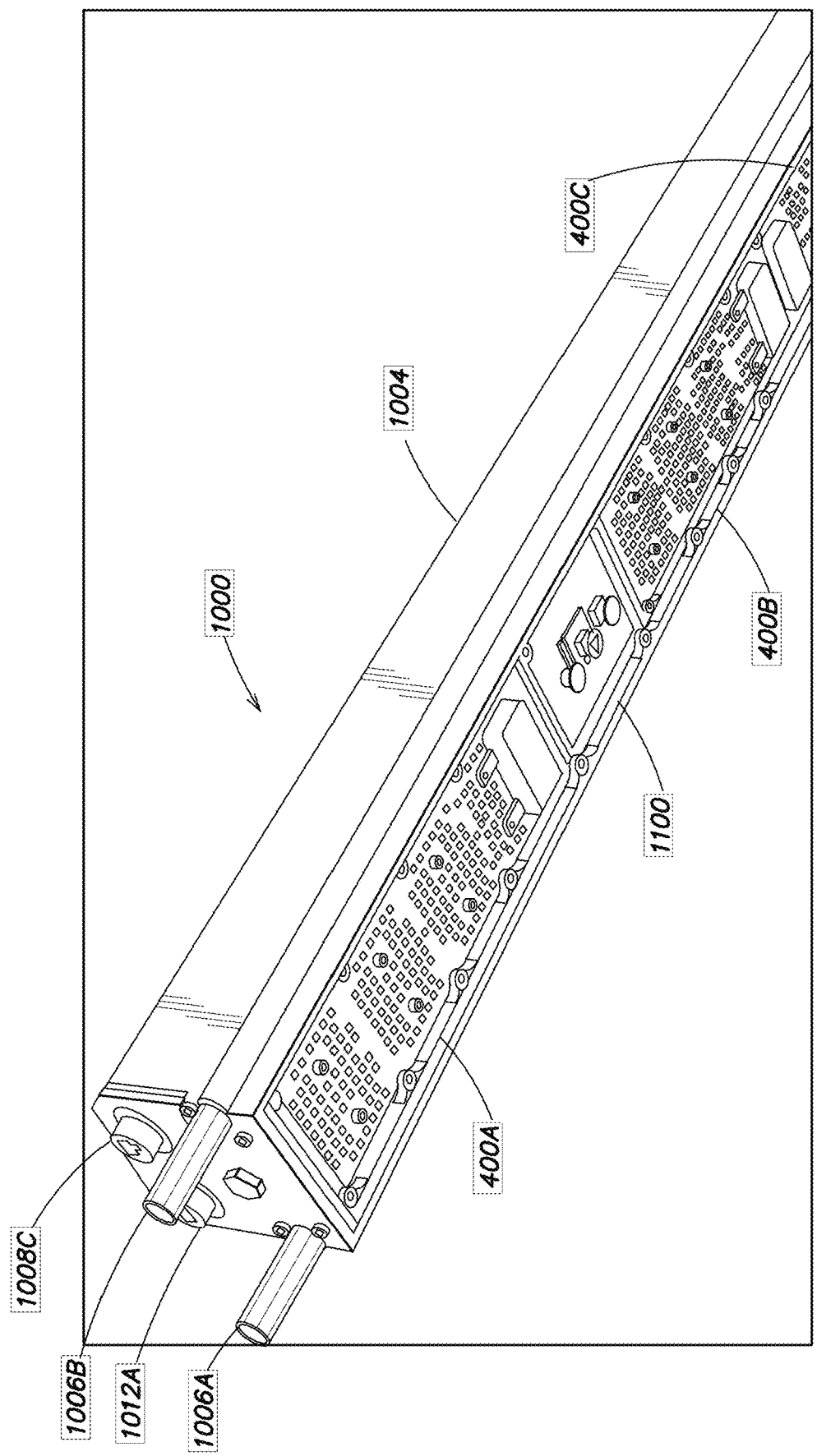
FIG. 7E shows a bottom, front, left perspective view of an exemplary lighting fixture with a multispectral imaging system, according to some implementations of the disclosure.
Figure 7G:
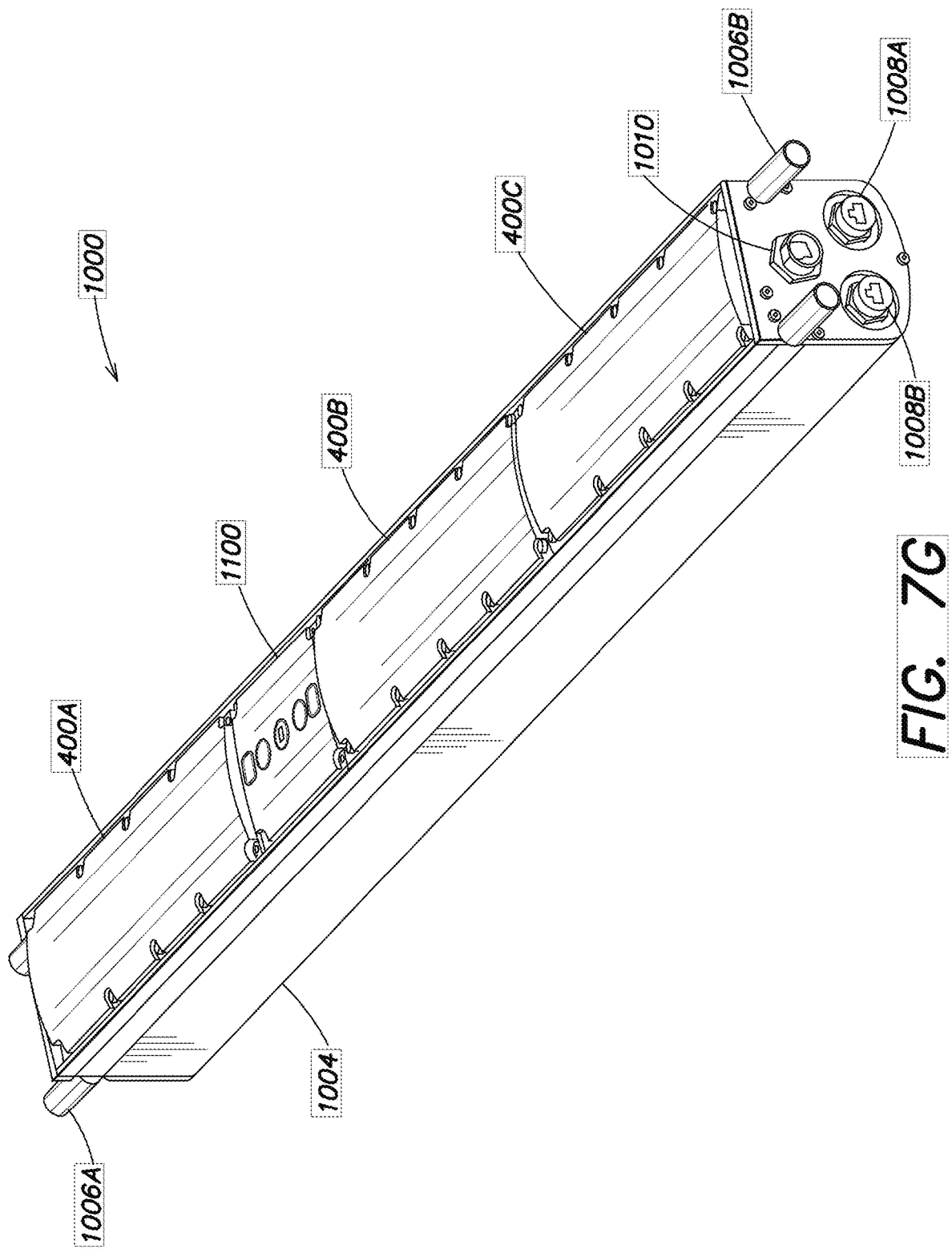
FIG. 7G shows a bottom, rear, right perspective view of the lighting fixture of FIG. 7E.
Figure 7H:
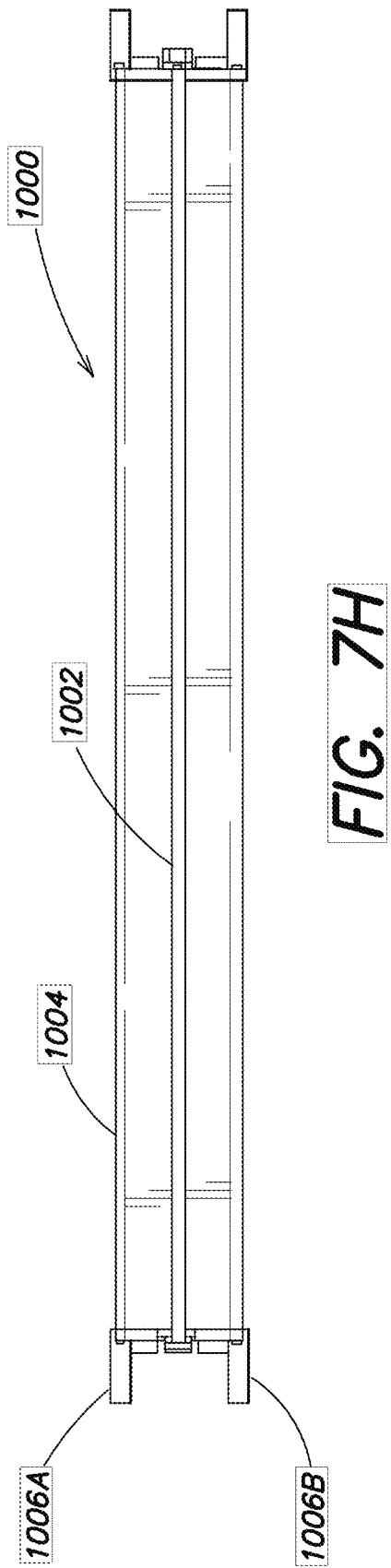
FIG. 7H shows a top view of the lighting fixture of FIG. 7E.
Figure 7I:
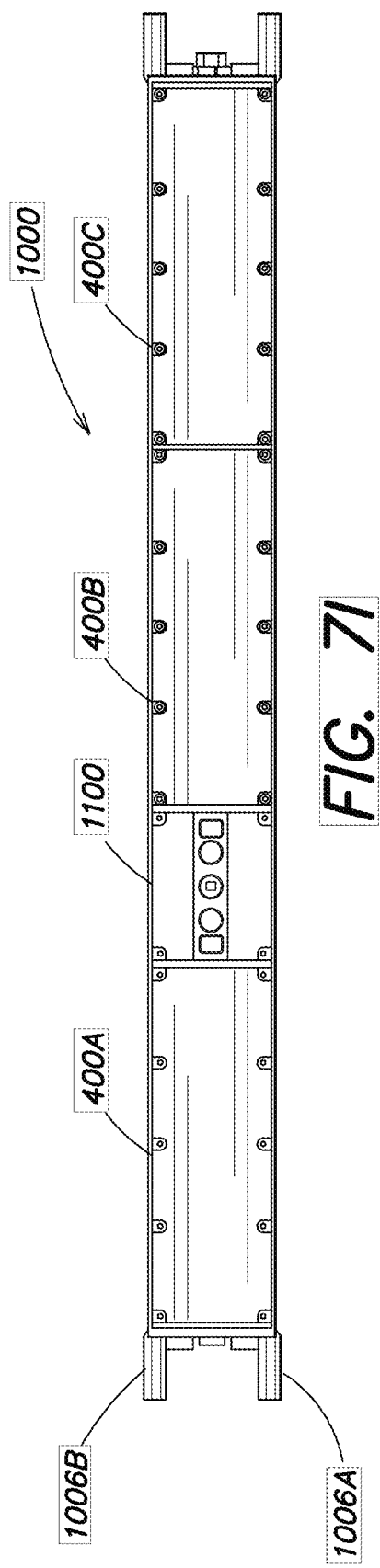
FIG. 7I shows a bottom view of the lighting fixture of FIG. 7E.
Figure 7L:
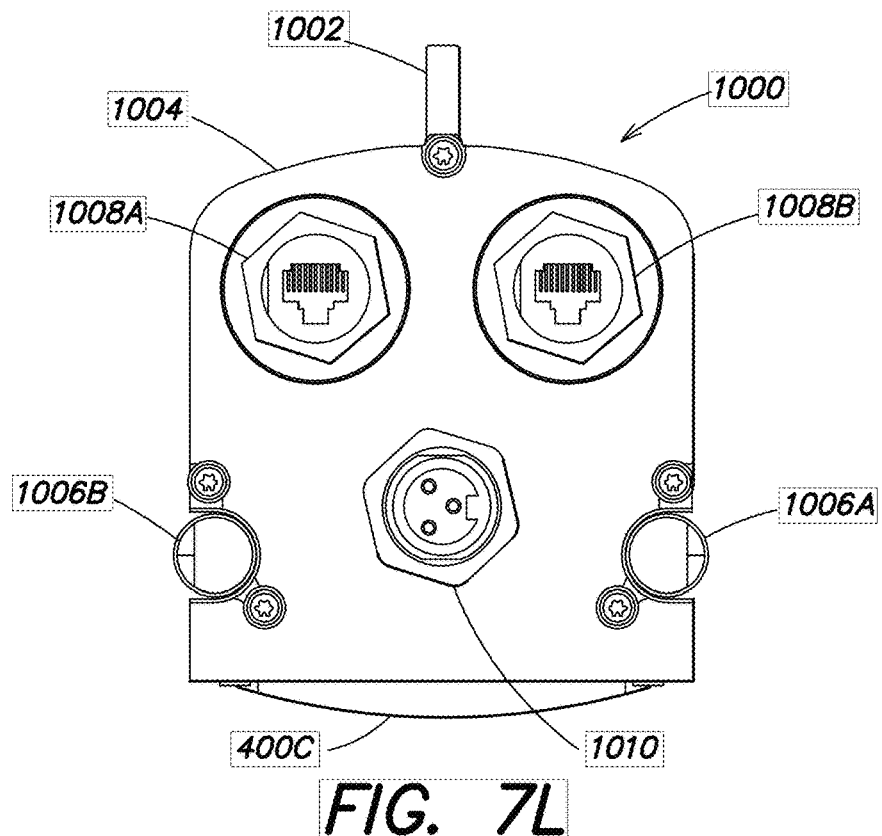
FIG. 7L shows a right view of the lighting fixture of FIG. 7E.
Figure 7M:
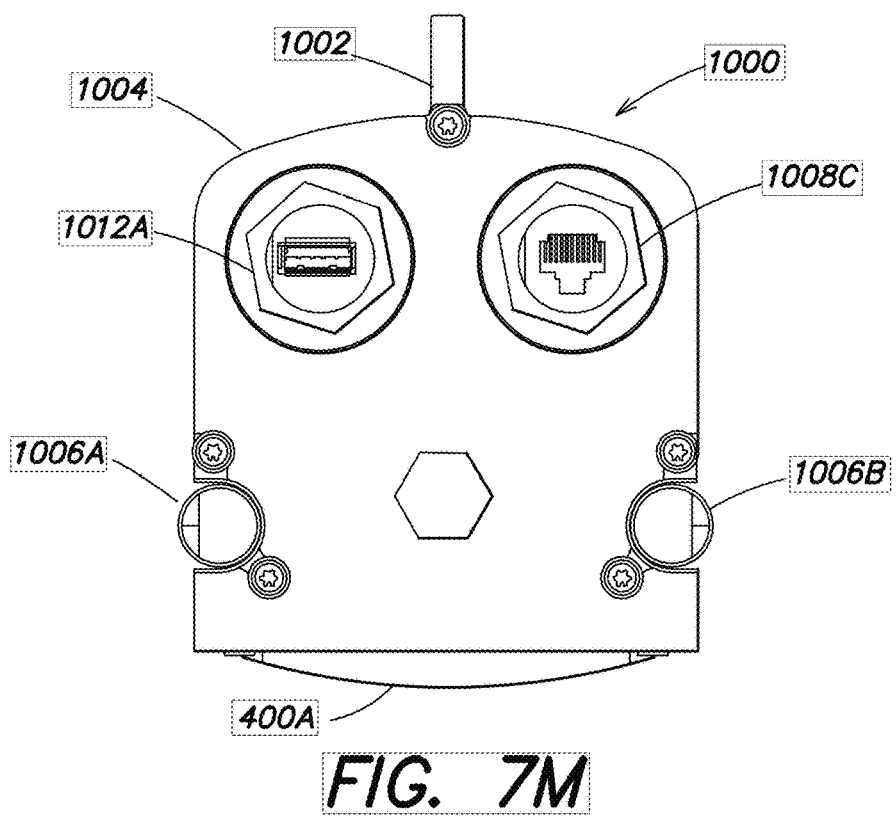
FIG. 7M shows a left view of the lighting fixture of FIG. 7E.
Figure 7N:
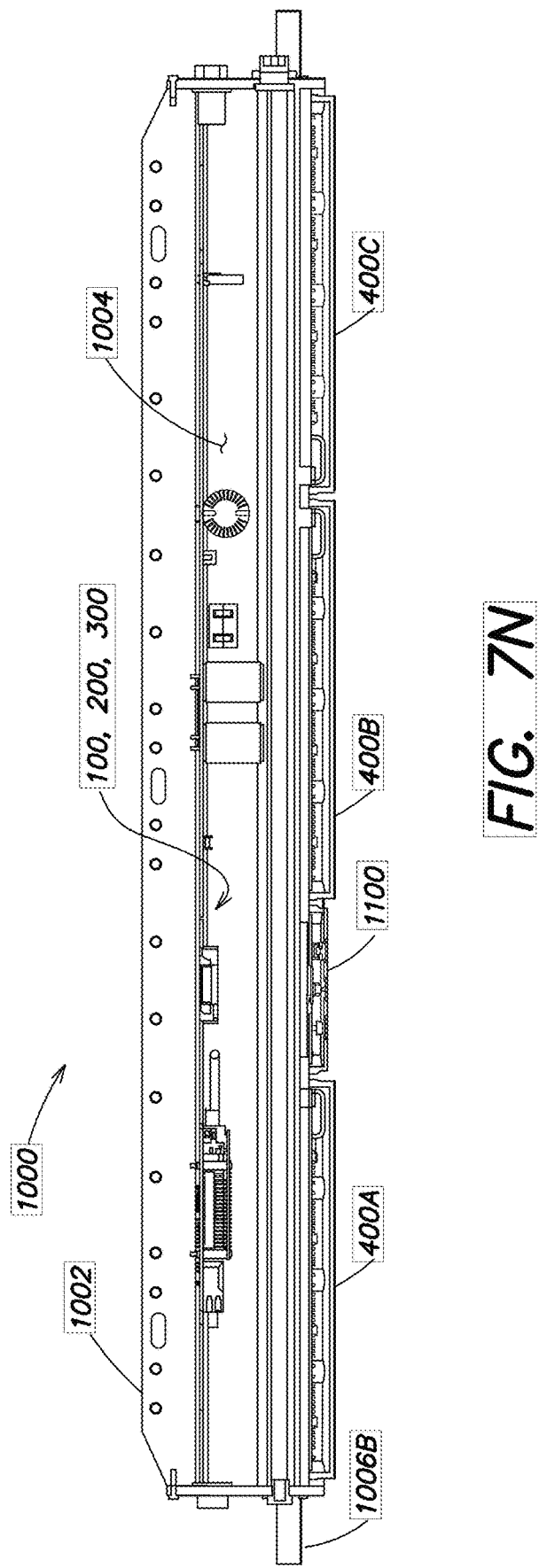
FIG. 7N shows a front cross-sectional view of the lighting fixture of FIG. 7E where the cross-section plane bisects the lighting fixture.
Figure 70:
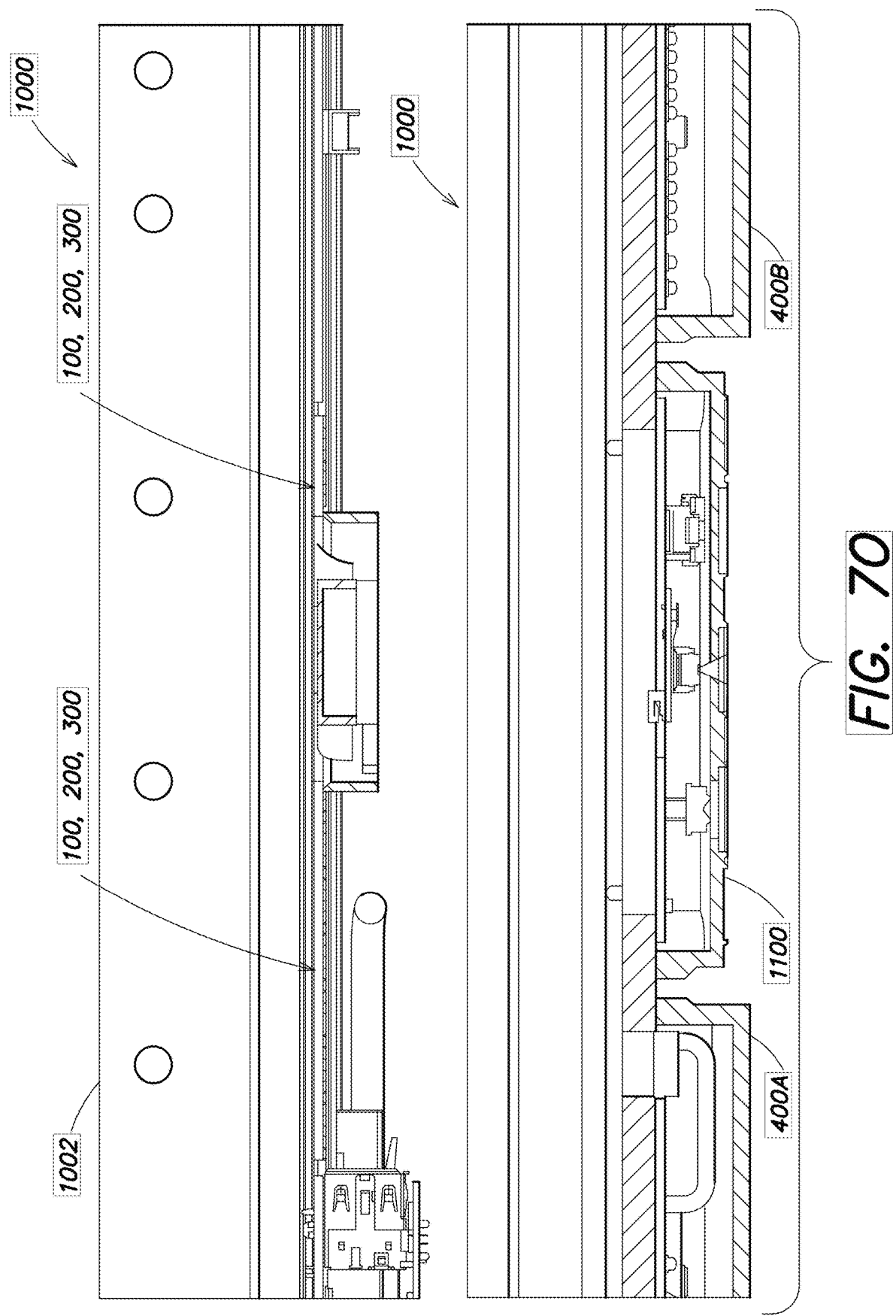
Figure 7P:
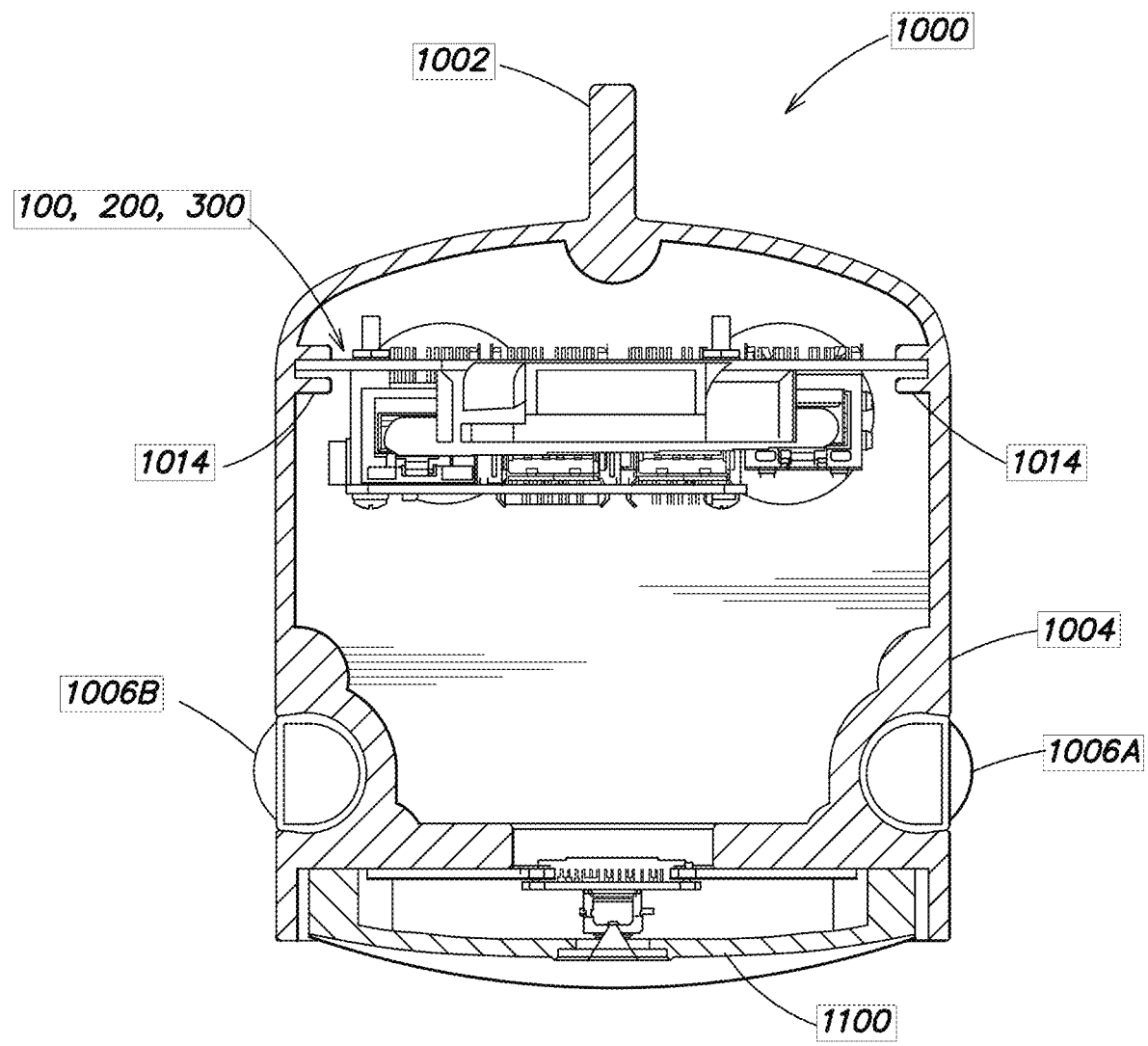
FIG. 7P shows a right cross-sectional view of the lighting fixture of FIG. 7E where the cross-section plane intersects the multispectral imaging system.

FIGS. 7D-1 and 7D-2 show various views of another lighting fixture 1000 that includes one or more onboard cameras and/or sensors 1005 and wireless communications devices 1003, according to some implementations of the disclosure. As shown, the camera(s)/sensor(s) 1005 and the wireless device 1003 may be mounted and/or integrated into the frame 1004 of the lighting fixture 1000. The camera(s)/sensor(s) 1005 and/or the wireless device 1003 may be used in combination with or as a substitute for sensors/communication devices coupled to the lighting fixture 1000 as an accessory to the various communication ports (e.g., the PoE ports 1008A-1008D, the USB ports 1012A-1012B). In some implementations, the camera(s)/sensor(s) 1005 and/or the wireless device 1003 may receive electrical power directly from the electrical power port 1010 (e.g., the port 1010 supplies AC power) or indirectly from another device (e.g., the processor 90 supplies DC power).

In some implementations, the frame 1004 may include one or more openings (not shown) to mechanically mount the camera/sensor 1005 and/or the wireless device 1003 (e.g., openings for bolt(s) or screw fastener(s) that align with corresponding openings on a housing or a printed circuit board in the camera(s)/sensor(s) 1005 and/or the wireless device 1003). The one or more openings may also provide an electrical feedthrough for the camera(s)/sensor(s) 1005 and/or the wireless device 1003. For example, the sensing components of the camera(s)/sensor(s) 1005 and/or the transmitter/receiver of the wireless device 1003 may be disposed on the exterior of the frame 1004 and electrically coupled to respective processors disposed inside the cavity of the frame 1004 via one or more wires. In some implementations, the frame 1004 may include an aperture and/or a recessed section to reduce or prevent obstructions to the field of view of the camera(s)/sensor(s) 1005. The frame 1004 may also provide mating features (e.g., a recessed section) for a gasket and/or a seal to protect sensitive components of the camera/sensor 1005 and/or wireless device 1003 (e.g., exposed electronic circuitry) disposed in the cavity of the frame 1004 from the environment.

The wireless communication device(s) 1003 may include one or more WiFi antennas and accompanying electric circuits (e.g., chipsets, processors) to facilitate wireless communication to/from the lighting fixture 1000. In some implementations, the wireless device 1003 may include a transmitter and/or a receiver to communicate with one or more remote devices (e.g., a computer, a server, a tablet, a smartphone). For example, the wireless device 1003 may include a transmitter to transmit various sensory data collected by the camera/sensor 1005 (or another sensor coupled to the PoE ports 1008A-1008D and/or the USB ports 1012A-1012B) to the remote device (e.g., for processing, recording). In another example, the wireless device 1003 may include a receiver to receive a signal from the remote device, which may include a command to adjust the operation of the lighting fixture 1000. Commands may include, but are not limited to, adjusting the light output of the LED module 400 (e.g., total intensity, spectral intensity distribution), the flow of a fluid coolant passing through the coolant pipes 1006A and 1006B (e.g., adjusting a valve to control flow rate), and adjusting the settings of various sensors (e.g., turning on/off the sensor, acquisition rate, operation mode of the sensor).

In some implementations, the electric circuit(s) of the wireless device 1003 may comprise discrete circuit boards (not shown) that are electrically coupled to the respective antennas of the wireless device 1003. The circuit boards, in turn, may be coupled to other circuitry in the lighting fixture 1000 (e.g., processor 90) to facilitate electrical communication between the respective components of the lighting fixture 1000. In some implementations, the wireless device 1003 may be directly coupled to one or more of the communication ports on the lighting fixture 1000 (e.g., the PoE ports 1008A-1008D and/or the USB ports 1012A-1012B) and/or another device (e.g., the camera/sensor 1005).

The wireless device 1003 may generally communicate with other remote devices using various communication protocols including, but not limited to LoRaWAN, WiSun, Zigbee, Bluetooth, 3G, 4G, and 5G. In some implementations, the wireless signals transmitted and/or received by the wireless device 1003 may be encrypted using various encryption protocols may be used including, but not limited to wired equivalent privacy (WEP), Wi-Fi protected access (WPA), WPA version 2 (WPA2), and WPA version 3 (WPA3). In some implementations, the wireless device 1003 may be used instead of the Ethernet cable 160 for data communication to/from the lighting fixture 1000. In this manner, a lighting system that includes multiple lighting fixtures 1000 may utilize respective wireless devices 1003 for communication (e.g., between lighting fixtures 1000, between the lighting fixture 1000 and the remote device), thus simplifying installation by reducing the amount of Ethernet cables 160 used. In some implementations, multiple lighting fixtures 1000 each employing wireless device(s) 1003 may be configured and arranged as a wireless mesh network of lighting fixtures.

The lighting fixture 1000 of FIGS. 7D-1 and 7D-2 may also include one or more cameras, other imaging devices (e.g., a thermal imager), or other sensors (collectively referred to with reference number 1005) disposed in or on (integrated with) the frame 1004 of the lighting fixture 1000. The camera(s)/sensor(s) 1005 may be used to acquire various information about the agricultural environment including, but not limited to imagery (video imagery or still imagery, as well as thermal imagery) of the plants and/or other subjects of interest in the environment around the lighting fixture 1000, lighting conditions, temperature, relative humidity, nutrient levels in the air and/or soil, and carbon dioxide ($CO_2$) concentrations. Examples of various types of sensors that may be included in the camera(s)/sensor(s) 1005 include, but are not limited to, one or more cameras responsive to radiation in a range of at least visible wavelengths and/or IR wavelengths, an air temperature sensor, a near infrared (NIR) leaf moisture sensor, a relative humidity sensor, a hyperspectral camera, a carbon dioxide sensor, an infrared (IR) leaf temperature sensor, an airflow sensor, and a root zone temperature sensor.

In some implementations, the camera(s)/sensor(s) 1005 may be configured to acquire sensory data proximate to the portion of the plants and/or other subjects of interest in the environment around the lighting fixture 1000 irradiated by the LED source(s) 400. In some example implementations employing multiple cameras/sensors 1005, the multiple cameras/sensors 1005 may be co-located on the frame 1004 of the lighting fixture 1000 (e.g., in sufficient proximity to one another) such that the respective fields of view (FOV) of the cameras and/or sensors are substantially overlapping or substantially the same. In this manner, different types of sensory data may correspond to the same region of the environment, thus enabling a more comprehensive analysis of the environment. In some implementations, the portion of the plants and/or other subjects of interest irradiated by the LED light source(s) 400 of the lighting fixture 1000 may be further subdivided into subregions that are each characterized by corresponding sets of cameras/sensors 1005 disposed on/integrated in the lighting fixture 1000.

In some implementations, the camera(s)/sensor(s) 1005 may include multiple cameras or other imaging devices (e.g., thermal imagers) that facilitate acquisition of images and other information within different spectral bands. For example, the lighting fixture 1000 may include cameras that acquire imagery in various spectral bands including, but not limited to the ultraviolet band (e.g., wavelengths between 10 nm and 400 nm), the visible band (e.g., wavelengths between 400 nm and 700 nm), the near infrared (NIR) band (e.g., wavelengths between 700 nm and 1.4 μm), the mid infrared (MIR) band (e.g., wavelengths between 1.4 μm and 8 μm), and the far infrared (FIR) band (e.g., wavelengths greater than 8 μm).

To this end, FIG. 7D-2 illustrates that one implementation of the lighting fixture 1000 may include three cameras/sensors 1005A, 1005B and 1005C. As show in FIG. 7D-2, the multiple cameras/sensors 1005A, 1005B and 1005C may be integrated with and disposed on the bottom portion of the lighting fixture 1000 adjacent to one or more light sources 400. Although FIG. 7D-2 illustrates three cameras/sensors located on one side of multiple light sources 400 on the bottom portion of the lighting fixture 1000, it should be appreciated that different numbers of cameras/sensors 1005 may be included in the lighting fixture 1000 according to the inventive concepts described herein, and that one or more cameras/sensors may be disposed on or otherwise integrated with the lighting fixture 1000 at various locations and/or positions on the lighting fixture other than those shown in FIG. 7D-2 (and as discussed further below in connection with other example implementations).

In some implementations, the camera(s)/sensor(s) 1005 may include one or more processors (e.g., a Raspberry Pi processor) and one or more of the cameras/sensors may be configured for operation with the one or more of the processors. In one example implementation of the lighting fixture shown in FIG. 7D-2, the lighting fixture 1000 includes a visible camera 1005A, an infrared camera 1005B, and/or an IR single point sensor 1005C. As shown, the multiple cameras/sensors may be co-located on the fixture 1000 proximate to each other (e.g., such that they have overlapping or significantly overlapping fields of view). The cameras/sensors 1005A, 1005B and 1005C may be controlled by one or more processors disposed in the cavity of the frame 1004.

One example of the camera/sensor 1005A includes, but is not limited to, the Raspberry Pi Camera Module v2. The v2 Camera Module has a Sony IMX219 8-megapixel sensor and may be used to acquire high-definition video and/or still photographs. The sensor supports 1080p30, 720p60, and VGA90 video modes in addition to still capture. The sensor attaches to the camera serial interface (CSI) port on the Raspberry Pi via a 15 cm ribbon cable. The camera works with various Raspberry Pi models including, but not limited to the Raspberry Pi 1, 2, and 3. The camera 1005A may be accessed and controlled using the multimedia abstraction layer (MMAL) and video for Linux (V4L) API's. Additionally, numerous third-party software libraries may be used to control the camera 1005A in various software environments (e.g., Python using the Picamera Python library).

One example of the camera/sensor 1005B includes, but is not limited to, the infrared Camera Module v2 (Pi NoIR). The v2 Pi NoIR has a Sony IMX219 8-megapixel sensor, which is the same as the camera used in the Raspberry Pi Camera Module v2 of 1005A. The difference is that the Pi NoIR does not include an infrared filter (NoIR=No Infrared) and is thus able to acquire imagery of at least a portion of the infrared spectrum (e.g., NIR), In some implementations, the Pi NoIR may be used together with a square of blue gel to monitor the health of green plants. Similar to the Pi Cam, the Pi NoIR may with various Raspberry Pi models including, but not limited to the Raspberry Pi 1, 2, and 3. Also, the Pi MAR camera may also be accessed and controlled in software using the MMAL and V4L API's as well as third-party libraries (e.g., Python using the Picamera Python library).

In some example implementations, the Pi NoIR Camera described above in connection with the camera 1005B may instead serve as the camera/sensor 1005A, such that the camera 1005A may be employed to capture images having spectral content in a range of approximately 356 nanometers through 950 nanometers (including the visible portion of the spectrum and at least a portion of the infrared spectrum, e.g., the NIR). In implementations in which the camera/sensor 1005A includes a broadband camera/sensor such as the Pi NoIR Camera, the camera/sensor 1005B may be a longwave IR thermal imager responsive to wavelengths in a range of from approximately 8 micrometers to approximately 14 micrometers (FIR). One example of such a thermal imager includes, but is not limited to, the FLIR Lepton 3.5 micro thermal imager, which provides 160×120 pixels of calibrated radiometric output.

One example of the IR single point sensor 1005C includes, but is not limited to, the Melexis MLX90614 infrared thermometer for non-contact temperature measurements. An IR sensitive thermopile detector chip and the signal conditioning application-specific integrated circuit (ASIC) are integrated in the same TO-39 can. The MLX90614 also includes a low noise amplifier, 17-bit analog-digital converter (ADC), and a powerful digital signal processor (DSP) unit to achieve a high accuracy and resolution for the thermometer. The thermometer may be factory calibrated with a digital SMBus output providing access to the measured temperature in the complete temperature range(s) with a resolution of 0.02° C. The digital output may be configured to use pulse width modulation (PWM). As a standard, the 10-bit PWM is configured to continuously transmit the measured temperature in range of −20° C. to 120° C., with an output resolution of 0.14° C.

In some implementations, the processor(s) may correspond to the processor 90 (e.g., the camera(s)/sensor(s) 1005 is/are coupled to the same circuitry board used to support the LED light source 400 and the various communication ports). In some implementations, the processor(s) associated with operation of the camera(s)/sensor(s) 1005 may be associated with one or more discrete circuit boards that are electrically coupled to the processor 90. For such cases, the processor 90 may be used to facilitate control of the camera(s)/sensor(s) 1005 via the respective processor(s). For example, the processor(s) may be Pi processor(s), which generally feature a Broadcom system on a chip (SoC) with an integrated advanced RISC machine (ARM)-compatible central processing unit (CPU) and on-chip graphics processing unit (GPU). Secure Digital (SD) cards may be used to store the operating system and program memory in either SD high capacity (SDHC) or MicroSDHC sizes. The boards may have multiple ports (e.g., one to four USB ports). HDMI and composite video may be supported for video output and a standard 3.5 mm tip-ring-sleeve jack for audio output. Lower-level output is provided by a number of GPIO pins, which support common protocols like I²C. The B-models have an 8P8C Ethernet port and the Pi 3 and Pi Zero W have on-board Wi-Fi 802.11n and Bluetooth.

In some implementations, the one or more cameras and/or sensors 1005 may be packaged as a separate module for ease of assembly and/or installation in connection with the lighting fixture 1000. Such a camera/sensor module may be mechanically mounted directly to the frame 1004 of the lighting fixture 1000 and electrically coupled to other systems in the lighting fixture 1000 (e.g., a cable or wire connecting the module to the processor 90). In one aspect, a separate module may make it easier to package the cameras/sensors 1005 and protect various components from exposure to water and/or moisture in the environment. In some implementations, multiple modules may be disposed on the frame 1004 where each module may contain one or more cameras/sensors 1005. A module with one set of cameras/sensors 1005 may also be readily replaced with another module with another set of cameras/sensors 1005. In this manner, the lighting fixture 1000 may be modular in design, thus enabling the installation of different modules with different functionalities on to the same frame 1004 during initial assembly of the lighting fixture 1000 and/or post-assembly (to change/update the modules after deployment).

In another exemplary implementation, FIGS. 7E-7P show several views of a lighting fixture 1000 equipped with cameras/sensors 1005 as introduced in the discussion above, in which the cameras/sensors are integrated as a module serving as a multispectral imaging system 1100 (also referred to herein as the "imaging system 1100"). As shown in the figures, in one example implementation the imaging system 1100 may be directly mounted to the frame 1004 between the LED light sources 400A and 400B. The lighting fixture 1000 may also include onboard cooling (e.g., cooling pipes 1006A and 1006B) and various communication ports (PoE ports 1008A-1008C, USB ports 1012A) for data transfer between the lighting fixture 1000 and another device (e.g., another lighting fixture 1000, a remote device, an accessory). As shown in the cross-sectional views of FIGS. 7N-7P, the imaging system 1100 may include electronic circuitry. In some implementations, the imaging system 1100 may be electrically coupled to other components of the lighting fixture 1000 (e.g., control circuitry boards 100, 200, 300) to receive power and/or to transfer data to/from the imaging system 1000.

The imaging system 1100 may be used to characterize the growth and/or health of plants in the environment over time. This may be accomplished, in part, by utilizing the imaging system 1100 by itself or in conjunction with one or more light sources (e.g., LED light sources 400A-400C) to irradiate plants and/or other subjects of interest with different wavelengths of radiation, and measure the spectral optical properties of the plants and/or other subjects of interest in their surroundings (e.g., in the environment of the lighting fixture 1000) over time, in response to irradiation at different wavelengths. The foregoing process may be referred to as "kinetic finite absorbance and reflectance spectroscopy," in which different finite spectra images and/or other information are collected for plants and/or other subjects of interest in response to irradiation at particular wavelengths, as a function of time, and then the acquired images/collected information are analyzed to determine physical changes in the plants and/or other subjects of interest.

As discussed further below, in one example implementation the imaging system 1100 may include one or more relatively narrow band or essentially monochromatic irradiators (e.g., also referred to herein as "flashes"). These irradiators may be controlled to provide irradiation (a "flash") of one or more plants and/or other subjects of interest while one or more of the cameras/sensors of the imaging system 1100 are operated to acquire an image and/or other information regarding the subject of interest irradiated by the relatively narrowband or essentially monochromatic flash.

Figure 7Q:
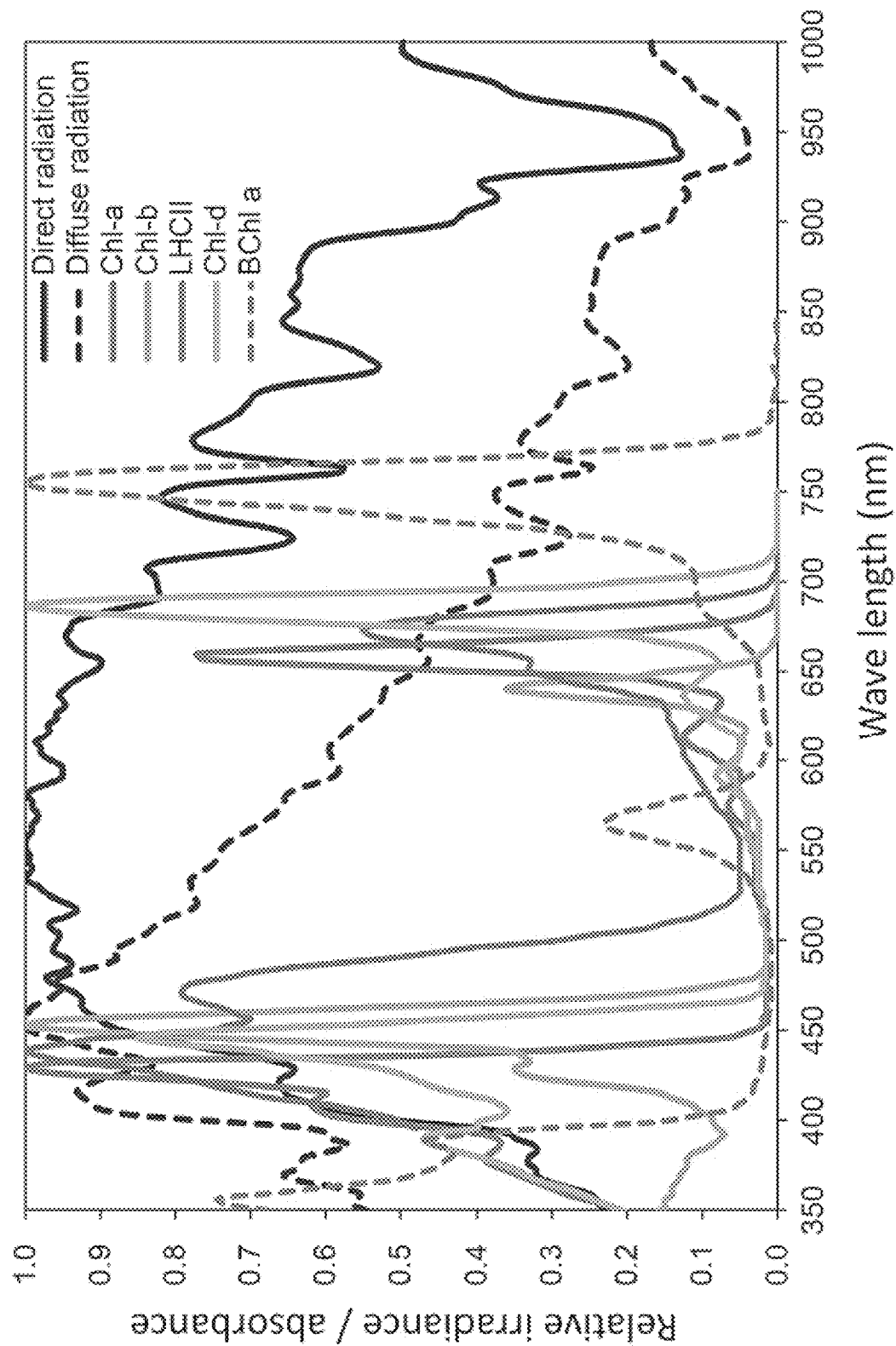
FIG. 7Q shows the spectral absorbance of various plant-related compounds.

The spectral optical properties of plants, as measured by the imaging system 1100, may be used to detect and quantify various chemical compounds related to plant development. For example, FIG. 7Q shows the spectral absorptive properties of various types of chlorophyll compounds. As shown, the various chemical compounds exhibit different absorption peaks, which may be used to identify and distinguish between the compounds. The presence of these compounds may vary between different plant species. For a particular plant species, the amount of these compounds relative to a nominal baseline, as measured by the imaging system 1100, may provide valuable information on various aspects of the plant's development including, but not limited to, the stage of development, prospective crop yield, appearance, nutritional composition, structural integrity, flowering, and pollination.

In one example, the light source may illuminate the plants with substantially broadband light (e.g., a white light source). In this case, the imaging system 1100 may include a spectrometer (e.g., an onboard monochromator) that measures the spectral reflective properties of the plants by separating the spectral components of the broadband light reflected by the plants. In another example, the light source may illuminate the plants with substantially monochromatic light at a particular wavelength and the imaging system 1100 may measure the amount of light reflected by the plants (e.g., a single point measurement, an image of the plants) at that wavelength. The emission wavelength of the light source may be tunable. Thus, the imaging system 1100 may acquire the spectral reflective properties of the plants at different wavelengths by adjusting the wavelength of light illuminating the plants. For this case, the imaging system 1100 may acquire the spectral properties of the plants without the use of a filter.

The data collected by the imaging system 1100 may be used to monitor the development of the plants and/or to provide feedback to adjust other components of the lighting fixture 1000 (e.g., the total intensity or spectral intensity of the light emitted by the LED light sources 400) in order to improve the health and growth of the plants. For example, if the imaging system 1100 detects damage to the plants caused by pests, the lighting fixture 1000 may be adjusted to illuminate the plants with more UV light as a form of repellant. In another example, the imaging system 1100 may acquire data over time to assess changes to the plant during a typical day/night cycle (e.g., blooming for short day/long day plants). This information may be used to alter when the plant blooms by adjusting the lighting fixture 1000 to illuminate the plants with more/less near infrared light (e.g., 730 nm light). In this manner, plants may be grown at a faster rate.

FIGS. 8A-8I and 8J-8Q show several views of the multispectral imaging system 1100 according to example inventive implementations with and without a housing 1120, respectively. As shown, the imaging system 1100 may include a circuit board 1110 that supports the cameras/sensors 1005A, 1005B and 1005C previously described. The imaging system 1100 may also include LED arrays 1140A and 1140B (collectively referred to as LED array 1140) to irradiate the plants with radiation at various wavelengths to facilitate acquisition of one or more corresponding multispectral images (in which radiation reflected or otherwise emitted by the subject plant(s) is sensed/captured by one or more of the cameras/sensors upon exposure to one or more flashes from an LED/LEDs having particular wavelength(s) of radiation). Thus, the imaging system 1100 provides both multispectral irradiation and sensing in a single, self-contained device. The imaging system 1100 may also include supplementary LED arrays 1150A and 1150B (collectively referred to as supplementary LED array 1150) to augment the LED array 1140 and/or to alter the chemical/morphological properties of the plants. The imaging system may also include a single point laser rangefinder 1170. The circuit board 1110 may include power electronic circuitry 1160 to support the operation of the LED arrays 1140 and 1150, cameras/sensors 1005, laser rangefinder 1170, and other components of the imaging system 1100. The imaging system 1100 may include the housing 1120 to protect the cameras/sensors 1005A, 1005B, and 1005C, the LED arrays 1140 and 1150, and other electronics from the surrounding environment.

The LED array 1140 may include one or more LED elements 1142. Each LED element 1142 of the array 1140 may emit radiation at a particular band of wavelengths or an essentially monochromatic wavelength and may be controlled independently from the other LED elements 1142. When one or more LED elements 1142 are operated to irradiate a desired portion of the environment (e.g., the plants below the lighting fixture 1000) with relatively narrow band or substantially monochromatic radiation, one or more of the cameras/sensors 1005 (e.g., camera 1005A) acquires a corresponding image that contains radiation reflected or otherwise emitted by the plant subjects in the field of view in response to exposure to radiation at the corresponding wavelength(s) of the operated LED element(s). Different LED elements 1142 may be activated to illuminate the desired portion of the environment with radiation at different wavelengths and the cameras/sensors 1005, in turn, may acquire corresponding images or other sensed information relating to reflected and/or emitted radiation resulting from the respective different wavelengths/wavelength bands of the activated LED elements. In some example implementations, after acquiring images and/or other information at multiple wavelengths/wavelength bands, a multispectral image may be formed by aligning and superimposing the respective acquired images onto each another. In this manner, the multispectral image may include spatial and spectral information regarding the desired portion of the environment (e.g., each pixel of the multispectral image contains corresponding spectral data).

The imaging system 1100 may generally include one or more LED arrays 1140. Each LED array 1140 may include one or more LED elements 1142. For instance, each LED array 1140 may include between about 1 to about 100 LED elements 1142. The LED elements 1142 in the LED array 1140 may be disposed proximate to each other on the circuit board 1110. The LED arrays 1140 may be arranged on the circuit board 1110 to provide a desired illumination profile. For example, the LED arrays 1140A and 1140B may include the same type of LED elements 1142, thus providing multiple radiation sources that emit radiation at the same wavelength. FIG. 8A shows the LED arrays 1140A and 1140B may be disposed on opposing sides of the camera 1005A. By irradiating the plants and/or their surroundings with radiation from opposing sides of the camera 1005A, the camera 1005A may acquire images under more uniform irradiation. Other illumination profiles may be achieved with different arrangements and/or using an optical element (e.g., shaping a portion of the housing 1120 in front of the LED array 1140, placing a separate diffuser or lens onto the LED array 1140).

The LED array 1140 may generally include LED elements 1142 that respectively emit radiation at different wavelengths. For example, the LED elements 1142 may emit radiation at wavelengths ranging between about 200 nm to about 2 μm. The number of LED elements 1142 and the wavelengths at which they emit light may be chosen, in part, based on known spectral absorption peaks of various chemical compounds associated with the plants (see FIG. 7Q) and/or other subjects of interest in the environment of the lighting fixture 1000. For example, the LED elements 1142 may be chosen to cover the absorption peaks of several different types of compounds from the UV to the NIR wavelength ranges. In some implementations, it may be preferable to use LED elements 1142 with a smaller spectral bandwidth (e.g., essentially monochromatic radiation) in order to provide greater spectral resolution when acquiring multispectral images of the plants and/or other subjects. For example, the spectral bandwidth of one or more of the LED elements 1142 considered to be essentially monochromatic may be less than about 50 nm. Other LED elements 1142 may emit radiation in a broader range of wavelengths; for example, one or more of the LED elements 1142 may be a white LED in which the generated radiation covers a band of wavelengths and may be specified as corresponding to a particular color temperature.

In some implementations, the LED elements 1142 respectively may be activated for a relatively short time period (i.e., turning on and off quickly) in succession (and optionally according to some pattern or order), thus exposing the plants to a brief "flash" of light when acquiring various information relating to reflected radiation using the camera(s)/sensor(s) 1005. For example, the LED elements 1142 may emit radiation for a duration of less than about 1 second. Activating the LED elements 1142 in this manner may have multiple benefits including, but not limited to (1) reducing the time delay between acquiring images/information at different wavelengths so that the multiple images/information acquired are representative of the same environmental conditions and (2) reducing the duration in which the plants and/or other imaging subjects are exposed to radiation. In some implementations, the camera(s)/sensor(s) 1005 may be synchronized with the LED elements 1142 such that the camera(s)/sensor(s) 1005 is/are triggered to acquire an image/information when the LED elements 1142 are activated. In this manner, a series of images/information may be collected by sequentially flashing the plants with radiation from different LED elements 1142 and capturing an image/information during each flash using the camera(s)/sensor(s) 1005. In yet other implementations, multiple LEDs having different spectral outputs may be activated together while one or more images and/or other information is acquired relating to radiation absorbed and/or reflected by the irradiated plants and/or other subjects.

In one example implementation, respective wavelengths of essentially monochromatic LED elements 1142 of the LED array 1140 may include, but are not limited to, 365 nm, 450 nm, 530 nm, 620 nm, 630 nm, 660 nm, 730 nm, 850 nm, 860 nm, 940 nm, and 950 nm. More generally, the LED elements 1142 of the LED array 1140 may have radiation wavelengths between approximately 365 nm to 540 nm, and between approximately 605 nm to 1100 nm.

In some implementations, it may be preferable for the LED elements 1142 in the LED array 1140 to emit radiation with a sufficient intensity to acquire images/information at a desired quality (e.g., the signal-to-noise ratio of the image/information is above a pre-defined threshold) without causing chemical and/or morphological changes to the plant (e.g., photomorphogenesis). In this manner, the various images/information acquired by the camera(s)/sensor(s) 1005 are representative of the plant in their non-illuminated state. For example, the LED elements 1142 may have a wattage rating less than about 6 Watts (the wattage rating may be correlated to the radiation output from the LED elements 1142).

The supplementary LED array 1150 may include additional LED elements 1152. The LED elements 1152 may have one or more of the same features as the LED elements 1142 described above. In one example, the LED elements 1152 may emit radiation at one or more of the same wavelengths as the LED elements 1142 in order to increase the overall intensity of radiation when acquiring images/information relating to the irradiated plants/other subjects (i.e., both LED elements 1142 and 1152 are activated). In some implementations, the LED elements 1152 may provide a radiation output greater than the LED elements 1142. For example, the LED elements 1152 may have a wattage rating greater than about 6 Watts. The higher radiation output provided by the LED elements 1152 may be used, in part, to intentionally induce chemical and/or morphological changes to plants in the environment. For example, the LED elements 1152 may provide a higher radiation output at 730 nm in order to alter the day/night cycle of the plants (e.g., changing when the plant blooms). In another example, the LED elements 1152 may provide UV light to ward off pests in the environment.

The housing 1120 may be used, in part, to enclose and protect the various components of the imaging system 1100 and to facilitate installation of the imaging system 1100 onto the frame 1004 of the lighting fixture 1000. For example, FIGS. 8A-8E show the housing 1120 includes multiple openings 1122 at each corner that align with a corresponding set of holes on the frame 1004 (not shown) to facilitate attachment via one or more bolts or screw fasteners, for example. In some implementations, the housing 1120 may form a substantially sealed enclosure in order to prevent moisture and/or water from contacting the various electronics, cameras, and sensors on the circuit board 1110. As shown in FIGS. 8C and 8E, the housing 1120 may include a groove along its periphery to support a gasket 1124. When the housing 1120 is coupled to the frame 1004, the gasket 1124 may deform to form a seal. In some implementations, the housing 1120 may form a substantially watertight seal with the frame 1004.

The housing 1120 may be formed from various plastic and/or ceramic materials. In some implementations, the housing 1120 may be formed from a material that is substantially transparent to light at wavelengths corresponding to at least the emission wavelengths of the LED elements 1142 and 1152. Thus, radiation emitted by the LED elements 1142 and 1152 may transmit through the housing 1120 when irradiating the plants and/or the surrounding environment. In some implementations, the housing 1120 may be shaped to redirect radiation emitted by the LED elements 1142 and 1152 along a desired direction. For example, the housing 1120 may be shaped to redirect radiation emitted at wider angles towards the plants disposed directly below the lighting fixture 1000 in order to more efficiently use the radiation for imaging/information acquisition. In some implementations, the surface finish of the housing 1120 may be altered to disperse radiation (e.g., a substantially smooth finish to provide specular illumination or a substantially rough finish to provide diffuse illumination).

In some implementations, the housing 1120 may be formed from a material that is not sufficiently transparent across the wavelength range of interest. For example, the camera 1005A may acquire imagery/information from the UV to NIR ranges while the camera 1005B may acquire imagery/information in the MIR and FIR ranges. Materials are typically not transparent across such a large wavelength range. Furthermore, in some instances parasitic absorption by the housing 1120 may affect the data collected by the camera(s)/sensor(s) 1005. In view of the foregoing, the housing 1120 may include multiple openings 1126 disposed near the camera(s)/sensor(s) 1005 that are shaped to support various optical elements tailored for the appropriate wavelength ranges of each camera/sensor 1005.

Figure 8B:
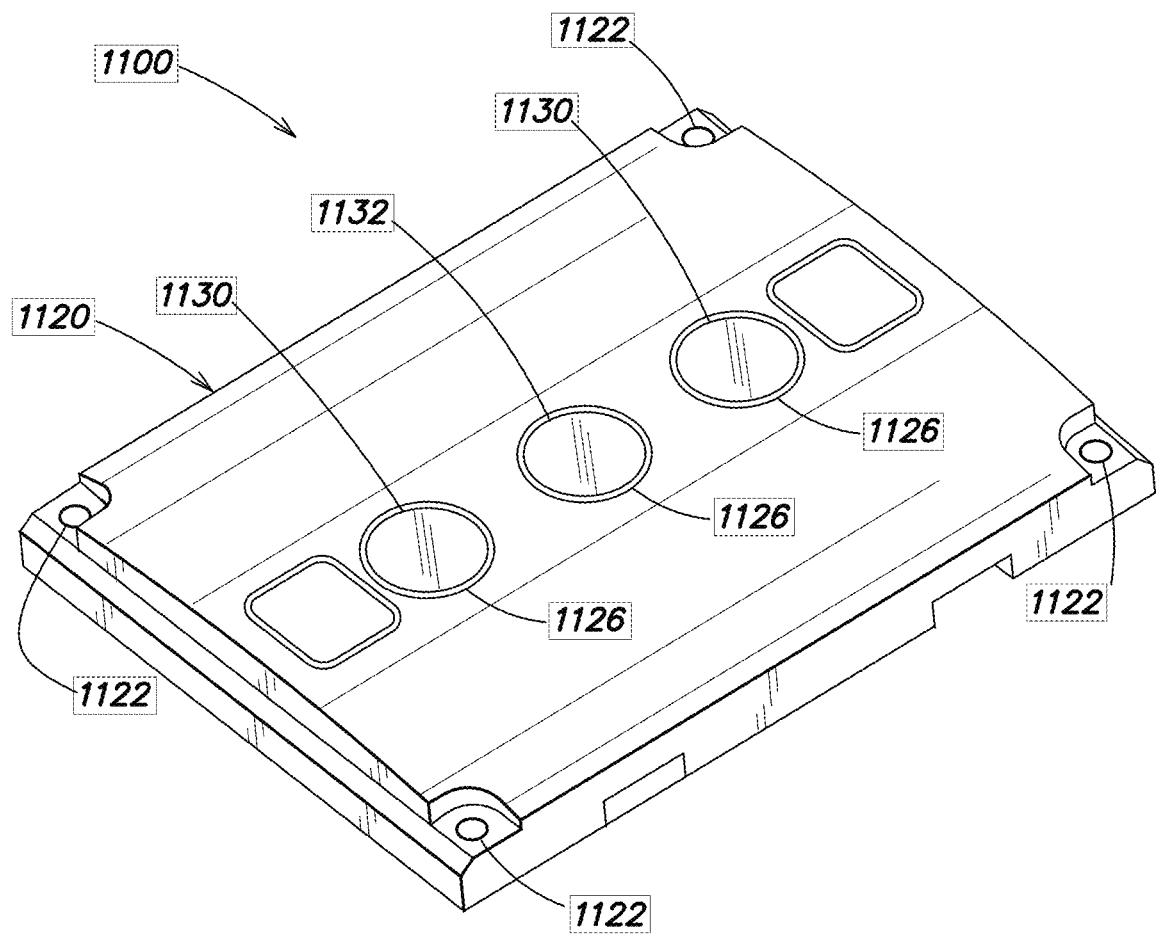
FIG. 8B shows a top, front, left perspective view of the imaging system of FIG. 8A.
Figure 8C:
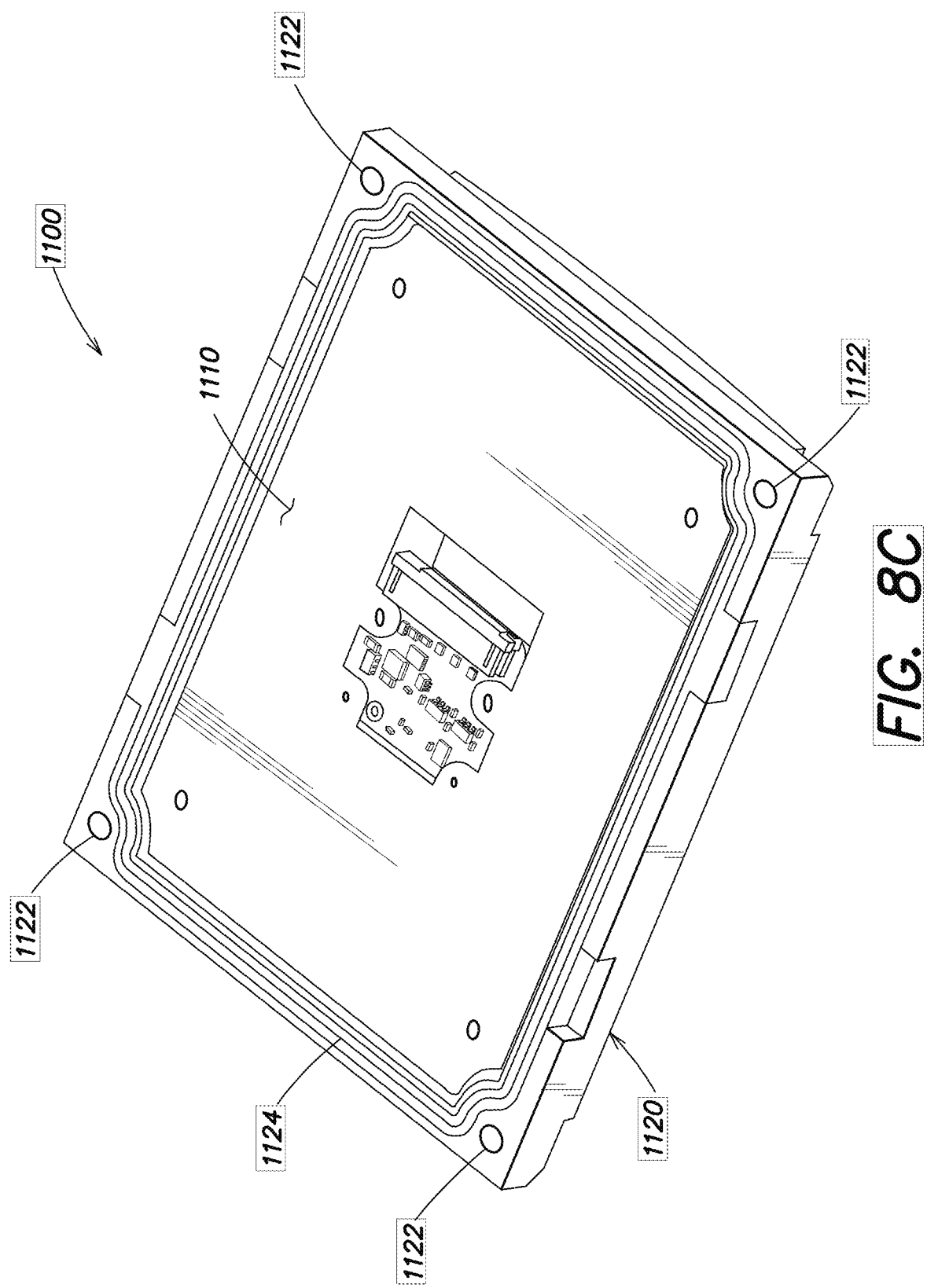
FIG. 8C shows a bottom, rear, right perspective view of the imaging system of FIG. 8A.
Figure 8D:
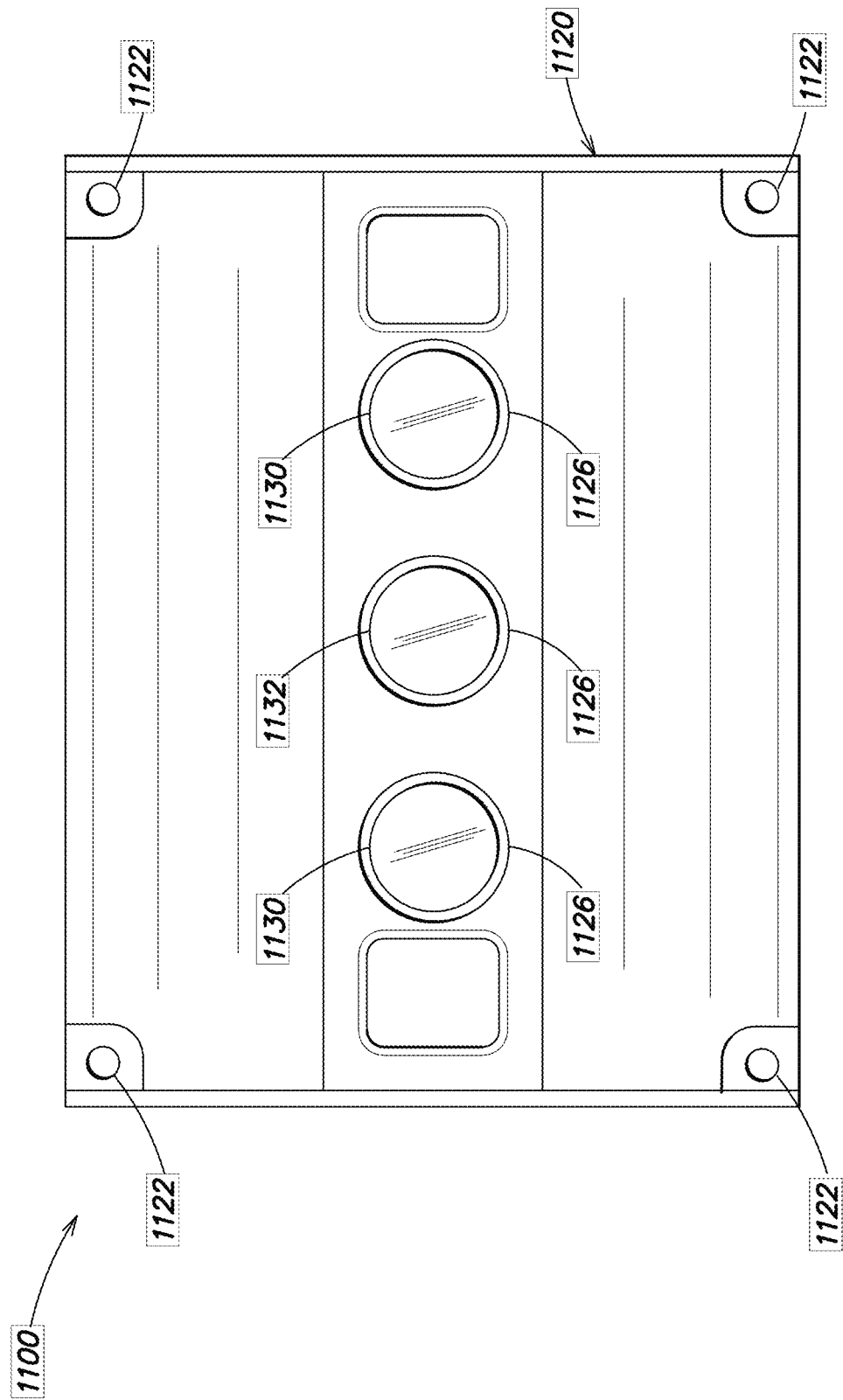
FIG. 8D shows a top view of the imaging system of FIG. 8A.
Figure 8E:
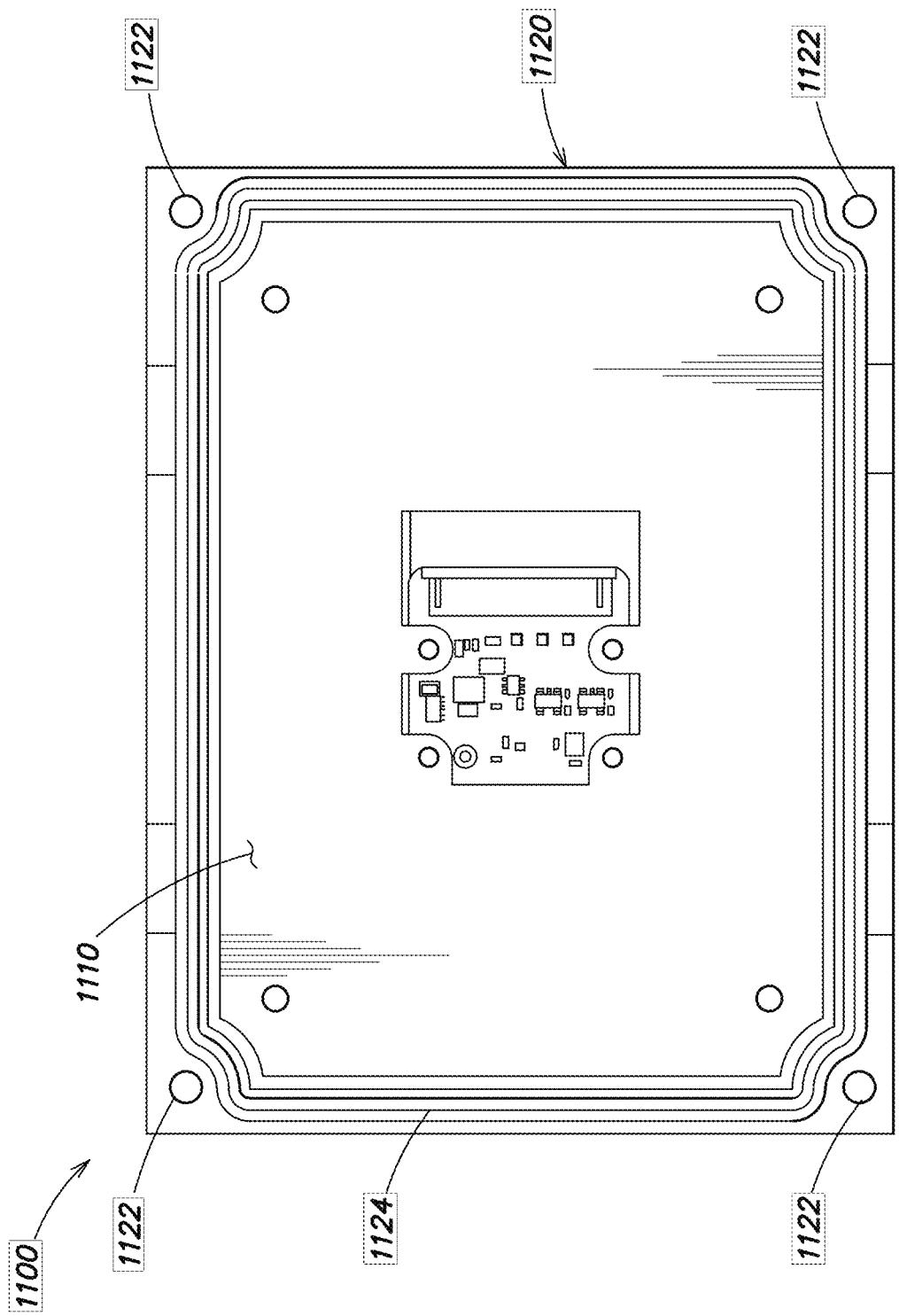
FIG. 8E shows a bottom view of the imaging system of FIG. 8A.
Figure 8J:
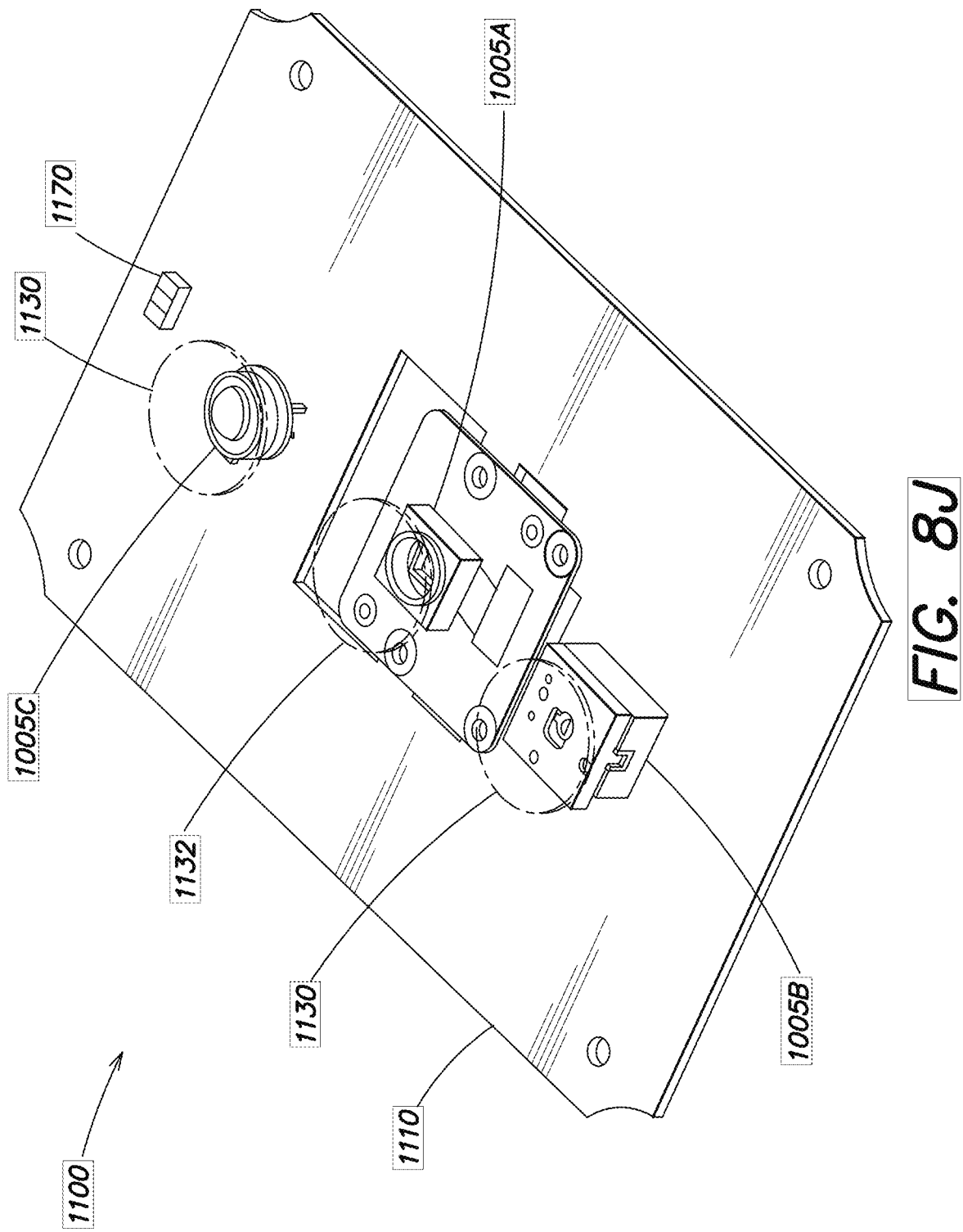
FIG. 8J shows a top, front, left perspective view of the imaging system of FIG. 8A without the housing.
Figure 8M:
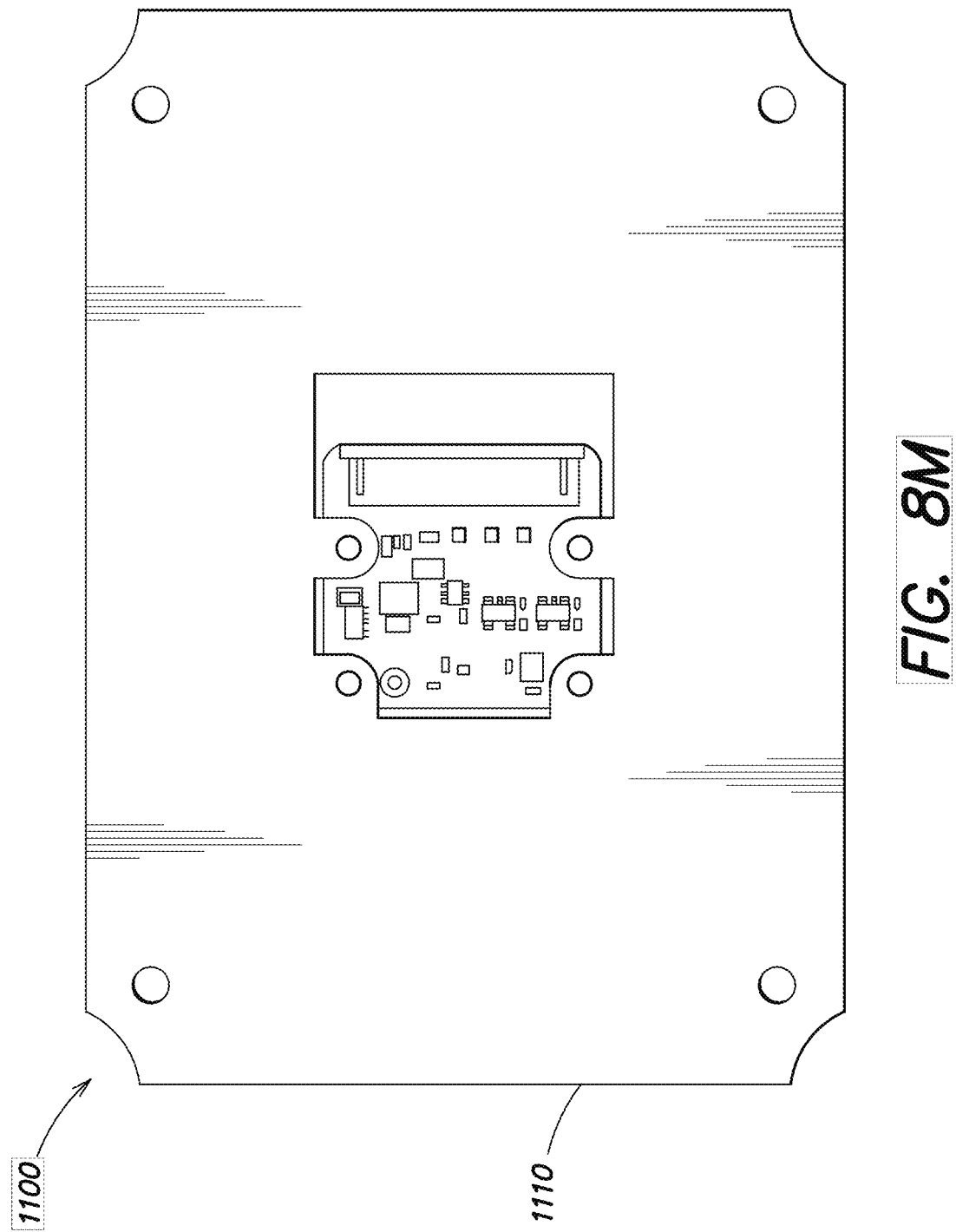
FIG. 8M shows a bottom view of the imaging system of FIG. 8I.

For example, FIGS. 8B and 8D show a germanium (Ge) window 1130 may be installed into the openings 1126 located directly above the camera 1005B and the sensor 1005C. The Ge window 1130 may be used, in part, as an infrared filter that substantially reduces (attenuates) the transmission of higher frequency (shorter wavelength) radiation, thus ensuring the camera 1005B and the sensor 1005C receive infrared light in the MIR and FIR ranges. Similarly, a glass window 1132 may be disposed in the opening 1126 located directly above the camera 1005A to transmit UV to NIR radiation. In some implementations, the Ge window 1130 and glass window 1132 may include an anti-reflection coating to increase the amount of light transmitted and detected by the respective camera(s)/sensor(s) 1005. It should be appreciated that the Ge window 1130 and glass window 1132 are two exemplary materials and may be substituted with other materials suitable for the respective wavelength range(s) of interest. For example, a zinc selenide (ZnSe) window may be used for the IR range. Magnesium fluoride ($MgF_2$), sapphire ($Al_2O_3$), and calcium fluoride ($CaF_2$) may be used for the UV and NIR ranges.

Figure 9A:
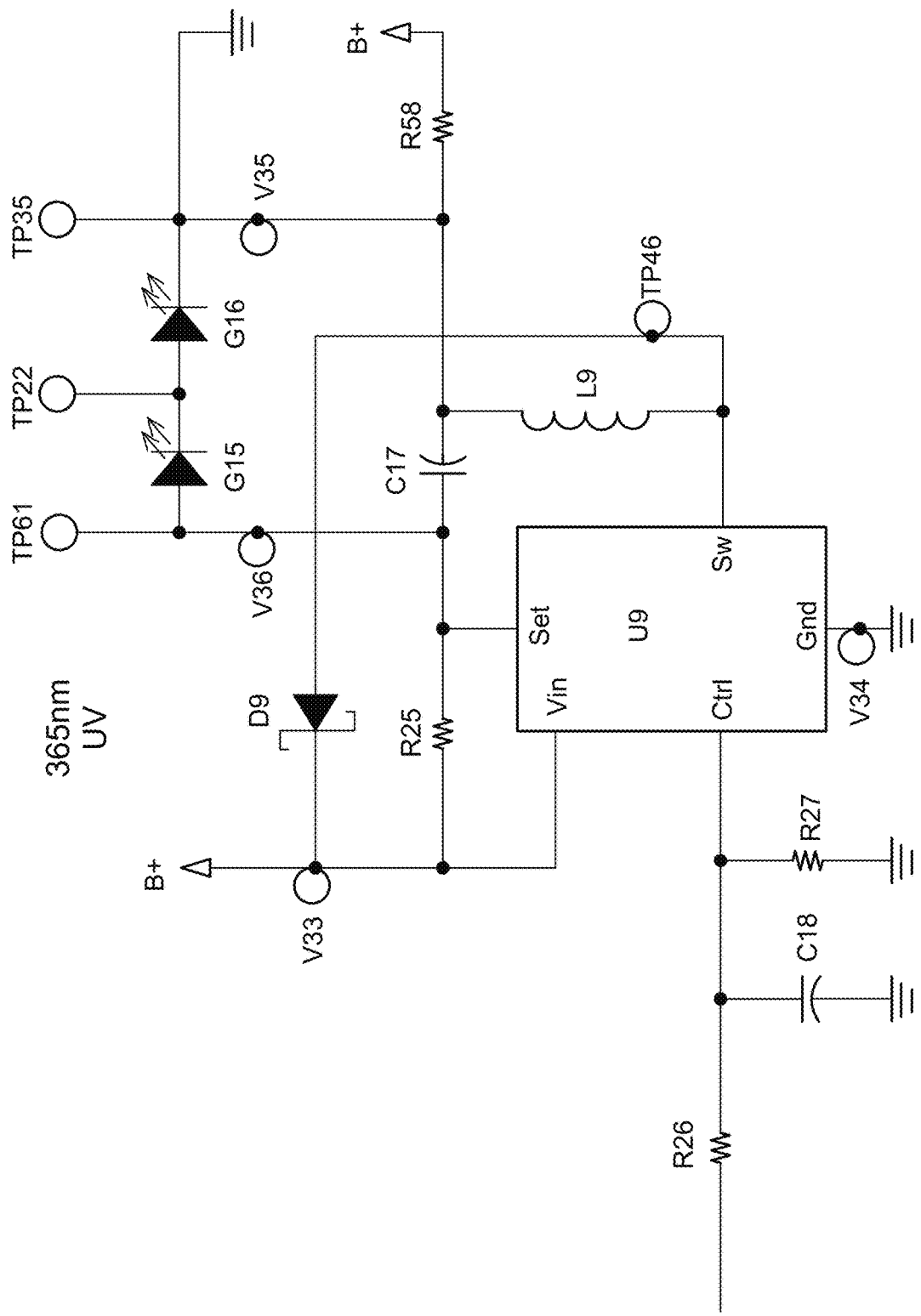
FIG. 9A shows a circuit diagram of a 365 nm ultraviolet (UV) light emitting diode (LED).
Figure 9B:
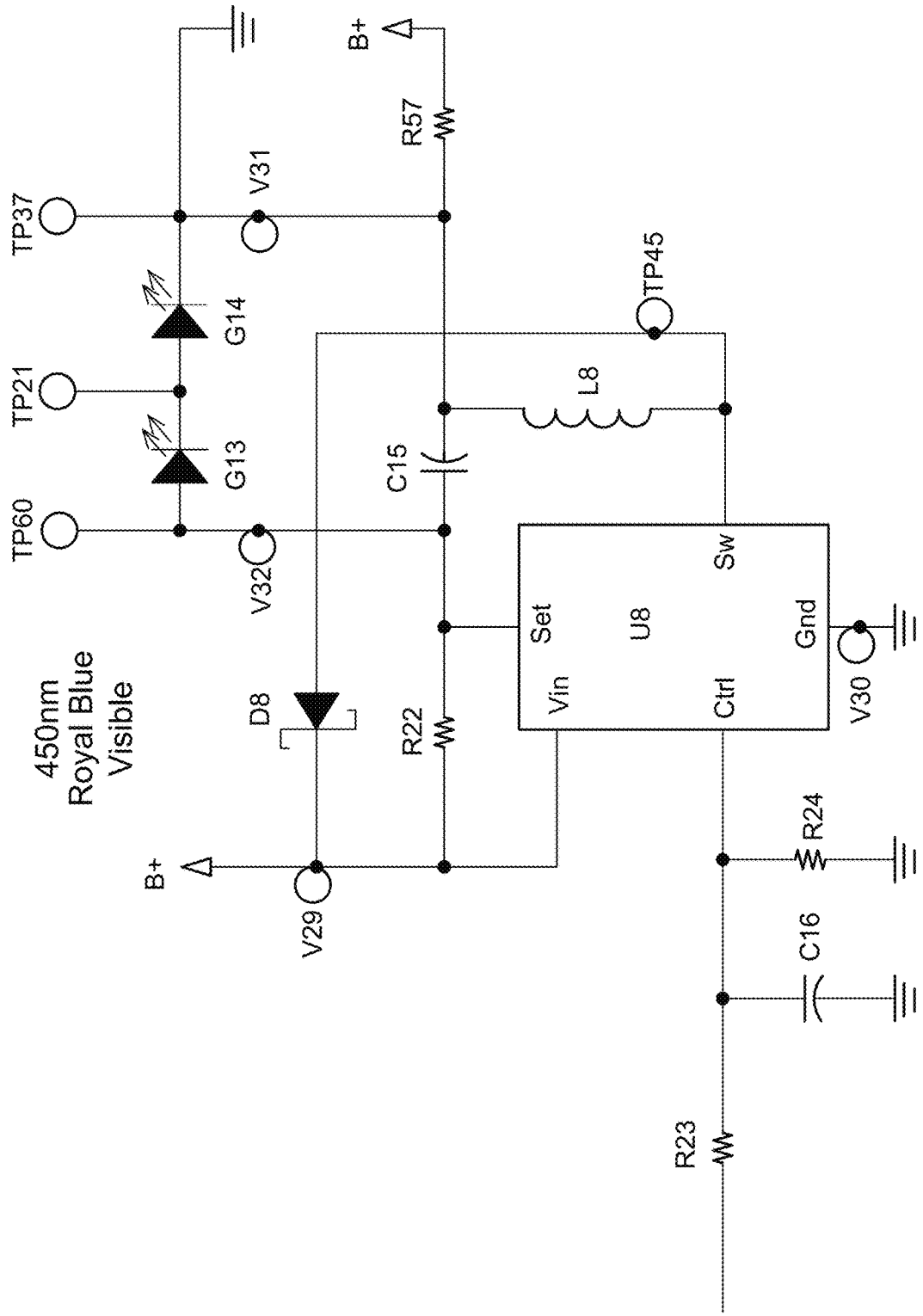
FIG. 9B shows a circuit diagram of a 450 nm royal blue visible LED.
Figure 9C:
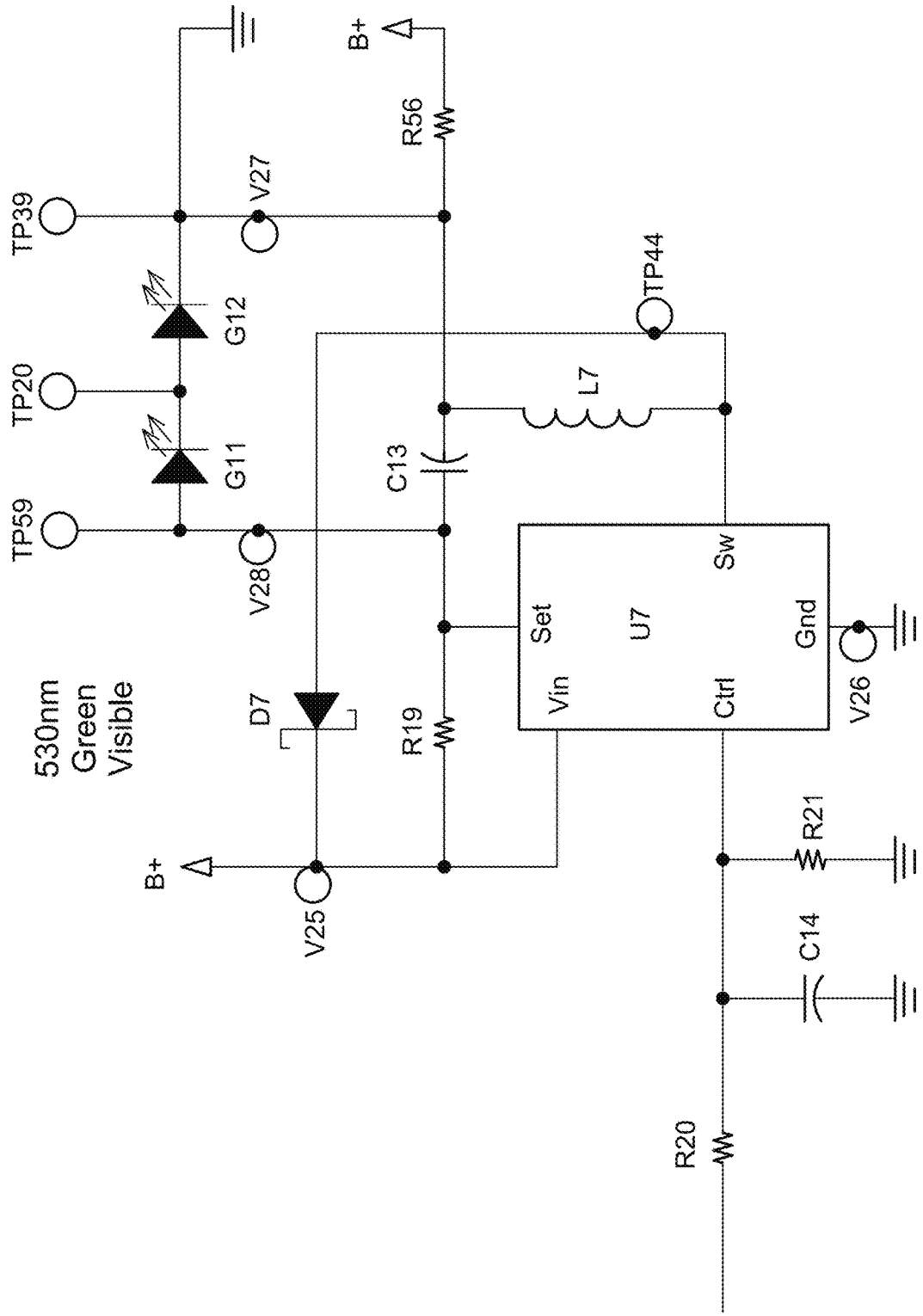
FIG. 9C shows a circuit diagram of a 530 nm green visible LED.
Figure 9D:
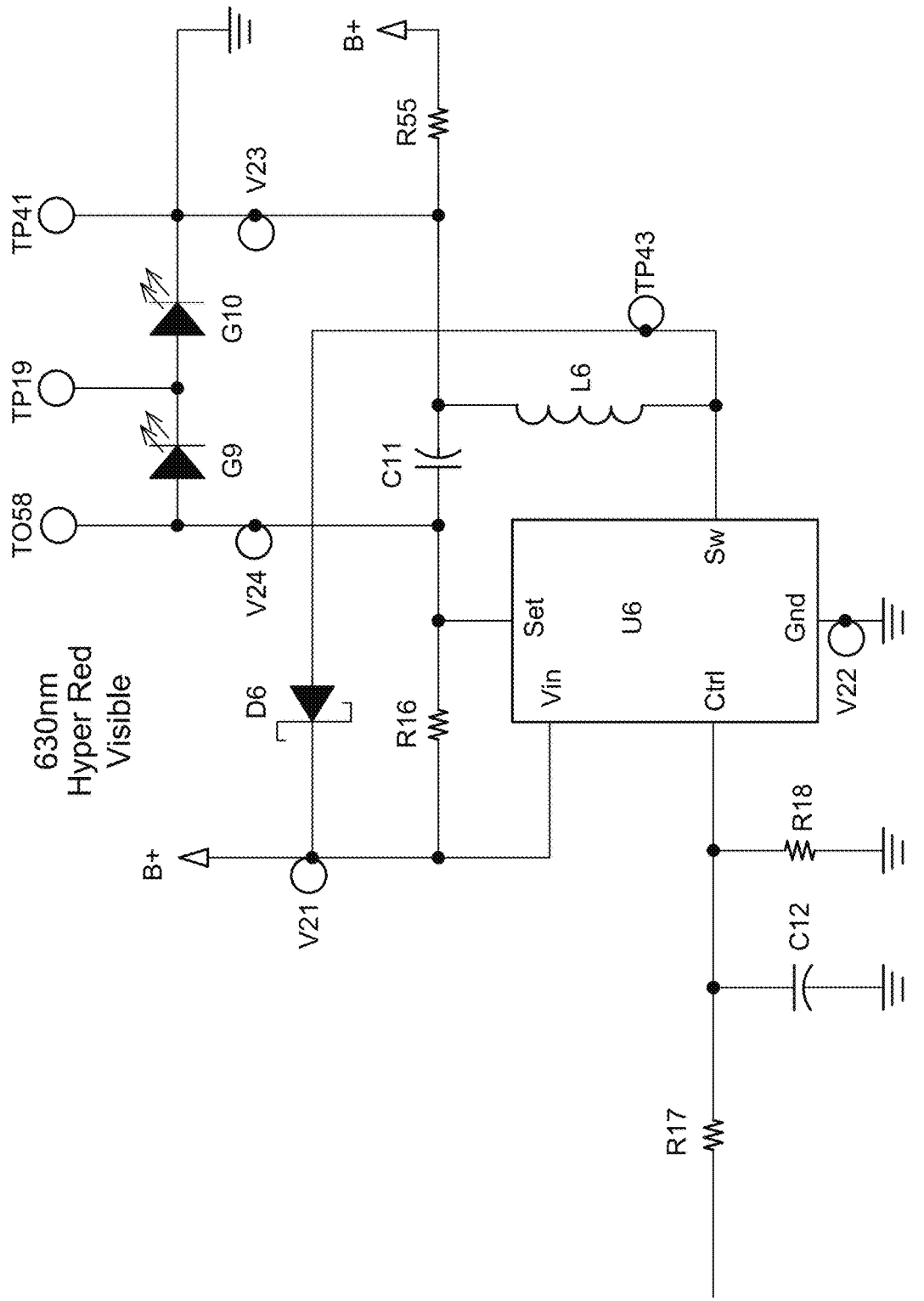
FIG. 9D shows a circuit diagram of a 630 nm hyper red visible LED.
Figure 9E:
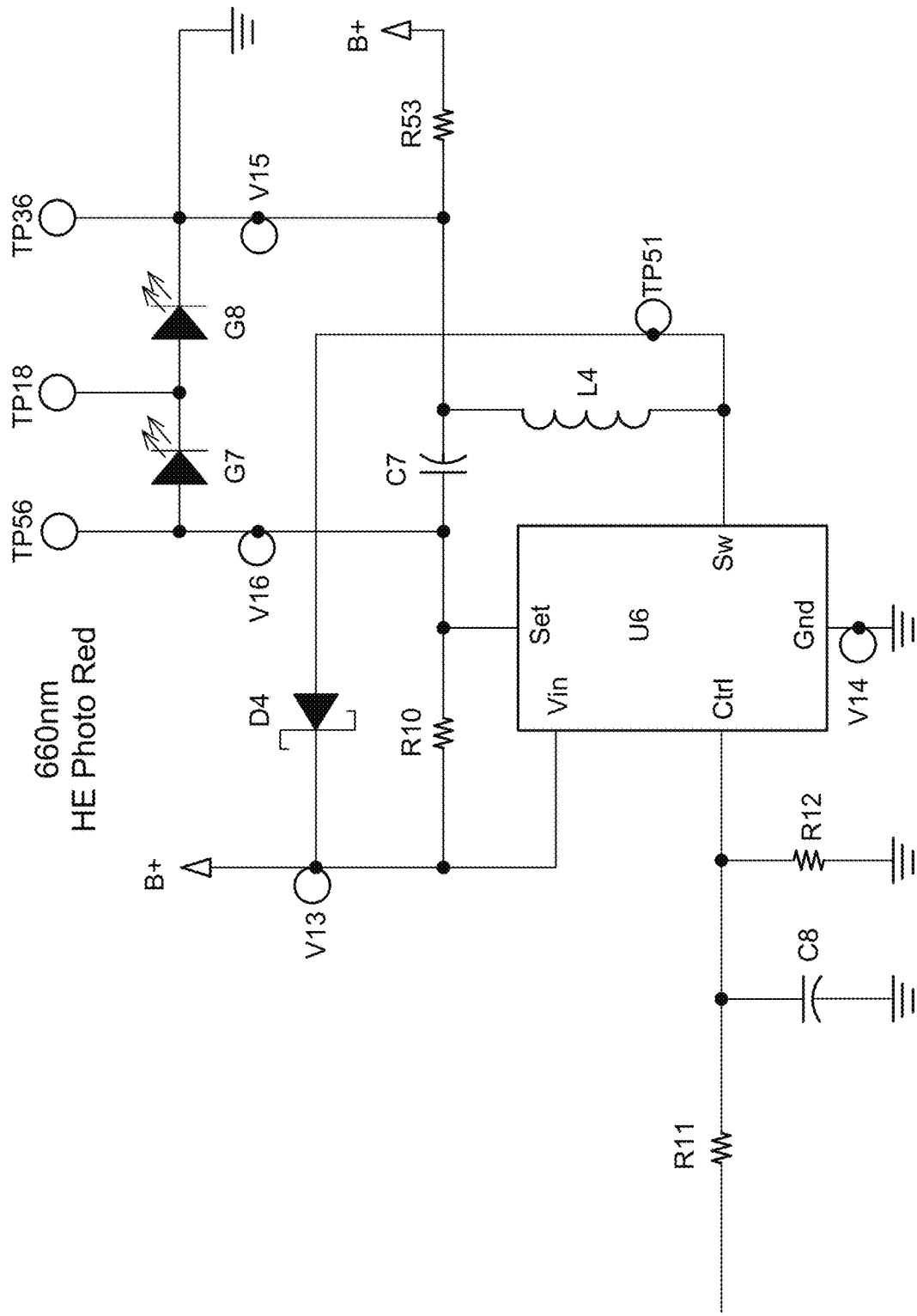
FIG. 9E shows a circuit diagram of a 660 nm HE photo red LED.
Figure 9F:
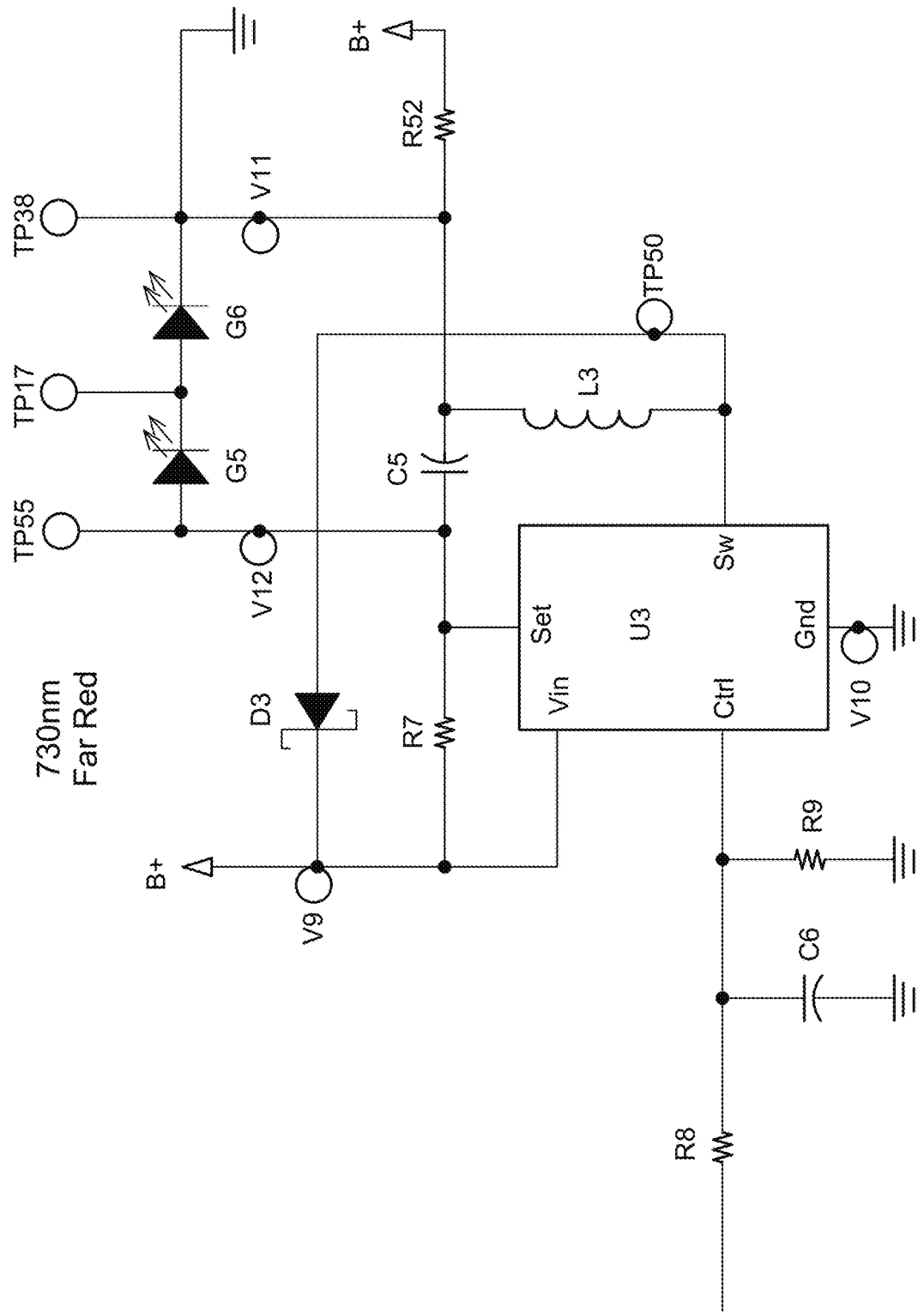
FIG. 9F shows a circuit diagram of a 730 nm far red LED.
Figure 9G:
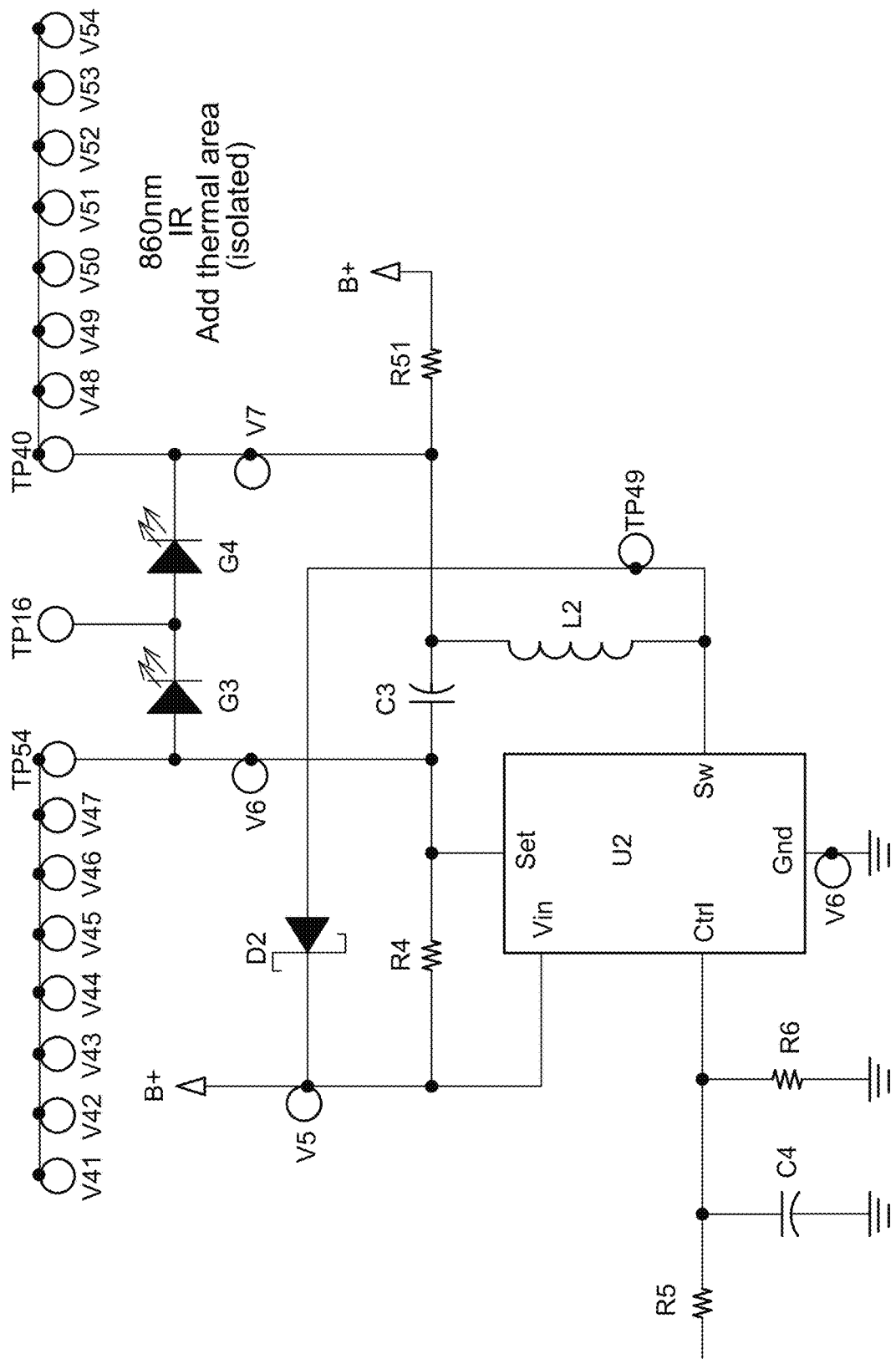
FIG. 9G shows a circuit diagram of a 860 nm infrared LED.
Figure 9H:
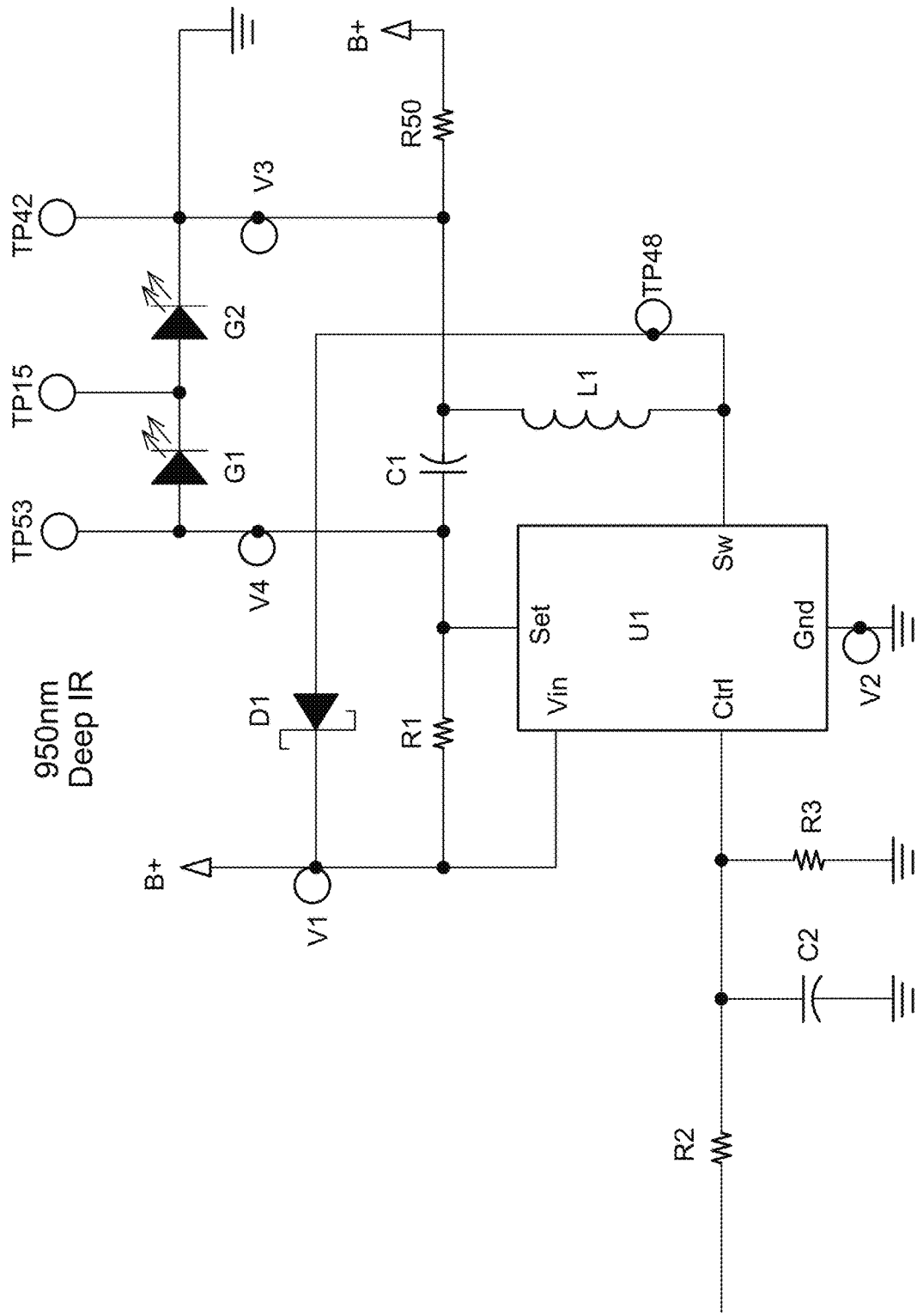
FIG. 9H shows a circuit diagram of a 950 nm deep infrared LED.
Figure 9I:
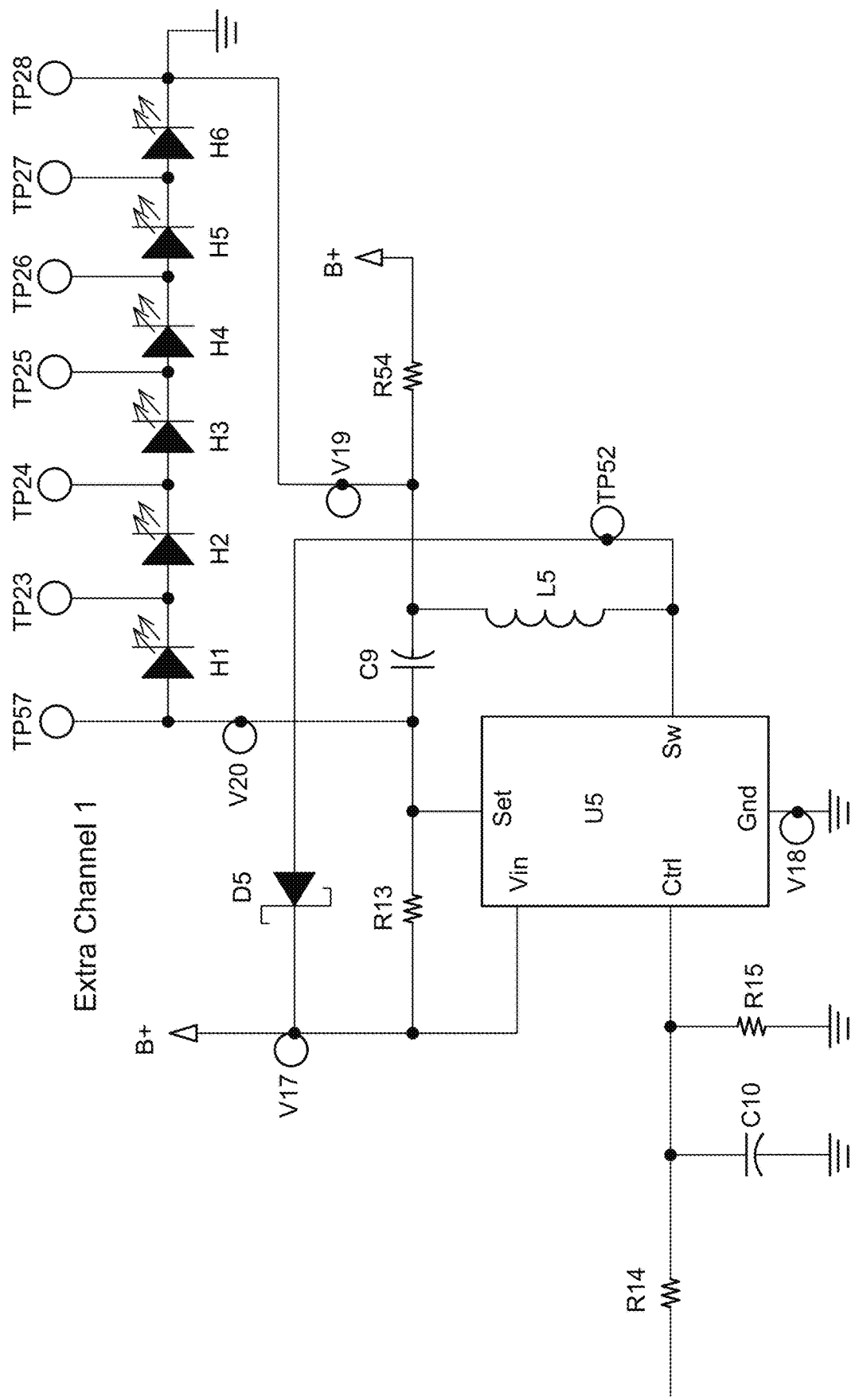
FIG. 9I shows a circuit diagram of a first extra channel.
Figure 9J:
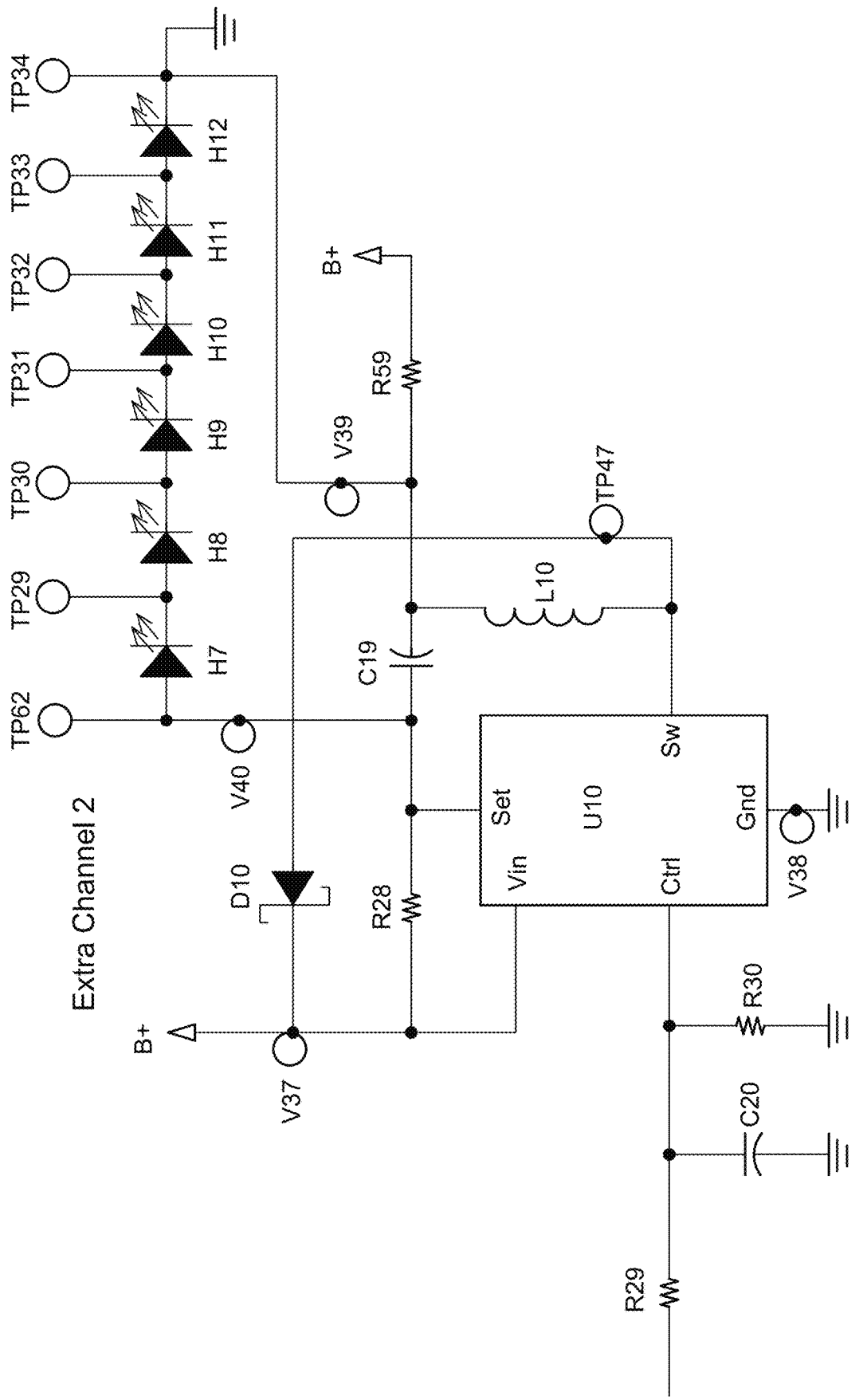
FIG. 9J shows a circuit diagram of a second extra channel.
Figure 9K:
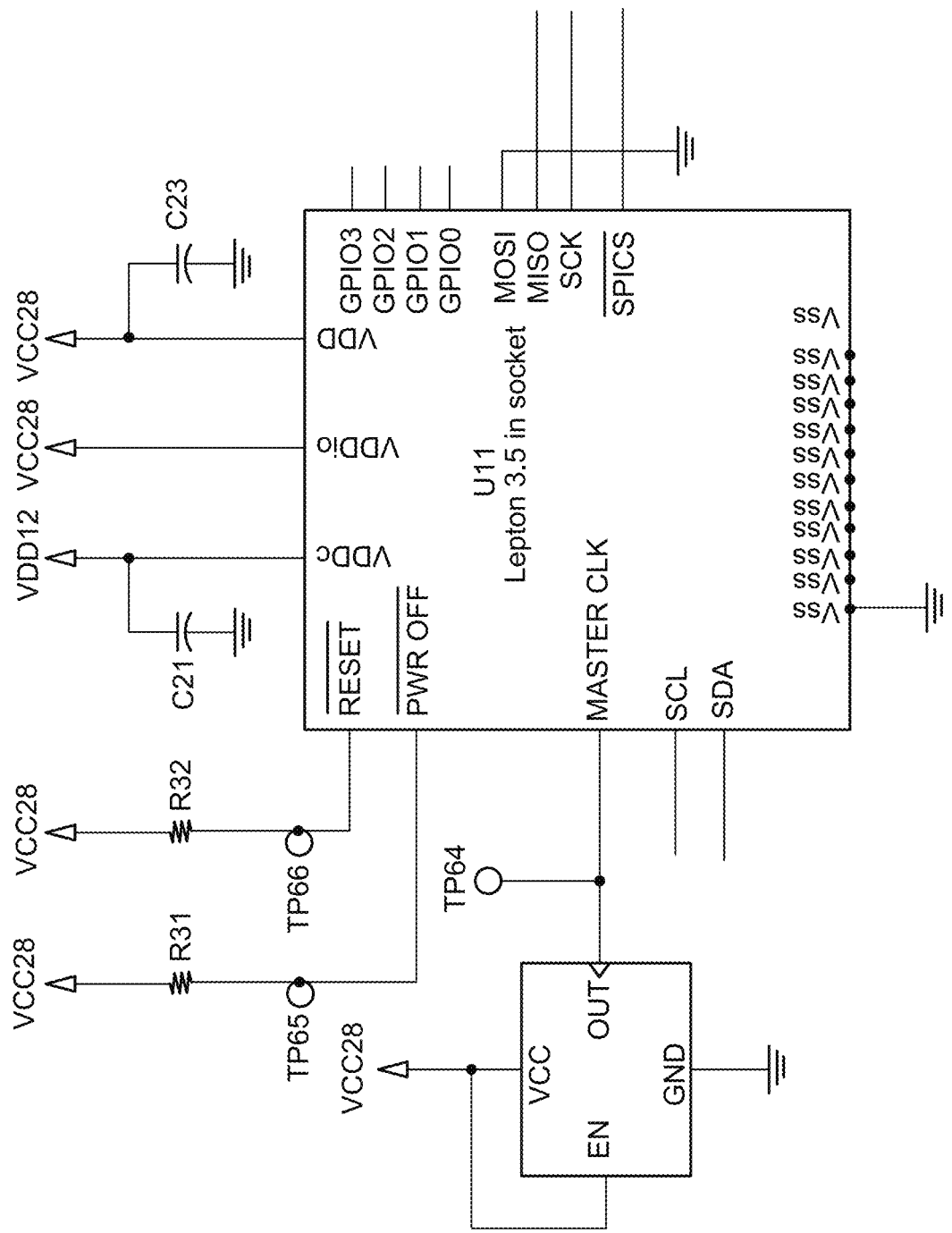
FIG. 9K shows a circuit diagram of a Lepton 3.5 socket.
Figure 9L:
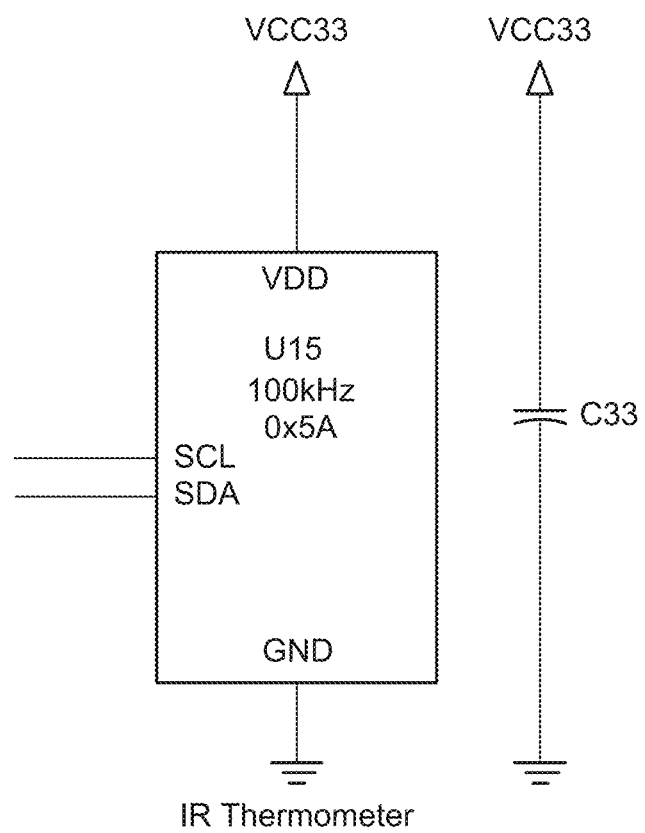
FIG. 9L shows a circuit diagram of an infrared thermometer.
Figure 9M:
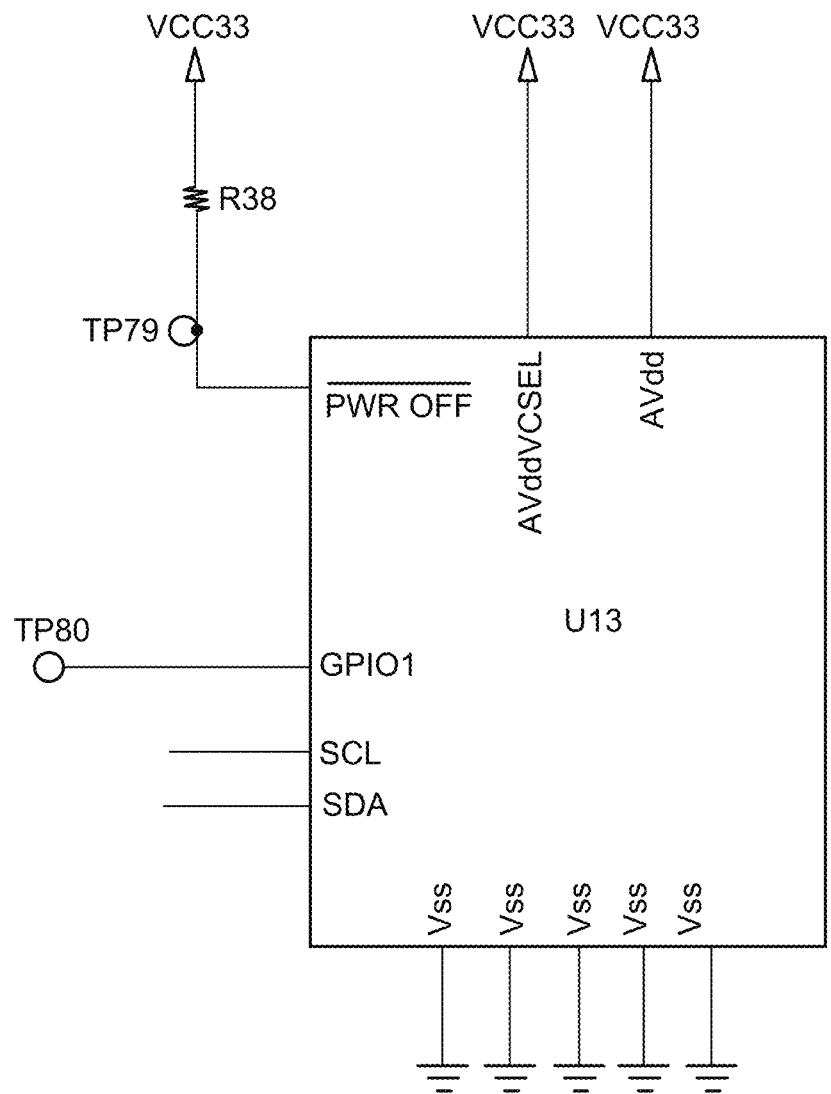
FIG. 9M shows a circuit diagram of a VL53L1X time-of-flight proximity sensor.
Figure 9N:
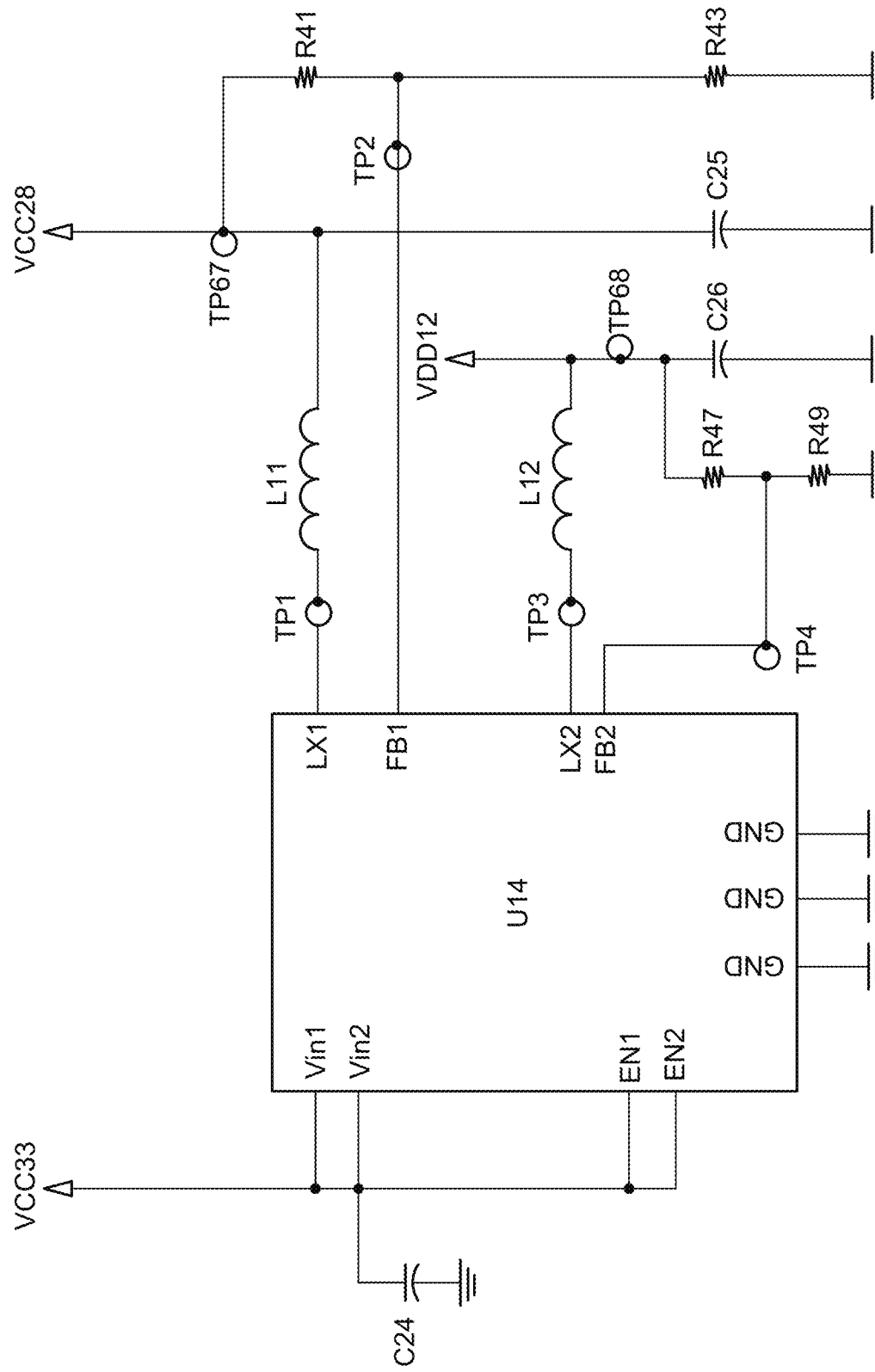
FIG. 9N shows a circuit diagram of a RT8020 pulse-width-modulated (PWM) converter.
Figures 1, 90:
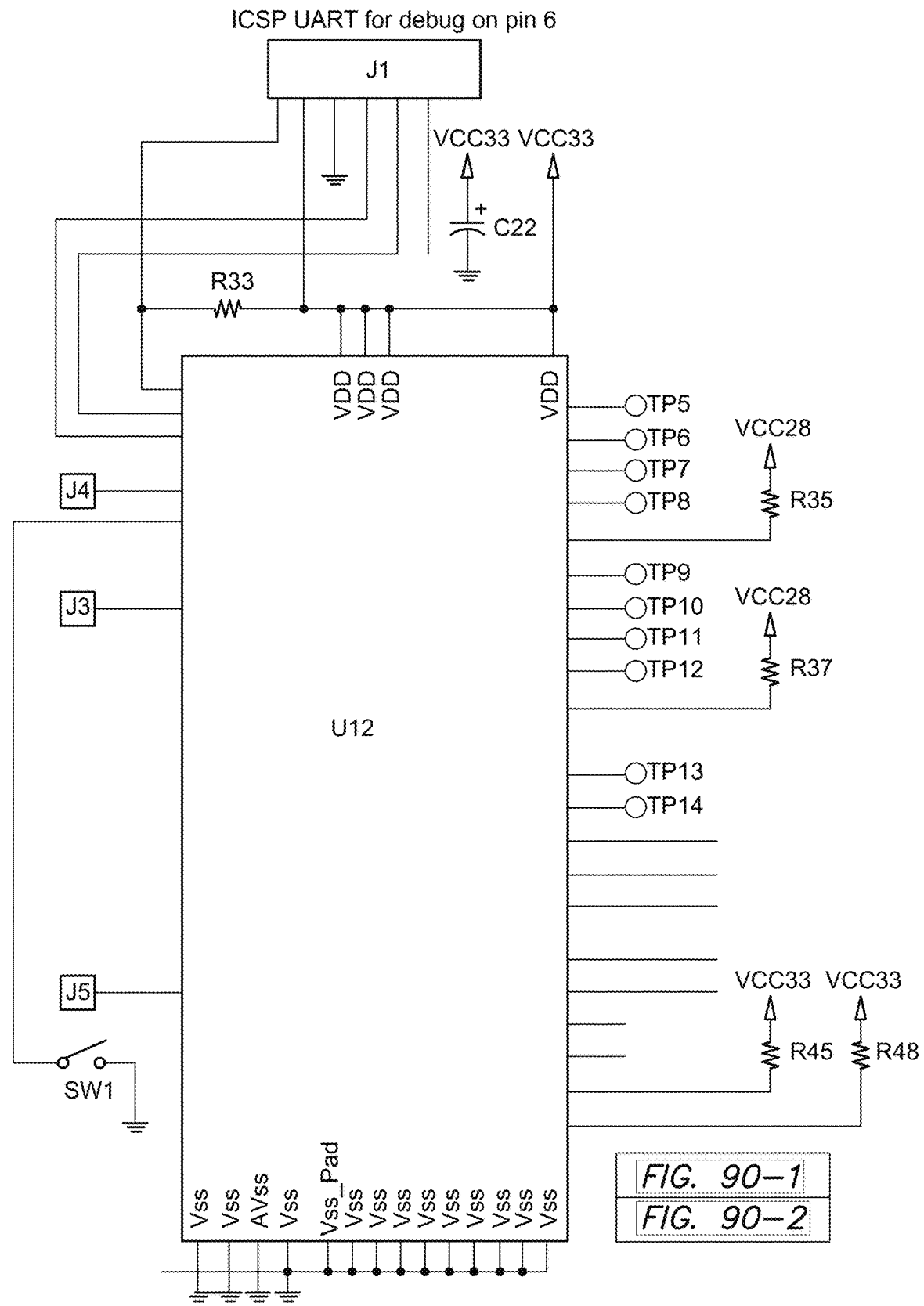

FIGS. 9A-9O show circuit diagrams for various components in the imaging system 1100 according to one exemplary implementation. FIGS. 9A-9H show circuit diagrams of respective drivers for a 365 nm ultraviolet (UV) LED, a 450 nm royal blue LED, a 530 nm green LED, a 630 nm red LED, a 660 nm red LED, a 730 nm far red LED, an 860 nm infrared LED, and a 950 nm infrared LED, respectively, which form the LED array 1140. FIGS. 9I and 9J show circuit diagrams for additional channels that may be used to support extra LED elements 1142. FIG. 9K shows a circuit diagram of a Lepton 3.5 socket used for IR imaging (e.g., the camera/sensor 1005B). FIG. 9L shows a circuit diagram of an infrared thermometer (e.g., the sensor 1005C). FIG. 9M shows a circuit diagram of a VL53L1X time-of-flight proximity sensor (e.g., see the single point laser rangefinder 1170 shown in FIG. 8A). FIG. 9N shows a circuit diagram of a RT8020 pulse-width-modulated (PWM) converter. FIG. 9O shows a circuit diagram of a digital signal converter to support the various components of the imaging system 1100.

Exemplary Lighting Systems With the Lighting Fixture

Figure 10A:
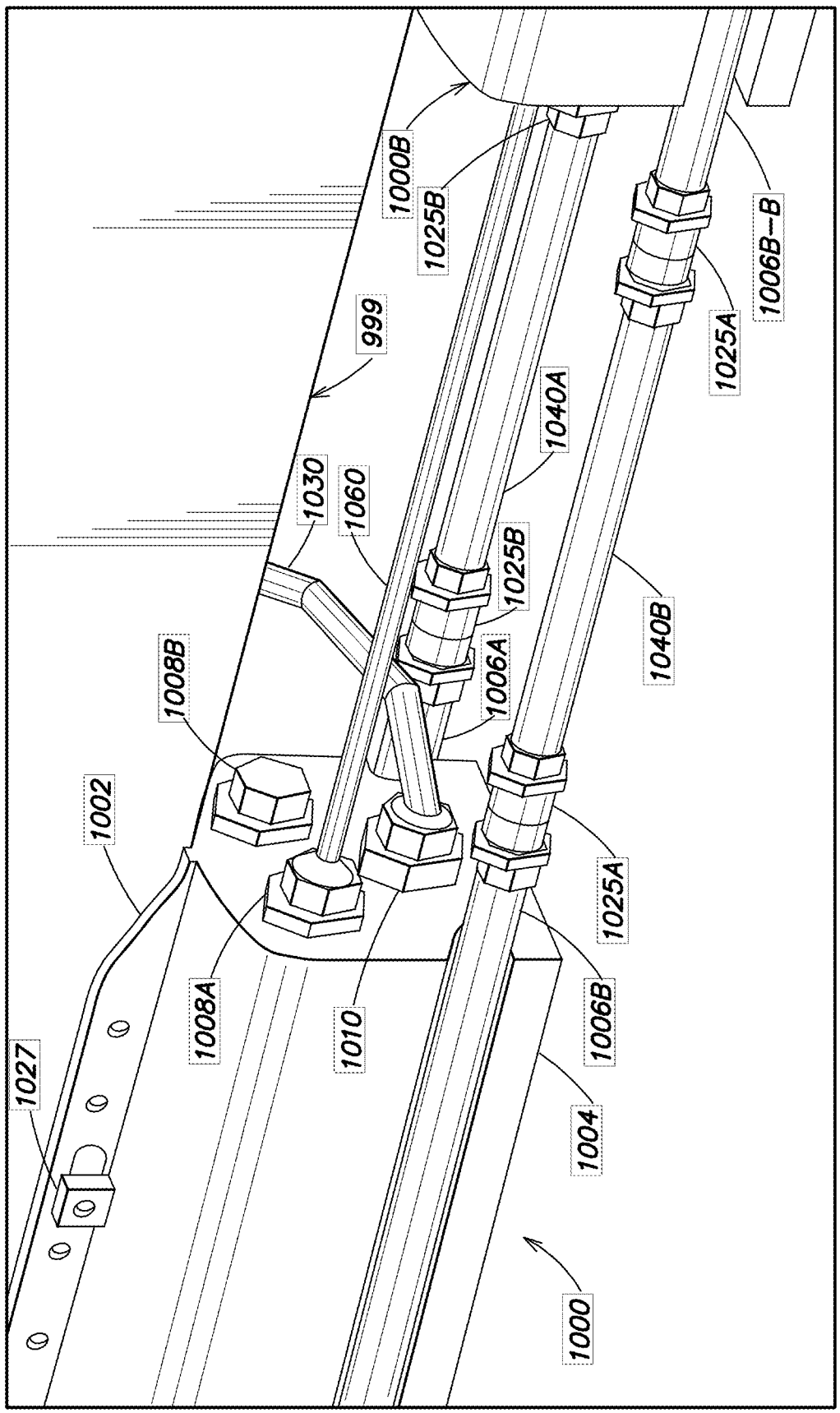
FIG. 10A shows a top perspective view of a first lighting fixture coupled to a second lighting fixture and a support structure, according to some implementations of the disclosure.

As described above, the lighting fixture 1000 may be coupled to other lighting fixtures 1000 in a daisy-chain configuration where electrical and piping connections are shared to facilitate assembly of a continuous electrical circuit and coolant circuit. For the coolant circuit, the daisy-chain configuration may be in series where the fluid coolant 800 exiting from one lighting fixture 1000 flows into a subsequent lighting fixture 1000 within the daisy-chain. The temperature of the fluid coolant 800 may increase further due to heat generated from the LED modules 400 of the subsequent lighting fixture 1000. It should be appreciated that so long as the temperature of the coolant fluid 800 is less than the temperature of the LED modules 400 in the lighting fixture 1000, the fluid coolant 800 may still capture heat from the lighting fixture 1000. Furthermore, in some implementations, heat rejection devices may be interspersed along the coolant circuit to reduce the temperature of the fluid coolant 800 and maintain sufficient heat dissipation as the fluid coolant 800 passes through multiple lighting fixtures 1000. An exemplary implementation detailing the manner in which two lighting fixtures 1000 and 1000-B may be coupled in a daisy-chain configuration is shown in FIG. 10A. In some implementations, the lighting fixture 1000 may be coupled to a support structure 999 using a bolt fastener 1027 placed through a hole in the light spine 1002 and secured to the side of the support structure 999 as shown in FIG. 10A.

The coolant pipes 1006A and 1006B of the lighting fixture 1000 may be coupled to a corresponding set of coolant pipes 1006A-B and 1006B-B from the other lighting fixture 1000-B using one or more intermediate pipes. As shown in FIG. 10A, the pair of coolant pipes 1006B and 1006B-B (1006A and 1006A-B) may be connected via a single intermediate pipe 1040B (1040A). Each intermediate pipe 1040B (1040A) may have push-to-connect fittings 1025A (1025B) disposed on both ends to facilitate connection to the coolant pipes 1006B and 1006B-B (1006A and 1006A-B). The shape of the intermediate pipe may vary depending on the desired distance and orientation between lighting fixtures 1000 and 1000-B. For example, the length of the intermediate pipe may be longer in order to space the lighting fixtures 1000 and 1000-B further apart to provide greater areal coverage or to traverse a gap separating two separate growing areas. In another example, the intermediate pipe may be curved such that the lighting fixtures 1000 and 1000-B are oriented at an angle relative to one another, e.g., 90 degrees, to accommodate variable shaped growing areas. In yet another example, the intermediate pipe may be substantially U-shaped to couple two parallel rows of lighting fixtures 1000 where the lighting fixtures 1000 and 1000-B are the last lighting fixtures 1000 in each respective row. In this manner, the coolant circuit may be continuous for multiple rows of lighting fixtures 1000.

Electrical power may be supplied to multiple lighting fixtures 1000 through a single power cable. An exemplary power cable 1030 coupled to the lighting fixture 1000 is shown in FIG. 10A. In some implementations, the power cable 1030 may be rated to support a particular electrical power and current input. For example, the power cable 1030 may be rated to supply at least 1000 W of electrical power and up to 15 A of current. Depending on the power and current requirements of the lighting fixture 1000, the power cable 1030 may be used to power multiple lighting fixtures 1000, thus reducing the amount of cabling and the number of electrical terminals (e.g., electrical outlets) that need to be installed in the controlled agricultural environment.

The lighting fixture 1000 may also be communicatively coupled to another lighting fixture 1000 to facilitate transmission of data and control signals to multiple lighting fixtures 1000. As shown in FIG. 10A, an Ethernet cable 1060 may be used to couple the PoE port 1008A of lighting fixture 1000 to the PoE port 1008C-B of lighting fixture 1000-B. Each of the lighting fixtures 1000 and 1000-B may include a processor to manage the flow of data and/or control signals. In some implementations, the lighting fixture 1000 may be used as a piggyback to facilitate the transfer of data and/or control signals to another lighting fixture 1000 located further along the daisy-chain. In this manner, multiple lighting fixtures 1000 spanning a large area may be communicatively coupled to a fewer number of network nodes (e.g., hubs, switches, routers) and without using excessive amounts of network cabling.

Figure 10B:
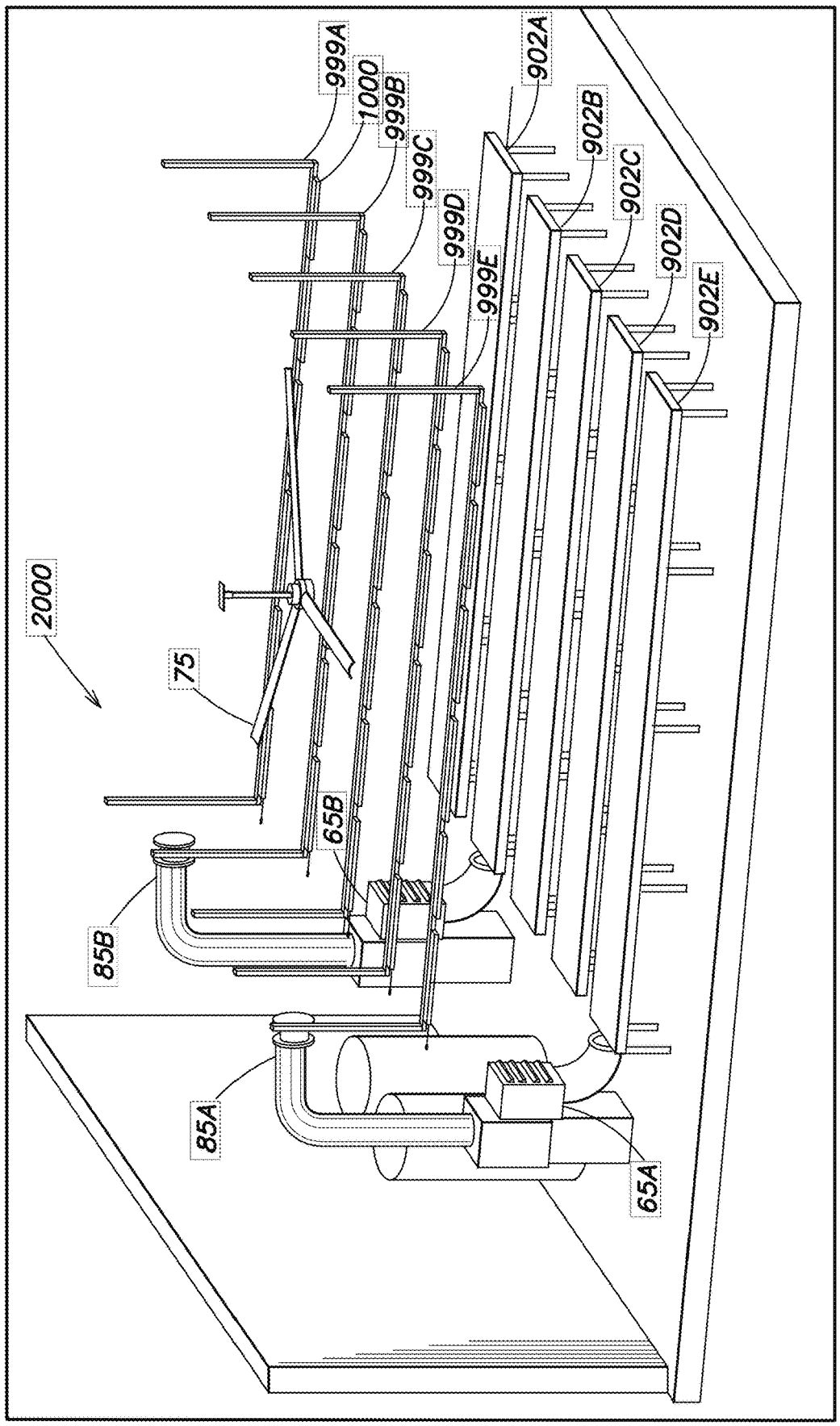
FIG. 10B shows a perspective view of a controlled agricultural environment showing multiple rows of fluid-cooled LED-based lighting fixtures coupled together forming a continuous electrical and coolant circuit, according to some implementations of the disclosure.

An exemplary arrangement of lighting fixtures 1000 in a controlled agricultural environment 2000 is shown in FIG. 10B. Multiple lighting fixtures 1000 may be arranged along a row spanning a growing area defined by the dimensions of a shelf 902A. Each lighting fixture 1000 in the row may be coupled to a support structure 999A disposed above the shelf 902A. The lighting fixtures 1000 in the row may be coupled together in a daisy chain configuration, as described above. Intermediate piping may be used to couple adjacent lighting fixtures 1000 such that fluid coolant 800 may circulate through the multiple lighting fixtures 1000 in a continuous manner from a single inlet and outlet for the row. One or more power cables may be used to supply electrical power to the lighting fixtures 1000. Ethernet cabling may be used to communicatively couple the lighting fixtures 1000 in a serial manner and to a common network node. As shown in FIG. 10B, the controlled agricultural environment 2000 may include multiple rows of lighting fixtures 1000 supported by support structures 999A-999E arranged above corresponding rows of shelves 902A-902E. The controlled agricultural environment 2000 may further include a fan 75, dehumidifiers 65A and 65B, and air conditioning ducts 85A and 85B for one or more air conditioners.

As previously shown in the exemplary controlled agricultural environments 2000A and 2000B in FIGS. 3 and 4, respectively, the lighting fixture 1000 may be incorporated into a coolant circuit 570 to facilitate the flow of fluid coolant 800 such that heat may be continuously removed from the lighting fixture 1000. In some implementations, the coolant circuit 570 may be designed to substantially remove heat from only the lighting fixture 1000 and is not intended to thermally interact with other components or regions of the controlled agricultural environment 2000A, as shown in the coolant circuit 570 in FIG. 3 for a retrofit application. In some implementations, however, the coolant circuit 570 may include additional piping subsystems designed to redistribute heat to a space near or within the controlled agricultural environment, such as the hydronics loops 700A and 700B shown in FIG. 4 for a hydronics application, and/or to store heat captured by the lighting fixture 1000 for later use.

A piping subsystem may be branched from the coolant circuit 570 such that the flow of fluid coolant 800 may be controllably adjusted (e.g., by a valve and a separate pump) without affecting the flow of fluid coolant 800 through the coolant circuit 570 and hence, without affecting the removal of heat from the lighting fixture 1000. However, in some instances, a piping subsystem may be placed in series with the coolant circuit 570 where the piping subsystem is also used on a continual basis. Some exemplary instances of a piping subsystem being used in series with the coolant circuit 570 includes, but is not limited to a heating system for a hot water system in a residential space, storing heat from the fluid coolant 800 in a thermal energy storage system, and charging a battery by converting heat from the fluid coolant 800 into electricity (e.g., using a thermoelectric device).

Figure 11A:
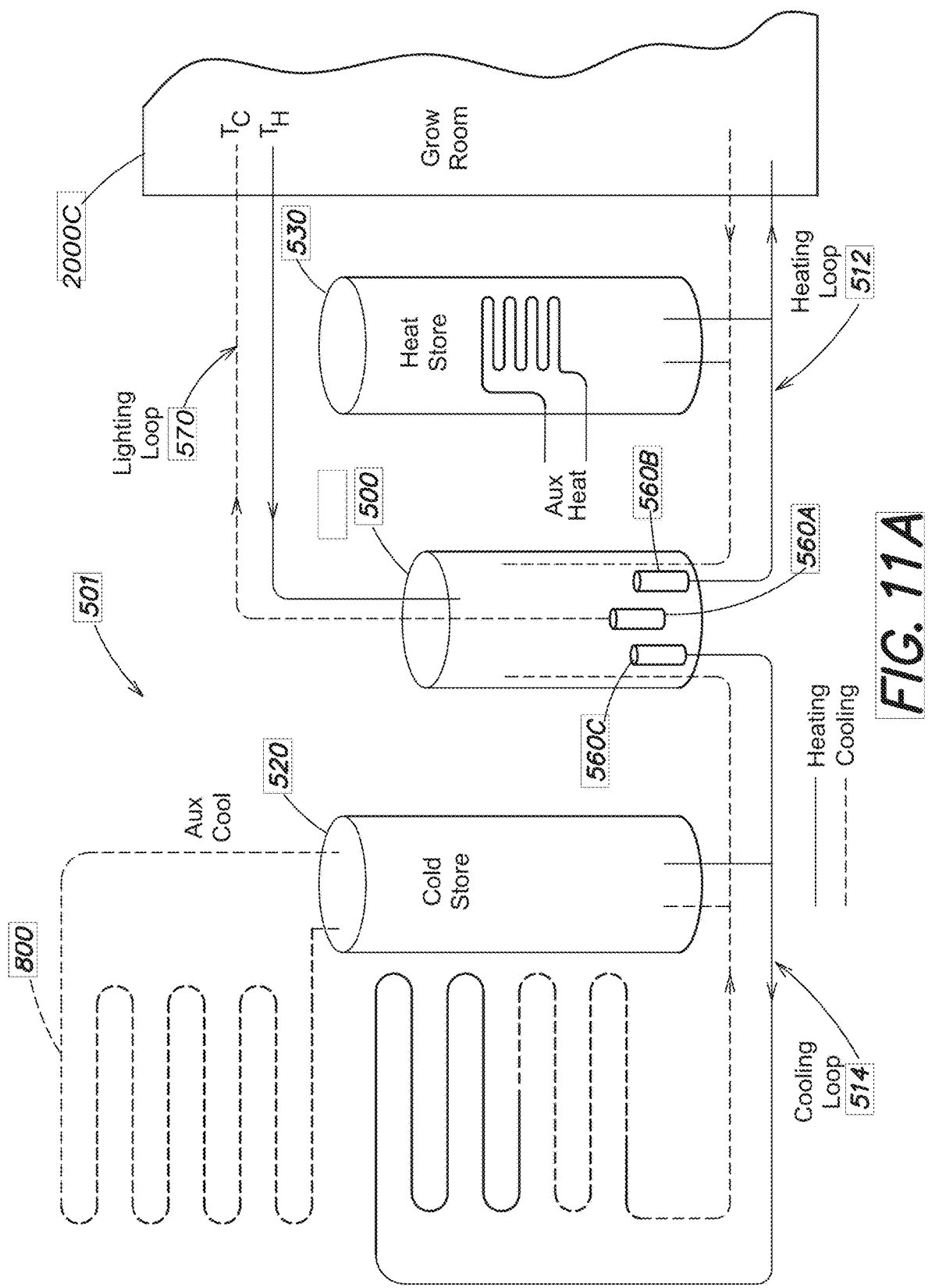
FIG. 11A shows an exemplary hydronics system including a fluid storage tank and multiple piping subsystems such as a lighting loop, a heating loop, and a cooling loop, according to some implementations of the disclosure.

FIG. 11A shows an exemplary hydronics system 501 that may be used in connection with a coolant circuit 570 as well as in other implementations of a controlled agricultural environment where one or more lighting fixtures 1000 are used. As shown, the hydronics system 501 may include a fluid storage tank 500 to store fluid coolant 800, which may be disposed internally or externally to the controlled agricultural environment. In some implementations, the fluid storage tank 500 may include separate compartments for relatively cooler fluid coolant 800 and relatively hotter fluid coolant 800 with sufficient thermal insulation to substantially isolate the compartments from one another and the surrounding environment. The fluid storage tank 500 may also be dimensioned to have a sufficiently large storage capacity such that the thermal time constant of the fluid storage tank 500 meets a desired rate of change in temperature during operation. For example, it may be desirable for the temperature of the fluid coolant 800 stored in the fluid storage tank 500 to remain substantially unchanged (e.g., 1° C. per hour) throughout the day to reduce fluctuations in the amount of heat supplied to various piping subsystems. However, if adjustments to the fluid coolant 800 temperature are desired, the amount of time needed for the adjustments to occur may be prohibitive due to the long thermal time constant. In such instances, multiple fluid storage tanks 500, each having a smaller capacity and thus a shorter thermal time constant, may be used instead.

Three submersible pumps 560A, 560B, and 560C may be disposed within the fluid storage tank 500 to pump fluid coolant 800 through three corresponding piping subsystems, namely, the coolant circuit 570 (also referred to in FIG. 9A as a "lighting loop"), a heating loop 512, and a cooling loop 514. The lighting loop 570 associated with the pump 560A is responsible for providing relatively cooler fluid coolant from the fluid storage tank 500 to one or more lighting fixtures 1000 (e.g., via the coolant circuit 570 as shown in FIGS. 3 and 4) and returning relatively hotter fluid coolant 800 from the one or more lighting fixtures 1000 to the fluid storage tank 500. In this manner, the lighting loop 570 may function as a heat source to heat fluid coolant 800 stored in the fluid storage tank 500 with heat being subsequently distributed to other piping subsystems. In some implementations, the lighting loop 570 may be used to heat at least a portion of the controlled agricultural environment 2000C via natural convection or thermal radiation to regulate and maintain temperature of the portion within a desired temperature envelope.

In some implementations, a secondary heating loop may be incorporated into the lighting loop 570 to more directly and controllably heat a portion of the controlled agricultural environment 2000C that may not be proximate to the lighting loop 570 (e.g., a growing area, as shown in FIG. 4). For example, the secondary heating loop may include a pump, a fan, and a fan coil. The pump may generate a flow of relatively hotter fluid coolant 800 through the fan coil, thus heating the fan coil. The fan may then generate a flow of hot air, thus heating the portion of the controlled agricultural environment 2000C via forced convection. In another example, the secondary heating loop may be routed through the root zone of the growing area to heat the soil or nutrient solution to a desired temperature via a combination of convection and conduction (e.g., see the hydronics loop 700A in FIG. 4). The secondary heating loop may include a flow controlling device (e.g., a valve) to control the amount of heat added to the portion of the controlled agricultural environment. For example, the secondary heating loop may be coupled to a thermostat that adjusts the heat added according to a day/night cycle.

The heating loop 512 associated with the pump 560B may also be used to heat a portion of the controlled agricultural environment 2000C or another space located separately to the controlled agricultural environment 2000C. For example, the heating loop 512 may be coupled to a heating, ventilation, and air conditioning (HVAC) system in a building to regulate the interior climate of the building, a heating system in a manufacturing plant to offset gas or electricity consumption, or a cogeneration plant to produce electricity and high-grade heat. In some implementations, the heating loop 512 may also be coupled to a heat store 530, which may provide additional capacity to store heat for future use by the controlled agricultural environment 2000C or another space.

The cooling loop 514 associated with the pump 560C may be used to cool the fluid coolant 800 stored in the fluid storage tank 500. In this manner, the temperature of the relatively cooler fluid coolant 800 entering the lighting loop 570 may be regulated and maintained, which may reduce the effects of thermal drift over time where the temperature of the relatively cooler fluid coolant 800 increases, thus reducing the amount of heat removed from the one or more lighting fixtures 1000. In some implementations, the cooling loop 514 may be a piping subsystem that captures heat to an exterior environment via natural convection and radiation along the length of the cooling loop 514. In some implementations, a heat rejection device may be incorporated into the cooling loop 514 to facilitate cooling of the fluid coolant 800. Various types of heat rejection devices may be used including, but not limited to cooling towers (e.g., see the cooling tower 557 in FIG. 3 or FIG. 4), evaporative coolers, "free" coolers, chillers, dry coolers, air source coolers, ground source heat exchangers, water source heat exchangers, or any combinations of the foregoing. In some implementations, the cooling loop 514 may also be coupled to a cold store 520, which may provide additional capacity to store relatively cooler fluid coolant 800 for future use by the controlled agricultural environment 2000C or another space.

In various implementations described herein, the temperature of the fluid coolant 800 stored in the fluid storage tank 500 and flowing through the lighting loop 570, heating loop 512, cooling loop 514, and one or more secondary loops coupled to any of the lighting loop 570, heating loop 512, cooling loop 514 may vary within an appreciable temperature range. In some implementations, the temperature of the fluid coolant 800 may range from about 20° C. to about 50° C. The flow rate of the fluid coolant 800 may range from about 1 gallon per minute to about 3 gallons per minute through the lighting loop 570. Similar or significantly different (e.g., higher) flow rates may be used by the heating loop 512 and the cooling loop 514. Furthermore, the various piping subsystems (e.g., the lighting loop 570, the heating loop 512, and the coolant loop 514) may be controlled via at least one of a pump, regulator, and/or valves. The at least one of a pump, regulator, and/or valves may be operated on various time cycles (e.g., daily, weekly, monthly, seasonal, other periodicities, or any combination thereof) to regulate and maintain desired thermal conditions, which may be dynamic as a function of time, in the controlled agricultural environment 2000C.

Additionally, while three piping subsystems are shown in FIG. 11A, it should be appreciated that any number and combination of piping subsystems may be used with the coolant circuit 570. For example, one or both of the heating loop 512 and the cooling loop 514 may be used in conjunction with the lighting loop 570. It should also be appreciated that while three submersible pumps 560A-560C are shown in FIG. 11A, any number of pumps may be used for a particular piping subsystem and the pumps 560A-560C may also be disposed externally to the fluid storage tank 500. The pumps may be various types of pumps including, but not limited to piston pumps, end-suction pumps, diaphragm pumps, gear pumps, lobed pumps, flexible-vane pumps, nutating pumps, peristaltic pumps, centrifugal pumps, diffuser pumps, propeller pumps, and peripheral pumps.

Figure 11B:
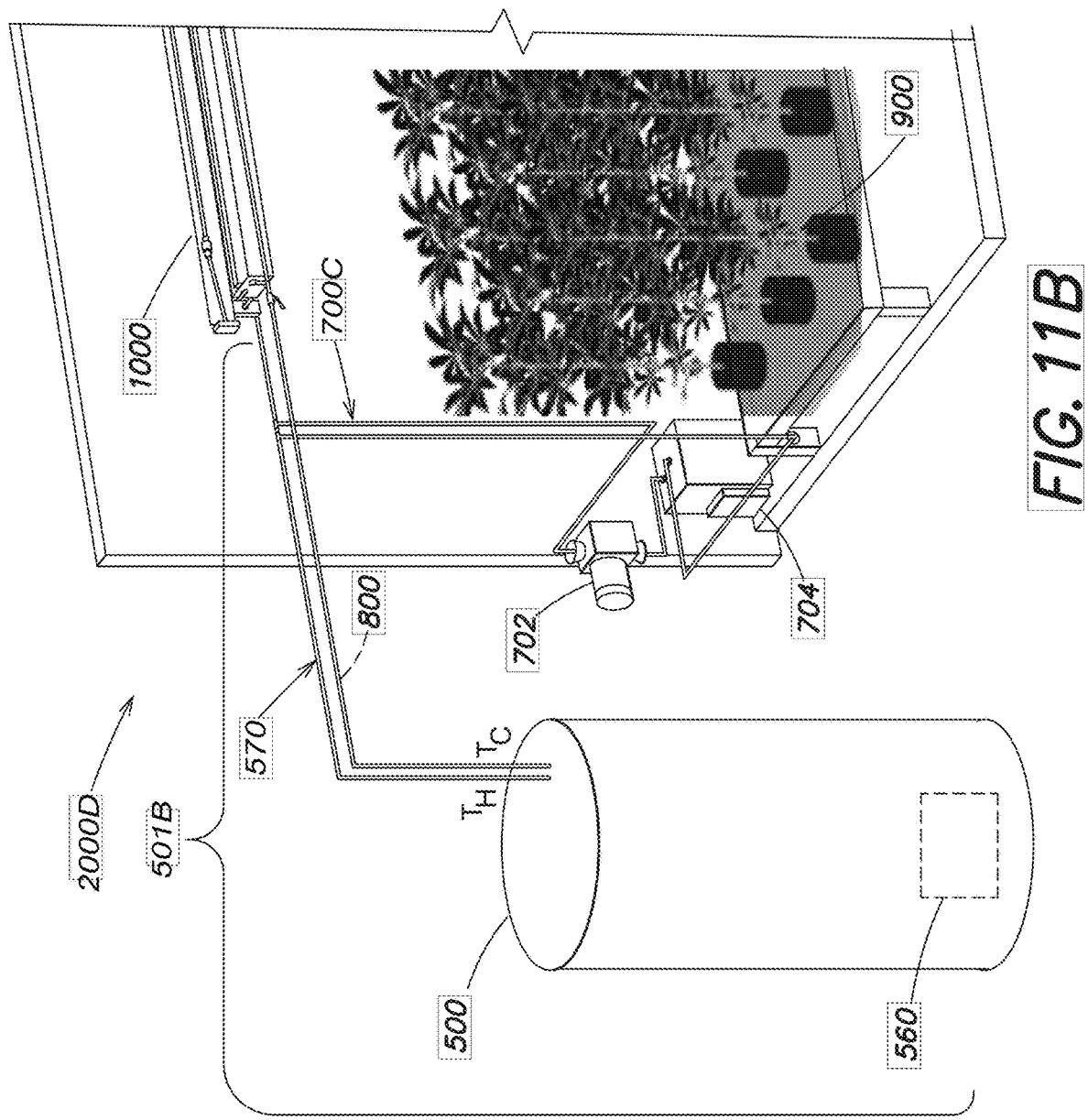
FIG. 11B shows a portion of an exemplary hydronics system coupled to a lighting fixture and a growing area, according to some implementations of the disclosure.

An exemplary implementation of a hydronics system 501B coupled to a lighting fixture 1000 and a coolant circuit ("lighting loop") 570 in a controlled agricultural environment 2000D is shown in FIG. 11B. The hydronics system 501B may include a fluid storage tank 500 having contained therein a submersible pump 560. The submersible pump 560 is used to pump relatively cooler fluid coolant 800 into a lighting loop 570, where the fluid coolant 800 is then heated as it passes through the lighting fixture 1000. Subsequently, the relatively hotter fluid coolant 800 exits the lighting loop 570 and enters the fluid storage tank 500 for storage. It should be appreciated that so long as the temperature of the fluid coolant 800 stored in the fluid storage tank 500 is less than the temperature of the fluid coolant 800 entering the fluid storage tank 500 from the lighting loop 570, heat generated by the lighting fixture 1000 may be removed. Over time, if the temperature of the fluid coolant 800 increases, the amount of heat that may be removed may decrease due to a smaller temperature difference. Thus, a heat rejection device may need to be incorporated into the hydronics system 501B to regulate the temperature of the fluid coolant 800 stored in the fluid storage tank 500.

The hydronics system 501B shown in FIG. 11B may also include a secondary heating loop 700C coupled to the portion of the lighting loop 570 where relatively hotter fluid coolant 800 heated by the lighting fixture 1000 flows through (e.g., similar to the hydronics loops 700A and 700B shown in FIG. 4). As shown, the secondary heating loop 700C may include a pump 704 and an electric fan with a fan coil 702. The pump 704 generates a flow of the relatively hotter fluid coolant 800 through the fan coil, thus heating the fan coil. The electric fan 702 may then blow heated air towards a plurality of plants 900 located below the lighting fixture 1000 to increase the temperature of the growing area as desired. The second heating loop 700C may be controlled using one or more controllable valves to toggle the secondary heating loop 700C and to adjust the temperature of the air blown by the electric fan 702.

Figure 11C:
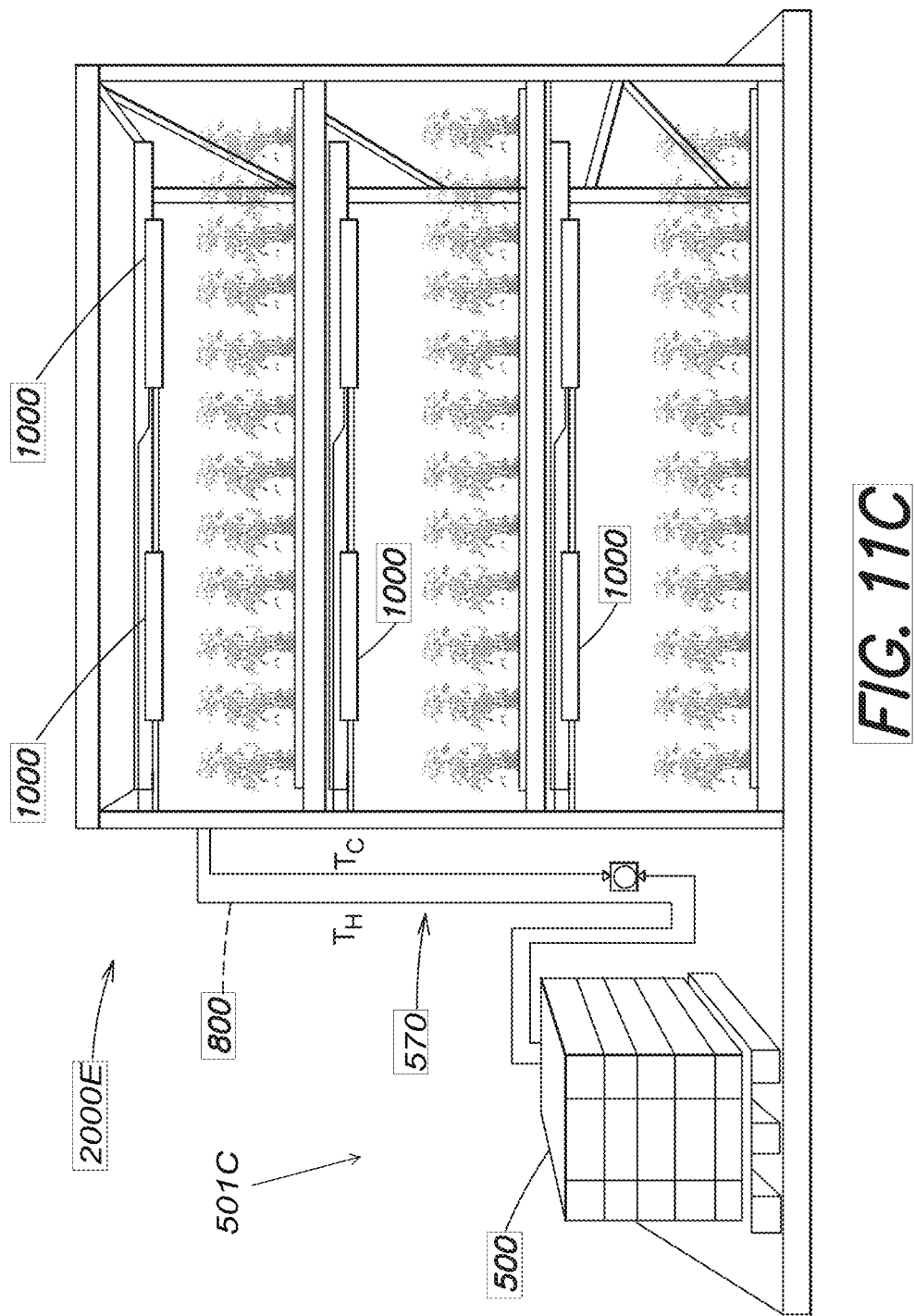
FIG. 11C shows a controlled agricultural environment where one or more fluid-cooled LED-based lighting fixtures are disposed in a vertically-stacked multiple-level growing area and coupled to a hydronics system, according to some implementations of the disclosure.

Another exemplary implementation of a hydronics system 501C disposed in a controlled agricultural environment 2000E is shown in FIG. 11C. As shown, the controlled agricultural environment 2000E may have a vertically-stacked multiple-level growing area. Each level of the growing area may include one or more lighting fixtures 1000 coupled to a lighting loop 570. The lighting loop 570 may be coupled to a fluid storage tank 500, which may again contain therein a submersible pump. Similar to the controlled agricultural environment 2000D of FIG. 11B, the hydronics system 501C may include secondary heating loops to separately heat each growing area in each level. The portions of the lighting loop 570 corresponding to each level may be coupled using a plumbing fitting with multiple inlets and outlets. Additionally, the portion of the lighting loop 570 coupled to the fluid storage tank 500 may support a higher flow rate to account for a reduction in flow rate once the fluid coolant 800 flows into each respective level of the growing area.

In some implementations, the lighting fixture 1000 may also function as a sensor platform supporting one or more sensors used to monitor environmental conditions in the controlled agricultural environment. The processor 90 in the lighting fixture 1000 may supply and regulate electrical power to the sensor through the communication ports 1009 (e.g., a USB port and a PoE port) and/or the camera(s)/sensor(s) 1005. The processor 90 may also include electronics to convert AC power to DC power, as will be described below, thus obviating the need for a separate AC to DC converter in each sensor deployed in the controlled agricultural environment.

The processor 90 may also be used to manage data communications (e.g., wired communication via the Ethernet cables 1060 or wireless communication via the wireless device 1003), including sending control signals to the sensor and receiving sensory data measured by the sensor for processing and/or transmission to a remote device (e.g., a remote computer or server). In some implementations, the remote device may include a network hub to communicate with multiple lighting fixtures 1000. The network hub may be wired (e.g., Ethernet cables 1060 are connected to the hub), wireless (e.g., wireless signals are transmitted/received to/from the wireless device 1003), or a combination of both. In some implementations, the network hub of the remote device may be only wireless, thus allowing a simpler installation by eliminating the Ethernet cables 1060. In some implementations, the network hub of the remote device may be wired to support greater network bandwidth and/or higher security (e.g., data communications may only be accessed at the remote device).

In this manner, the lighting fixture 1000 may provide integration of one or more sensors of various types, supplementing the need for separate power and data communications systems. Furthermore, the data measured by the one or more sensors may be used to adjust and control operation of one or more lighting fixtures 1000 (e.g., adjusting the PAR output from the lighting fixture 1000), one or more coolant circuits or other fluid coolant loops (e.g., adjusting the fluid flow through the coolant circuit/lighting loop, heating loop, and cooling loops shown in FIG. 9A), one or more fans, one or more dehumidifiers, or one or more air conditioners in the controlled agricultural environment. In some implementations, various environmental conditions are measured and controlled to provide target vapor pressure deficits in the environment.

Figure 12:
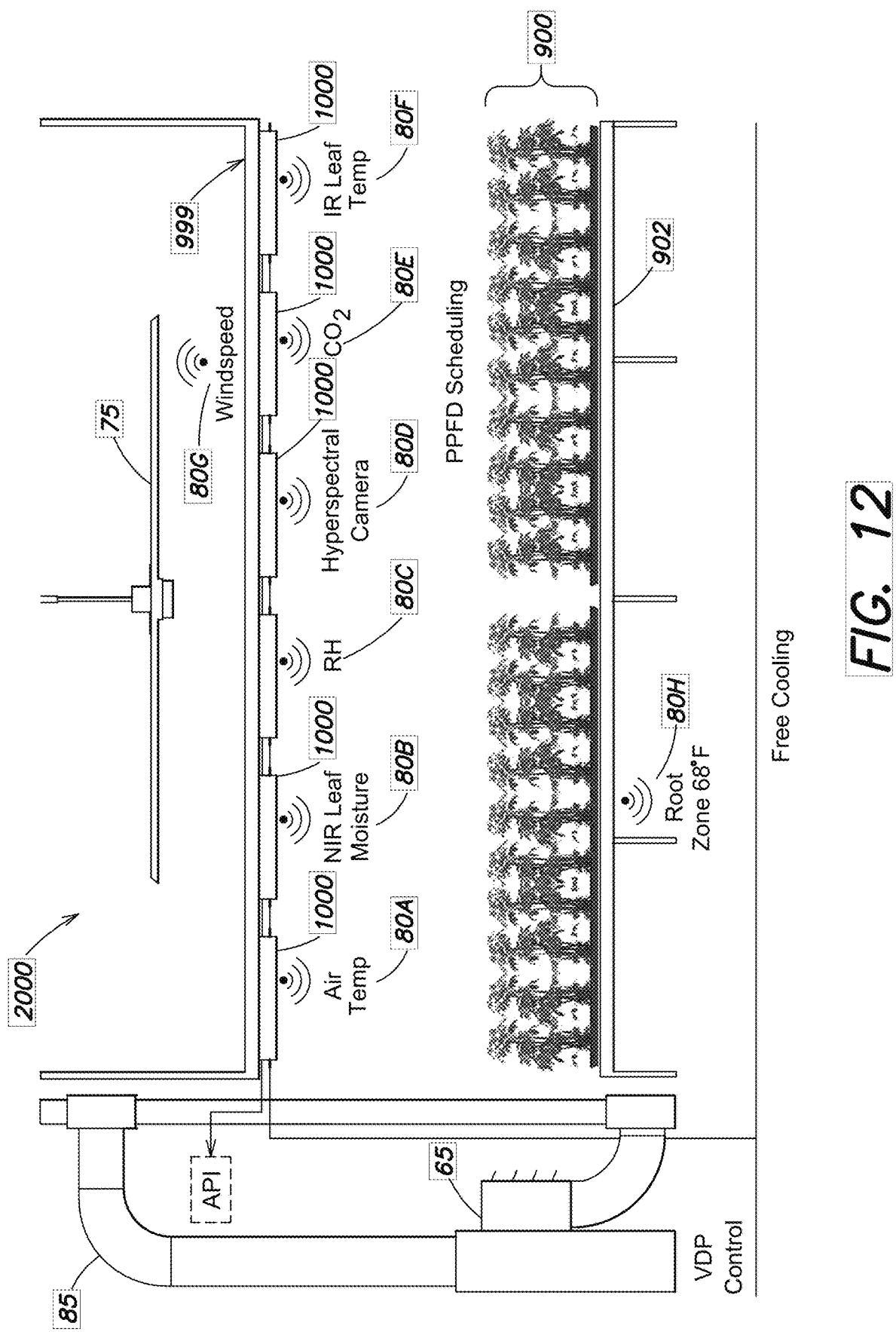
FIG. 12 shows a side view of a controlled agricultural environment with a plurality of fluid-cooled LED-based lighting fixtures and a plurality of sensors to facilitate monitoring of environmental conditions, according to some implementation of the disclosure.

An exemplary implementation of a controlled agricultural environment 2000 detailing the integration of various sensors via multiple lighting fixtures 1000 is shown in FIG. 12. Similar to FIG. 10B, multiple lighting fixtures 1000 may be mounted to a support structure 999 disposed above a plurality of plants 900 arranged on a shelf 902. The controlled agricultural environment 2000 may include one or more dehumidifiers 65, one or more air conditioners 85, and one or more fans 75. A variety of sensors may be supported by the lighting fixture 1000 including, but not limited to an air temperature sensor 80A, a near infrared (NIR) leaf moisture sensor 80B, a relative humidity sensor 80C, a hyperspectral camera 80D, a carbon dioxide sensor 80E, an infrared (IR) leaf temperature sensor 80F, an airflow sensor 80G, and a root zone temperature sensor 80H. The hyperspectral camera 80D refers to a type of camera that measures light within numerous energy bands (e.g., hundreds) where each band is narrower (e.g., 10 nm) than conventional imaging systems. Finite spectral cameras (also referred to as multispectral cameras) may also be used in the controlled agricultural environment 2000 to measure light using a fewer number of energy bands (e.g. 3 to 10) where each band is broader (e.g., greater than 20 nm). The cameras utilized in the controlled agricultural environment 2000 may measure light across various portions of the electromagnetic spectrum including, but not limited to ultraviolet, visible, near-infrared, mid-infrared, and far-infrared wavelengths. The lighting fixture 1000 may also be used to support other auxiliary devices including, but not limited to one or more fans, security cameras, smart phones, and multi-spectral cameras (e.g., to analyze soil moisture and nutrient content). In this manner, various auxiliary devices may be distributed in the controlled agricultural environment due to the flexible placement of communication ports 1009 on the respective lighting fixtures 1000.

An Exemplary Electrical Design of a Lighting Fixture

Figure 13A:
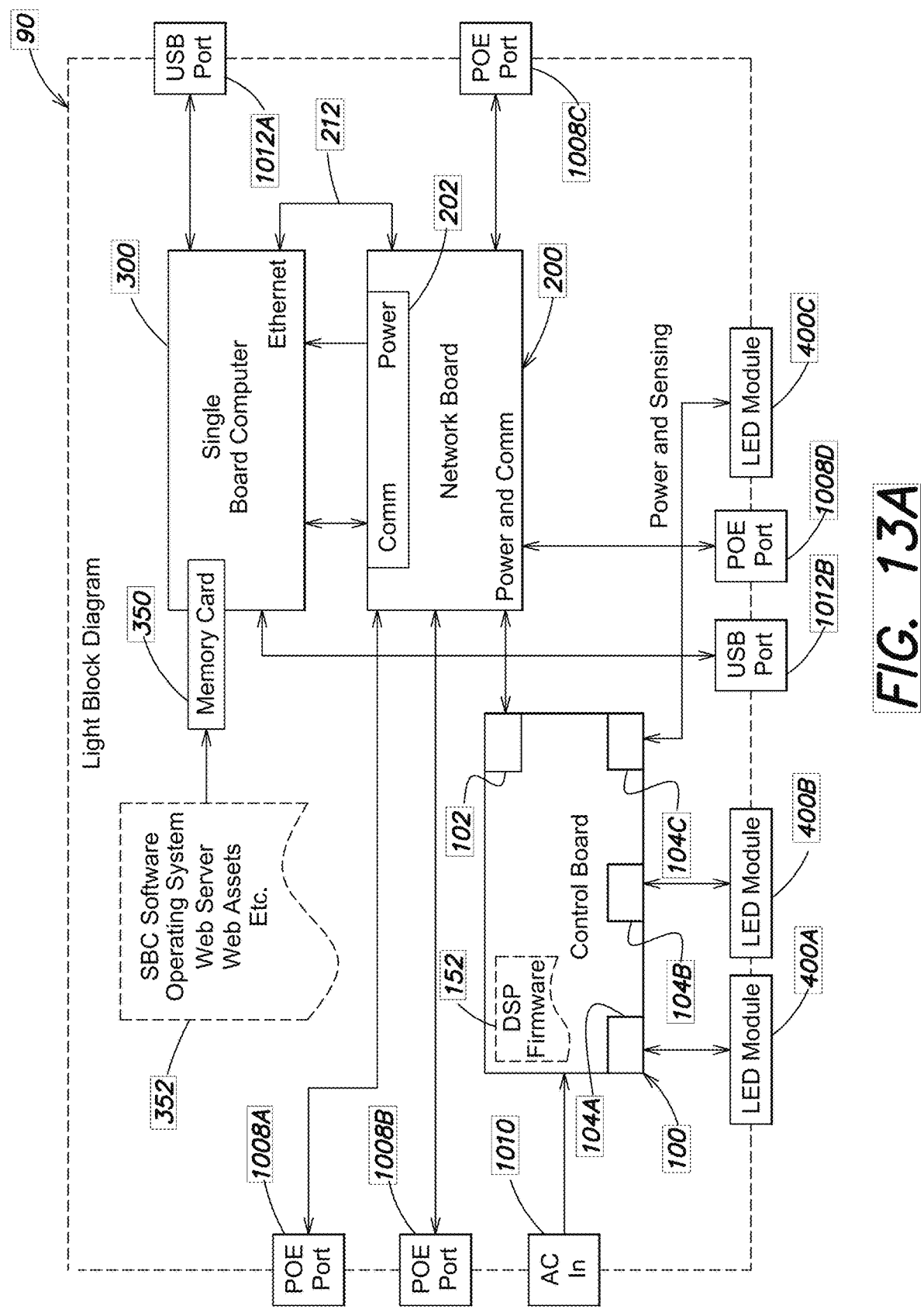
FIG. 13A is a block diagram detailing various electronics components of a processor including a control board, a network board, and a single board computer, according to some implementations of the disclosure.

The processor 90 may be used to facilitate multiple functionalities pertinent to the operation of the lighting fixture 1000 including, but not limited to power conversion, network connectivity, and data processing in the operation of the lighting fixture 1000. In some implementations, the processor 90 may be comprised of discrete electronics assemblies that are electrically coupled together where each electronics assembly provides one or more distinct functionalities. For example, FIG. 13A shows a block diagram detailing various electronic components and circuitry in the processor 90 to meet these functionalities according to one inventive implementation. The processor 90 may include a control board 100, a network board 200, and a single board computer 300.

The control board 100 may be used to regulate and distribute electrical power to other components of the lighting fixture 1000. As shown in FIG. 13A, the control board 100 may receive AC power through an electrical power port 1010 and convert the AC power to DC power. The control board 100 may then supply DC power and other control signals to other electronics in the lighting fixture 400. For example, the control board 100 may be directly coupled to multiple LED modules 400A, 400B, and 400C via ports/connectors 104A, 104B, and 104C, respectively, on the control board 100. The control board 100 may also be coupled to the network board 200, providing both electrical power and control signals to the network board 200. The control board 100 may also include onboard memory, in which digital signal processing (DSP) firmware 152 is stored to facilitate generation of control signals as described below.

Figure 13B:
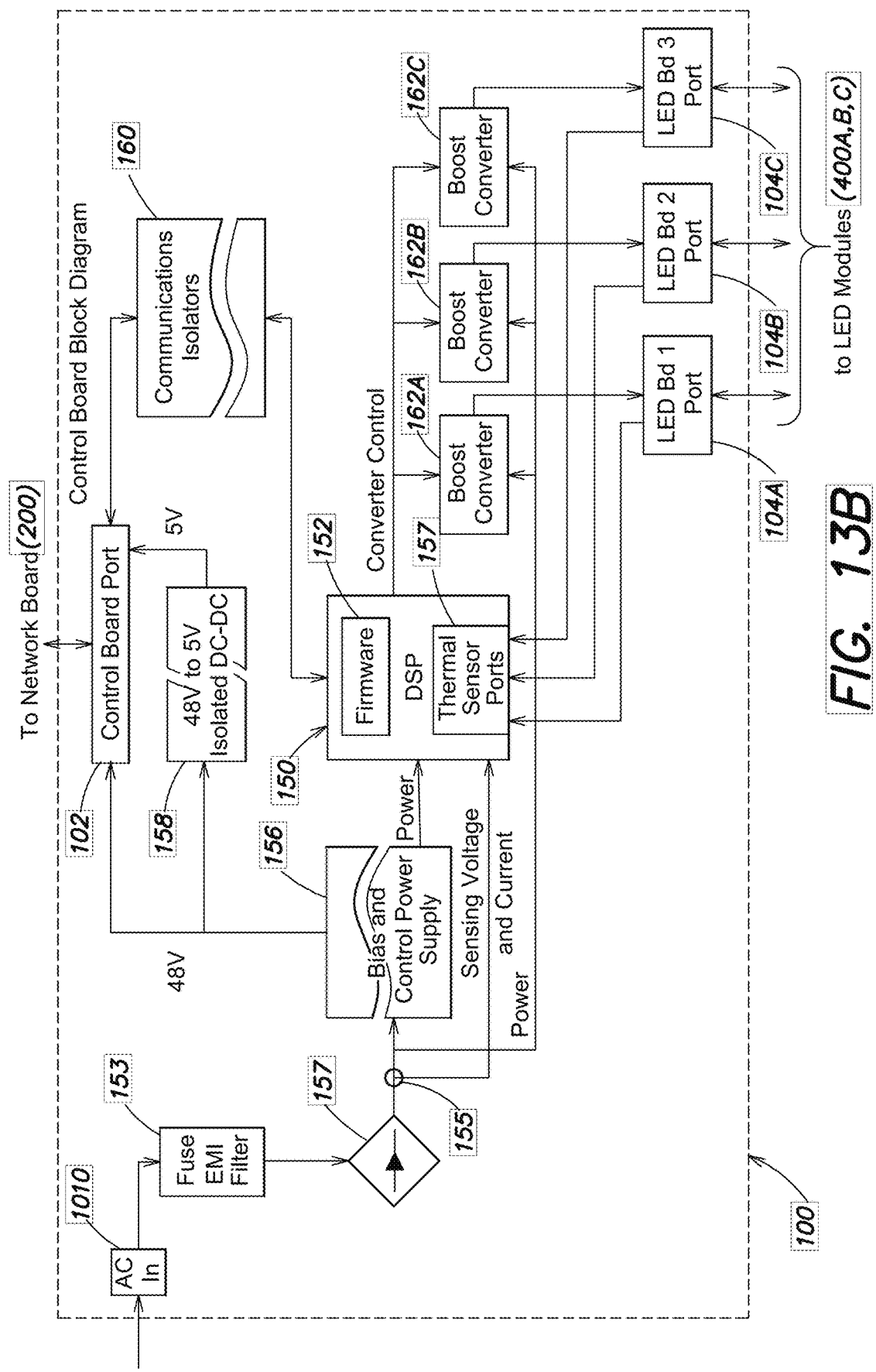
FIG. 13B is a block diagram providing additional detail of the control board of FIG. 13A.

A more detailed block diagram of the control board 100 in FIG. 13A is shown in FIG. 13B. The control board 100 may include a fuse/electromagnetic interference (EMI) filter 153 to provide safety and reduce noise input into the lighting fixture 1000. A rectifier 154 may be used to convert AC power to DC power. An AC line sensor 155 may be used to monitor the voltage and current of the DC power input. DC power may then be passed directly to a bias and control power supply 156, which may be used to distribute DC power to other components of the lighting fixture 1000 including the network board 200 and a digital signal processor (DSP) 150. A DC-DC converter 158 may also be included to supply different voltage inputs to the network board 200. For example, the bias and control power supply 156 may supply 48 V and 5 V to power different circuitry on the network board 200 and the single board computer 300. The 5 V input may be down converted from the 48 V line via the DC-DC converter 158. The DSP 150 may provide control signals by executing the firmware 152 described above to various components including the network board 200, via one or more communications isolators 160. The DSP 150 may also provide control signals to one or more boost converters 162A, 162B, and 162C, which may be used to regulate electricity supplied to the corresponding LED modules 400A-400C via ports 104A-104C. The boost converters 162A-162C may receive DC power directly once converted from AC power via the rectifier 154. The DSP 150 may receive power from the bias and control power supply 156, a voltage and current measurement from the AC line sensor 155, and thermal sensor inputs via the thermal sensor ports 154, which may be used to monitor the temperature of the LED modules 400A-400C.

The network board 200 may be used to manage data communication between the lighting fixture 1000 and various devices coupled to the lighting fixture 1000 including, but not limited to other lighting fixtures 1000 and one or more auxiliary sensors coupled to the lighting fixture 1000. As shown in FIG. 13A, in some implementations, the network board 200 may control one or more PoE ports 1008A, 1008B, 1008C, and 1008D of the lighting fixture 1000. The network board 200 may receive electrical power and control signals from the control board 100 via a control board port 102. The network board 200 may also supply electrical power and control signals to the single board computer 300 via a single board computer port 202. The network board 200 may also support a dedicated Ethernet cable connection 212 through an Ethernet port 213 between the network board 200 and the single board computer 300 to manage data transfer through the PoE ports 1008A-1008D.

Figure 13C:
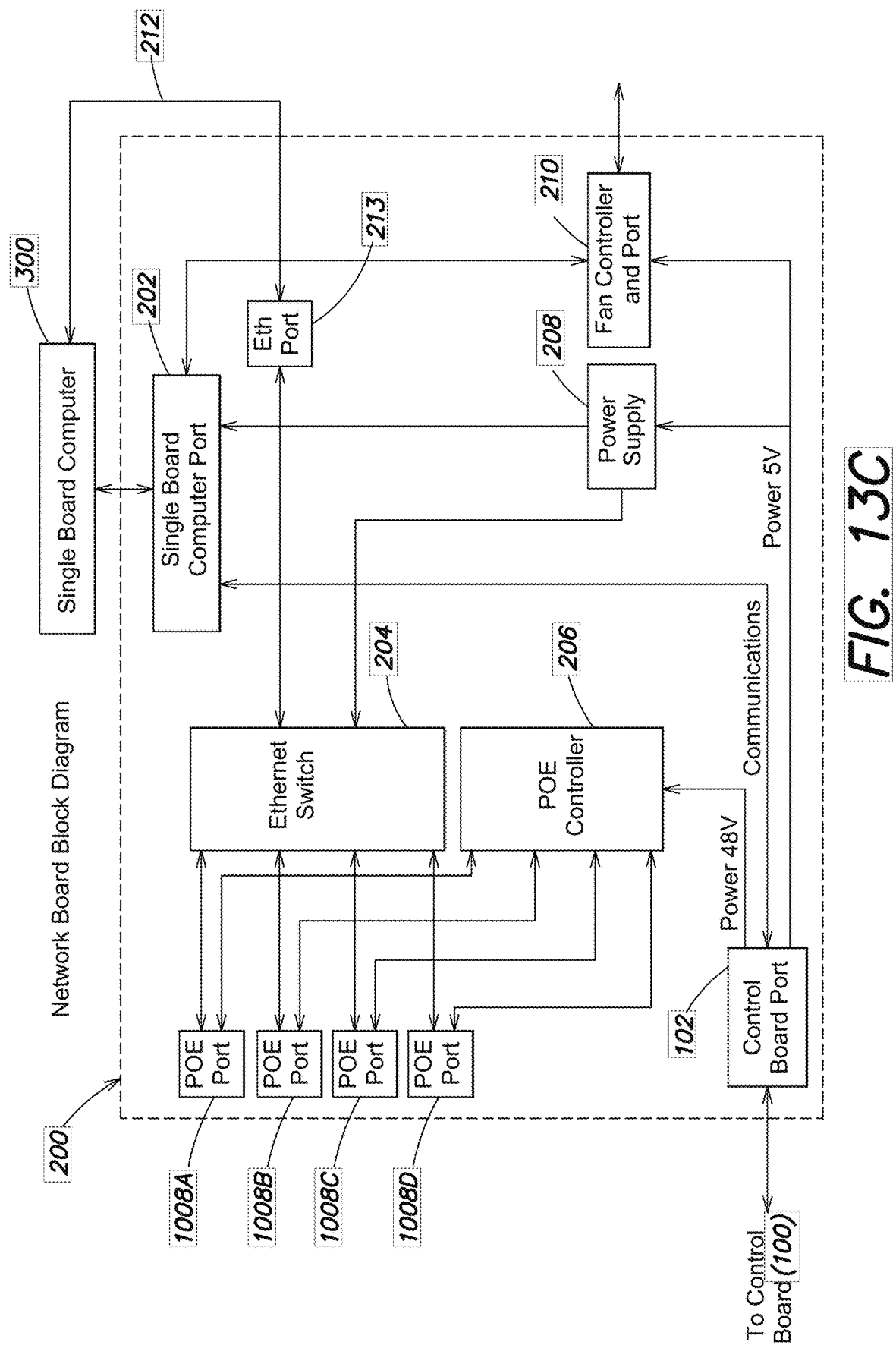
FIG. 13C is a block diagram providing additional detail of the network board of FIG. 13A.

A more detailed block diagram of the network board 200 in FIG. 13A is shown in FIG. 13C. The control board port 102 may be used to supply electrical power at different voltages, e.g., 48 V and 5 V, to a PoE controller 206, a power supply 208, and a fan controller and port 210. The control board port 102 may also directly relay control signals from the control board 100 to the single board computer 300 via the single board computer port 202. In some implementations, the control board port 102 may be arranged as a piggyback board to the network board 200. The PoE controller 206 may be used to regulate and supply electrical power to the PoE ports 1008A-1008D. The power supply 208 may supply electrical power to the single board computer 300, through the single board computer port 202, and to an Ethernet switch 204. The Ethernet switch 204 is communicatively coupled to the PoE ports 1008A-1008D and to the single board computer 300 via the Ethernet port 213, which supports the dedicated Ethernet cable connection 212. The Ethernet switch 204 may be used to facilitate receipt and transmission of data and/or control signals to and from the PoE ports 1008A-1008D.

The single board computer 300 may provide several functions to the processor 90 including, but not limited to managing the operation of the control board 100 and the network board 200 and data processing. As shown in FIG. 13A, the single board computer 300 may also be used to support the functionality of USB ports 1012A and 1012B on the lighting fixture 1000. The single board computer 300 may include a memory card 350 that contains (has stored thereon) various data and computer executable code 352 including, but not limited to, session border controller (SBC) software, an operating system, web server software and other web server assets.

The processor 90 may be used to manage the voltage and current supplied to various components of the lighting fixture 1000, e.g., a power cable, the LED modules 400A-400C, in order to reduce the likelihood of damage under different operating conditions. For example, the lighting fixture 1000 may be operated under low voltage conditions where 1200 W may be supplied to the LED modules 400A-400C and 65 W for auxiliary sensors. The power cable used to supply electricity to the lighting fixture 1000 from an external source, e.g., a building electrical supply system, may be rated to sustain a current up to 15 A. The processor 90 may be used to limit the current through the lighting fixture 1000 to 5 A such that three lighting fixtures 400A-

400C may be powered by a single power cable 1030. If the current draw of the lighting fixture 1000 approaches 5 A, the processor 90 may reduce the power draw of the lighting fixture. In this manner, the three lighting fixtures 400A-400C may collectively avoid a total current draw that exceeds 15 A, thus reducing the likelihood of damaging the power cable.

In some implementations, the processor 90 may enforce a current draw limit using an active feedback control loop. For instance, the DSP 150 of the control board 100 may be used to actively measure the voltage and current supplied to the lighting fixture 1000 via the AC line sensor 155. Depending on the magnitude and/or rate of change of the measured voltage and current, the DSP 150 may then adjust the voltage and current supplied to each of the LED modules 400A-400C such that the current drawn by the lighting fixture 1000 is maintained below the current draw limit. This process may be conducted in an iterative manner where measurements of the voltage and current supplied to the lighting fixture 1000 and subsequent adjustments to the voltage and current supplied to the LED modules 400A-400C repeatedly occur at a preset timescale. The timescale may vary from about 1 ms to about 60 s. The amount the voltage and current are varied during each increment may also vary according to the rate of change of the voltage and current supplied to the lighting fixture 1000. In some implementations, the stability of the active feedback control loop may be controlled by incorporating a proportional integral differential (PID) controller into the processor 90.

Figure 14A:
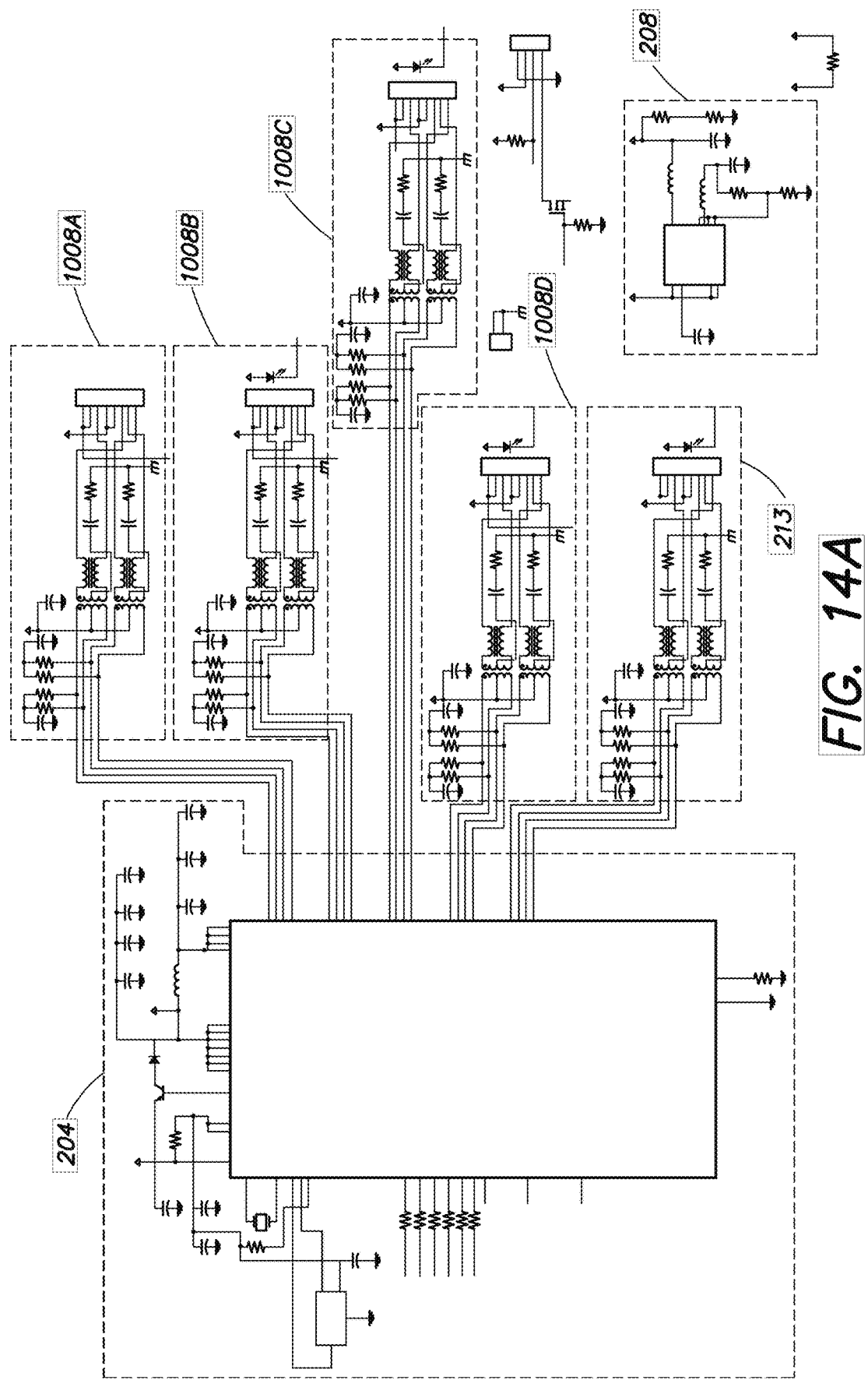
FIG. 14A is a circuit diagram detailing various electronic components of a network board, according to some implementations of the disclosure.
Figure 14B:
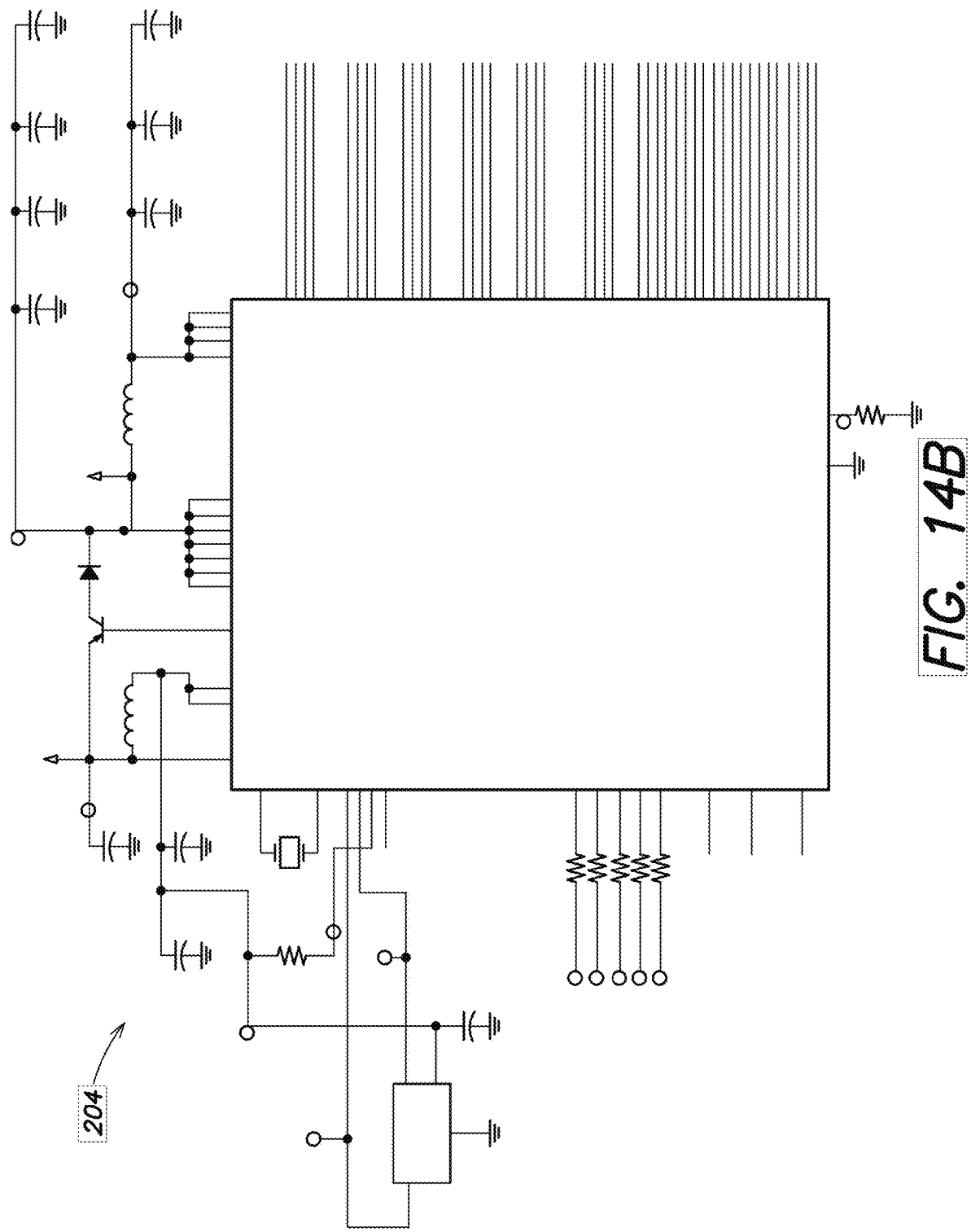
FIG. 14B is an expanded view of the Ethernet switch of FIG. 14A.
Figure 14C:
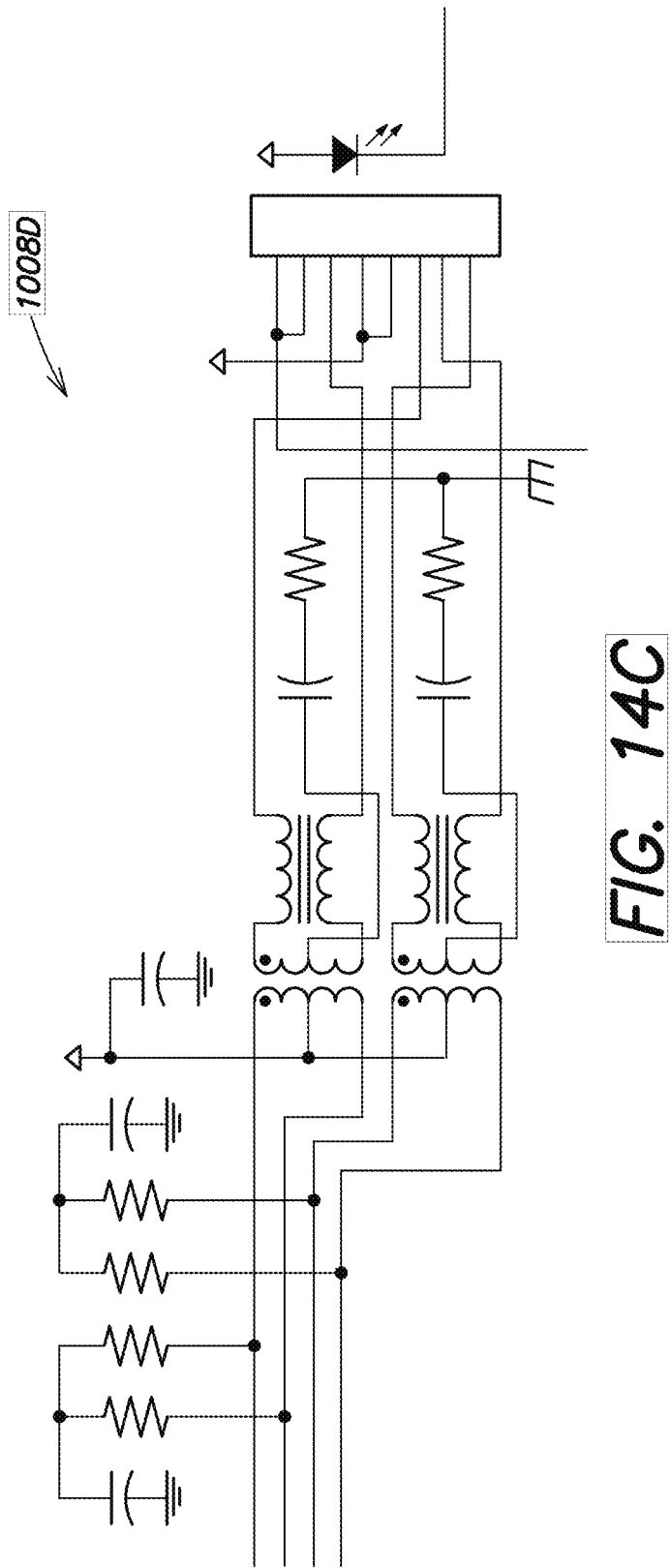
FIG. 14C is an expanded view of the PoE port of FIG. 14A.
Figure 14D:
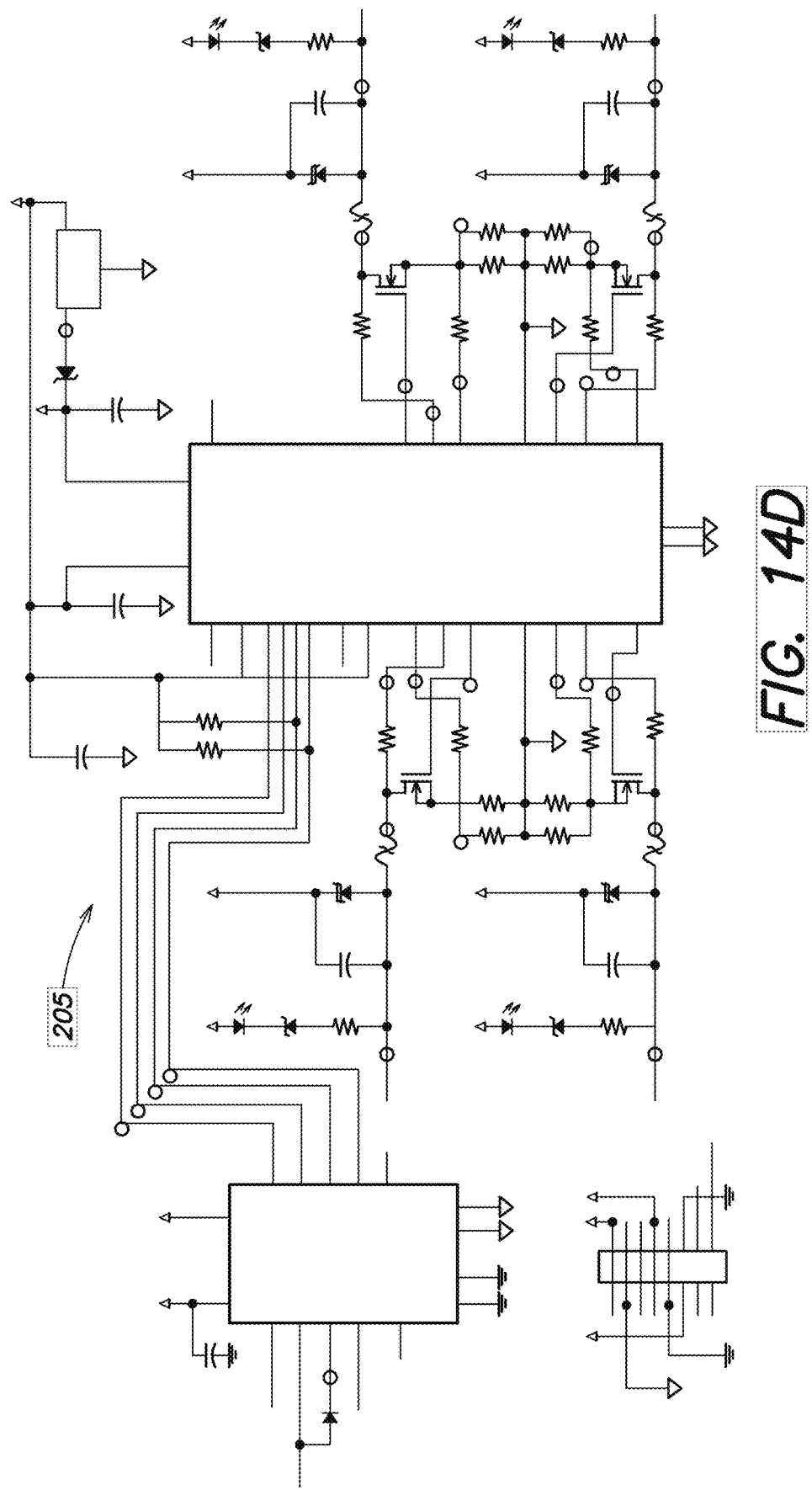
FIG. 14D is a circuit diagram of the PoE controller of FIG. 14A.
Figure 15:
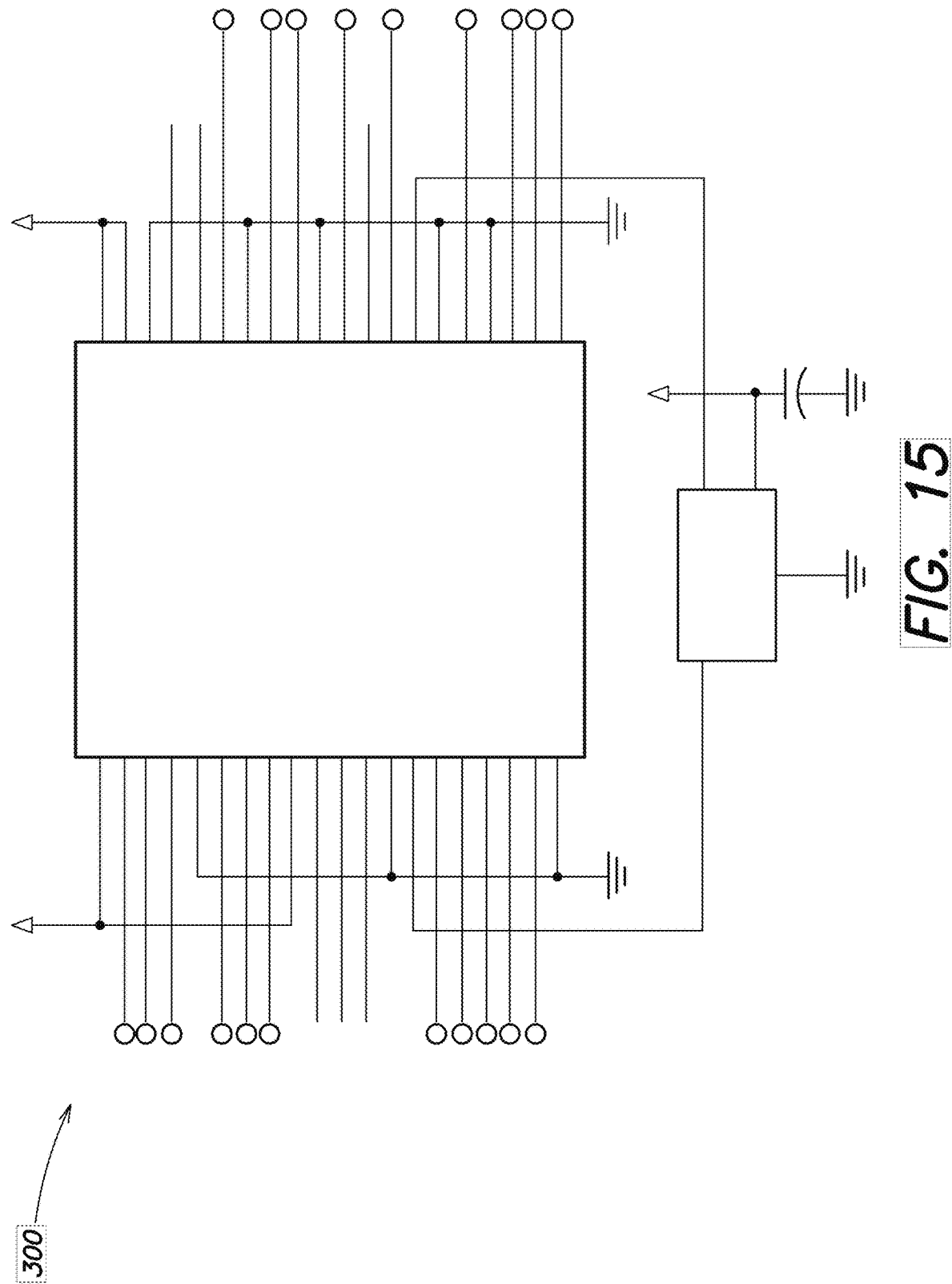
FIG. 15 is a circuit diagram of a single board computer, according to some implementations of the disclosure.
Figure 16A:
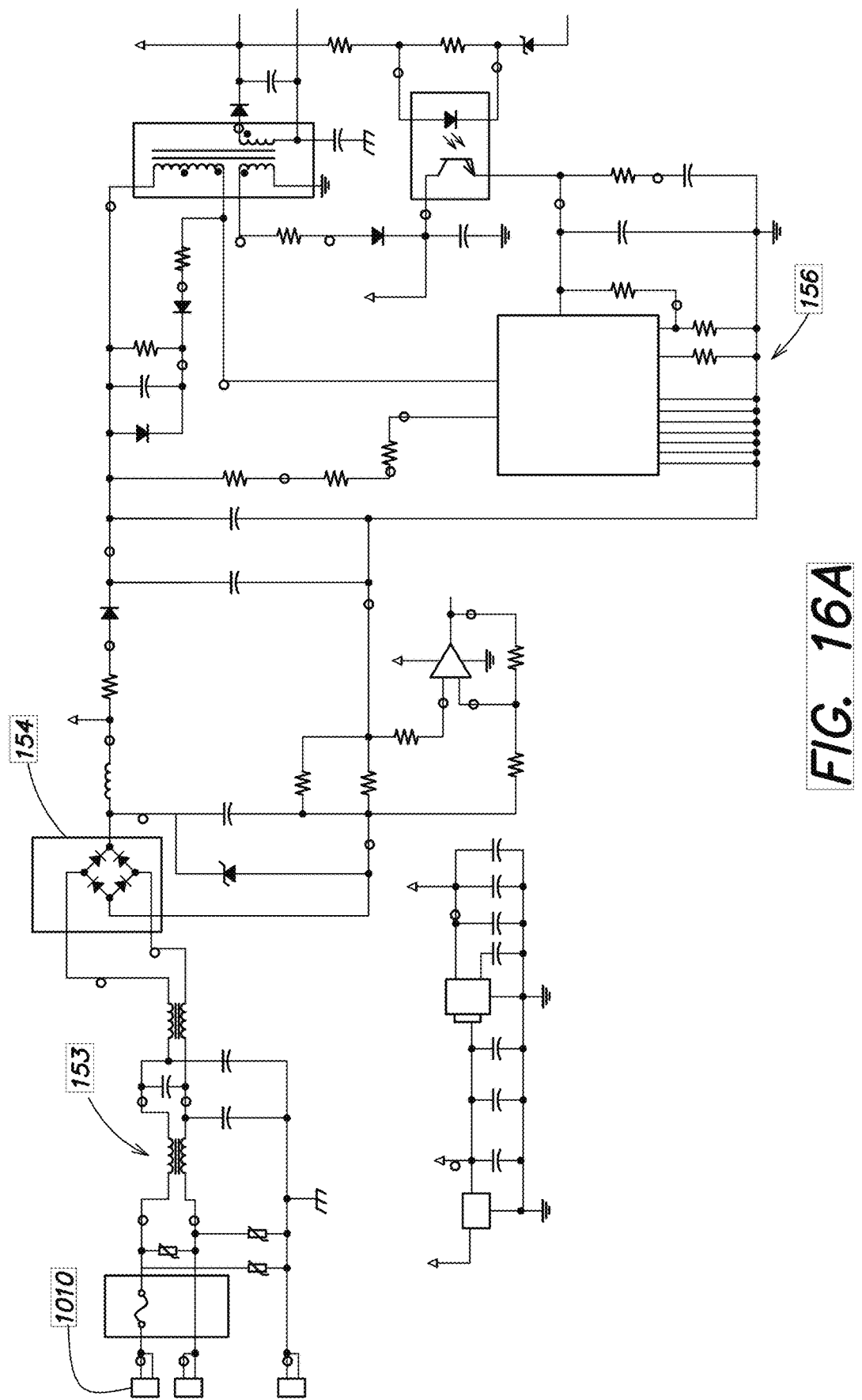
FIG. 16A is a circuit diagram detailing various electrical components of a control board, according to some implementations of the disclosure.
Figure 16B:
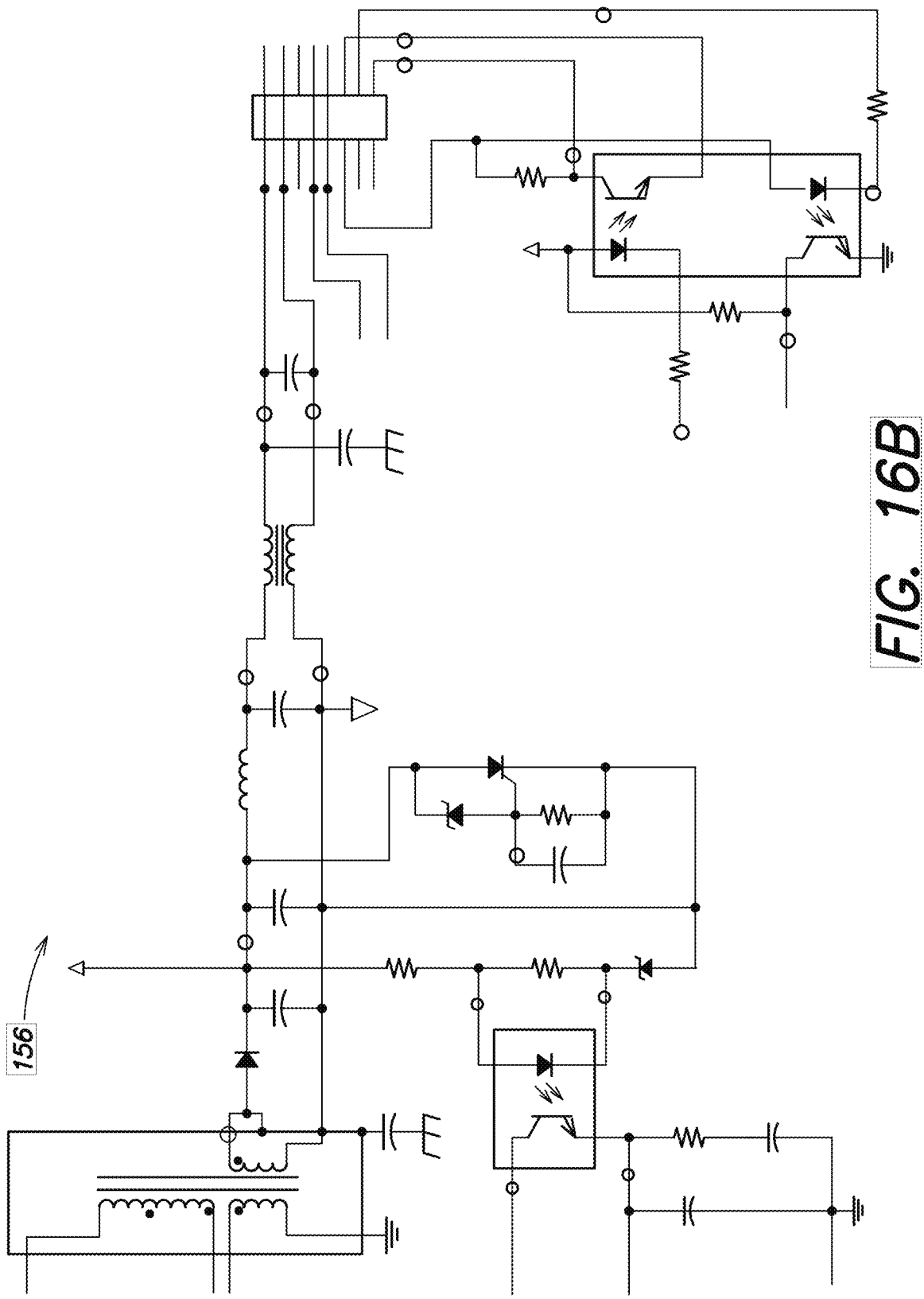
FIG. 16B is a circuit diagram detailing the bias and control power supply of the control board of FIG. 16A.
Figure 16C:
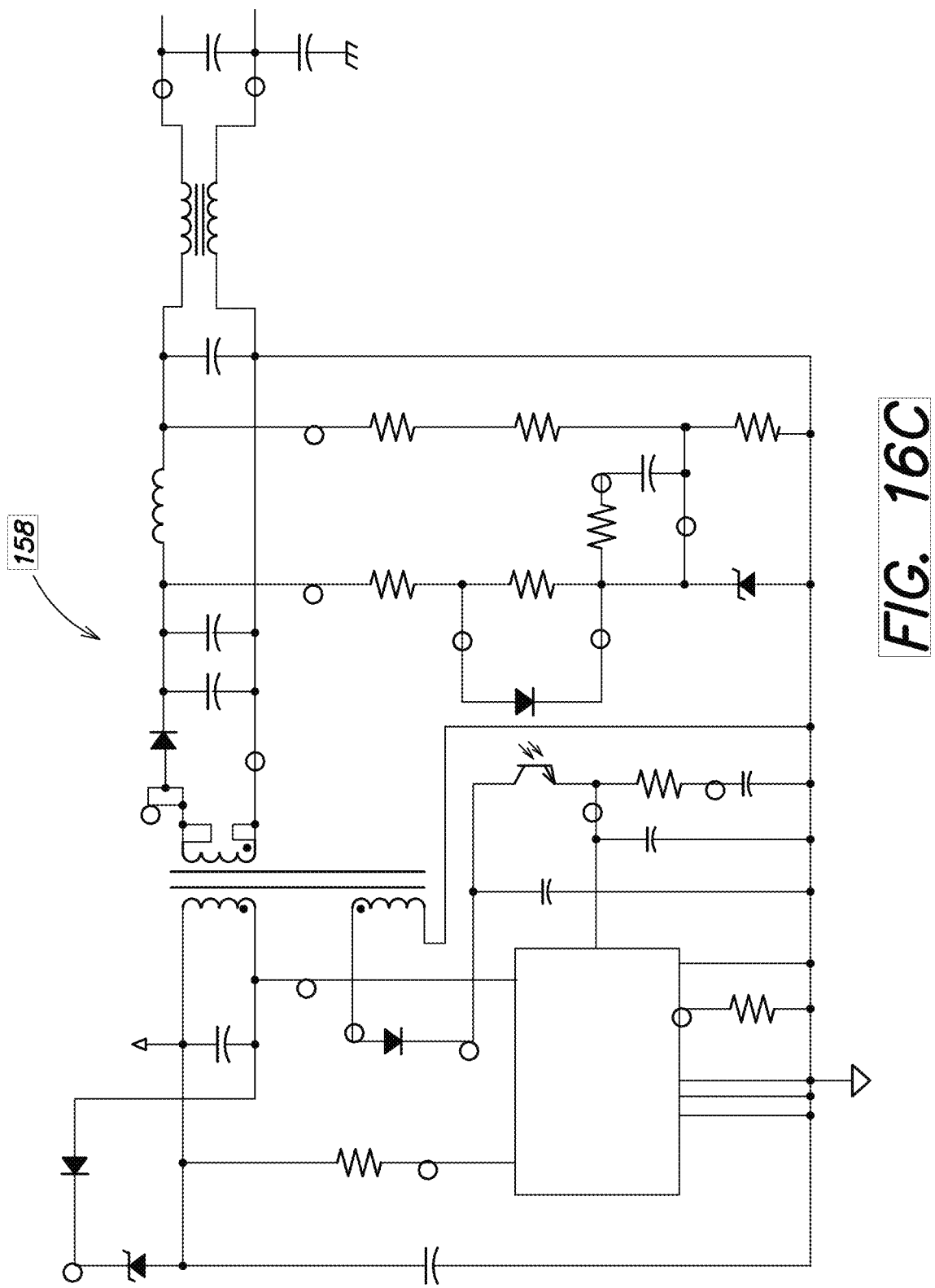
FIG. 16C is a circuit diagram detailing the DC-DC converter of the control board of FIG. 16A.
Figure 16D:
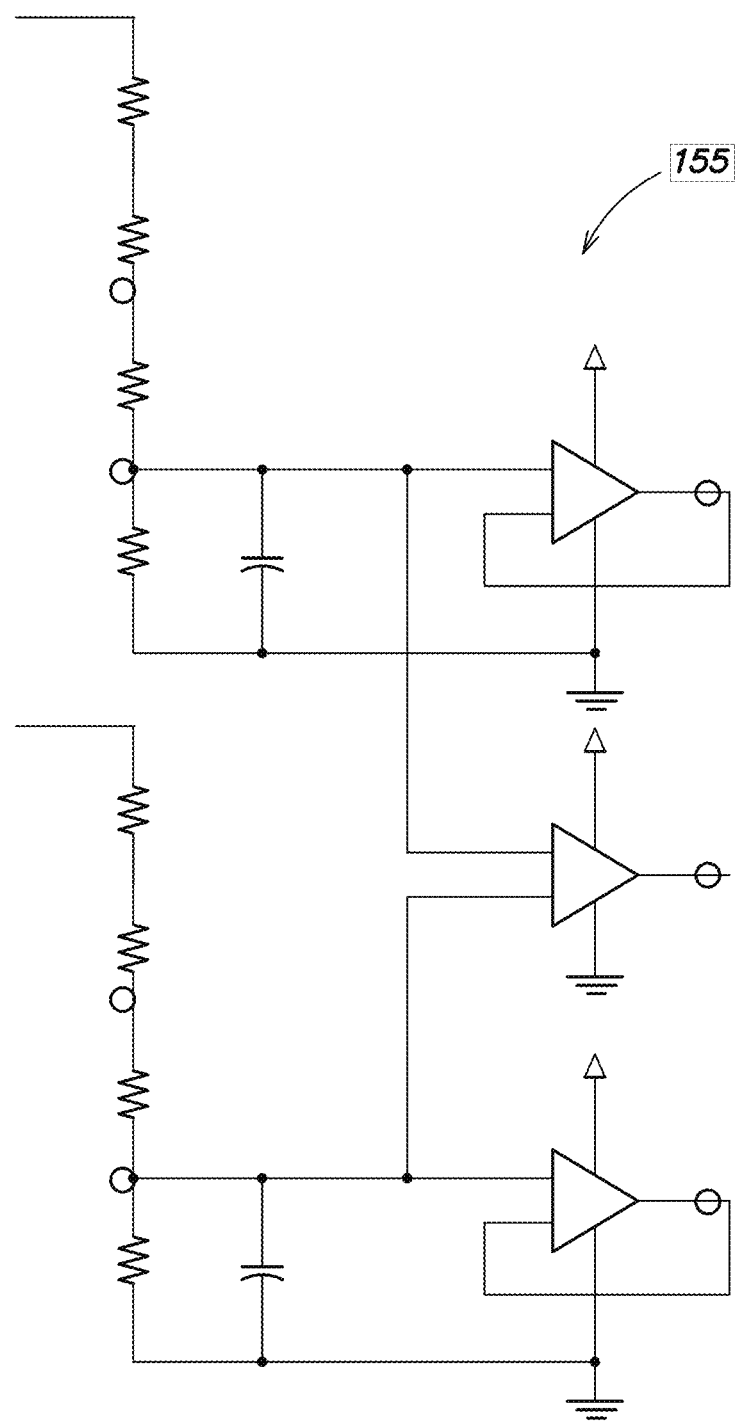
FIG. 16D is a circuit diagram detailing the AC line sensor of the control board of FIG. 16A.
Figure 16E:
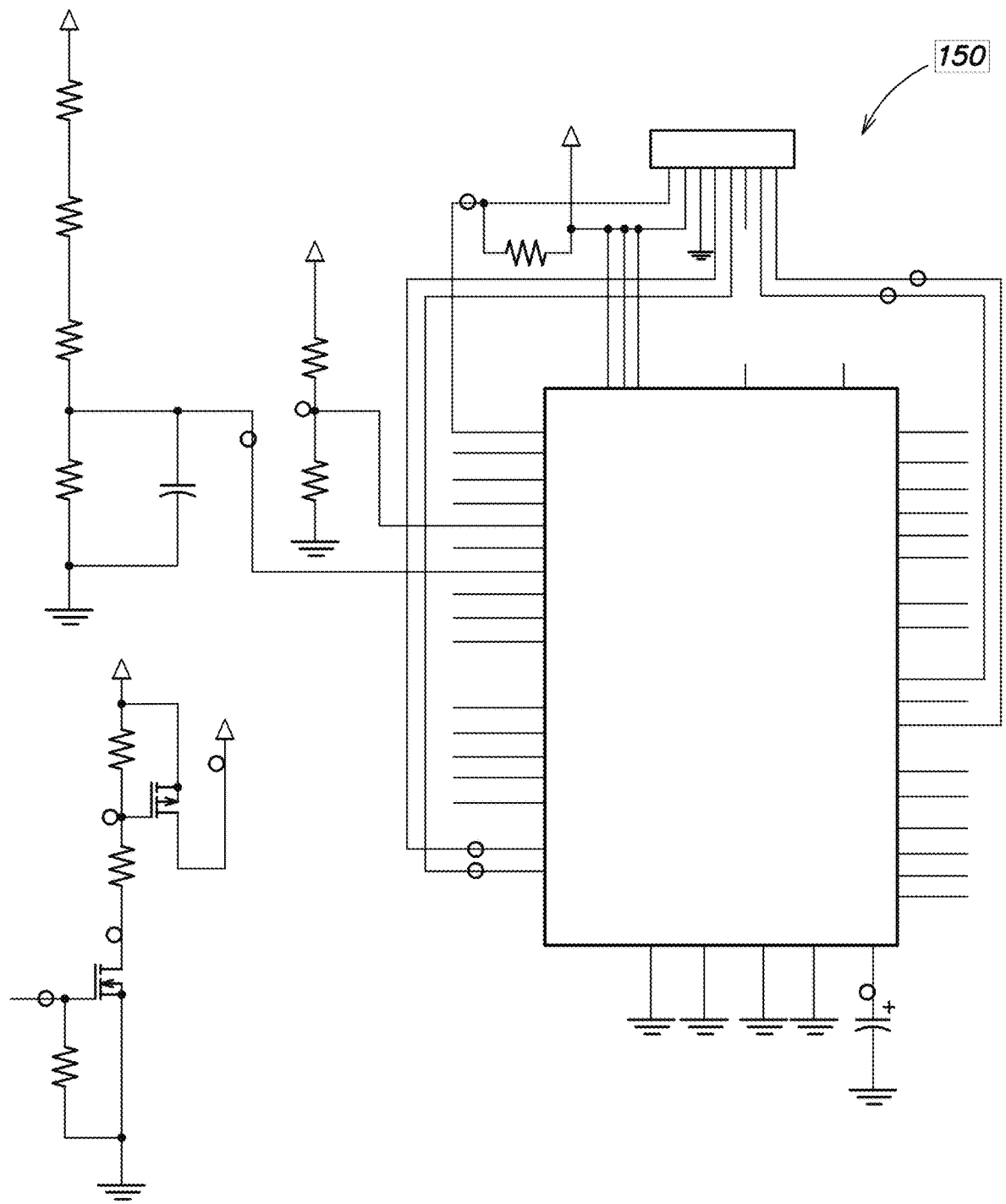
FIG. 16E is a circuit diagram detailing the DSP of the control board of FIG. 16A.
Figure 16F:
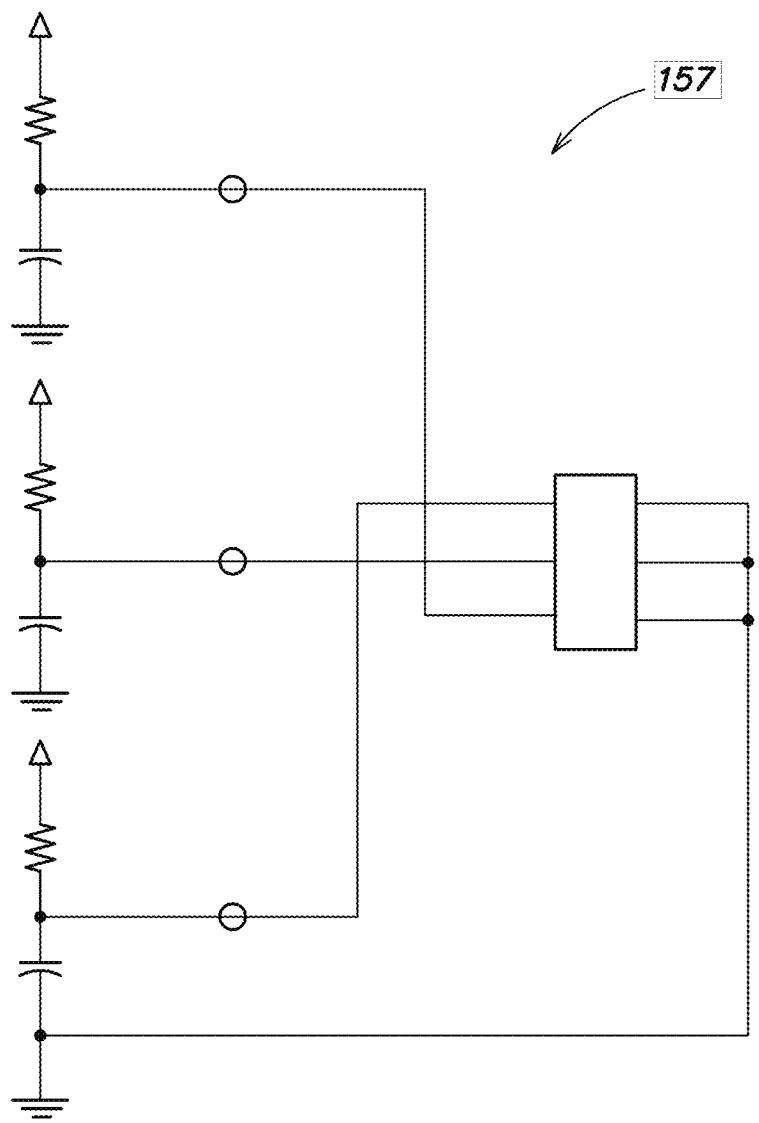
FIG. 16F is a circuit diagram detailing the temperature sensor circuitry of the control board of FIG. 16A.
Figure 16G:
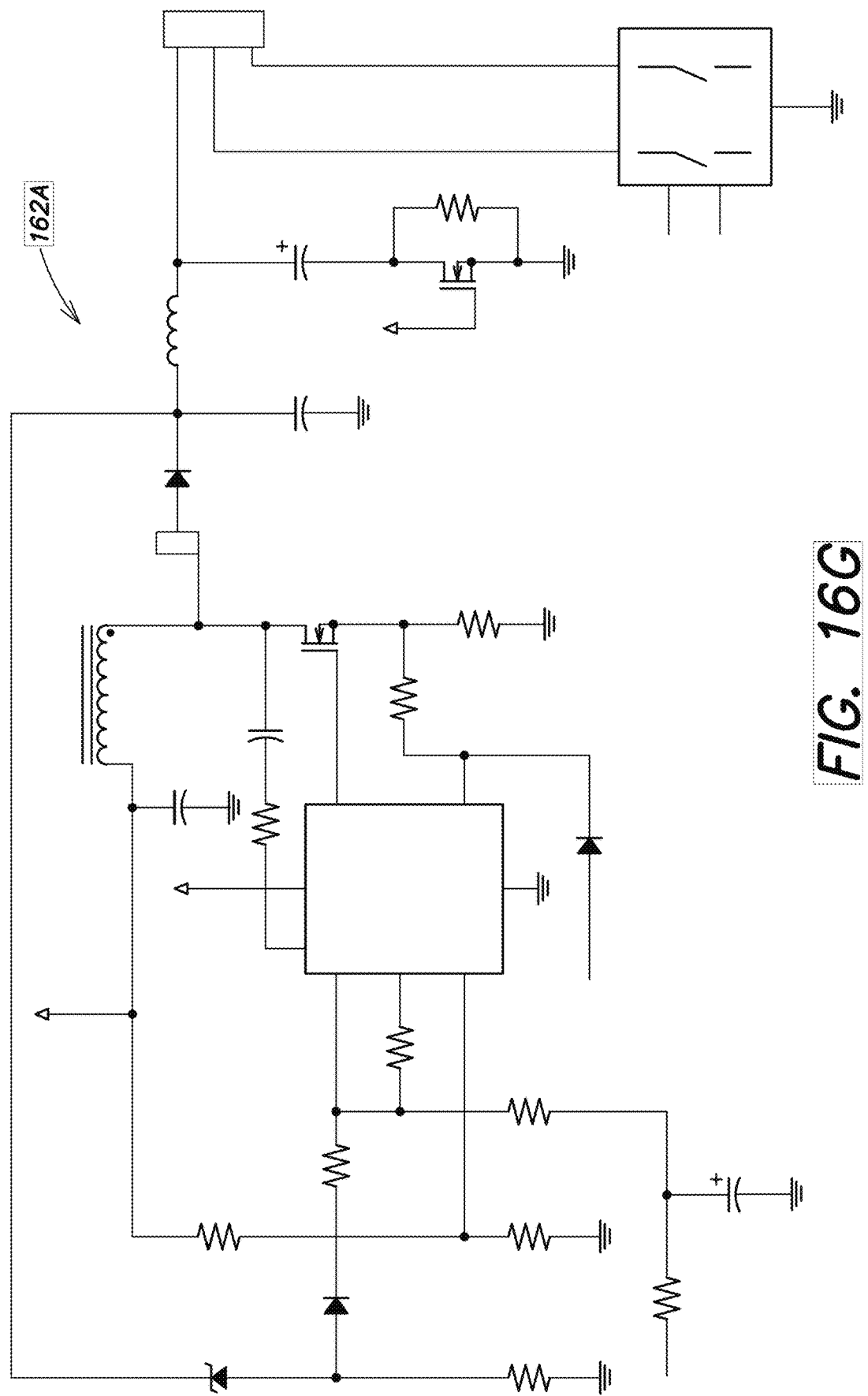
FIG. 16G is a circuit diagram detailing the boost circuit of the control board of FIG. 16A.
Figure 16H:
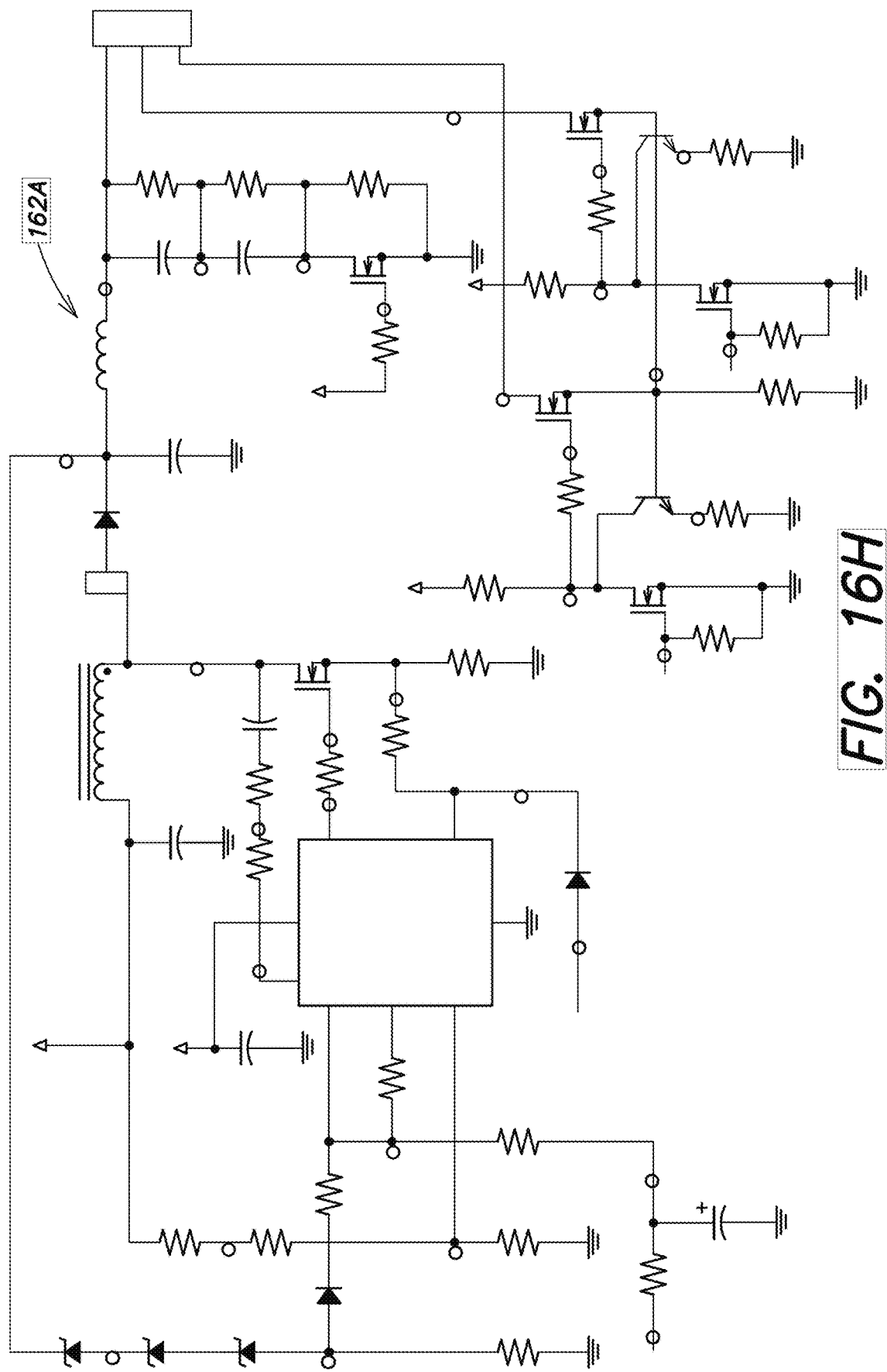
FIG. 16H is a circuit diagram further detailing the boost circuit of FIG. 16G.

FIGS. 14A-14D, 13, 16A-16H show circuit diagrams of various electrical components of a processor 90 according to one implementation. FIG. 14A shows a circuit diagram of an Ethernet switch 204 from a network board 200 and the electrical connections to PoE ports 1008A-1008D and an Ethernet port 213 for communication to a single board computer 300. FIG. 14A also shows a circuit diagram of a power supply 208 from the network board 200. For visual clarity, FIGS. 14B and 14C show expanded views of the Ethernet switch 204 and the PoE port 1008D from FIG. 14A, respectively. FIG. 14D shows a circuit diagram of a PoE controller 206 from the network board 200. FIG. 15 shows a circuit diagram of a single board computer 300 detailing various input and output connections. FIG. 16A shows circuit diagrams for an electrical power port 1010, fuse/EMI filter 153, a rectifier 154, and a first portion of a bias and control power supply 156 from a control board 100. FIG. 16B shows a second portion of the bias and control power supply 156 shown in FIG. 16A. FIGS. 16C-16F show a DC-DC converter 158, an AC line sensor 155, a DSP 150, and thermal sensor ports 154 from the control board 100. FIGS. 16G and 16H show circuit diagrams of an exemplary boost circuit 162A from the control board 100.

An Exemplary Leased Lighting System

The lighting fixture 1000 disclosed herein may also be utilized in a leased lighting system where a customer pays a recurring fee to rent and operate the lighting fixture 1000 (e.g., provide lighting using the lighting fixture 1000). In this system, the costs typically associated with purchasing the lighting fixture 1000 hardware and installation may be substantially reduced, thus providing substantial savings to the customer. The manufacturer providing the operation of the lighting fixture 1000 may earn a profit over time through continuing payments by the customer. In some implementations, the leased lighting system may be based on payment of a fee to operate the lighting fixture 1000 for a preset period of time. The lighting fixture 1000 may be communicatively coupled to a server via the processor 90. The server may remotely regulate operation of the lighting fixture, enabling the lighting fixture 1000 to provide lighting so long as the customer provides necessary payment to maintain the lease.

Figure 17A:
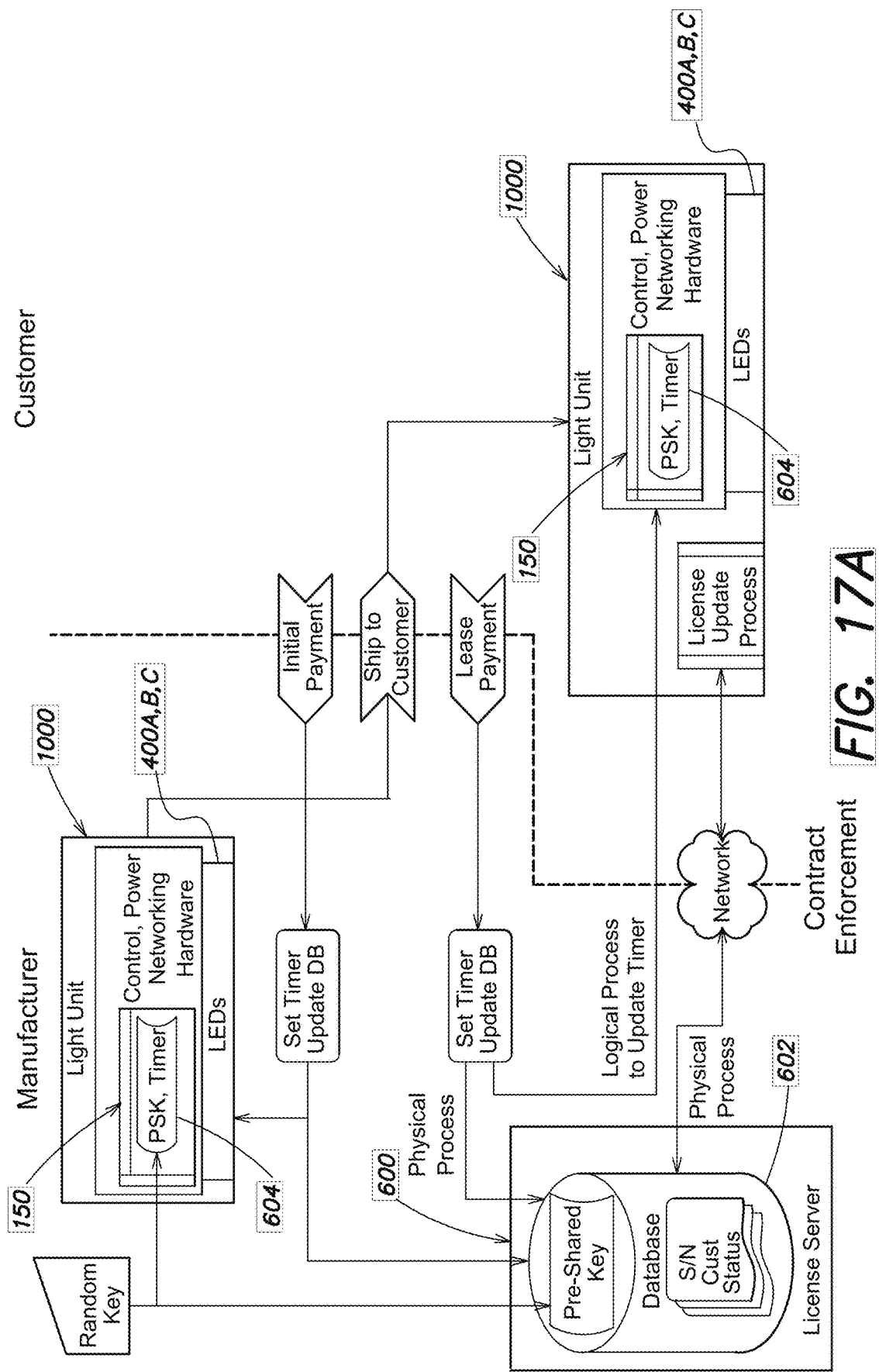
FIG. 17A is a flow diagram of a contract enforcement method, according to some implementations of the disclosure.

An exemplary implementation of a contract enforcement method where the lighting fixture 1000 is communicatively coupled to a license server 600 is shown in FIG. 17A. As shown, the license server 600 may include a database 602 containing information including, but not limited to a serial number for one or more lighting fixtures 1000 installed by a customer and a customer status (e.g., a payment status) for the customer to which the one or more lighting fixtures 1000 are leased. The database may also include a pre-shared key 604, which is also installed onto each lighting fixture 1000, e.g., such as in protected internal storage of the DSP 150 of the lighting fixture 1000, by the manufacturer, together with a timer, prior to shipment to the customer. Upon initial payment by the customer, the manufacturer may setup an initial timer update in the database 1000 to provide for some time period for initial lighting, after which an additional lease payment is required. Once the lighting fixture 1000 is deployed to the customer, the expiration of the timer may trigger a license update process. Once the additional lease payment is made, the manufacturer operating the license server 600 may update the database 602 with a new timer value, which is communicated to the lighting fixture 1000. Communication may occur via a proprietary communication protocol.

Figure 17B:
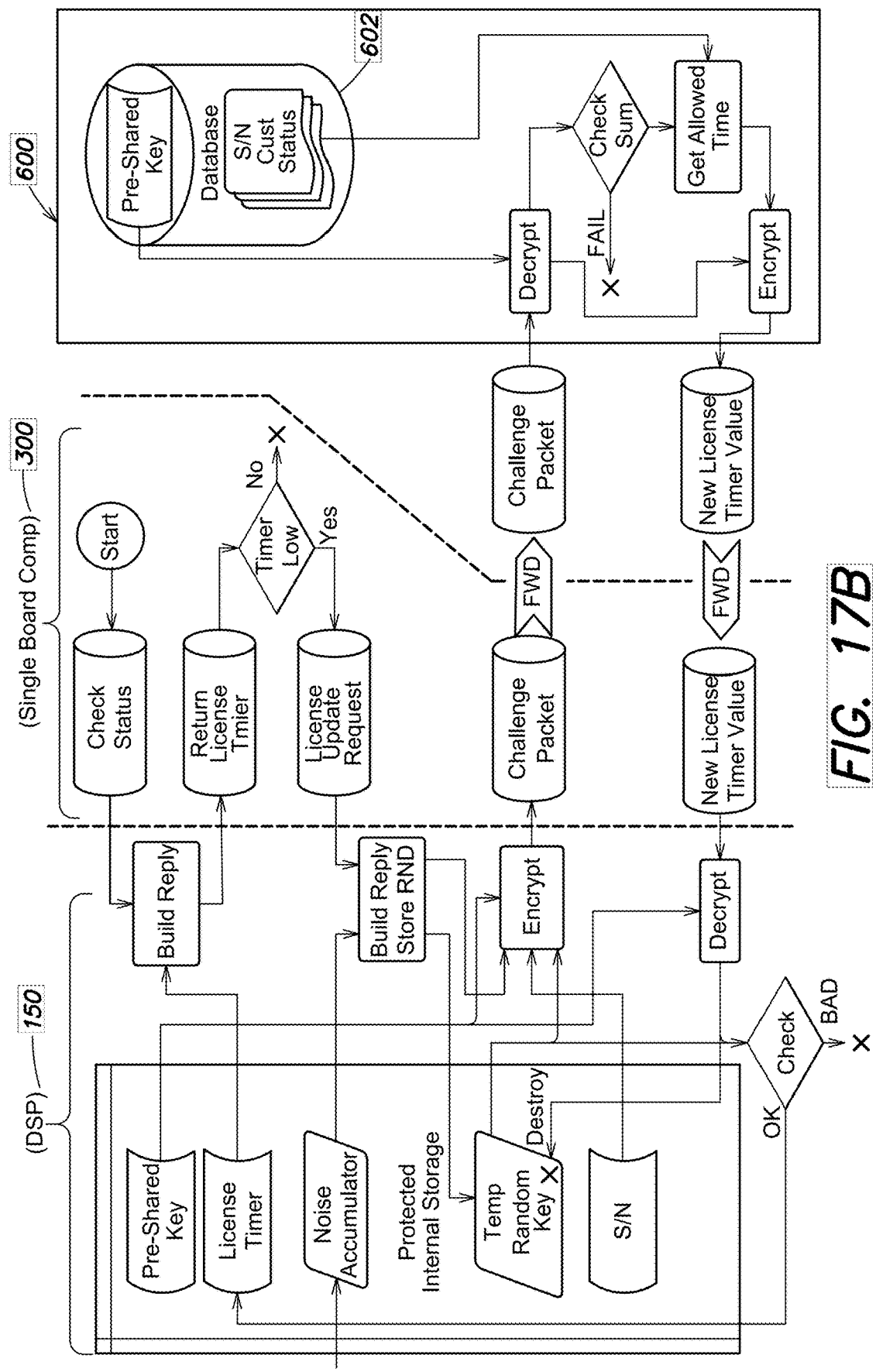
FIG. 17B is a flow diagram of a method to update a license in a leased lighting system, according to some implementations of the disclosure.

An exemplary implementation of a process to update a license for a leased lighting model with one or more lighting fixtures 1000 is shown in FIG. 17B. In this exemplary process, the DSP 150 and the single board computer 300 of the processor 90 may be coupled to the license server 600 and database 602 via the Internet to facilitate operation by the manufacturer of the one or more lighting fixtures 1000 or a leasing agent. As described above, the pre-shared key 604 and license timer may be stored in the protected internal storage of the DSP 150 by the manufacturer together with the serial number of the lighting fixture 1000. The single board computer 300 may periodically check the status of the license timer. Once the license timer is near expiration, the single board computer 300 may initiate with the DSP 150 a license update request. This request may include a "challenge packet" generated by the DSP 150, which is forwarded by the single board computer 300 to the license server 600. The challenge packet may include encrypted information based, at least in part, on the serial number of the lighting fixture 1000 and a temporary random key generated using a noise accumulator. The challenge packet may then be decrypted by the license server 600. If the challenge packet is found to be valid and payment is made for additional lighting, the license server 600 may then determine a new allowed timer value. The new allowed timer value may then be encrypted and sent back to the single board computer 300, which passes the encrypted timer value to the DSP 150. The DSP 150 may then decrypt the new timer value based on the pre-shared key 604. If the new timer value is found to be valid, the DSP 150 may update the license timer stored in the protected internal storage of the DSP 150.

CONCLUSION

All parameters, dimensions, materials, and configurations described herein are meant to be exemplary and the actual parameters, dimensions, materials, and/or configurations will depend upon the specific application or applications for which the inventive teachings is/are used. It is to be understood that the foregoing embodiments are presented primarily by way of example and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein.

In addition, any combination of two or more such features, systems, articles, materials, kits, and/or methods, if such features, systems, articles, materials, kits, and/or methods are not mutually inconsistent, is included within the inventive scope of the present disclosure. Other substitutions, modifications, changes, and omissions may be made in the design, operating conditions and arrangement of respective elements of the exemplary implementations without departing from the scope of the present disclosure. The use of a numerical range does not preclude equivalents that fall outside the range that fulfill the same function, in the same way, to produce the same result.

The above-described embodiments can be implemented in multiple ways. For example, embodiments may be implemented using hardware, software or a combination thereof. When implemented in software, the software code can be executed on a suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in a suitable form, including a local area network or a wide area network, such as an enterprise network, an intelligent network (IN) or the Internet. Such networks may be based on a suitable technology, may operate according to a suitable protocol, and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine. Some implementations may specifically employ one or more of a particular operating system or platform and a particular programming language and/or scripting tool to facilitate execution.

Also, various inventive concepts may be embodied as one or more methods, of which at least one example has been provided. The acts performed as part of the method may in some instances be ordered in different ways. Accordingly, in some inventive implementations, respective acts of a given method may be performed in an order different than specifically illustrated, which may include performing some acts simultaneously (even if such acts are shown as sequential acts in illustrative embodiments).

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A fluid-cooled LED-based lighting fixture, comprising:
an extruded aluminum frame including at least a first channel formed therein, a second channel formed therein, and at least one enclosed cavity formed therein, the extruded aluminum frame further including a fin protruding from the frame and having a plurality of holes to facilitate mechanical coupling of the lighting fixture to at least one support structure;
at least one LED light source mechanically supported by the extruded aluminum frame;
a first copper pipe to carry a fluid coolant to extract heat generated by at least the at least one LED light source during operation of the lighting fixture, wherein the first copper pipe is press-fit into the first channel of the extruded aluminum frame so as to establish a first thermal connection between the first copper pipe and the extruded aluminum frame;
a second copper pipe to carry the fluid coolant, wherein the second copper pipe is press-fit into the second channel of the extruded aluminum frame so as to establish a second thermal connection between the second copper pipe and the extruded aluminum frame;
control circuitry, disposed in the at least one enclosed cavity of the extruded aluminum frame, to receive AC power and to control the at least one LED light source;
at least one camera disposed in or on the extruded aluminum frame; and
a plurality of ports, electrically coupled to at least some of the control circuitry, to provide DC power to at least one auxiliary device coupled to at least one of the plurality of ports.

2. The lighting fixture of claim 1, further comprising:
at least one wireless communications device disposed in or on the extruded aluminum frame.

3. The lighting fixture of claim 1, wherein the at least one camera comprises a first imaging or sensing device responsive to a first spectrum of radiation, the first spectrum of radiation including at least one of a visible band of radiation or a near infrared (NIR) band of radiation.

4. The lighting fixture of claim 3, wherein the at least one camera further comprises a second imaging or sensing device responsive to a second spectrum of radiation different than the first spectrum of radiation.

5. The lighting fixture of claim 4, wherein the at least one camera further comprises a third imaging or sensing device responsive to a third spectrum of radiation different than the first spectrum of radiation and the second spectrum of radiation.

6. The lighting fixture of claim 5, wherein:
the first spectrum of radiation includes at least a visible band of radiation;
the second spectrum of radiation includes a first infrared band of radiation; and
the third spectrum of radiation includes a second infrared band of radiation.

7. The lighting fixture of claim 4, wherein the at least one LED comprises:
a first plurality of LEDs to illuminate a plant with photosynthetically active radiation (PAR); and
a second plurality of LEDs to irradiate at least one object in an environment of the lighting fixture to facilitate sensing by the at least one camera or sensor, the second plurality of LEDs emitting radiation having at least:
a first wavelength or first wavelength band of radiation; and
a second wavelength or second wavelength band of radiation different from the first wavelength or first wavelength band of radiation.

8. The lighting fixture of claim 7, further comprising:
a multi spectral imaging module comprising:
a housing coupled to the extruded aluminum frame;
the second plurality of LEDs disposed in the housing; and
the at least one camera disposed in the housing.

9. A fluid-cooled LED-based lighting fixture, comprising:
an extruded aluminum frame including at least a first channel formed therein, a second channel formed therein, and at least one enclosed cavity formed therein, the extruded aluminum frame further including a fin protruding from the frame and having a plurality of holes to facilitate mechanical coupling of the lighting fixture to at least one support structure;
at least one LED light source mechanically supported by the extruded aluminum frame, the at least one LED comprising:
a first plurality of LEDs to provide illumination in an environment of the lighting fixture during operation of the lighting fixture; and
a second plurality of LEDs to irradiate at least one object in the environment of the lighting fixture with at least:
a first wavelength or first wavelength band of radiation; and
a second wavelength or second wavelength band of radiation different from the first wavelength or first wavelength band of radiation;
a first copper pipe to carry a fluid coolant to extract heat generated by at least the at least one LED light source during operation of the lighting fixture, wherein the first copper pipe is press-fit into the first channel of the extruded aluminum frame so as to establish a first thermal connection between the first copper pipe and the extruded aluminum frame;
a second copper pipe to carry the fluid coolant, wherein the second copper pipe is press-fit into the second channel of the extruded aluminum frame so as to establish a second thermal connection between the second copper pipe and the extruded aluminum frame;
control circuitry, disposed in the at least one enclosed cavity of the extruded aluminum frame, to receive AC power and to control the at least one LED light source;
at least one camera disposed in or on the extruded aluminum frame;
at least one wireless communications device disposed in or on the extruded aluminum frame; and a plurality of ports, electrically coupled to at least some of the control circuitry, to provide DC power to at least one auxiliary device coupled to at least one of the plurality of ports, wherein the second plurality of LEDs facilitates sensing, by the at least one camera, of reflected or emitted radiation reflected or emitted by the at least one object in the environment in response to irradiation by the second plurality of LEDs.

10. The lighting fixture of claim 9, wherein the second plurality of LEDs comprises:
a plurality of visible LEDs to irradiate the at least one object with multiple first wavelengths or first wavelength bands of radiation in a visible band of radiation; and
a plurality of infrared LEDs to irradiate the at least one object with multiple second wavelengths or second wavelength bands of radiation in an infrared band of radiation.

11. The lighting fixture of claim 9, wherein the second plurality of LEDs further comprises:
at least one ultraviolet LED to irradiate the at least one object with a third wavelength or third wavelength band of radiation in an ultraviolet band of radiation.

12. The lighting fixture of claim 9, wherein the at least one camera comprises:
a first imaging or sensing device responsive to a first spectrum of radiation, the first spectrum of radiation including at least a visible band of radiation;
a second imaging or sensing device responsive to a second spectrum of radiation different than the first spectrum of radiation, the second spectrum of radiation including a first infrared band of radiation; and
a third imaging or sensing device responsive to a third spectrum of radiation different than the first spectrum of radiation and the second spectrum of radiation, the third spectrum of radiation including a second infrared band of radiation.

13. The lighting fixture of claim 9, further comprising:
a multi spectral imaging module comprising:
a housing coupled to the extruded aluminum frame;
the second plurality of LEDs disposed in the housing; and
the at least one camera disposed in the housing,
wherein at least a portion of the housing is transparent to radiation in at least the first wavelength or first wavelength band of radiation and the second wavelength or second wavelength band of radiation.

14. A lighting and imaging system, comprising:
a first housing;
a first LED light source, mechanically supported by the first housing, to illuminate a plant with photosynthetically active radiation (PAR);
a multi spectral imaging module comprising:
a second housing coupled to the first housing;
at least one of a camera or a sensor disposed in the second housing;
a second LED light source, disposed in the second housing, to irradiate at least one object in an environment of a lighting fixture to facilitate sensing, by the at least one camera or sensor, of reflected or emitted radiation reflected or emitted by the at least one object in response to irradiation by the second LED light source, the second LED light source comprising:
at least one first LED to emit first essentially monochromatic or relatively narrowband radiation; and
at least one second LED to emit second essentially monochromatic or relatively narrowband radiation different from the first essentially monochromatic or relatively narrowband radiation; and
at least one processor, coupled to the second LED light source and the at least one of the camera or the sensor, to sequentially control the at least one first LED and the at least one second LED and monitor the at least one camera or sensor by:
A) controlling the at least one first LED to emit the first essentially monochromatic or relatively narrowband radiation to irradiate the at least one object;
B) during A), acquiring first information from the at least one of the camera or the sensor representing first reflected or emitted radiation from the at least one object based on the first essentially monochromatic or relatively narrowband radiation irradiating the at least one object;
C) controlling the at least one second LED to emit the second essentially monochromatic or relatively narrowband radiation; and
D) during C), acquiring second information from the at least one of the camera or the sensor representing second reflected or emitted radiation from the at least one object based on the second essentially monochromatic or relatively narrowband radiation irradiating the at least one object.

15. The system of claim 14, further comprising:
a copper pipe, coupled to the first housing, to flow a fluid coolant that extracts heat generated by at least one of the first LED light source or the second LED light source during operation of the lighting and imaging system.

16. The system of claim 15, further comprising:
an antenna, coupled to the first housing, to:
transmit at least one of the first information or the second information to a remote device; and/or
receive at least one signal from the remote device that is used by the at least one processor to:
adjust at least one of the PAR or the flow of the fluid coolant; and/or
control the second LED light source.

17. The system of claim 14, wherein the at least one camera or sensor comprises:
a first camera to acquire visible imagery of at least a portion of the at least one object;
a second camera to acquire infrared imagery of at least a portion of the at least one object; and
a single point sensor to measure a temperature based on infrared radiation from at least a portion of the at least one object,
wherein the first camera, the second camera, and the single point sensor are located proximate to each other so as to have substantially overlapping fields of view.

18. The system of claim 14, wherein the at least one processor is configured to generate different finite spectra images based respectively on the first information representing the first reflected or emitted radiation and the second information representing the second reflected or emitted radiation.

19. The system of claim 18, wherein the at least one processor is further configured to generate at least one multispectral image by aligning and superimposing the different finite spectra images, wherein respective pixels of the at least one multispectral image include spatial and spectral information.

20. The system of claim 14, wherein:

the at least one object includes the plant; and the at least one processor is further configured to repeat A), B), C), and D) at least once and analyze the first information and the second information to detect physical changes in the plant over time.

21. The system of claim 14, wherein the at least one object includes the plant, and wherein the at least one first LED and the at least one second LED respectively emit the first essentially monochromatic or relatively narrowband radiation and the second essentially monochromatic or relatively narrowband radiation with a sufficient intensity to acquire the first information and the second information without causing chemical and/or morphological changes to the plant.

22. The system of claim 14, wherein the at least one object includes the plant, and wherein the at least one processor is further configured to:

E) analyze the first information and the second information based at least in part on spectral absorptive properties of one or more types of chlorophyll compounds; and F) detect and/or quantify one or more chemical compounds in the plant based at least in part on E).

23. The system of claim 14, wherein the at least one processor is further configured to adjust the PAR provided by the first LED light source based at least in part on at least one of the first information or the second information.

24. A method for controlling a lighting and imaging system to illuminate and acquire images of an agricultural environment, the lighting and imaging system comprising:

a fluid-cooled first LED light source to illuminate at least one plant with photosynthetically active radiation (PAR); and a multi spectral imaging module coupled to the fluid-cooled first LED light source and comprising:

at least one of a camera or a sensor; and a second LED light source comprising:

at least one first LED to emit first essentially monochromatic or relatively narrowband radiation; and at least one second LED to emit second essentially monochromatic or relatively narrowband radiation different from the first essentially monochromatic or relatively narrowband radiation, the method comprising:

A) controlling the at least one first LED to emit the first essentially monochromatic or relatively narrowband radiation to irradiate the at least one plant;

B) during A), acquiring first information from the at least one of the camera or the sensor representing first reflected or emitted radiation from the at least one plant based on the first essentially monochromatic or relatively narrowband radiation irradiating the at least one plant;

C) controlling the at least one second LED to emit the second essentially monochromatic or relatively narrowband radiation; and D) during C), acquiring second information from the at least one of the camera or the sensor representing second reflected or emitted radiation from the at least one plant based on the second essentially monochromatic or relatively narrowband radiation irradiating the at least one plant.

25. The method of claim 24, further comprising:

E) generating different finite spectra images based respectively on the first information representing the first reflected or emitted radiation and the second information representing the second reflected or emitted radiation.

26. The method of claim 25, further comprising:

F) generating at least one multispectral image by aligning and superimposing the different finite spectra images in E), such that respective pixels of the at least one multispectral image include spatial and spectral information based at least in part on the first information and the second information.

27. The method of claim 24, further comprising:

E) repeating A), B), C), and D) at least once; and

F) analyzing at least one of the first information or the second information to detect physical changes in the at least one plant over time.

28. The method of claim 24, further comprising:

E) analyzing the first information and the second information based at least in part on spectral absorptive properties of one or more types of chlorophyll compounds; and F) detecting and/or quantifying one or more chemical compounds in the plant based at least in part on E).

29. The method of claim 28, wherein:

F) comprises detecting an amount of the one or more chemical compounds relative to a nominal baseline for the one or more types of chlorophyll compounds.

30. The method of claim 24, further comprising:

adjusting the PAR provided by the fluid-cooled first LED light source based at least in part on at least one of the first information or the second information.

* * * * *